US009359338B2

(12) United States Patent
Zhang et al.

(10) Patent No.: US 9,359,338 B2
(45) Date of Patent: Jun. 7, 2016

(54) CYCLOPROPANECARBOXAMIDO-SUBSTITUTE AROMATIC COMPOUNDS AS ANTI-TUMOR AGENTS

(71) Applicant: Crown Bioscience Inc. (Taiwan), Taipei (TW)

(72) Inventors: Deyi Zhang, Taicang (CN); Ruihao Zhang, Taicang (CN); Boyu Zhong, Taicang (CN); Chuan Shih, Taicang (CN)

(73) Assignee: CROWN BIOSCIENCE INC. (Taiwan), Xinyi Dist. Taipei (TW)

( * ) Notice: Subject to any disclaimer, the term of this patent is extended or adjusted under 35 U.S.C. 154(b) by 0 days.

(21) Appl. No.: 14/408,943

(22) PCT Filed: Jun. 24, 2013

(86) PCT No.: PCT/CN2013/000731
§ 371 (c)(1),
(2) Date: Dec. 17, 2014

(87) PCT Pub. No.: WO2014/000418
PCT Pub. Date: Jan. 3, 2014

(65) Prior Publication Data
US 2015/0197511 A1 Jul. 16, 2015

(30) Foreign Application Priority Data

Jun. 26, 2012 (CN) .......................... 2012 1 0213116
Apr. 16, 2013 (CN) .......................... 2013 1 0172393

(51) Int. Cl.
| | |
|---|---|
| C07D 401/12 | (2006.01) |
| A61K 31/4427 | (2006.01) |
| C07D 413/12 | (2006.01) |
| A61K 31/44 | (2006.01) |
| C07D 403/12 | (2006.01) |
| A61K 31/505 | (2006.01) |
| A61K 31/506 | (2006.01) |
| C07D 213/75 | (2006.01) |
| C07D 239/47 | (2006.01) |
| C07D 213/68 | (2006.01) |
| C07D 213/72 | (2006.01) |
| C07D 405/12 | (2006.01) |

(52) U.S. Cl.
CPC .............. *C07D 413/12* (2013.01); *A61K 31/44* (2013.01); *A61K 31/4427* (2013.01); *A61K 31/505* (2013.01); *A61K 31/506* (2013.01); *C07D 213/68* (2013.01); *C07D 213/72* (2013.01); *C07D 213/75* (2013.01); *C07D 239/47* (2013.01); *C07D 401/12* (2013.01); *C07D 403/12* (2013.01); *C07D 405/12* (2013.01)

(58) Field of Classification Search
CPC .. C07D 401/12; C07D 403/12; C07D 213/72; C07D 213/75; C07D 239/47; A61K 31/44; A61K 31/4427; A61K 31/505; A61K 31/506

USPC ........... 544/319; 546/261, 297; 514/269, 335, 514/349
See application file for complete search history.

(56) References Cited

U.S. PATENT DOCUMENTS

| | | |
|---|---|---|
| 2003/0216446 A1 | 11/2003 | Dumas et al. |
| 2008/0234332 A1 | 9/2008 | Cai et al. |
| 2010/0311980 A1 | 12/2010 | Rao et al. |

FOREIGN PATENT DOCUMENTS

| | | |
|---|---|---|
| CN | 1303380 A | 7/2001 |
| CN | 1630638 A | 6/2005 |
| CN | 101163691 A | 4/2008 |
| CN | 101421253 A | 4/2009 |
| JP | 2005-272474 A | 10/2005 |
| JP | 2007-51400 A | 6/2007 |
| WO | 02/32872 A1 | 4/2002 |
| WO | 03/068746 A1 | 8/2003 |
| WO | 2004/078748 A2 | 9/2004 |
| WO | 2005/051366 A2 | 6/2005 |
| WO | 2007/119055 A1 | 10/2007 |
| WO | 2008/033747 A2 | 3/2008 |
| WO | 2008/115263 A2 | 9/2008 |
| WO | 2009/034308 A2 | 3/2009 |
| WO | 2009/042646 A1 | 4/2009 |
| WO | 2011/158042 A2 | 12/2011 |

OTHER PUBLICATIONS

Johnson et al., Relationships between drug activity in NCI preclinical in vitro and in vivo models and early clinical trials, British Journal of Cancer, 84(10):1424-1431,2001.*
Pearce et al., Failure modes in anticancer drug discovery and development, Cancer Drug Design and Discovery Edited by Stephen Neidle, Chapter 18, pp. 424-435 (2008).*
Simone, Oncology: Introduction, Cecil Textbook of Medicine, 20th Edition, vol. 1, pp. 1004-1101 O, 1995.*
Gura et al., Systems for identifying new drugs are often faulty, Science, 278:1041-1042, 1997.*
Youzhi Li et al., Suppressino of cancer relapse and metastasis by inhibiting cancer stemness, PNAS, vol. 112, No. 6, pp. 1839-1844 (2015).*
Kolch et al., Raf-1 protein kinase is required for growth of induced NIH/3T3 cells, Nature, vol. 349, pp. 426-428 (1991).*
International Search Report for International Application No. PCT/CN2013/000731 dated Oct. 3, 2013.
Cohen, "Protein kinases—the major drug targets of the twenty-first century?," *Nat. Rev. Drug Discov.*, vol. 1(4), pp. 309-315 (2002).

(Continued)

*Primary Examiner* — Deepak Rao
(74) *Attorney, Agent, or Firm* — Jun He Law Offices P.C.; James J. Zhu

(57) ABSTRACT

Provided are cyclopropanecarboxamido-substituted aromatic compounds that inhibit protein kinases and their use in anti-tumor area. In particular, tyrosine-kinase inhibitors and Raf-kinase inhibitors as anti-tumor agents, their preparation, pharmaceutical composition, and their use in the treatment of cancer are also provided.

32 Claims, No Drawings

(56) References Cited

OTHER PUBLICATIONS

Folkman, "What Is the Evidence That Tumors Are Angiogenesis Dependent?," *National Cancer Institute*, vol. 82, pp. 4-6, (1990).
Thompson, et al., "Recent progress in targeting the Raf/MEK/ERK pathway with inhibitors in cancer drug discovery," *Curr. Opin. Pharmacology*, vol. 5, pp. 350-356 (2005).
Office Action with English translation for Chinese Patent Application No. 201310172393.X, mailed Nov. 19, 2014, 16 pages.
European Search Report for European Application No. 13810683.6 dated Oct. 15, 2015.
Office Action dated Feb. 2, 2016 in JP 2015-518790, 4 pages.

* cited by examiner

CYCLOPROPANECARBOXAMIDO-SUBSTITUTE AROMATIC COMPOUNDS AS ANTI-TUMOR AGENTS

CROSS-REFERENCE TO RELATED APPLICATIONS

This application is the U.S. National Stage entry of PCT/CN2013/000731, filed Jun. 24, 2013, which claims priority to China Application No. 201310172393.X, filed Apr. 16, 2013, and China Application No. 201210213116.4, filed Jun. 26, 2012, and each is incorporated herein in its entirety.

TECHNICAL FIELD

The present invention relates to novel cyclopropanecarboxamido-substituted aromatic compounds that inhibit protein kinases and their use in anti-tumor area. In particular, the invention relates to novel tyrosine-kinase inhibitors and Raf-kinase inhibitors as anti-tumor agents, their preparation, pharmaceutical composition, and their use in the treatment of cancer.

BACKGROUND OF THE INVENTION

Protein kinases have become targets of intense drug discovery efforts for the past 10-15 years (Cohen, Nat. Rev. Drug Discov., 2002, 1(4), 309-315; Sebolt-Leopold, Nature Review Cancer, 2004, 4, 937-947). Small molecule inhibitors of Ras-Raf-Mek-Erk pathway have been the focus of many studies (Thompson, et al., Curr. Opin. Pharmacology, 2005, 5, 1-7; US patent Application 2003/0216446). Raf inhibitors have been proposed to be used in inhibiting cancer cell growth and in the treatment of cancers, including histiocytic lymphoma, lung adenocarcinoma, small-cell lung cancer, pancreatic cancer, and breast cancer. Recently, the approval of Zelboraf® (Vemurafenib by Plexxikon/Roche) for B-Raf mutated metastatic melanoma further demonstrates the attractiveness of the target.

Disruption of VEGFR signaling is a very attractive target in cancer therapy, as angiogenesis is a prerequisite for all solid tumor growth (Folkman, J. National Cancer Institute, 1990, 82, 4-6) and that the mature endothelium remains relatively quiescent (except for female reproductive system and wound healing), consequently, targeting of pro-angiogenesis pathway becomes a strategy being widely pursued to provide new therapeutics in cancer area.

WO2008/115263 to Curis relates to Raf kinase inhibitors containing zinc-binding and their use in the treatment of Raf related diseases and disorders such as cancer. The said derivatives may further act as HDAC inhibitors.

WO2008/033747 to Curis relates to the compositions, methods, and applications of a novel approach to selective inhibition of several cellular or molecular targets with a single small molecule. More specifically, the present invention relates to multi-functional small molecules wherein one functionality is capable of inhibiting histone deacetylases (HDAC) and the other functionality is capable of inhibiting a different cellular or molecular pathway involved in aberrant cell proliferation, differentiation or survival.

WO2009/042646 to Curis relates to the compositions, methods, and applications of a novel approach to selective inhibition of several cellular or molecular targets with a single small molecule. More specifically, the present invention relates to multi-functional small molecules capable of inhibiting a different cellular or molecular pathway involved in aberrant cell proliferation, differentiation or survival.

WO2002/32872 (EP1415987) to Eisai relates to nitrogeneous aromatic ring compounds as anti-cancer agents.

The present invention provides novel cyclopropanecarboxamido-substituted aromatic compounds which have improved anti-tumor activity and longer half-life in vivo over known, structurally-related compounds. These novel compounds are kinase inhibitors, preferably Raf inhibitors and VEGFR-2 (KDR/Flk-1) inhibitors. Since Raf is a key component of Ras-Raf-Mek-Erk pathway and VEGFR-2 is critical in angiogenesis, inhibitors of these kinases will be useful in pharmaceutical compositions for human and veterinary use where inhibition of Raf pathway or VEGFR-mediated angiogenesis is indicated, e.g., treatment of tumor or cancerous cell growth mediated by Raf and/or VEGFR-2 kinases. In particular, the compounds or the invention are useful in the treatment of human and animal solid tumors.

DESCRIPTION OF THE INVENTION

The objective of the present invention is to provide a series of amides of nitrogen-containing heteroaryls with anti-tumor activities.

In one aspect, the present invention novel compounds of formula (I), and pharmaceutically acceptable salts thereof

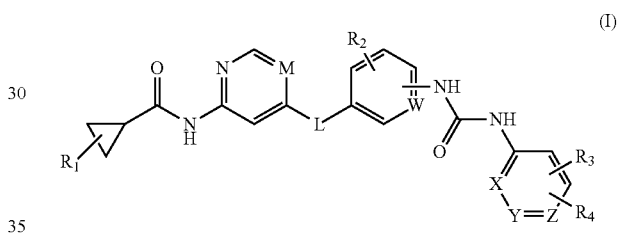

wherein:
$R_1$ is hydrogen, $C_{1-6}$ alkyl, $C_{1-6}$ haloalkyl, halo, or cyano;
M is CH or N;
L is O, NH, or $N(CH_3)$;
A is $CR_5$ or N;
W is $CR_6$ or N;
$R_2$, $R_5$ and $R_6$ are independently hydrogen, $C_{1-6}$ alkyl, $C_{1-6}$ haloalkyl, halo, $C_{3-7}$ cycloalkyl or cyano;
X, Y, and Z are independently CH or N;
$R_3$, $R_4$ are independently hydrogen, halo, cyano, $C_{1-6}$ alkyl, $C_{1-6}$ haloalkyl, $C_{2-6}$ alkenyl, hydroxyl-$C_{1-6}$ alkyl, di-($C_{1-6}$ alkylamino)-$C_{1-6}$ alkyl, amino, $C_{1-6}$ alkylamino, $C_{3-7}$ cycloalkylamino, di-($C_{1-6}$ alkyl)amino, amino-$C_{1-6}$ alkylamino, $C_{1-6}$ alkoxy-$C_{1-6}$ alkylamino, $C_{1-6}$ alkoxycarbonyl-$C_{1-6}$ alkylamino, di-($C_{1-6}$ alkoxy-$C_{1-6}$ alkyl)amino, aminocarbonyl, $C_{1-6}$ alkylaminocarbonyl, di-($C_{1-6}$ alkyl) aminocarbonyl, $C_{3-7}$ cycloalkylaminocarbonyl, $C_{1-6}$ alkoxy, $C_{3-7}$ cycloalkoxy, hydroxyl-$C_{1-6}$ alkoxy, $C_{1-6}$ haloalkoxy, amino-$C_{1-6}$ alkyl, amino-$C_{1-6}$ alkoxy, $C_{1-6}$ alkylsulfonyl, $C_{2-6}$ alkenylsulfonyl, $C_{3-7}$ cycloalkylsulfonyl, heterocycle optionally substituted by B, aryl optionally substituted by B, heteroaryl optionally substituted by B, $C_{1-6}$ alkylsulfonylamino, $C_{2-6}$ alkenylsulfonylamino, $C_{3-7}$ cycloalkylsulfonylamino, amido, $C_{1-6}$ alkylcarbonylamino, $C_{2-6}$ alkenylcarbonylamino, $C_{3-7}$ cyclooalkylcarbonylamino, $C_{1-6}$ alkoxycarbonylamino, $C_{3-7}$ cycloalkoxycarbonylamino, ureido, $C_{3-7}$ cycloalkyl, $C_{3-7}$ halocycloalkyl, heterocyclyl-oxy, piperidinylamino, N-methyl-piperidinyl-4-carbonyl, piperazinyl-$C_{1-6}$ alkyl, pyrrolylcarbonylamino, N-methyl-piperidinylcarbonylamino or heterocyclyl-$C_{1-6}$ alkoxy; or $R_3$ and $R_4$ can form a 3 to 8-membered ring together with atoms in the aromatic ring to which they are attached; and B is hydrogen, $C_{1-6}$ alkyl, $C_{1-6}$ haloalkyl, halo, hydroxyl, aryl, amino, $C_{1-6}$ alkylamino, $C_{3-7}$ cycloalkylamino, di-($C_{1-6}$ alkyl)amino, cyano, or $C_{3-7}$ cycloalkyl.

In one embodiment, the NHCONH and L substituents on the central aromatic ring are in a 1,3-configuration.

In another embodiment, the NHCONH and L substituents on the central aromatic ring are in a 1,4-configuration.

In another embodiment, L is O.

In another embodiment, L is NH or N(CH$_3$).

In another embodiment, X, Y, and Z are all CH.

In another embodiment, one of X, Y, or Z is N and the other two are CH.

In another embodiment, M is CH.

In another embodiment, M is N.

In another embodiment, A is CR$_5$.

In another embodiment, A is N.

In another embodiment, W is CR$_6$.

In another embodiment, W is N.

In another embodiment, $R_1$ is hydrogen or $C_{1-3}$ alkyl.

In another embodiment, $R_2$, $R_5$ and $R_6$ are independently hydrogen, $C_{1-3}$ alkyl, $C_{1-3}$ haloalkyl, halo, or cyano.

In another embodiment, $R_3$ and $R_4$ are independently hydrogen, halo, cyano, $C_{1-6}$ alkyl, $C_{1-6}$ haloalkyl, $C_{2-6}$ alkenyl, hydroxyl-$C_{1-6}$ alkyl, di-($C_{1-6}$ alkylamino)-$C_{1-6}$ alkyl, amino, $C_{1-6}$ alkylamino, $C_{3-7}$ cycloalkylamino, di-($C_{1-6}$ alkyl)amino, amino-$C_{1-6}$ alkylamino, $C_{1-6}$ alkoxy-$C_{1-6}$ alkylamino, $C_{1-6}$ alkoxycarbonyl-$C_{1-6}$ alkylamino, di-($C_{1-6}$ alkoxy-$C_{1-6}$ alkyl)amino, aminocarbonyl, $C_{1-6}$ alkylaminocarbonyl, di-($C_{1-6}$ alkyl)aminocarbonyl, $C_{3-7}$ cycloalkylaminocarbonyl, $C_{1-6}$ alkoxy, $C_{3-7}$ cycloalkoxy, hydroxyl-$C_{1-6}$ alkoxy, $C_{1-6}$ haloalkoxy, amino-$C_{1-6}$ alkyl, amino-$C_{1-6}$ alkoxy, $C_{1-6}$ alkylsulfonyl, $C_{2-6}$ alkenylsulfonyl, $C_{3-7}$ cycloalkylsulfonyl, heterocycle optionally substituted by B, aryl optionally substituted by B, heteroaryl optionally substituted by B, $C_{1-6}$ alkylsulfonylamino, $C_{2-6}$ alkenylsulfonylamino, $C_{3-7}$ clcyoalkylsulfonylamino, amido, $C_{1-6}$ alkylcarbonylamino, $C_{2-6}$ alkenylcarbonylamino, $C_{3-7}$ clcyoalkylcarbonylamino, $C_{1-6}$ alkoxycarbonylamino, $C_{3-7}$ cycloalkoxycarbonylamino, ureido, $C_{3-7}$ cycloalkyl, $C_{3-7}$ halocycloalkyl, heterocyclyl-oxy, piperidinylamino, N-methyl-piperidinyl-4-carbonyl, piperazinyl-$C_{1-6}$ alkyl, pyrrolylcarbonylamino, N-methyl-piperidinylcarbonylamino or heterocyclyl-$C_{1-6}$ alkoxy.

In another embodiment, one or both of $R_3$ and $R_4$ are independently a heterocyclyl-oxy group selected from pyrrolyloxy, piperidinyloxy, furanyloxy and azetidinyloxy.

In another embodiment, one or both of $R_3$ and $R_4$ are independently an optionally substituted aryl group selected from phenyl and naphthyl.

In another embodiment, one or both of $R_3$ and $R_4$ are independently an optionally substituted hereroaryl group selected from furyl, pyridinyl, pyridazinyl, pyrimidinyl, pyrazinyl, thienyl, isoxazolyl, oxazolyl, oxadiazolyl, imidazolyl, pyrrolyl, pyrazolyl, triazolyl, tetrazolyl, thiazolyl, isothiazolyl, 1,2,3-thiadiazolyl, benzimidazolyl, indolyl, indazolyl, benzoisothiazolyl, benzoxazolyl, benzoisoxazolyl, qunioliniyl and isoquinolinyl.

In another embodiment, the hereroaryl is pyridinyl, oxazolyl, or triazolyl.

In another embodiment, one or both of $R_3$ and $R_4$ are independently an optionally substituted heterocyclyl group selected from piperidinyl, piperazinyl, homopiperazinyl, azepinyl, azetidinyl, pyrrolidinyl, pyrazolidinyl, imidazolidinyl, imidazolinyl, oxazolidinyl, isoxazolidinyl, morpholinyl, thiazolidinyl, isothiazolidinyl, quinuclidinyl, thiadiazolidinyl, benzothiazolidinyl, benzopynolidinyl, dihydrofuranyl, tetrahydrofuranyl, dihydropyranyl, tetrahydropyranyl, thiomorpholinyl, 1-oxo-thiomorpholinyl, 1,1-dioxothiomorpholinyl, dihydroquinolinyl, dihydroisoquinolinyl, tetrahydroquinolinyl and tetrahydroisoquinolinyl.

In another embodiment, the optionally substituted heterocyclyl is N($R_7$)piperazinyl, N($R_7$)piperidin-4-yl, pyrrolidinyl, 2-oxopyrrolidinyl, morpholinyl, 2-methylmorpholinyl, 2,6-dimethylmorpholinyl, 2-oxomorpholinyl, 3-(dimethylamino)pyrrolidinyl, 2-oxo-5-methyloxazolidin-3-yl, 3,3-difluoroazetidinyl, fluoropiperidinyl, hydroxylpiperidinyl, or 1,1,-dioxothiomorpholinyl, and $R_7$ is hydrogen, $C_{1-3}$ alkyl, $C_{1-3}$ haloalkyl, $C_{3-6}$ cycloalkyl, $C_{1-5}$ acyl or $C_{3-6}$ cycloalkylacyl.

In another embodiment, B is hydrogen, $C_{1-3}$ alkyl, $C_{1-3}$ haloalkyl, halo, hydroxyl, aryl, amino, $C_{1-3}$ alkylamino, $C_{3-5}$ cycloalkylamino, di-($C_{1-3}$ alkyl)amino, cyano, or $C_{3-5}$ cycloalkyl.

In another embodiment, B is hydrogen, halo, hydroxyl, $C_{1-3}$ alkyl, $C_{1-3}$ haloalkyl, di-($C_{1-3}$ alkyl)amino.

In another embodiment, $R_3$ and $R_4$ are independently halo, cyano or $C_{1-3}$ haloalkyl.

In another embodiment, $R_3$ and $R_4$ together form a 3 to 8-membered ring with the atoms in the aromatic ring to which they are attached.

Other embodiments of the compounds include Examples 1-242, and pharmaceutically acceptable salts thereof.

It is understood that the invention also contemplates all possible combinations of the embodiments listed above.

The compounds of the present invention have improved anti-tumor activity and longer half-life in vivo. For example, compared to the marketed drug sorafenib which is structurally somewhat similar to the compound in example 137 of this invention, the in vitro IC$_{50}$ of compound 137 at B-Raf is four times more potent than that of sorafenib. In pre-clinical animal studies, sorafenib has a shorter half-life than many of the compounds in this invention; its in vivo anti-tumor activities are also weaker than that of many of the compounds in the present invention. Clinically, sorafenib is given twice daily with 200-400 mg each time. The preferred compounds in the present invention are expected to be given once daily with much lower dose.

A key difference between compounds in the present invention and those known in the art is the use of (substituted) cyclopropanecarboxamido group as the substituent on the aromatic rings. It is this (substituted)cyclopropanecarboxamido group that plays a key and irreplaceable role in providing the desired properties to compounds in the present invention. For example, when the cyclopropanecarboxamido group in example 22 is replaced by a cyclobutanecarboxamido group, the IC$_{50}$ of the resulting compound is decreased by twenty folds in pERK assay using MDA-MB-231 cell line; whereas the replacement of cyclopropanecarboxamido group in example 7 with either cyclobutanecarboxamido group or propionamido group results in more than twenty fold loss of activity in pERK assay using MDA-MB-231 cell line. These examples further demonstrate the pivotal role that (substituted)cyclopropanecarboxamido group plays in the structures and properties of compounds in the present invention.

A second aspect of the invention relates to the processes for preparing the compounds of the invention and to the synthetic intermediates useful in such process as described below. Compounds of the present invention can be prepared in a number of conventional methods. Some suitable methods for preparing the compounds are described in the examples. Typically, compounds of formula (I) can be prepared with the methods below.

Because of the fixed (properly substituted) cyclopropanecarboxamide structural feature, it would be more efficient when a fragment containing this functional feature is allowed to couple with another fragment through urea bond formation to make the final products. There are many ways of forming ureas, including reaction of amines with isocynates; or reaction of amines with phenyl carbamates or other analogs. For example, Compounds in Formula (I) may be prepared through the following approach:

1) Amines with optionally substituted phenylisocynates or other arylisocynates

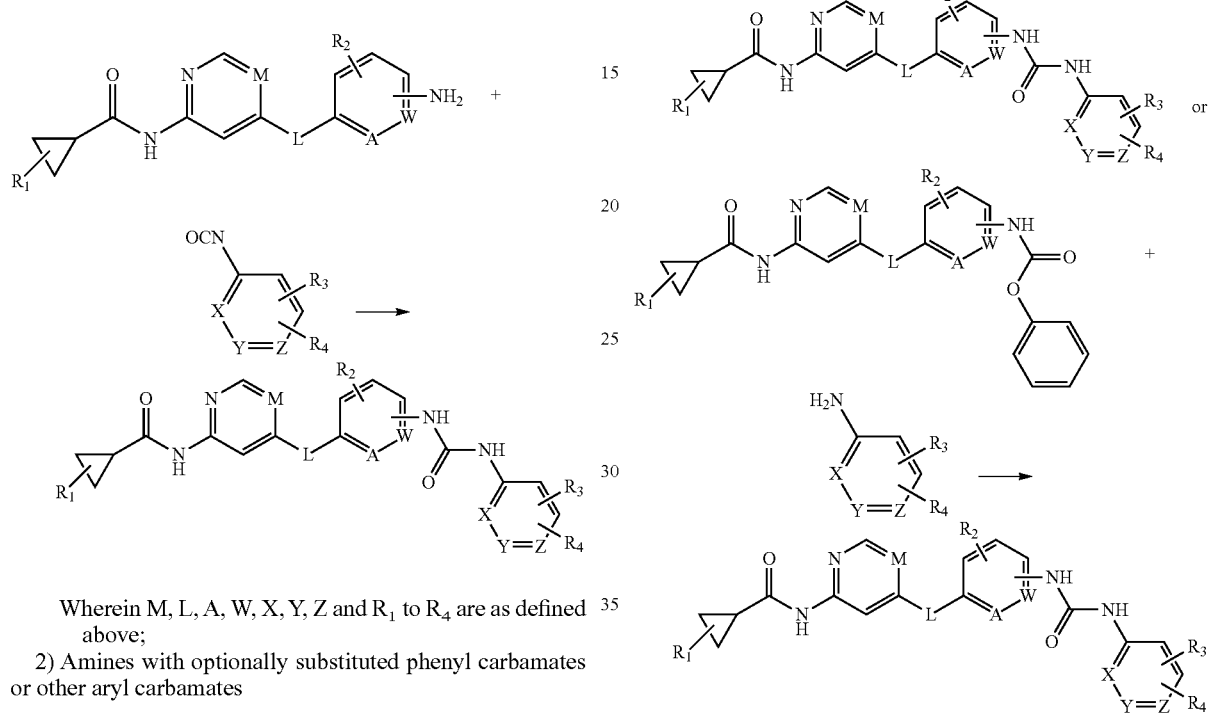

Wherein M, L, A, W, X, Y, Z and $R_1$ to $R_4$ are as defined above;

2) Amines with optionally substituted phenyl carbamates or other aryl carbamates

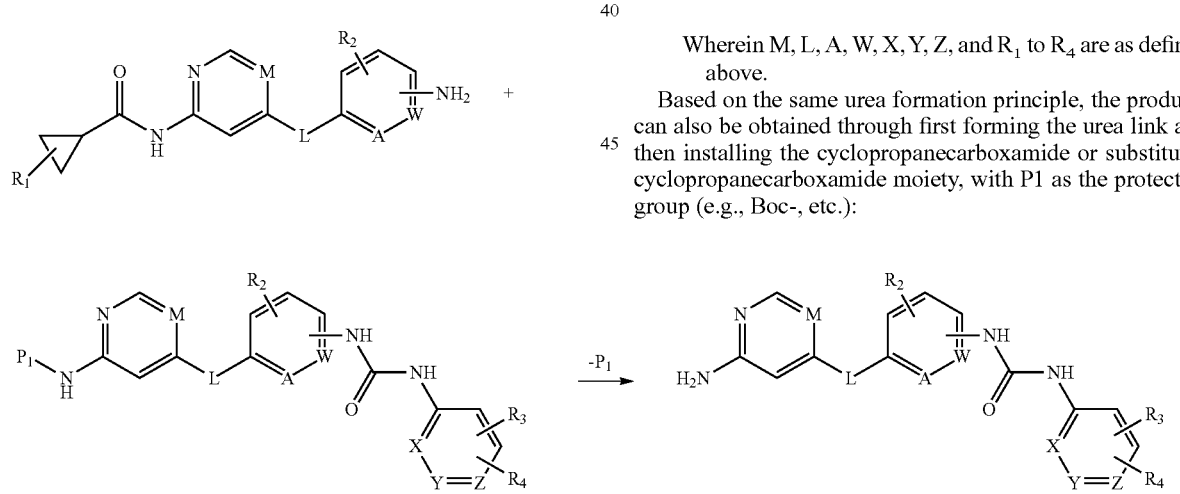

Wherein M, L, A, W, X, Y, Z, and $R_1$ to $R_4$ are as defined above.

Based on the same urea formation principle, the products can also be obtained through first forming the urea link and then installing the cyclopropanecarboxamide or substituted cyclopropanecarboxamide moiety, with P1 as the protective group (e.g., Boc-, etc.):

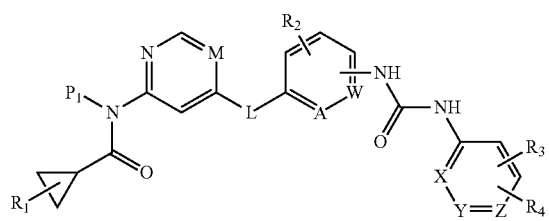 → 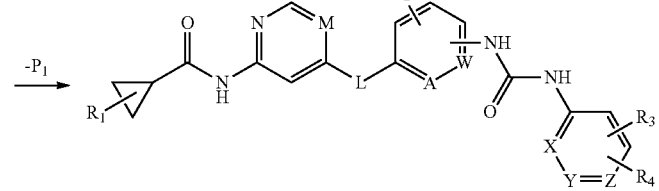

Wherein M, L, A, W, X, Y, Z, and $R_1$ to $R_4$ are as defined above.

In a third aspect, the present invention provides pharmaceutical compositions comprising compounds of formula (I), or pharmaceutically acceptable salts thereof, together with a pharmaceutically acceptable carrier or excipient.

In a fourth aspect, the present invention provides a method of treating cancer using compounds of formula (I), or pharmaceutically acceptable salts thereof.

In a fifth aspect, the present invention provides use of a compound of formula (I), or a pharmaceutically acceptable salt thereof, in the preparation of medicament for the treatment of cancer.

Compounds of this invention inhibit KDR and B-Raf kinases at the enzyme levels, they also inhibit Erk phosphorylation and PLC-PRF-5 cell proliferation at the cellular levels. These compounds can be used to treat hyperproliferative disorders such as cancers, especially colon cancer, breast cancer, lung cancer, prostate cancer, pancreatic cancer, gastrointestinal cancer, bladder cancer, ovarian cancer, melanoma, neuroblastoma, cervical cancer, kidney or renal cancer, leukemia and lymphoma. They are especially useful in treating or inhibiting solid tumors, for example, breast cancer, colon cancer, lung and prostate cancer. These compounds can be used as treatment for AML, ALL and GIST.

The compounds of the present invention are preferably formulated as pharmaceutical compositions administered by a variety of routes. Such pharmaceutical compositions and processes for preparing them are well known in the art. See, e.g., REMINGTON: THE SCIENCE AND PRACTICE OF PHARMACY (A. Gennaro, et al., eds, 19$^{th}$ ed. Mack Publishing Co., 1995)

Unless otherwise defined, the following definitions refer to the various terms used above and throughout the disclosure:

The term "halo" refers to fluoro-, chloro-, bromo- and iodo-; with fluoro-, chloro- and bromo-preferred.

The term "$C_{1-6}$ alkyl", alone or in combination with other groups, refers to monovalent, linear chain or branched chain alkyl groups containing from 1 to 6 carbon atoms. Exemplary $C_{1-6}$ alkyl groups include but not limited to methyl, ethyl, n-propyl, iso-propyl, n-butyl, sec-butyl and tert-butyl groups. More preferred are $C_{1-4}$ alkyls.

The term "haloalkyl" refers to alkyl groups in which one or more hydrogen atoms are substituted with the same or different halogens. Exemplary haloalkyl groups include —CH$_2$Cl, —CH$_2$CF$_3$, CH$_2$CCl$_3$, pan-fluoroalkyl (e.g., —CF$_3$), etc.

The term "$C_{3-7}$ cycloalkyl", alone or in combination with other groups, refers to, unless otherwise defined, fully saturated hydrocarbon rings of 3 to 7 carbon atoms. For example, cyclopropyl, cyclobutyl, cyclohexyl.

The term "$C_{3-6}$ cycloalkylacyl" also called "cycloalkanecarbonyl" refers to acyl groups in which the carbonyl is directly attached to saturated hydrocarbon rings of 3-6 carbon atoms. For example, cyclopropylacyl.

The term "$C_{1-6}$ alkoxy" refers to, alone or in combination with other groups, R'—O—, where R' is $C_{1-6}$ alkyl.

The term "$C_{2-6}$ alkenyl" refers to, alone or in combination with other groups, linear or branched-chain monovalent groups of 2 to 6 carbon atoms with at least one carbon-carbon double bond. Examples include vinyl, 2-propenyl.

The term "aryl" refers to, alone or in combination with other groups, a monovalent, mono- or bi-cyclic aromatic carbon ring system. The preferred aryls include, but are not limited to, phenyl, naphthyl, methylphenyl and dimethylphenyl.

The term "heterocyclyl" refers to, alone or in combination with other groups, 3 to 8-membered non-aromatic mono- or bi-cyclic heteroatom-containing ring systems where one or two heteroatoms may be selected from N, O, or S(O)$_n$ (n is an integral of 0 to 2). Examples of "heterocyclyl" include, but are not limited to, optionally substituted piperidinyl, piperazinyl, homopiperazinyl, azepinyl, azetidinyl, pyrrolidinyl, pyrazolidinyl, imidazolidinyl, imidazolinyl, oxazolidinyl, isoxazolidinyl, morpholinyl, thiazolidinyl, isothiazolidinyl, quinuclidinyl, thiadiazolidinyl, benzothiazolidinyl, benzopyrrolidinyl, dihydrofuranyl, tetrahydrofuranyl, dihydropyranyl, tetrahydropyranyl, thiomorpholinyl, 1-oxo-thiomorpholinyl, 1,1-dioxothiomorpholinyl, dihydroquinolinyl, dihydroisoquinolinyl, tetrahydroquinolinyl, tetrahydroisoquinolinyl, etc.

The term "heteroaryl" refers to five- to six-membered monocyclic or nine to ten-membered bicyclic aromatic rings containing one, two or three heteroatoms selected from nitrogen, oxygen and/or sulfur atoms. Examples include, but are not limited to, furyl, pyridinyl, pyridazinyl, pyrimidinyl, pyrazinyl, thienyl, isoxazolyl, oxazolyl, oxadiazolyl, imidazolyl, pyrrolyl, pyrazolyl, triazolyl, tetrazolyl, thiazolyl, isothiazolyl, 1,2,3-thiadiazolyl, benzimidazolyl, indolyl, indazolyl, benzoisothiazolyl, benzoxazolyl, benzoisoxazolyl, quniolinyl and isoquinolinyl. The preferred heteroaryls are pyridinyl, oxazolyl and triazolyl.

The term "pharmaceutically acceptable salt" refers to those salts which are, within the scope of sound medical judgement, suitable for use in contact of the tissues of human and lower animals without undue toxicity, irritation, allergic reactions and the like. The salts are organic or inorganic salts of a compound of the invention which maintain the biological activities of it as drawn in Formula (I). The salts may be prepared from suitable, non-toxic organic or inorganic acids reacting with free base, or organic and inorganic bases reacting with acid group in the compounds of invention. Examples of acid addition salts include those salts derived from inorganic acids and organic acids. Examples of inorganic acid include, but are not limited to, hydrochloric acid, hydrobromic acid, hydroiodic acid, sulfuric acid, animosulfonic acid, phosphoric acid, nitric acid; examples of organic acids include, but are not limited to, para-toluenesulfonic acid, salicylic acid, methanesulfonic acid, oxalic acid, succinic acid, citric acid, maleic acid, lactic acid, fumaric acid, etc.

Examples of base addition salts include those derived from ammonium hydroxide, sodium hydroxide, potassium hydroxide, quaternary ammonium hydroxide such as tetramethylammonium hydroxide. Conversion of an acid or base compound into a salt is well known in the art to improve its physicochemical properties, chemical stability, moisture absorption property, liquidity and solubility.

"Pharmaceutically acceptable" carrier, excipient refers to those carriers and excipients which are compatible to the administration of the compounds to the subjects, and are non-toxic.

The "therapeutically effective amount" of a compound of this invention means an amount of the compound that effectively prevents or delays the progression of the disease, or attenuates, ameliorates some of the symptoms of the disease or extends the life of patients. Determination of therapeutically effective amount depends on a variety of factors well known in medical arts.

The therapeutically effective amount or dose may vary in a wide range, and can be determined by known arts in this field. The specific therapeutically effective dose level for any particular patient will depend upon a variety of factors including the activity of specific compound being employed, route of administration, duration of treatment, and the age, body weight, general health, sex and diet of the patient. In general, the total daily dose of the compound for a 70 Kg adult, when administered orally or parenterally, may range from 10 mg to 10,000 mg, preferably from about 200 mg to 1,000 mg, albeit some evidences show higher dose level may be acceptable. Total daily dose of the compounds of this invention may be administered in a single dose or multiple doses, for parenteral administration, the total daily dose may be delivered through continuous infusion.

All compound names listed herein are generated with Symyx Draw 3.3 program from Accelrys.

Abbreviations used in this application are listed below:

DCM: dichloromethane; PE: petroleum ether; THF: tetrahydrofuran; DMF: N,N,-dimethylformamide; DIEA: diisopropylethylamine; DMSO: dimethylsulfoxide; TEA: triethylamine; TFA: trifluoroacetic acid; MW: microwave; NMP: N-methyl-2-pyrrolidone; mCPBA: meta-chloroperoxybenzoic acid; BAST: bis-(2-methoxyethyl)aminosulfur trifluoride; EDCI: 1-ethyl-3-(3-dimethylaminopropyl)carbodiimide hydrochloride; TLC: thin-layer chromatography; EtOAc: ethyl acetate; MeOH: methanol; EtOH: ethanol;

MS data is obtained with ESI-MS (electrospray ionization mass spectrometry) method through a LC/MS system.

INTERMEDIATES

Preparation of Intermediate A

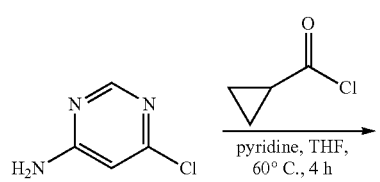

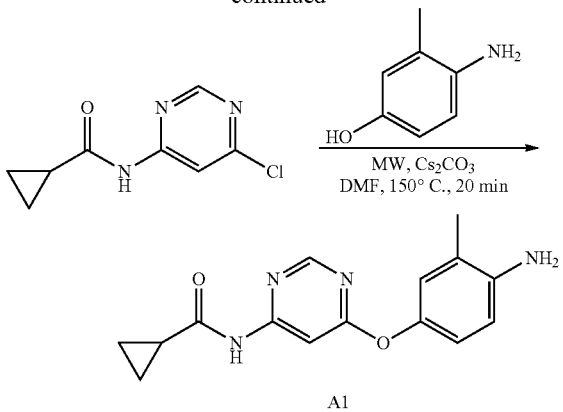

Step 1: Synthesis of N-(6-chloropyrimidin-4-yl)cyclopropanecarboxamide

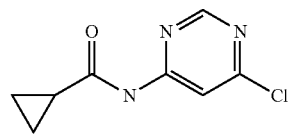 [SMILES: O=C(Nc1cc(Cl)ncn1)C1CC1]

Add slowly cyclopropanecarbonyl chloride (10.6 g, 102.3 mmol) to a mixture of 4-amino-6-chloro-pyrimidine (12 g, 91 mmol), pyridine (18 g, 227.5 mmol) in THF (150 mL) at 0° C. Stir the reaction at 60° C. for 4 hrs.

TLC (DCM:MeOH=20:1) shows that the reaction is complete. Cool the reaction to 0° C., add water (100 mL), extract with EtOAc (100 mL×2). Combine the organic layers, wash with diluted aqueous HCl (1M, 150 mL) and brine sequentially, dry over anhydrous Na$_2$SO$_4$. Evaporation under reduced pressure affords crude product (16 g, crude yield 88.8%). MS: (M+1): 198.1. Use crude product directly in next step without further purification.

Step 2: Synthesis of N-[6-(4-amino-3-methyl-phenoxy)pyrimidin-4-yl]cyclopropanecarboxamide

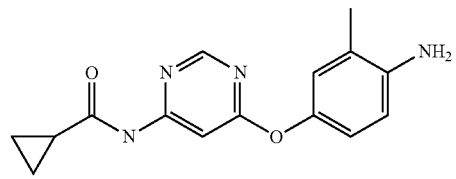 [SMILES: Cc1cc(Oc2cc(NC(=O)C3CC3)ncn2)ccc1N]

Mix the cyclopropanecarboxamide derivative obtained in Step 1 (400 mg, 2.03 mmol), 4-amino-3-methyl-phenol (272 mg, 2.23 mmol) and Cs$_2$CO$_3$ (1.3 g, 4.06 mmol) in DMF (10 mL). Stir the reaction at 150° C. under microwave conditions for 30 min.

TLC (EtOAc:PE=2:1) shows the reaction is complete. Cool the reaction to room temperature; add water (15 mL). Extract with EtOAc (15 mL×2). Wash the combined organic layers with brine, dry over anhydrous Na$_2$SO$_4$. Evaporation under reduced pressure affords crude product. Purification by chromatography (silica gel, EtOAc:petroleum ether=1:1) provides the title compound as a light-yellow solid (450 mg, 78.1%). MS: (M+1): 285.2.

Intermediates A2-A5 can be synthesized with similar method (Table A1).

TABLE A1
Intermediates A1-A5
| Number | Starting material | Intermediate | MS [M + 1]+ |
|---|---|---|---|
| A1 | | | 285.2 |
| A2 | | | 305.1 |
| A3 | | | 289.2 |
| A4 | | | 305.1 |
| A5 | | | 303.2 |
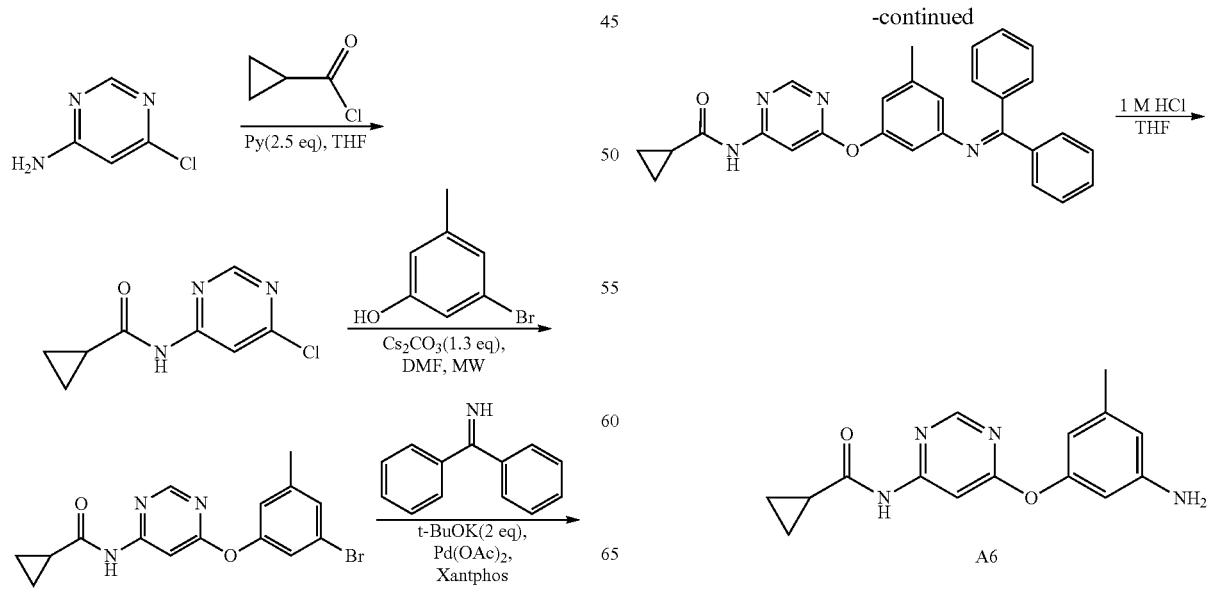

Step 1: Synthesis of N-(6-chloropyrimidin-4-yl)cyclopropanecarboxamide (see Step 1 for A1)

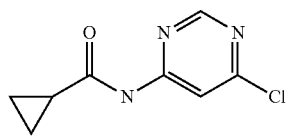 [SMILES: O=C(Nc1cc(Cl)ncn1)C1CC1]

Step 2: Synthesis of N-[6-(3-bromo-5-methyl-phenoxy)pyrimidin-4-yl]cyclopropanecarboxamide

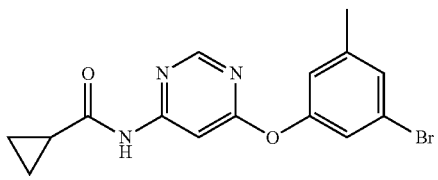 [SMILES: Cc1cc(Br)cc(Oc2cc(NC(=O)C3CC3)ncn2)c1]

Add N-(6-chloropyrimidin-4-yl)cyclopropanecarboxamide (1 g, 5.07 mmol), 3-bromo-5-methyl-phenol (950 mg, 5.07 mmol), $Cs_2CO_3$ (2.14 g, 6.60 mmol) and DMF (10 mL) to a microwave reaction vessel (25 mL). Heat the reaction under microwave conditions at 150° C. for 1 hr.

Cool to room temperature, add water (50 mL), extract with EtOAc (100 mL×2), combine organic layers, dry over anhydrous $Na_2SO_4$. Concentration and purification by chromatography (silica gel, EtOAc:PE=1:3) afford the title compound (1.2 g, 67.9%). MS: (M+1): 348.1.

Step 3: Synthesis of N-[6-[3-(benzhydrylideneamino)-5-methyl-phenoxy]pyrimidin-4-yl]cyclopropanecarboxamide

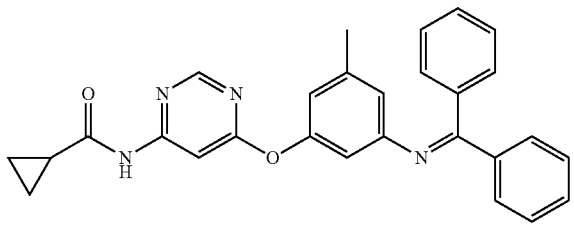 [SMILES: Cc1cc(N=C(c2ccccc2)c2ccccc2)cc(Oc2cc(NC(=O)C3CC3)ncn2)c1]

Mix the cyclopropanecarboxamide derivative obtained in Step 2 (400 mg, 1.15 mmol), benzophenone imine (624 mg, 3.45 mmol), t-BuOK (257 mg, 2.3 mmol) and 1,4-dioxane in a 250 mL flask, add Xantphos (133 mg, 0.23 mmol), $Pd(OAc)_2$ (26 mg, 0.115 mmol). Stir the reaction under $N_2$ at 120° C. for 15 hrs.

TLC shows reaction is complete. Remove the solid through suction filtration. Concentration and purification by chromatography (silica gel, EtOAc:PE=1:3) afford the title compound (450 mg, 87.4%). MS: (M+1): 449.3.

Step 4: Synthesis of N-[6-(3-amino-5-methyl-phenoxy)pyrimidin-4-yl]cyclopropanecarboxamide

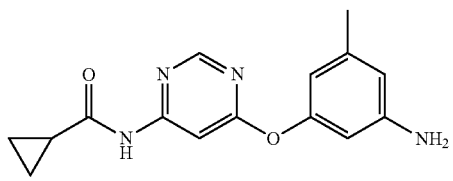 [SMILES: Cc1cc(N)cc(Oc2cc(NC(=O)C3CC3)ncn2)c1]

Add 1M HCl aqueous solution (10 mL) to a solution of the imine obtained in Step 3 (450 mg, 1.0 mmol) in THF (10 mL), stir the reaction at room temperature for 1 hr. Basicify with saturated $NaHCO_3$ solution, extract with EtOAc (30 mL×2). Combine the organic layers, dry over anhydrous $Na_2SO_4$. Concentration and purification by chromatography (silica gel, EtOAc:PE=1:1) afford the title compound (230 mg, 80.8%). MS: (M+1): 285.2.

Intermediates A7-A8 can be synthesized with similar method (Table A2)

TABLE A2

| Intermediates A6-A8 | | | |
|---|---|---|---|
| Number | Starting material | Intermediate | MS [M + 1]⁺ |
| A6 | 3-bromo-5-methyl-phenol | N-[6-(3-amino-5-methyl-phenoxy)pyrimidin-4-yl]cyclopropanecarboxamide | 285.2 |
| A7 | 3-bromo-5-fluoro-phenol | N-[6-(3-amino-5-fluoro-phenoxy)pyrimidin-4-yl]cyclopropanecarboxamide | 289.2 |

TABLE A2-continued

Intermediates A6-A8

| Number | Starting material | Intermediate | MS [M + 1]+ |
|---|---|---|---|
| A8 | 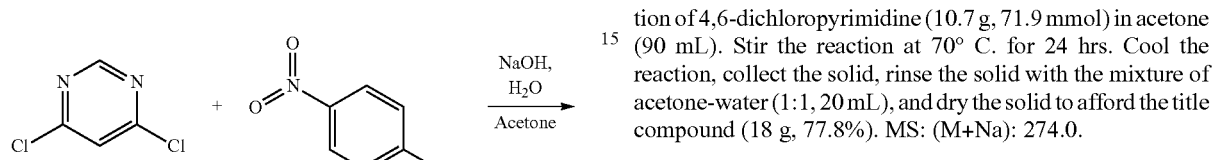 | | 296.2 |

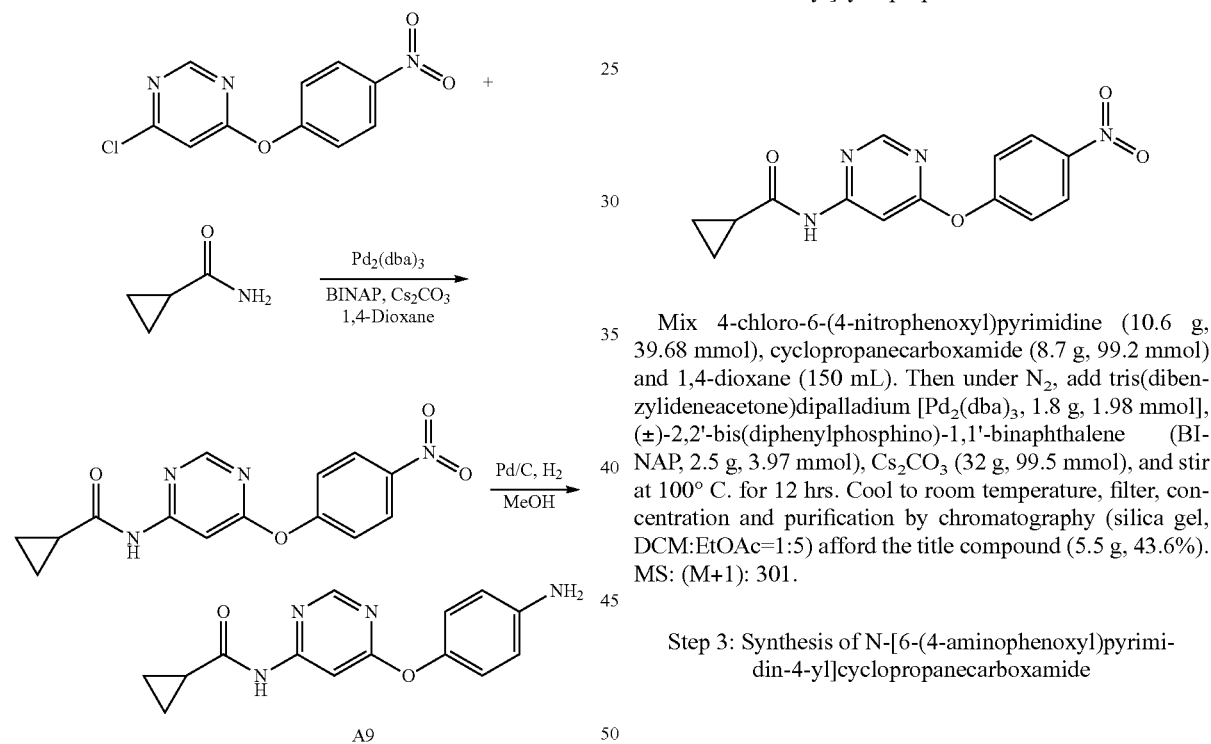

Step 1: Synthesis of 4-chloro-6-(4-nitrophenoxyl)pyrimidine

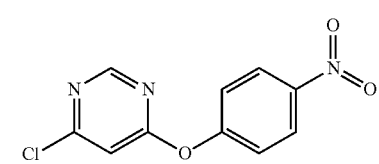 [SMILES: O=[N+]([O-])c1ccc(Oc2cc(Cl)ncn2)cc1]

Dissolve NaOH (2.8 g, 71.9 mmol) in water (90 mL) at 0° C. Add para-nitrophenol (10 g, 71.9 mmol), and then a solution of 4,6-dichloropyrimidine (10.7 g, 71.9 mmol) in acetone (90 mL). Stir the reaction at 70° C. for 24 hrs. Cool the reaction, collect the solid, rinse the solid with the mixture of acetone-water (1:1, 20 mL), and dry the solid to afford the title compound (18 g, 77.8%). MS: (M+Na): 274.0.

Step 2: Synthesis of N-[6-(4-nitrophenoxyl)pyrimidin-4-yl]cyclopropanecarboxamide Mix 4-chloro-6-(4-nitrophenoxyl)pyrimidine (10.6 g, 39.68 mmol), cyclopropanecarboxamide (8.7 g, 99.2 mmol) and 1,4-dioxane (150 mL). Then under $N_2$, add tris(dibenzylideneacetone)dipalladium [$Pd_2(dba)_3$, 1.8 g, 1.98 mmol], (±)-2,2'-bis(diphenylphosphino)-1,1'-binaphthalene (BINAP, 2.5 g, 3.97 mmol), $Cs_2CO_3$ (32 g, 99.5 mmol), and stir at 100° C. for 12 hrs. Cool to room temperature, filter, concentration and purification by chromatography (silica gel, DCM:EtOAc=1:5) afford the title compound (5.5 g, 43.6%). MS: (M+1): 301.

Step 3: Synthesis of N-[6-(4-aminophenoxyl)pyrimidin-4-yl]cyclopropanecarboxamide Dissolve N-[6-(4-nitrophenoxyl)pyrimidin-4-yl]cyclopropanecarboxamide (2.2 g, 7.33 mmol) in DCM (50 mL), add Pd/C (10%, 340 mg), flush with $H_2$, and stir at room temperature under $H_2$ for 2 hrs. After the reaction is complete, flush with $N_2$, and then filter, concentrate the filtrate, purify the crude product by chromatography (silica gel, EtOAc:PE=1:1) to provide the title compound (1.8 g, 91%). MS: (M+1): 271.

Intermediates A10-A16 can be synthesized by similar method (Table A3).

TABLE A3
Intermediates A9-A16
| Number | Starting material | Intermediate | MS [M + 1]+ |
|---|---|---|---|
| A9 | 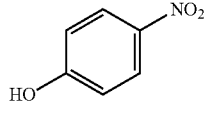 | 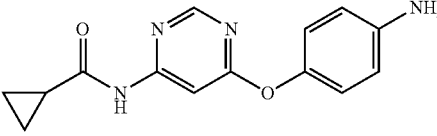 | 271 |
| A10 | 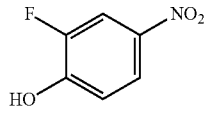 | 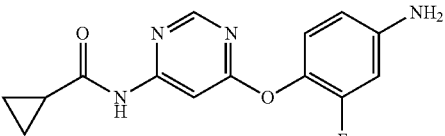 [SMILES: Nc1ccc(Oc2cc(NC(=O)C3CC3)ncn2)cc1] | 289.2 |
| A11 | 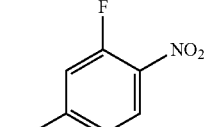 | 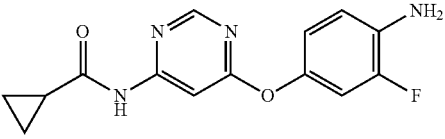 [SMILES: Nc1ccc(Oc2cc(NC(=O)C3CC3)ncn2)cc1F] | 289.2 |
| A12 | 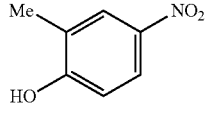 | 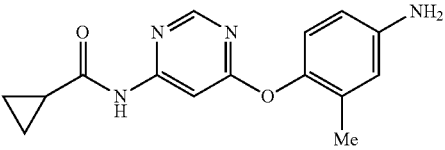 [SMILES: Cc1cc(N)ccc1Oc1cc(NC(=O)C2CC2)ncn1] | 284.2 |
| A13 | 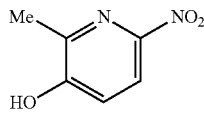 | 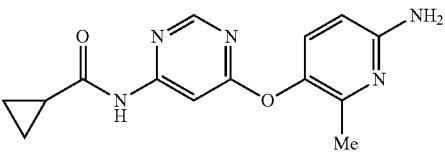 | 286 |
| A14 | 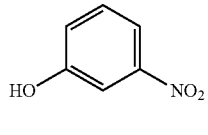 | 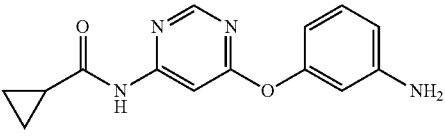 [SMILES: Nc1cccc(Oc2cc(NC(=O)C3CC3)ncn2)c1] | 271.1 |
| A15 | 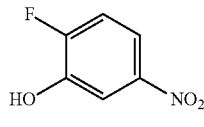 | 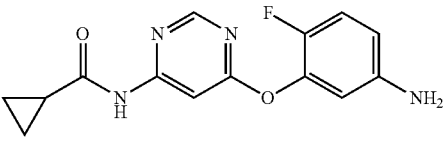 [SMILES: Nc1ccc(F)c(Oc2cc(NC(=O)C3CC3)ncn2)c1] | 289 |
| A16 | 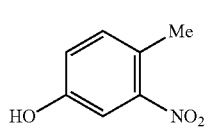 | 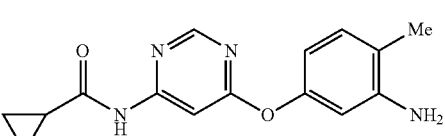 | 285.2 |

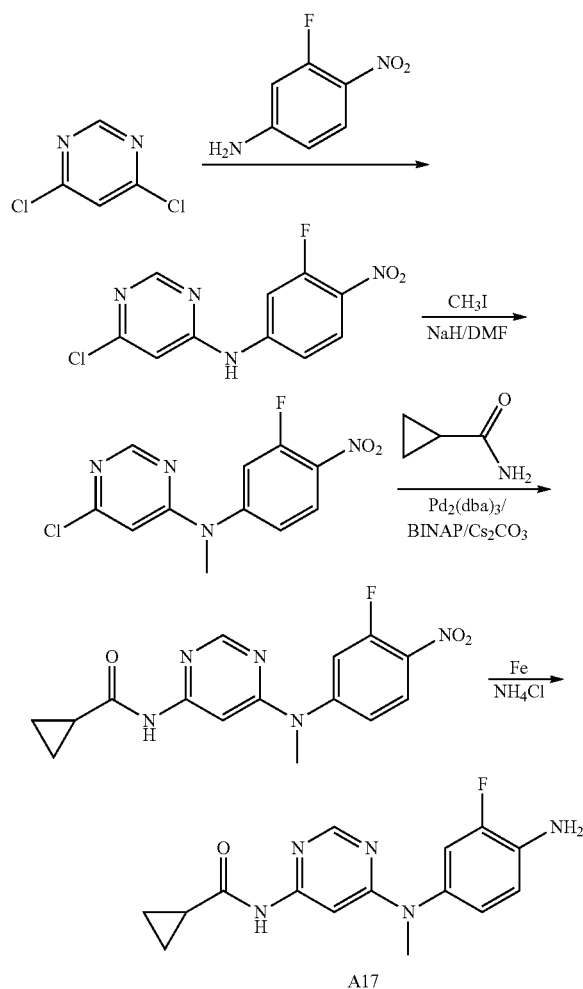

A17

Step 1: Synthesis of 6-chloro-N-(3-fluoro-4-nitro-phenyl)pyrimidin-4-amine

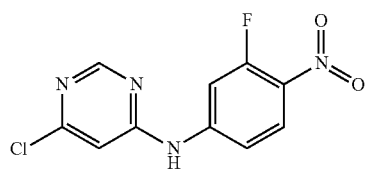 [SMILES: O=[N+]([O-])c1ccc(Nc2cc(Cl)ncn2)cc1F]

Mix 4,6-dichloroppimidine (3 g, 20.1 mmol), 3-fluoro-4-nitroaniline (2.4 g, 15.5 mmol), isopropanol (20 mL) and concentrated HCl (3 mL) in a 100 mL flask, heat at 120° C. under $N_2$ for 4 hrs.

TLC (PE:EtOAc=3:1) shows the reaction is complete. Cool to room temperature, add water (20 mL), carefully adjust pH=8 with saturated $NaHCO_3$ solution. Extract with EtOAc (100 mL×2), combine the organic layers; wash with brine (100 mL), dry over anhydrous $Na_2SO_4$. Filtration and concentration afford crude product. Add the mixture of EtOAc and PE (1:1, 100 mL), stir and filter to give the title compound (1.38 g, 67%). MS: (M+1): 269.1.

Step 2: Synthesis of 6-chloro-N-(3-fluoro-4-nitro-phenyl)-N-methyl-pyrimidin-4-amine

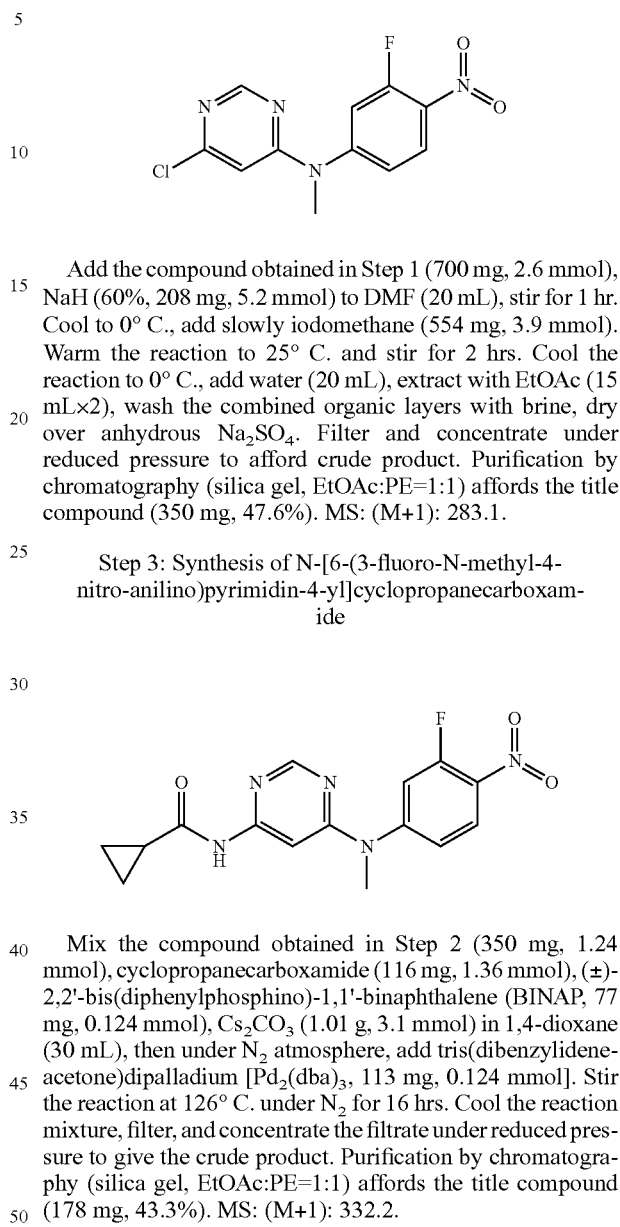

Add the compound obtained in Step 1 (700 mg, 2.6 mmol), NaH (60%, 208 mg, 5.2 mmol) to DMF (20 mL), stir for 1 hr. Cool to 0° C., add slowly iodomethane (554 mg, 3.9 mmol). Warm the reaction to 25° C. and stir for 2 hrs. Cool the reaction to 0° C., add water (20 mL), extract with EtOAc (15 mL×2), wash the combined organic layers with brine, dry over anhydrous $Na_2SO_4$. Filter and concentrate under reduced pressure to afford crude product. Purification by chromatography (silica gel, EtOAc:PE=1:1) affords the title compound (350 mg, 47.6%). MS: (M+1): 283.1.

Step 3: Synthesis of N-[6-(3-fluoro-N-methyl-4-nitro-anilino)pyrimidin-4-yl]cyclopropanecarboxamide Mix the compound obtained in Step 2 (350 mg, 1.24 mmol), cyclopropanecarboxamide (116 mg, 1.36 mmol), (±)-2,2'-bis(diphenylphosphino)-1,1'-binaphthalene (BINAP, 77 mg, 0.124 mmol), $Cs_2CO_3$ (1.01 g, 3.1 mmol) in 1,4-dioxane (30 mL), then under $N_2$ atmosphere, add tris(dibenzylideneacetone)dipalladium [$Pd_2(dba)_3$, 113 mg, 0.124 mmol]. Stir the reaction at 126° C. under $N_2$ for 16 hrs. Cool the reaction mixture, filter, and concentrate the filtrate under reduced pressure to give the crude product. Purification by chromatography (silica gel, EtOAc:PE=1:1) affords the title compound (178 mg, 43.3%). MS: (M+1): 332.2.

Step 4: Synthesis of N-[6-(4-amino-3-fluoro-N-methyl-anilino)pyrimidin-4-yl]cyclopropanecarboxamide

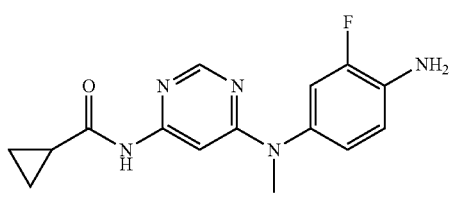 [SMILES: CN(c1ccc(N)c(F)c1)c1cc(NC(=O)C2CC2)ncn1]

Dissolve the compound obtained in Step 3 (180 mg, 0.543 mmol) in ethanol (20 mL), add iron powder (150 mg, 2.72 mmol) and saturated NH₄Cl solution (10 mL). Stir the reaction at 75° C. for 2 hrs. TLC (DCM:MeOH=20:1) shows the reaction is complete. Cool the reaction to 0° C., add water (20 mL), extract with EtOAc (30 mL×2), combine the organic layers, wash with brine (30 mL), dry over anhydrous Na₂SO₄, filter and concentrate to give the crude product (150 mg). Use it directly without further purification. MS: (M+1): 302.2.

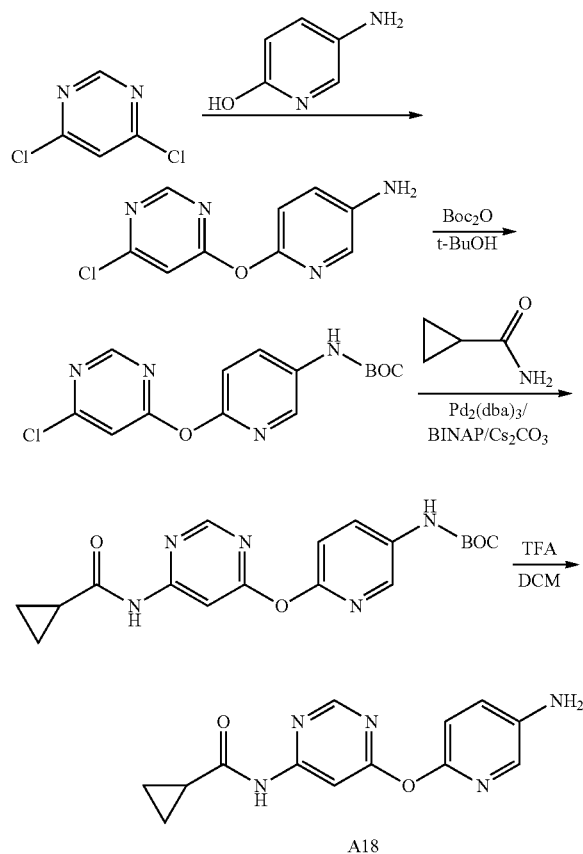

A18

Step 1: Synthesis of 6-(6-chloropyrimidin-4-yl)oxypyridin-3-amine

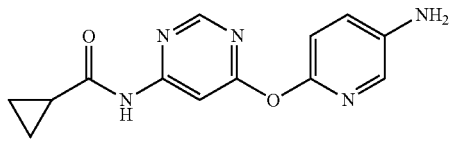

Add 5-aminopyridin-2-ol (500 mg, 4.545 mmol), t-BuOK (555 mg, 4.545 mmol) in DMF (20 mL), stir at 25° C. for 30 min. Cool to 0° C., add slowly 4,6-dichloropyrimidine (614 mg, 4.13 mmol). Stir the reaction under N₂ for 1 hr. TLC (EtOAc:PE=1:1) shows the reaction is complete. Cool the mixture to 0° C., add water (20 mL), extract with EtOAc (20 mL×2). Combine the organic layers; wash with brine, dry over anhydrous Na₂SO₄. Filter and concentrate under reduced pressure to give crude product. Purification by chromatography (silica gel, EtOAc:PE=1:1) affords the title compound (650 mg, 70.8%). MS: (M+1): 223.1.

Step 2: Synthesis of tert-butyl N-[6-(6-chloropyrimidin-4-yl)oxy-3-pyridyl]carbamate

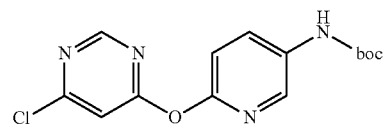

Add the compound obtained in Step 1 (650 mg, 2.93 mmol) and Boc₂O (766 mg, 3.51 mmol) in t-BuOH (20 mL) and heat at 50° C. for 16 hrs. TLC (EtOAc:PE=1:1) shows the reaction is complete. Concentrate under reduced pressure to give crude product. Purification by chromatography (silica gel, EtOAc:PE=1:1) affords the title compound (610 mg, 64.6%). MS: (M+1): 323.1.

Step 3: Synthesis of tert-butyl N-[6-[6-(cyclopropanecarbonylamino)pyrimidin-4-yl]oxy-3-pyridyl]carbamate

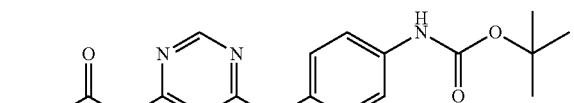

Mix the compound obtained in Step 2 (610 mg, 1.9 mmol), cyclopropanecarboxamide (193 mg, 2.27 mmol), (±)-2,2'-bis(diphenylphosphino)-1,1'-binaphthalene (BINAP, 118 mg, 0.19 mmol), Cs₂CO₃ (1.238 g, 3.8 mmol) and tris(dibenzylideneacetone)dipalladium [Pd₂(dba)₃, 122 mg, 0.133 mmol] in 1,4-dioxane (30 mL). Stir the reaction at 120° C. under N₂ for 16 hrs. Cool the reaction, filter, concentrate the filtrate under reduced pressure to give the crude product. Purification by chromatography (silica gel, EtOAc:PE=1:1) affords the title compound (500 mg, 70.8%). MS: (M+1): 372.2.

Step 4: Synthesis of N-[6-[(5-amino-2-pyridyl)oxy]pyrimidin-4-yl]cyclopropanecarboxamide Add the compound obtained in Step 3 (500 mg, 1.9 mmol) to DCM (30 mL), cool to 0° C., add slowly trifluoroacetic acid (10 mL), then stir the reaction at 25° C. for 4 hrs. TLC (DCM:MeOH=20:1) shows the reaction is complete. Cool the reaction to 0° C., adjust to pH=8-9 with saturated NaHCO₃ solution. Extract with DCM (30 mL×2), combine the organic layers; wash with brine (30 mL), dry over anhydrous Na₂SO₄. Filter and concentrate under reduced pressure to give crude product. Rinse the solid with ether, dry under reduced pressure to give the product (180 mg, 49.3%). MS: (M+1): 272.2.

Intermediate A19 can be synthesized with similar method (Table A4).

TABLE A4

Intermediates A17-A19

| Number | Starting material | Intermediate | MS [M + 1]+ |
|---|---|---|---|
| A17 | 4-amino-2-fluoro-1-nitrobenzene structure (F, NO2, H2N) | cyclopropanecarboxamide-pyrimidine-N(Me)-phenyl(NH2, F) structure | 302.2 |
| A18 | 5-nitro-2-hydroxypyridine | cyclopropanecarboxamide-pyrimidine-O-pyridine-NH2 | 272.2 |
| A19 | 4-methyl-3-nitrophenol | cyclopropanecarboxamide-pyrimidine-O-(4-methyl-pyridine)-NH2 | 286.2 |

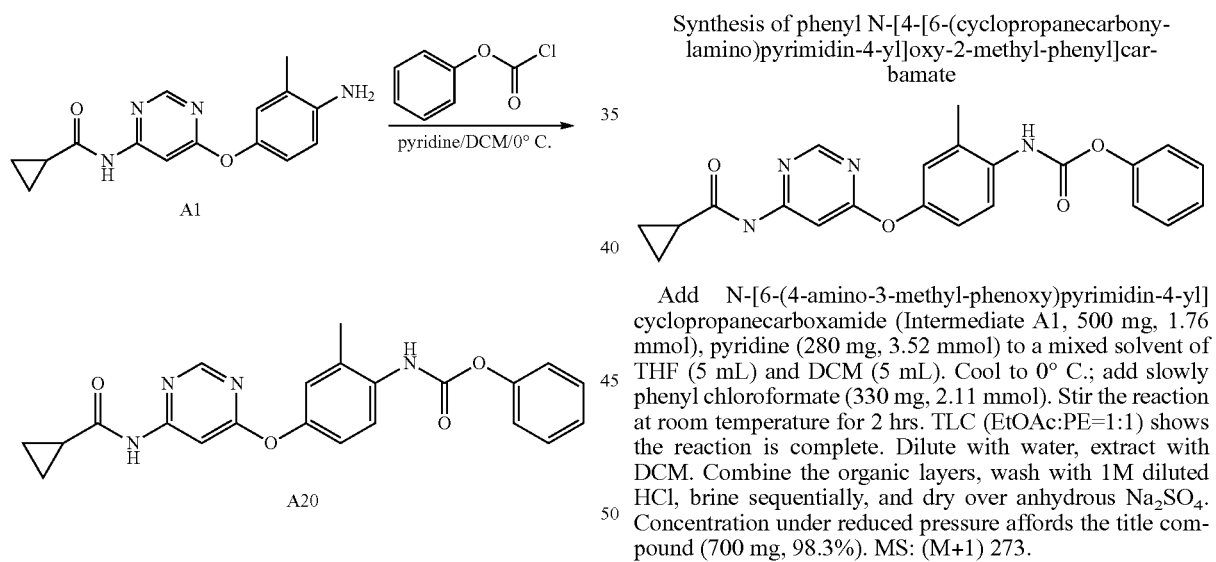

Synthesis of phenyl N-[4-[6-(cyclopropanecarbonylamino)pyrimidin-4-yl]oxy-2-methyl-phenyl]carbamate Add N-[6-(4-amino-3-methyl-phenoxy)pyrimidin-4-yl] cyclopropanecarboxamide (Intermediate A1, 500 mg, 1.76 mmol), pyridine (280 mg, 3.52 mmol) to a mixed solvent of THF (5 mL) and DCM (5 mL). Cool to 0° C.; add slowly phenyl chloroformate (330 mg, 2.11 mmol). Stir the reaction at room temperature for 2 hrs. TLC (EtOAc:PE=1:1) shows the reaction is complete. Dilute with water, extract with DCM. Combine the organic layers, wash with 1M diluted HCl, brine sequentially, and dry over anhydrous Na2SO4. Concentration under reduced pressure affords the title compound (700 mg, 98.3%). MS: (M+1) 273.

TABLE A5

Intermediate A20

| Number | Starting material | Intermediate | MS [M + 1]+ |
|---|---|---|---|
| A20 | A1 (cyclopropanecarboxamide-pyrimidine-O-(2-methyl-4-amino)phenyl) | phenyl carbamate product | 273 |

Preparation of Intermediate B

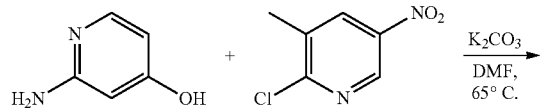

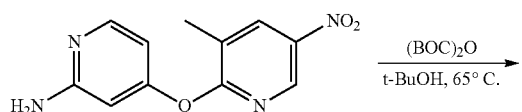

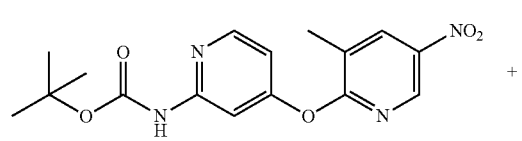

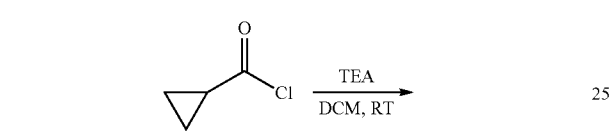

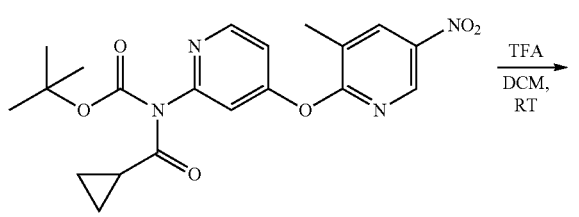

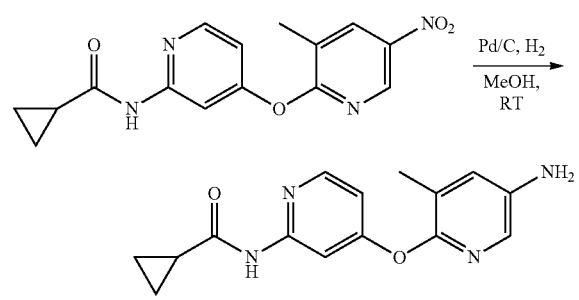

B1

Step 1: Synthesis of 4-[(3-methyl-5-nitro-2-pyridyl)oxy]pyridin-2-amine

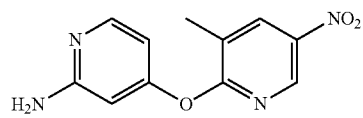 [SMILES: Cc1cc([N+](=O)[O-])cnc1Oc1ccnc(N)c1]

Mix 2-aminopyridin-4-ol (3.3 g, 30 mmol), 2-chloro-3-methyl-5-nitropyridine (5.17 g, 30 mmol) in anhydrous DMF (50 mL), add $K_2CO_3$ (8.28 g, 60 mmol). Stir the reaction at 90° C. overnight. Concentrate under reduced pressure to give crude product. Purification by chromatography (silica gel, EtOAc:PE=1:1) affords the title compound (3.3 g, 45%). MS: (M+1): 247.1.

Step 2: Synthesis of tert-butyl N-[4-[(3-methyl-5-nitro-2-pyridyl)oxy]-2-pyridyl]carbamate

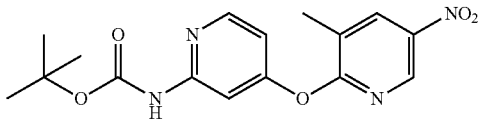 [SMILES: Cc1cc([N+](=O)[O-])cnc1Oc1ccnc(NC(=O)OC(C)(C)C)c1]

Add 4-[(3-methyl-5-nitro-2-pyridyl)oxy]pyridin-2-amine (400 mg, 1.62 mmol), $Boc_2O$ (388 mg, 1.78 mmol) to t-BuOH (10 mL). Stir the reaction at 50° C. for 12 hrs. Concentrate to give the crude product. Purification by chromatography (silica gel, EtOAc:PE=1:3) affords the title compound (400 mg, 71%). MS: (M+1): 347.

Step 3: Synthesis of tert-butyl N-(cyclopropanecarbonyl)-N-[4-[(3-methyl-5-nitro-2-pyridyl)oxy]-2-pyridyl]carbamate

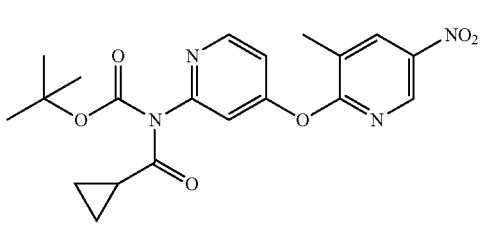 [SMILES: Cc1cc([N+](=O)[O-])cnc1Oc1ccnc(N(C(=O)OC(C)(C)C)C(=O)C2CC2)c1]

Add N-[4-[(3-methyl-5-nitro-2-pyridyl)oxy]-2-pyridyl]carbamate (300 mg, 0.87 mmol), $Et_3N$ (350 mg, 3.47 mmol) to anhydrous DCM (5 mL), cool to 0° C., add cyclopropanecarbonyl chloride (360 mg, 3.47 mmol) dropwise. Stir at room temperature for 2 hrs. Concentrate to give the crude product. Purification by chromatography (silica gel, EtOAc:PE=1:3) affords the title compound (350 mg, 97%). MS: (M+1): 415.

Step 4: Synthesis of N-[4-[(3-methyl-5-nitro-2-pyridyl)oxy]-2-pyridyl]cyclopropanecarboxamide

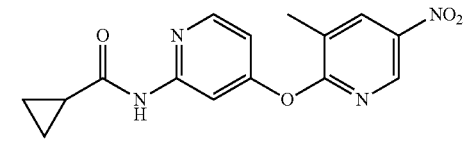 [SMILES: Cc1cc([N+](=O)[O-])cnc1Oc1ccnc(NC(=O)C2CC2)c1]

Add tert-butyl N-(cyclopropanecarbonyl)-N-[4-[(3-methyl-5-nitro-2-pyridyl)oxy]-2-pyridyl]carbamate (350 mg, 0.84 mmol) in DCM (10 mL), add trifluoroacetic acid (2 mL). Stir the reaction at room temperature for 2 hrs. Concentrate to give the crude product. Purification by chromatography (silica gel, EtOAc:PE=1:3) affords the title compound (260 mg, 98%). MS: (M+1): 315.

Step 5: Synthesis of N-[4-[(5-amino-3-methyl-2-pyridyl)oxy]-2-pyridyl]cyclopropanecarboxamide

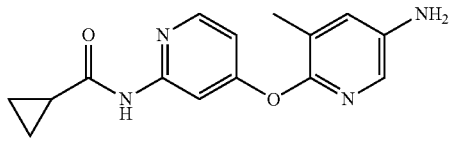

Dissolve N-[4-[(3-methyl-5-nitro-2-pyridyl)oxy]-2-pyridyl]cyclopropanecarboxamide (269 mg, 0.83 mmol) in MeOH (5 mL) and DCM (5 mL). Add Pd/C (10%, 104 mg), flush with $H_2$. Stir the reaction under $H_2$ at room temperature for 2 hrs. After the reaction, flush with $N_2$, filter the reaction mixture; concentrate the filtrate under reduced pressure to give the crude product. Purification by chromatography (silica gel, EtOAc:PE=1:1) affords the title compound (70 mg, 30%). MS: (M+1): 285.

Intermediates B2-B9 can be synthesized using similar method (Table B1).

TABLE B1

| Number | Starting material | Intermediate | MS [M + 1]⁺ |
|---|---|---|---|
| B1 | | | 285.2 |
| B2 | | | 285.2 |
| B3 | | | NA |
| B4 | | | NA |
| B5 | | | 271.1 |
| B6 | | | 270.2 |
| B7 | | | 288 |

TABLE B1-continued

Intermediates B1-B9

| Number | Starting material | Intermediate | MS [M + 1]+ |
|---|---|---|---|
| B8 | (4-fluoro-2-methyl-nitrobenzene) | (cyclopropanecarboxamide-pyridyloxy-methylaniline) | 284.2 |
| B9 | (3,5-difluoro-nitrobenzene) | (cyclopropanecarboxamide-pyridyloxy-fluoroaniline) | 288 |

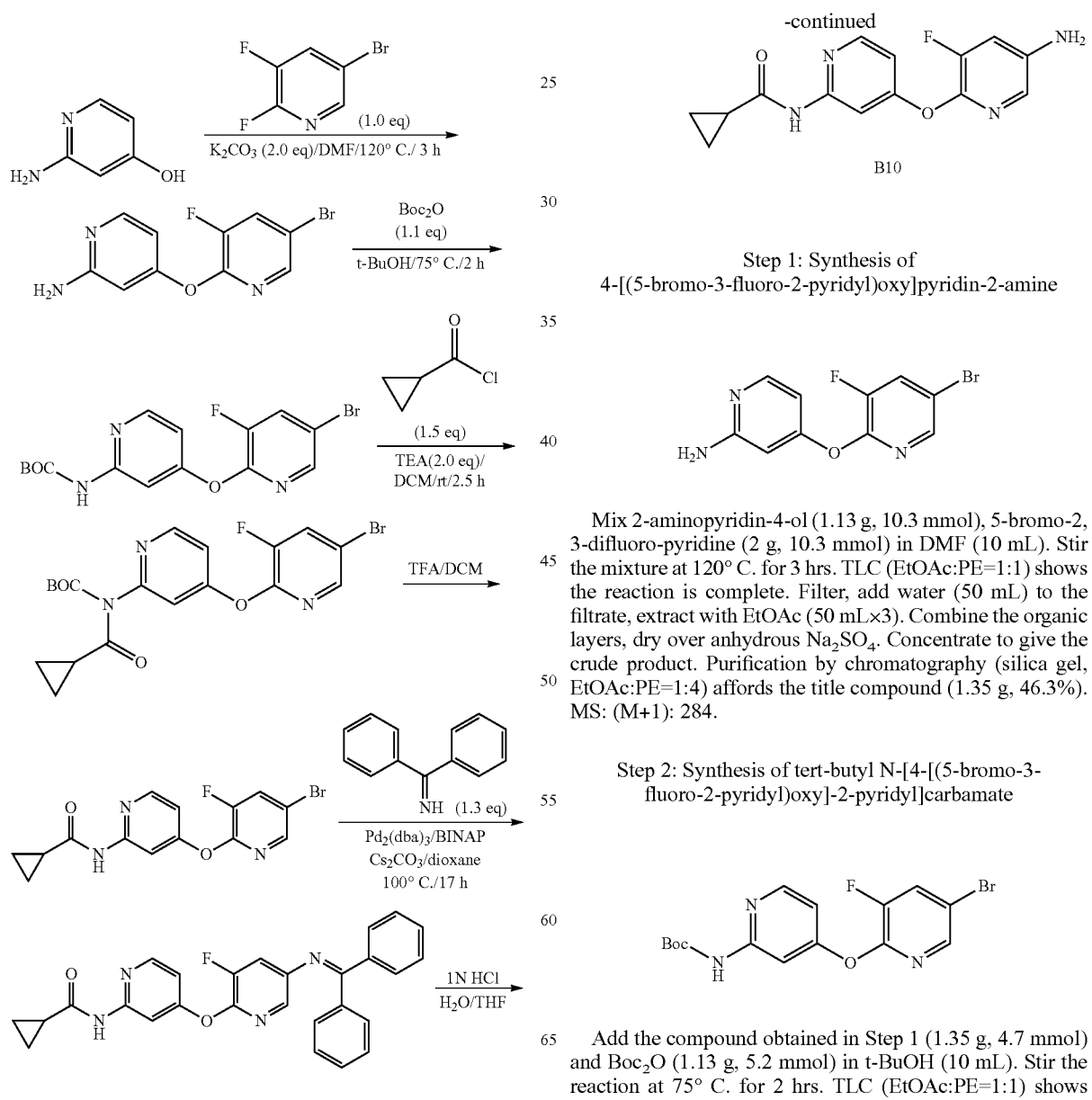

B10

Step 1: Synthesis of 4-[(5-bromo-3-fluoro-2-pyridyl)oxy]pyridin-2-amine

Mix 2-aminopyridin-4-ol (1.13 g, 10.3 mmol), 5-bromo-2,3-difluoro-pyridine (2 g, 10.3 mmol) in DMF (10 mL). Stir the mixture at 120° C. for 3 hrs. TLC (EtOAc:PE=1:1) shows the reaction is complete. Filter, add water (50 mL) to the filtrate, extract with EtOAc (50 mL×3). Combine the organic layers, dry over anhydrous Na₂SO₄. Concentrate to give the crude product. Purification by chromatography (silica gel, EtOAc:PE=1:4) affords the title compound (1.35 g, 46.3%). MS: (M+1): 284.

Step 2: Synthesis of tert-butyl N-[4-[(5-bromo-3-fluoro-2-pyridyl)oxy]-2-pyridyl]carbamate Add the compound obtained in Step 1 (1.35 g, 4.7 mmol) and Boc₂O (1.13 g, 5.2 mmol) in t-BuOH (10 mL). Stir the reaction at 75° C. for 2 hrs. TLC (EtOAc:PE=1:1) shows reaction is complete. Concentrate under reduced pressure to give the crude product (1.8 g) which is used without further purification.

Step 3: Synthesis of tert-butyl N-[4-[(5-bromo-3-fluoro-2-pyridyl)oxy]-2-pyridyl]-Nyclopropanecarbonyl)carbamate

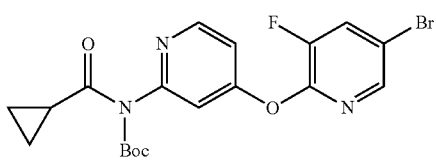 [SMILES: CC(C)(C)OC(=O)N(C(=O)C1CC1)c1cc(Oc2ncc(Br)cc2F)ccn1]

Add the compound obtained in Step 2 (1.8 g, 4.7 mmol), Et₃N (0.95 g, 9.4 mmol) to DCM (10 mL), then add cyclopropanecarbonyl chloride (0.95 g, 7.0 mmol). Stir the reaction at room temperature for 2.5 hrs. TLC (EtOAc:PE=1:1) shows the reaction is complete. Add water (10 mL) to quench the reaction. Extract with DCM (10 mL×3), combine the organic layers, dry over anhydrous Na₂SO₄. Concentrate under reduced pressure to give the crude product (2.14 g) which is used without further purification.

Step 4: Synthesis of N-[4-[(5-bromo-3-fluoro-2-pyridyl)oxyl-2-pyridyl]cyclopropanecarboxamide

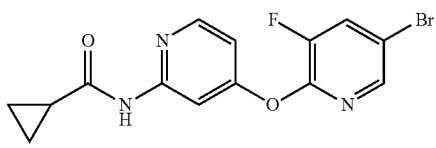 [SMILES: O=C(Nc1cc(Oc2ncc(Br)cc2F)ccn1)C1CC1]

Dissolve the crude product obtained in Step 3 (2.14 g, 4.7 mmol) in HCl solution in 1,4-dioxane (5 M, 10 mL). Stir the reaction at room temperature for 17 hrs. LC/MS shows reaction is complete. Remove the solvent under reduced pressure, suspend the solid in DCM and add carefully saturated NaHCO₃ solution. Separate the organic layer. Extract the aqueous layer with DCM. Combine the organic layers, dry over anhydrous Na₂SO₄. Concentrate to give the crude product. Purification by chromatography (silica gel, EtOAc:PE=1:3) affords the title compound (0.9 g, 54% from step 2). MS: (M+1): 352.

Step 5: Synthesis of N-[4-[[5-(benzhydrylideneamino)-3-fluoro-2-pyridyl]oxy]-2-pyridyl]cyclopropanecarboxamide

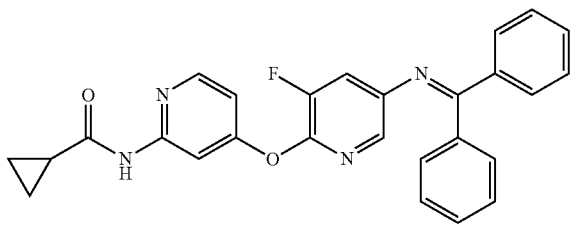 [SMILES: O=C(Nc1cc(Oc2ncc(N=C(c3ccccc3)c3ccccc3)cc2F)ccn1)C1CC1]

Add the compound obtained in Step 4 (0.9 g, 2.5 mmol), benzophenone imine (0.59 g, 3.25 mmol), tris(dibenzylideneacetone)dipalladium [Pd₂(dba)₃, 200 mg, 0.25 mmol], (±)-2,2'-bis(diphenylphosphino)-1,1'-binaphthalene (BINAP, 250 mg, 0.375 mmol), Cs₂CO₃ (1.6 g, 5.0 mmol) in 1,4-dioxane (10 mL). Stir the mixture under N₂ at 100° C. for 16 hrs. Cool to room temperature, filter, and concentrate the filtrate to give the crude product. Purification by chromatography (silica gel, EtOAc:PE=1:3) affords the title compound (0.8 g, 69%). MS: (M+1): 453.

Step 6: Synthesis of N-[4-[(5-amino-3-fluoro-2-pyridyl)oxy]-2-pyridyl]cyclopropanecarboxamide

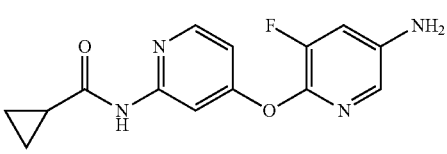 [SMILES: Nc1cnc(Oc2ccnc(NC(=O)C3CC3)c2)c(F)c1]

Dissolve the compound obtained in Step 5 (0.8 g, 1.77 mmol) in THF (10 mL), add water (1 mL) and 1N aqueous HCl (3 mL). Stir the reaction at room temperature for 2 hrs. TLC (EtOAc:PE=1:1) shows the reaction is complete. Extract with EtOAc. Wash the organic layer with saturated NaHCO₃ solution and brine respectively. Collect the organic layer, dry over anhydrous Na₂SO₄. Concentrate to give the crude product. Purification by chromatography (silica gel, EtOAc:PE=5:1) affords the title compound (0.4 g, 78%).

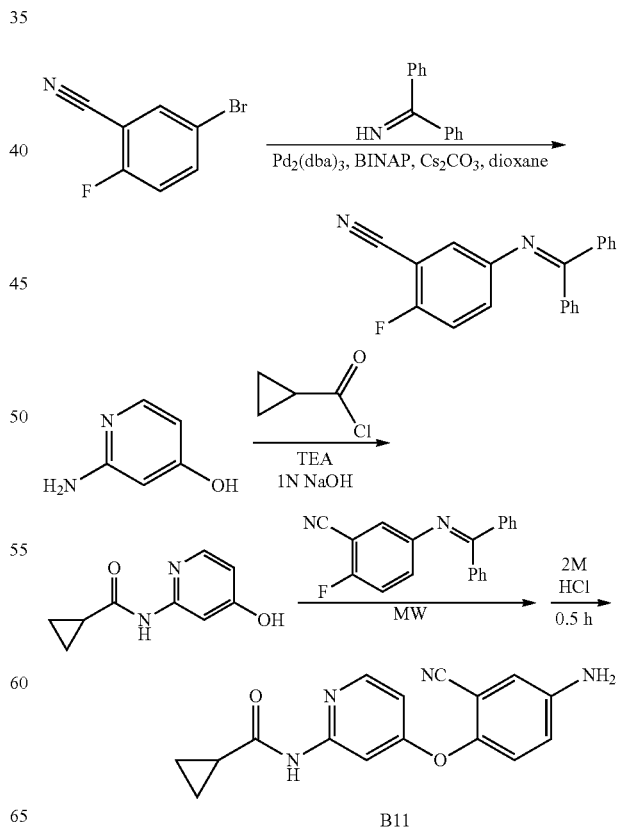

B11

Step 1: Synthesis of N-(4-hydroxy-2-pyridyl)cyclopropanecarboxamide

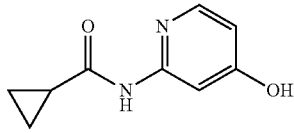 [SMILES: O=C(Nc1cc(O)ccn1)C1CC1]

Dissolve 2-amino-pyridin-4-ol (5 g, 45.4 mmol) in DCM (30 mL), add Et$_3$N (13.8 g, 136 mmol) and then cyclopropanecarbonyl chloride (14.2 g, 136 mmol) dropwise while keeping the temperature below 10° C. After addition, stir the reaction at room temperature for 16 hrs. Remove the solvent under reduced pressure, dissolve the residue in THF (40 mL), adjust pH=12 with 1N NaOH solution. Stir the mixture for 3 hrs. Concentrate to give the crude product. Purification by chromatography (silica gel, EtOAc:MeOH=9:1) affords the title compound (2.6 g, 32%).

Step 2: Synthesis of 5-(benzhydrylideneamino)-2-fluoro-benzonitrile

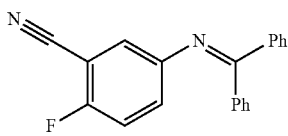 [SMILES: N#Cc1cc(N=C(c2ccccc2)c2ccccc2)ccc1F]

Add 5-bromo-2-fluoro-benzonitrile (0.5 g, 2.5 mmol), benzophenone imine (0.543 g, 3 mmol), (±)-2,2'-bis(diphenylphosphino)-1,1'-binaphthalene (BINAP, 60 mg, 0.1 mmol), tris(dibenzylideneacetone)dipalladium [Pd$_2$(dba)$_3$, 50 mg, 0.05 mmol], and Cs$_2$CO$_3$ (1.6 g, 4.9 mmol) in 1,4-dioxane (20 mL). Stir the reaction under N$_2$ at 110° C. for 16 hrs. Cool to room temperature, filter the solid, and concentrate the filtrate to give the crude product. Purification by chromatography (silica gel, EtOAc:PE=1:3) affords the title compound (0.78 g, 99%). MS: (M+1): 301.

Step 3: Synthesis of N-[4-(4-amino-2-cyano-phenoxy)-2-pyridyl]cyclopropanecarboxamide

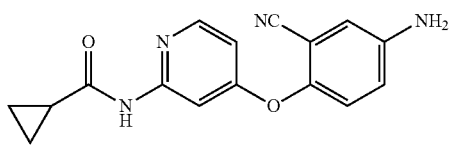 [SMILES: N#Cc1cc(N)ccc1Oc1ccnc(NC(=O)C2CC2)c1]

Mix N-(4-hydroxy-2-pyridyl)cyclopropanecarboxamide (179 mg, 1 mmol), 5-(benzhydrylideneamino)-2-fluoro-benzonitrile (0.3 g, 1 mmol), Cs$_2$CO$_3$ (0.28 g, 2 mmol) and DMF (10 mL) in a microwave reaction vessel. Use microwave to heat the reaction at 150° C. for 30 min. TLC (EtOAc:PE=2:1) shows the reaction is complete. Cool the reaction to room temperature. Add water (15 mL), extract with EtOAc (15 mL×2). Combine the organic layers; wash with brine, dry over anhydrous Na$_2$SO$_4$. Concentrate under reduced pressure to give the crude imine intermediate. Purification by chromatography (silica gel, EtOAc:PE=1:1) provides the imine intermediate (255 mg, 55.4%). MS: (M+1): 459.3.

Dissolve this imine intermediate in THF (10 mL), add 1M aqueous HCl (10 mL), stir for 1 hr. Adjust pH=7, extract with EtOAc (50 mL×3), combine the organic layers, wash with brine, dry over anhydrous Na$_2$SO$_4$. Concentrate under reduced pressure to give the crude product. Purification by chromatography (silica gel, EtOAc:PE=3:1) affords the title compound (124 mg, 78%). MS: (M+1): 295.2.

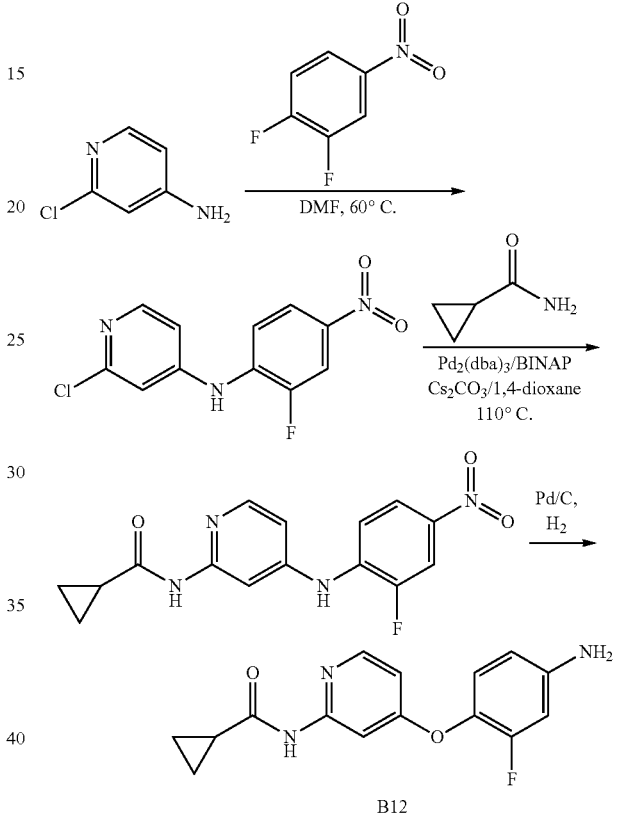

B12

Step 1: Synthesis of 2-chloro-N-(2-fluoro-4-nitrophenyl)pyridin-4-amine

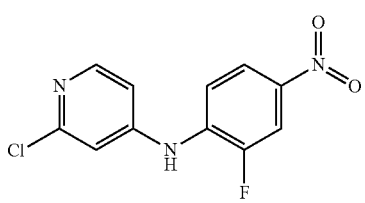 [SMILES: O=[N+]([O-])c1ccc(Nc2ccnc(Cl)c2)c(F)c1]

Add 2-chloropyridin-4-amine (500 mg, 3.9 mmol), 1,2-difluoro-4-nitrobenzene (620 mg, 3.9 mmol), Cs$_2$CO$_3$ (3.2 g, 9.8 mmol) to DMF (15 mL). Stir the reaction at 110° C. for 16 hrs. Cool to room temperature, add water (100 mL), extract with EtOAc (15 mL×3). Combine the organic layers and wash with brine, dry over anhydrous Na$_2$SO$_4$. Concentrate under reduced pressure to give the crude product. Purification by chromatography (silica gel, EtOAc:PE=1:4) affords the title compound (280 mg, 27%). MS: (M+1): 268.1.

Step 2: Synthesis of N-[4-(2-fluoro-4-nitro-anilino)-2-pyridyl]cyclopropanecarboxamide

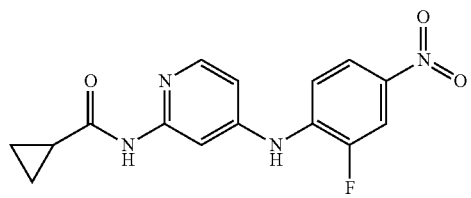 [SMILES: O=C(Nc1cc(Nc2ccc([N+](=O)[O-])cc2F)ccn1)C1CC1]

Mix 2-chloro-N-(2-fluoro-4-nitro-phenyl)pyridin-4-amine (280 mg, 1.05 mmol), cyclopropanecarboxamide (267 mg, 3.15 mmol), Cs$_2$CO$_3$ (863 mg, 2.63 mmol), (±)-2,2'-bis(diphenylphosphino)-1,1'-binaphthalene (BINAP, 65 mg, 1.05 mmol), tris(dibenzylideneacetone)dipalladium [Pd$_2$(dba)$_3$, 48 mg, 0.053 mmol] and 1,4-dioxane (6 mL) in a 50 mL round bottom flask, heat at 100° C. under N$_2$ for 16 hrs. Cool the reaction to 25° C., add water (40 mL), extract with EtOAc (10 mL×2). Combine the organic layers; wash with brine (15 mL), dry over anhydrous Na$_2$SO$_4$. Concentrate under reduced pressure to give the crude product. Purification by chromatography (silica gel, PE:EtOAc=7:3) affords the target compound (180 mg, 54%). MS: (M+1): 317.1.

Step 3: Synthesis of N-[4-(4-amino-2-fluoro-anilino)-2-pyridyl]cyclopropanecarboxamide

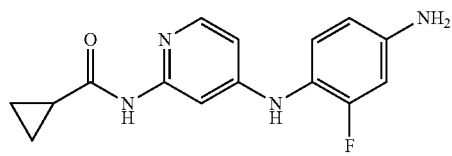 [SMILES: Nc1ccc(Nc2ccnc(NC(=O)C3CC3)c2)c(F)c1]

Dissolve the compound obtained in Step 2 (180 mg, 0.57 mmol) in methanol (6 mL), add wet Pd/C (10%, 70 mg), flush with H$_2$, and stir the reaction at room temperature under H$_2$ atmosphere for 16 hrs. After the reaction, remove H$_2$, filter the reaction mixture and concentrate the filtrate to get the crude product (100 mg). Use the crude product directly without further purification. MS: (M+1): 287.2.

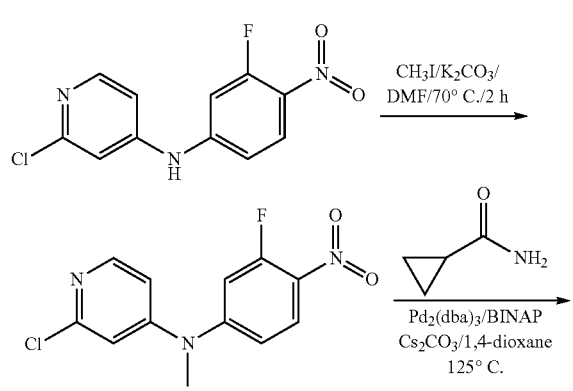

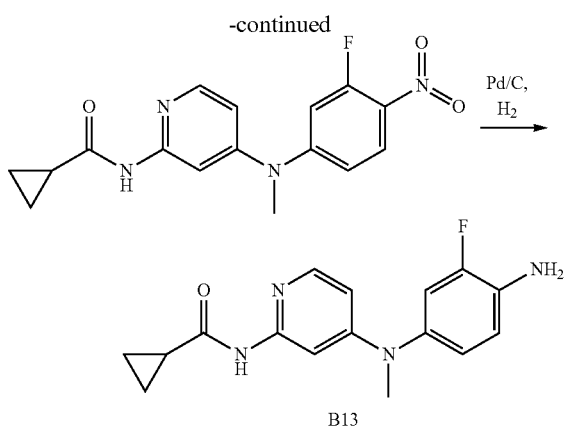

B13

Step 1: Synthesis of 2-chloro-N-(3-fluoro-4-nitro-phenyl)-N-methyl-pyridin-4-amine

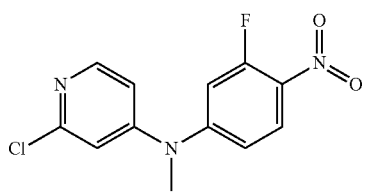 [SMILES: CN(c1ccnc(Cl)c1)c1ccc([N+](=O)[O-])c(F)c1]

Add 2-chloro-N-(3-fluoro-4-nitro-phenyl)pyridin-4-amine (300 mg, 1.12 mmol), methyl iodide (174 mg, 1.23 mmol) and K$_2$CO$_3$ (201 mg, 1.45 mmol) in DMF (6 mL). Stir the reaction at 70° C. for 3 hrs. TLC (EtOAc:PE=1:1) shows the reaction is complete, cool the reaction to 0° C., add water, extract with EtOAc. Combine the organic layers. Wash with brine, dry over anhydrous Na$_2$SO$_4$. Concentrate to give the crude product. Purification by chromatography (silica gel, EtOAc:PE=1:1) affords the title compound (190 mg, 45%). MS: (M+1): 282.2.

Step 2: Synthesis of N-[4-(3-fluoro-4-nitro-anilino)-2-pyridyl]cyclopropanecarboxamide

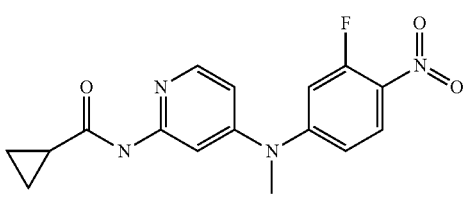 [SMILES: CN(c1ccnc(NC(=O)C2CC2)c1)c1ccc([N+](=O)[O-])c(F)c1]

Add 2-chloro-N-(3-fluoro-4-nitro-phenyl)-N-methyl-pyridin-4-amine (190 mg, 0.68 mmol), cyclopropanecarboxamide (85 mg, 2.03 mmol), Cs$_2$CO$_3$ (440 mg, 1.35 mmol), (±)-2,2'-bis(diphenylphosphino)-1,1'-binaphthalene (BINAP, 43 mg, 0.05 mmol) and tris(dibenzylideneacetone)dipalladium [Pd$_2$(dba)$_3$, 42 mg, 0.07 mmol] in 1,4-dioxane (6 mL) under N$_2$. Heat the reaction at 125° C. for 16 hrs. TLC (EtOAc:PE=2:1) shows the reaction is complete. Cool to room temperature, filter, and concentrate the filtrate under reduced pressure to give the crude product. Purification by chromatography (silica gel, EtOAc:PE=2:1) affords the target compound (160 mg, 71.7%). MS: (M+1): 331.

Step 3: Synthesis of N-[4-(4-amino-3-fluoro-anilino)-2-pyridyl]cyclopropanecarboxamide

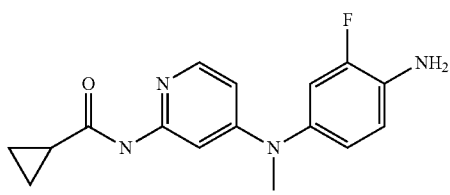 [SMILES: CN(c1ccnc(NC(=O)C2CC2)c1)c1ccc(N)c(F)c1]

Dissolve the compound obtained in Step 2 (160 mg, 0.48 mmol) in methanol (15 mL) and dichloromethane (15 mL). Add Pd/C (10%, 32 mg), flush with $H_2$. Stir the reaction at room temperature for 3.5 hrs under $H_2$. LC/MS shows the reaction is complete. Remove the $H_2$, filter the reaction mixture, and concentrate the filtrate under reduced pressure to give the crude product (120 mg). MS: (M+1): 301.

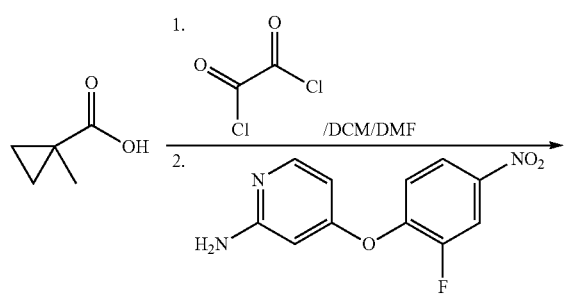

B14

Step 1: Synthesis of N-[4-(2-fluoro-4-nitro-phenoxy)-2-pyridyl]-1-methyl-cyclopropanecarboxamide

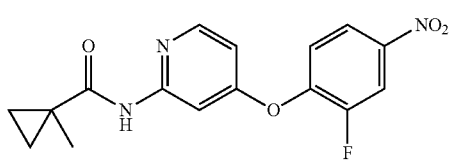 [SMILES: CC1(C(=O)Nc2cc(Oc3ccc([N+](=O)[O-])cc3F)ccn2)CC1]

Add oxalyl chloride (760 mg, 60 mmol) slowly to a solution of 1-methylcyclopropanecarboxylic acid (500 mg, 5.0 mmol) in DCM (10 mL) at 0° C., add a few drops of DMF. Stir the reaction at 0° C. for 30 min, and then stir at room temperature for hrs. Remove the volatiles under reduced pressure to give the crude 1-methylcyclopropanecarbonyl chloride.

Add the solution of the above 1-methylcyclopropanecarbonyl chloride in DCM slowly to a solution of 4-(2-fluoro-4-nitro-phenoxy)pyridin-2-amine (500 mg, 2.0 mmol) and $Et_3N$ (505 mg, 5.0 mmol) in DCM (15 mL) at 0° C. Stir the reaction at room temperature for 15 hrs. TLC (EtOAc:PE=1:1) shows the reaction is complete. Concentrate the mixture to give the crude product. Purification by chromatography (silica gel, EtOAc:PE=1:1) affords the target compound (160 mg, 24%). MS: (M+1): 332.2.

Step 2: Synthesis of N-[4-(4-amino-2-fluoro-phenoxy)-2-pyridyl]-1-methyl-cyclopropanecarboxamide

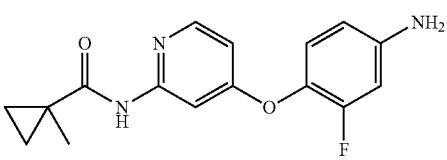 [SMILES: CC1(C(=O)Nc2cc(Oc3ccc(N)cc3F)ccn2)CC1]

Dissolve N-[4-(2-fluoro-4-nitro-phenoxy)-2-pyridyl]-1-methyl-cyclopropanecarboxamide (160 mg, 0.48 mmol) in DCM (30 mL), add Pd/C (10%, 55 mg), flush with $H_2$. Stir the reaction at room temperature under $H_2$ atmosphere for 2 hrs. Filter the reaction mixture; concentrate the filtrate under reduced pressure to give the crude product (100 mg) which is used without further purification. MS: (M+1): 302.2.

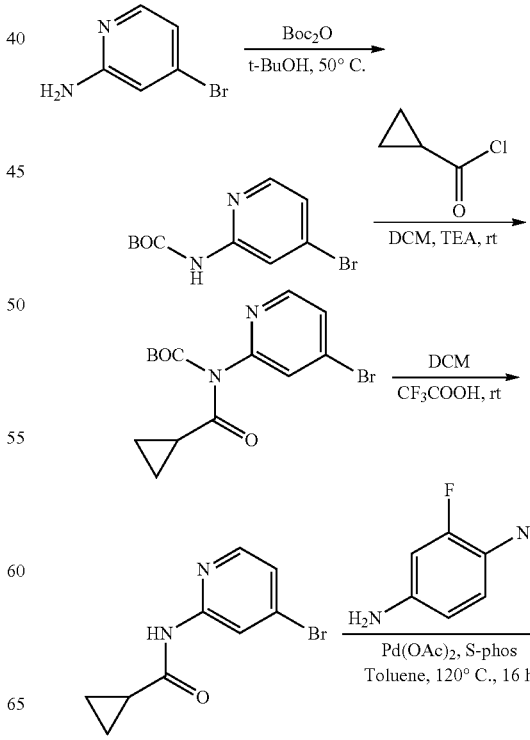

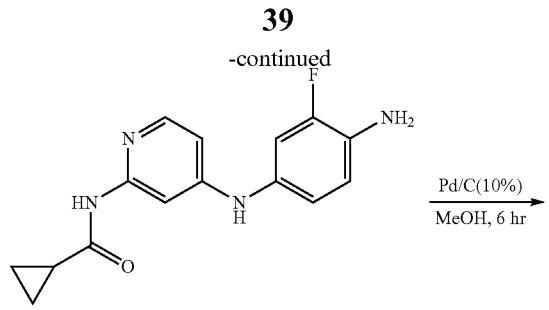

temperature for 2 hrs. Pour the reaction mixture to water (50 mL), extract with EtOAc (15 mL×3), combine the organic layers and wash with brine (100 mL). Dry over anhydrous $Na_2SO_4$; concentrate under reduced pressure to give the crude product (1.55 g) which is used without further purification. MS: (M+1): 241.0

Step 3: Synthesis of N-(4-bromo-2-pyridyl)cyclopropanecarboxamide

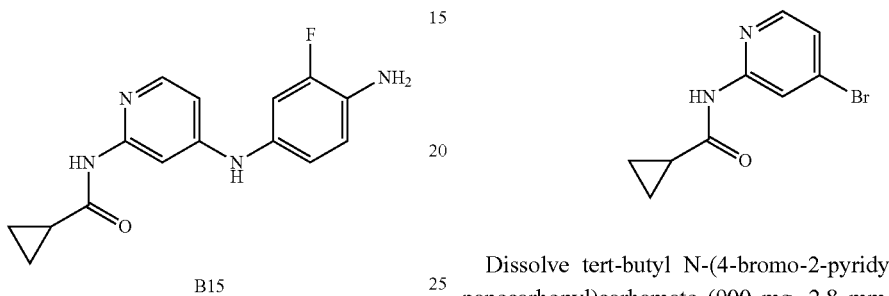

B15

Step 1: Synthesis of tert-butyl N-(4-bromo-2-pyridyl)carbamate

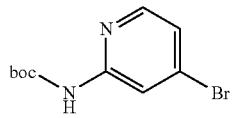

Dissolve 2-amino-4-bromopyridine (1.0 g, 5.8 mmol), di-tert-butyl dicarbonate ($Boc_2O$, 1.4 g, 6.4 mmol) in t-BuOH (15 mL), heat the mixture at 50° C. overnight. Cool to room temperature, pour to water (50 mL), extract with EtOAc (15 mL×3). Combine the organic layers, dry over anhydrous $Na_2SO_4$; concentrate under reduced pressure to afford the crude product (1.24 g) which is used without further purification. MS: (M+1): 219.0.

Step 2: Synthesis of tert-butyl N-(4-bromo-2-pyridyl)-N-(cyclopropanecarbonyl)carbamate

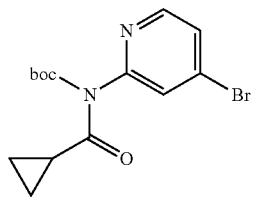

Add cyclopropanecarbonyl chloride (1.42 g, 13.68 mmol) slowly to a solution of tert-butyl N-(4-bromo-2-pyridyl)carbamate (1.24 g, 4.6 mmol), $Et_3N$ (1.38 g, 13.68 mmol) in DCM (15 mL) at 0° C. After addition, stir the reaction at room temperature for 2 hrs. Pour the reaction mixture to water (50 mL), extract with EtOAc (15 mL×3), combine the organic layers and wash with brine (100 mL). Dry over anhydrous $Na_2SO_4$; concentrate under reduced pressure to give the crude product (1.55 g) which is used without further purification. MS: (M+1): 241.0

Step 3: Synthesis of N-(4-bromo-2-pyridyl)cyclopropanecarboxamide

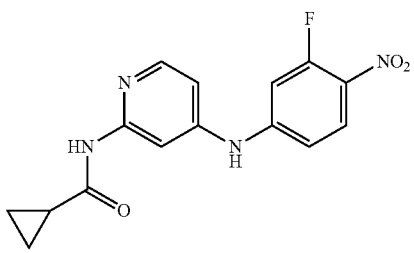

Dissolve tert-butyl N-(4-bromo-2-pyridyl)-N-(cyclopropanecarbonyl)carbamate (900 mg, 2.8 mmol) in DCM (8 mL), add slowly trifluoroacetic acid (4 mL). Stir the reaction at room temperature for 3 hrs. Pour the reaction mixture to water (50 mL), adjust to pH=7 with saturated $NaHCO_3$ solution. Extract with EtOAc (15 mL×3), combine the organic layers; wash with brine (100 mL), dry over anhydrous $Na_2SO_4$. Concentrate under reduced pressure to give the crude product (670 mg) which is used without further purification. MS: (M+1): 243.1.

Step 4: Synthesis of N-[4-(3-fluoro-4-nitro-anilino)-2-pyridyl]cyclopropanecarboxamide Under $N_2$, mix N-(4-bromo-2-pyridyl)cyclopropanecarboxamide (460 mg, 1.9 mmol), 3-fluoro-4-nitroaniline (359 mg, 2.3 mmol), palladium(II) acetate [$Pd(OAc)_2$, 43.2 mg, 0.19 mmol], 2-dicyclohexylphosphino-2',6'-dimethoxybiphenyl (S-Phos, 158 mg, 0.38 mmol), $Cs_2CO_3$ (1.2 g, 3.8 mmol) and anhydrous toluene (10 mL). Stir the mixture at 120° C. under $N_2$ for 16 hrs. Cool to room temperature, pour the reaction mixture to water (50 mL), extract with EtOAc (15 mL×3), combine the organic layers and dry over anhydrous $Na_2SO_4$. Concentrate under reduced pressure to give the crude product. Purification by chromatography (silica gel, PE:EtOAc=54:46) affords the target compound (160 mg, 22%). MS: (M+1): 317.2.

Step 5: Synthesis of N-[4-(4-amino-3-fluoro-anilino)-2-pyridyl]cyclopropanecarboxamide

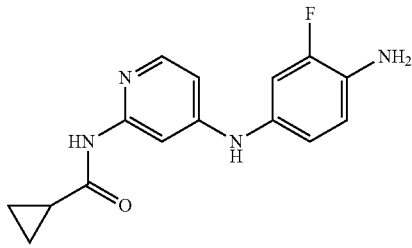 [SMILES: O=C(Nc1cc(Nc2ccc([N+](=O)[O-])c(F)c2)ccn1)C1CC1]

Dissolve N-[4-(3-fluoro-4-nitro-anilino)-2-pyridyl]cyclopropanecarboxamide (160 mg, 0.51 mmol) in methanol (10 mL), add wet Pd/C (10%, 60 mg), flush with H₂ and then stir the reaction under H₂ atmosphere at room temperature for 6 hrs. Remove H₂, filter the mixture. Concentrate the filtrate under reduced pressure to give the crude product (140 mg) which is used directly without further purification. MS: (M+1): 287.2.

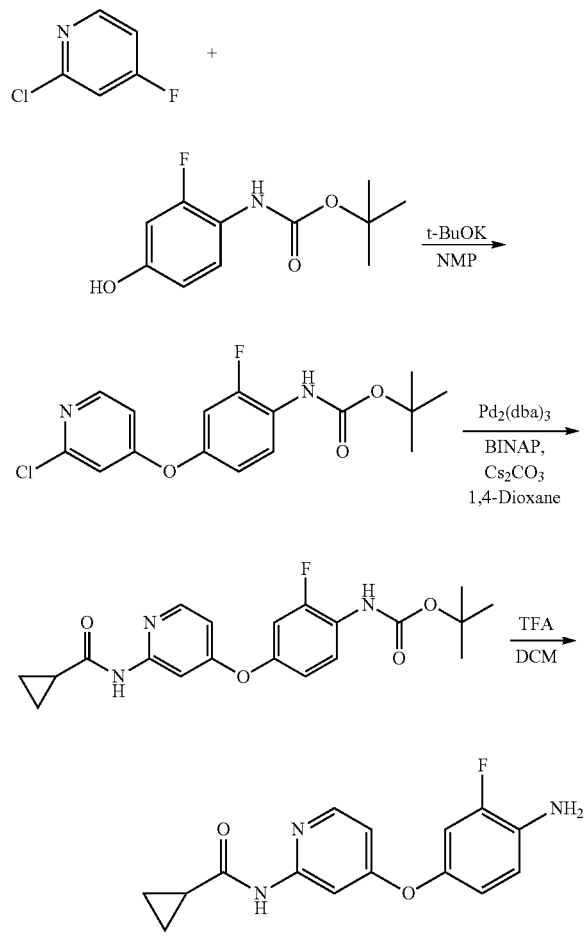

Step 1: Synthesis of tert-butyl N-[4-[(2-chloro-4-pyridyl)oxy]-2-fluoro-phenyl]carbamate

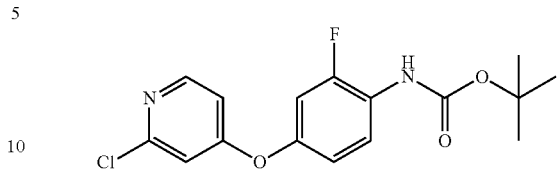

Dissolve tert-butyl N-(2-fluoro-4-hydroxy-phenyl)carbamate (10.47 g, 46.1 mmol) in N-methyl-2-pyrrolidone (NMP, 100 mL), add t-BuOK (5.67 g, 50.5 mmol) and stir at 0° C. for 30 min. Add 2-chloro-4-fluoropyridine (5.5 g, 41.9 mmol), then stir at 70° C. under N₂ for 12 hrs. Quench the reaction with water, extract with EtOAc (300 mL×3), combine the organic layers, wash with brine (300 mL×2), dry over anhydrous Na₂SO₄. Concentrate under reduced pressure to give the crude product. Purification by chromatography (silica gel, EtOAc:PE=1:4) affords the title compound (11.23 g, 79.5%). MS: (M+1): 339.

Step 2: Synthesis of tert-butyl N-[4-[[2-(cyclopropanecarbonylamino)-4-pyridyl]oxy]-2-fluoro-phenyl]carbamate

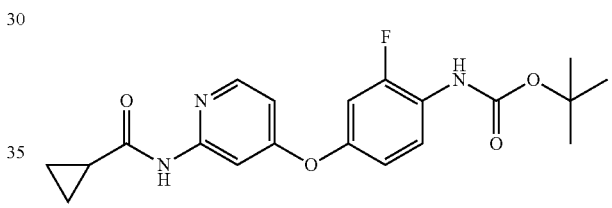

Dissolve tert-butyl N-[4-[(2-chloro-4-pyridyl)oxy]-2-fluoro-phenyl]carbamate (13 g, 14.7 mmol), cyclopropanecarboxamide (8.1 g, 36.7 mmol) in 1,4-dioxane (240 mL). Then add tris(dibenzylideneacetone)dipalladium(0) [Pd₂(dba)₃, 1.75 g, 0.73 mmol), (±)-2,2'-bis(diphenylphosphino)-1,1'-binaphthalene (BINAP, 2.38 g, 1.47 mmol) and Cs₂CO₃ (24.8 g, 29.4 mmol) under N₂. Stir the reaction at 100° C. for 12 hrs. Cool to room temperature, filter, and concentrate the filtrate to give the crude product. Purification by chromatography (silica gel, DCM:EtOAc-1:5) affords the title compound (12.14 g, 83.2%). MS: (M+1): 388.

Step 3: Synthesis of N-[4-(4-amino-3-fluoro-phenoxy)-2-pyridyl]cyclopropanecarboxamide

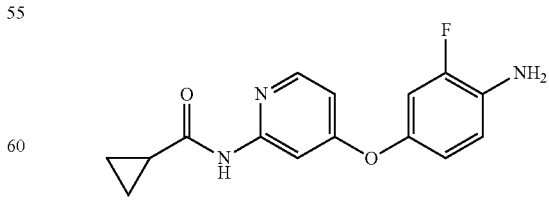

Dissolve tert-butyl N-[4-[[2-(cyclopropanecarbonylamino)-4-pyridyl]oxy]-2-fluoro-phenyl]carbamate (12.14 g, 31.28 mmol) in DCM (280 mL), add trifluoroacetic acid (35 mL). Stir the reaction at room temperature for 5 hrs. Remove the volatiles under reduced pressure. Add EtOAc (300 mL), washed with saturated NaHCO$_3$ solution (300 mL×2), and brine (300 mL×2). Dry the organic layer with anhydrous Na$_2$SO$_4$. Concentrate to give the crude product. Purification by chromatography (silica gel, EtOAc:PE=1:1) affords the title compound (7 g, 78.4%). MS: (M+1): 288.

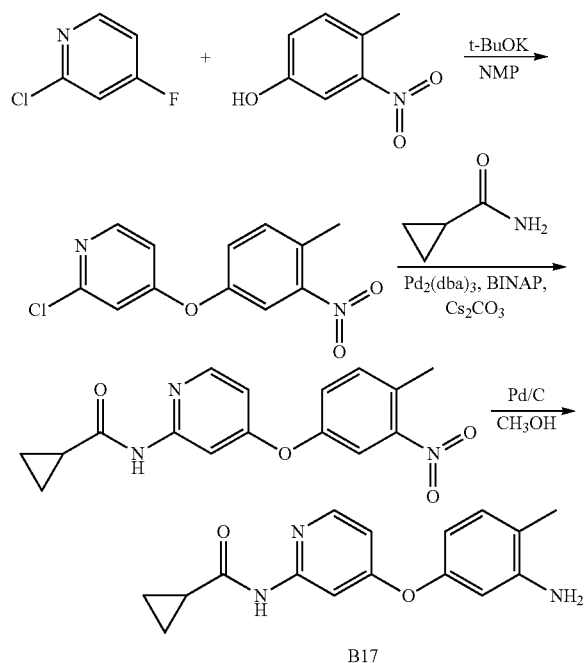

B17

Step 1: Synthesis of 2-chloro-4-(4-methyl-3-nitro-phenoxy)pyridine

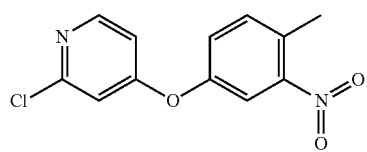 [SMILES: Cc1ccc(Oc2ccnc(Cl)c2)cc1[N+](=O)[O-]]

Add 4-methyl-3-nitrophenol (6.95 g, 45.46 mmol) and t-BuOK (5.94 g, 53.03 mmol) to N-methylpyrrolidin-2-one (100 mL), stir for 30 min, then add 2-chloro-4-fluoro-pyridine (5 g, 37.88 mmol) and stir the reaction at 70° C. overnight. TLC (PE:EtOAc=3:1) shows the reaction is complete. Add water (250 mL) to the reaction mixture, extract with EtOAc (100 mL×4), combine the organic layers, wash with water, brine respectively and dry over Na$_2$SO$_4$. Concentrate to give the crude product. Purification by chromatography (silica gel, EtOAc:PE=1:4) affords the title compound (5.8 g, 58%). MS: (M+1): 265.1.

Step 2: Synthesis of N-[4-(4-methyl-3-nitro-phenoxy)-2-pyridyl]cyclopropanecarboxamide

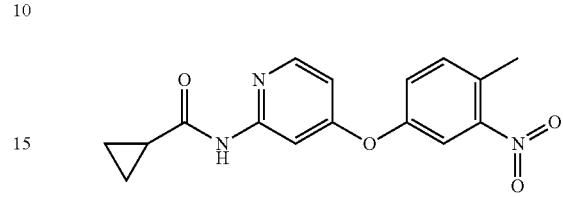

Add the compound obtained in Step 1 (5.0 g, 18.87 mmol), cyclopropanecarboxamide (4.81 g, 56.61 mmol) to 1,4-dioxane (100 mL). Then under N$_2$, add tris(dibenzylideneacetone)dipalladium [Pd$_2$(dba)$_3$, 0.86 g, 0.94 mmol], (±)-2,2'-bis(diphenylphosphino)-1,1'-binaphthalene (BINAP, 1.17 g, 1.89 mmol), Cs$_2$CO$_3$ (12.27 g, 37.74 mmol). Stir the reaction under N$_2$ at 100° C. overnight. TLC (PE:EtOAc=2:1) shows the reaction is complete. Cool the reaction to room temperature, filter, and concentrate the filtrate to get the crude product. Purification by chromatography (silica gel, EtOAc:PE=1:4) affords the title compound (3.0 g, 51%). MS: (M+1): 314.2.

Step 3: Synthesis of N-[4-(3-amino-4-methyl-phenoxy)-2-pyridyl]cyclopropanecarboxamide

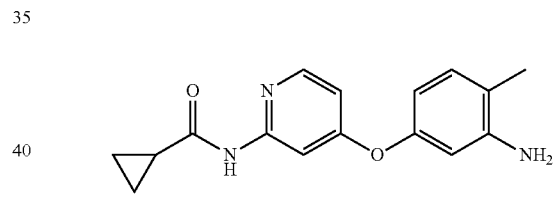

Dissolve the above nitro compound (3.0 g, 9.6 mmol) in methanol (150 mL), add Pd/C (10%, 0.9 g) to the solution, flush with H$_2$ and stir under H$_2$ atmosphere at room temperature overnight. TLC (PE:EtOAc=2:1) shows reaction is complete. Filter and concentrate the filtrate under reduced pressure to give a crude product. Purification by chromatography (silica gel, EtOAc:PE=1:2) affords the title compound (1.90 g, 70%). MS: (M+1): 284.2.

Intermediate B18 can be synthesized with similar method (Table B2).

TABLE B2

| | Intermediate B10-B18 | | |
|---|---|---|---|
| Number | Starting material | Intermediate | MS [M + 1]$^+$ |
| B10 | ![F,F,Br-pyridine] | ![structure] | 289.1 |

TABLE B2-continued

Intermediate B10-B18

| Number | Starting material | Intermediate | MS [M + 1]+ |
|---|---|---|---|
| B11 | 5-amino-2-fluorobenzonitrile | cyclopropanecarboxamide pyridine linked via O to 4-amino-2-cyanophenyl | 295.2 |
| B12 | 3,4-difluoronitrobenzene | cyclopropanecarboxamide pyridine linked via NH to 4-amino-2-fluorophenyl | 287.2 |
| B13 | 2,4-difluoronitrobenzene | cyclopropanecarboxamide pyridine linked via N(Me) to 4-amino-2-fluorophenyl | 301 |
| B14 | 3,4-difluoronitrobenzene | 1-methylcyclopropanecarboxamide pyridine linked via O to 4-amino-2-fluorophenyl | 302.2 |
| B15 | 4-amino-2-fluoronitrobenzene | cyclopropanecarboxamide pyridine linked via O to 4-amino-3-fluorophenyl | 287.2 |
| B16 | boc-protected 2-fluoro-4-hydroxyaniline | cyclopropanecarboxamide pyridine linked via O to 4-amino-3-fluorophenyl | 288 |
| B17 | 3-nitro-4-methylphenol | cyclopropanecarboxamide pyridine linked via O to 3-amino-4-methylphenyl | 284.2 |
| B18 | 4-amino-2-methylphenol | cyclopropanecarboxamide pyridine linked via O to 4-amino-2-methylphenyl | 284.2 |

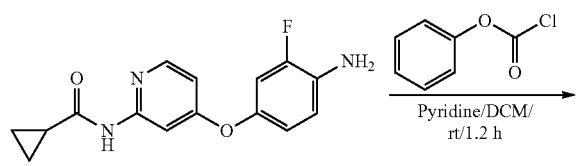

Mix N-[4-(4-amino-3-fluoro-phenoxy)-2-pyridyl]cyclopropanecarboxamide (500 mg, 1.7 mmol), DCM (8 mL) and pyridine (345 mg) and cool to 0-5° C. Add a solution of phenyl chloroformate (350 mg, 2.2 mmol) in DCM (1 mL). Stir the reaction at room temperature for 1.5 hrs. TLC (EtOAc:PE=1;1) shows the reaction is complete. Quench the reaction with water (5 mL). Wash the organic layer with 1N HCl solution, saturated NaHCO₃ solution and brine respectively. Dry the organic layer with anhydrous Na₂SO₄. Filter and concentrate to give the crude product (710 mg) which is used without further purification. MS: (M+1): 408.

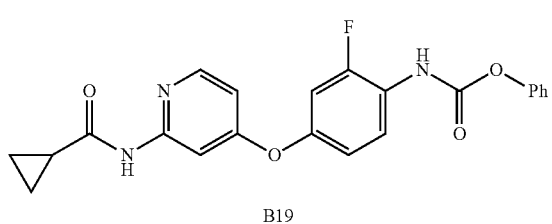

B19

Intermediates B20-21 can be synthesized with similar method (Table B3).

TABLE B3

Intermediates B19-B21

| Number | Starting material | Intermediate | MS [M + 1]⁺ |
|---|---|---|---|
| B19 | B16 | | 408 |
| B20 | B7 | | 408 |
| B21 | B6 | | NA |

Step 1: Synthesis of phenyl N-[4-[[2-(cyclopropanecarbonylamino)-4-pyridyl]oxy]-2-fluoro-phenyl]carbamate

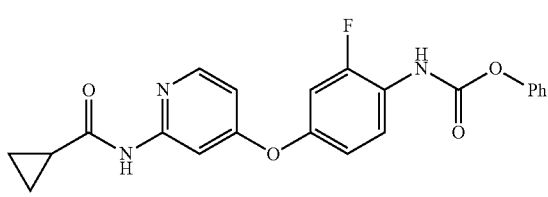 [SMILES: O=C(Nc1ccc(Oc2ccnc(NC(=O)C3CC3)c2)cc1F)Oc1ccccc1]

Preparation of Intermediate C

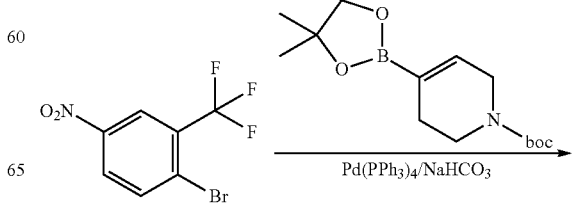

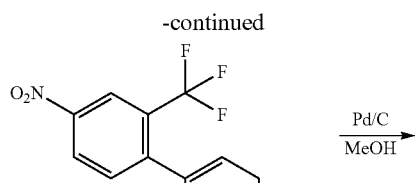

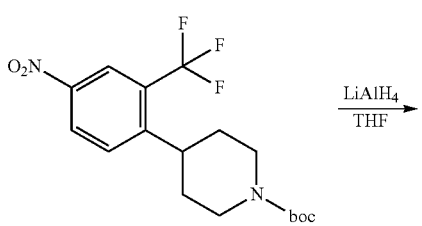

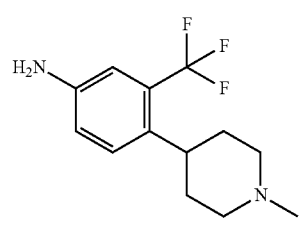

C1

Step 1: Synthesis of tert-butyl 4-(4-nitro-2-(trifluoromethyl)phenyl)-5,6-dihydropyridine-1(2H)-carboxylate

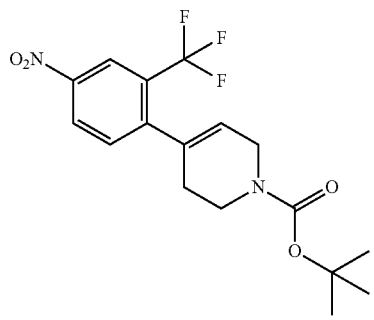 [SMILES: CC(C)(C)OC(=O)N1CC=C(c2ccc([N+](=O)[O-])cc2C(F)(F)F)CC1]

Add 2-bromo-5-nitrobenzotrifluoride (250 mg, 0.926 mmol) to dioxane (3 mL), then add tert-butyl 4-(4,4,5,5-tetramethyl-1,3,2-dioxaborolan-2-yl)-5,6-dihydropyridine-1(2H)-carboxylate (207 mg, 0.926 mmol), tetrakis(triphenylphosphine)palladium [Pd(PPh₃)₄, 35 mg, 0.03 mmol] and saturated sodium bicarbonate solution (1 mL) under nitrogen atmosphere. Stir the reaction mixture overnight at 120° C. TLC (PE:EtOAc=5:1) shows the reaction is complete. Partition the mixture between EtOAc and water, dry the organic layer over sodium sulfate, filter and concentrate the filtrate under reduced pressure. Purify the residue by flash chromatography (silica gel, PE:EtOAc=5:1) to afford the desired product (289 mg, 84%).

Step 2: Synthesis of tert-butyl 4-(4-amino-2-(trifluoromethyl)phenyl)piperidine-1-carboxylate

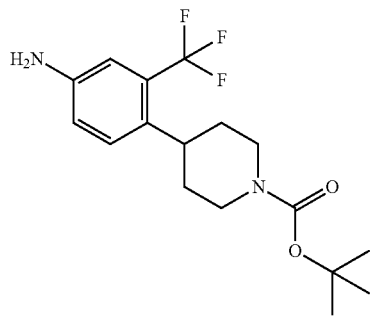

Stir the mixture of tert-butyl 4-(4-nitro-2-(trifluoromethyl)phenyl)-5,6-dihydropyridine-1(2H)-carboxylate (289 mg, 0.776 mmol), methanol (50 mL) and Pd/C (10%, 25 mg) under hydrogen atmosphere for 30 hrs. Remove H₂, filter the mixture and concentrate the filtrate under reduced pressure. Purify the residue with flash chromatography (silica gel, PE:EtOAc=5:1) to afford the desired product (151 mg, 84%).

Step 3: Synthesis of 4-(1-methylpiperidin-4-yl)-3-(trifluoromethyl)aniline

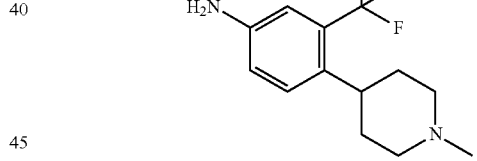

Add LiAlH₄ (66.5 mg, 1.75 mmol) at 0° C. to the mixture of tert-butyl 4-(4-amino-2-(trifluoromethyl)phenyl)piperidine-1-carboxylat (151 mg, 0.438 mmol) in THF (3 mL), stir the reaction mixture overnight at room temperature. Quench the reaction with 15% sodium hydroxide solution, filter and concentrate the filtrate under reduced pressure. Purify the residue by flash chromatography (silica gel, DCM:MeOH=15:1) to afford the desired product (70 mg, 56%). MS: (M+1): 259.1.

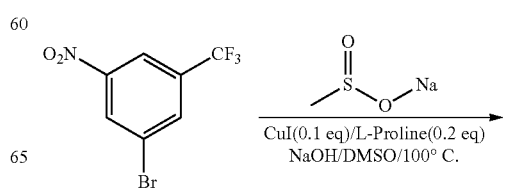

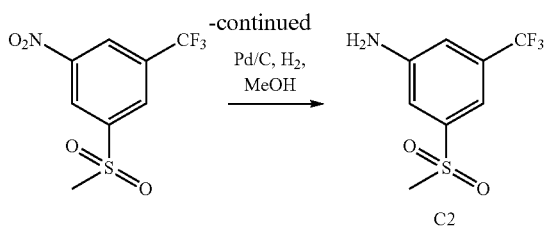

Step 1: Synthesis of 1-(methylsulfonyl)-3-nitro-5-(trifluoromethyl)benzene

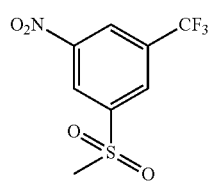 [SMILES: CS(=O)(=O)c1cc([N+](=O)[O-])cc(C(F)(F)F)c1]

Stir the mixture of 1-bromo-3-nitro-5-(trifluoromethyl)benzene (6 g, 22.2 mmol), sodium methanesulfinate (2.8 g, 26.7 mmol), cuprous iodide (0.5 g, 2.22 mmol), L(−)-proline (0.5 g, 4.44 mmol) and sodium hydroxide (0.088 g, 4.44 mmol) in DMSO (20 mL) at 100° C. for 15 hrs under nitrogen atmosphere. Add water, extract the mixture with ethyl acetate (200 mL×3), combine the organic layers, dry over anhydrous sodium sulfate, and concentrate the mixture under reduced pressure. Purify the residue by flash chromatography to afford the desired product (2 g, 33.3%).

Step 2: Synthesis of 3-(methylsulfonyl)-5-(trifluoromethyl)aniline

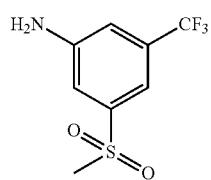

Stir the mixture of 1-(methylsulfonyl)-3-nitro-5-(trifluoromethyl)benzene (2 g, 7.43 mmol), Pd/C (10%, 500 mg) in methanol (100 mL) under hydrogen atmosphere at room temperature for 15 hrs. Filter off the solid and concentrate the filtrate under reduced pressure. Purify the residue with flash chromatography (silica gel, EtOAc:PE=1:5) to afford the desired product (1.3 g, 73%). MS: (M+23): 262.0.

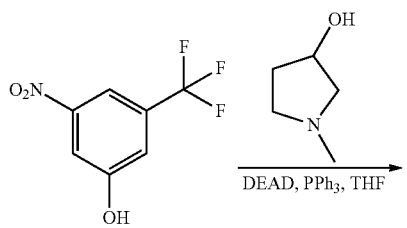

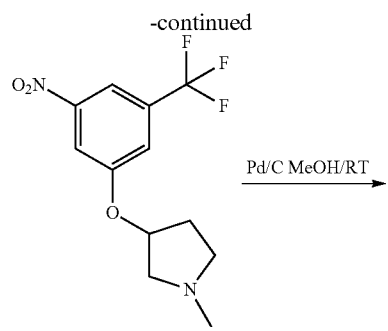

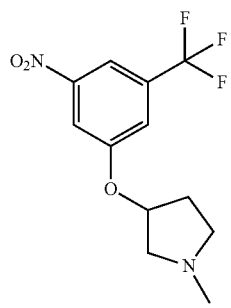 [SMILES: CN1CCC(Oc2cc([N+](=O)[O-])cc(C(F)(F)F)c2)C1]

Step 1: Synthesis of 1-methyl-3-(3-nitro-5-(trifluoromethyl)phenoxy)pyrrolidine

Add 3-nitro-5-(trifluoromethyl)phenol (1.6 g, 7.7 mmol), 1-methylpyrrolidin-3-ol (940 mg, 9.3 mmol), triphenylphosphine (3.4 g, 11.6 mmol) in THF (20 mL), stir on ice bath, then add diethyl azodicarboxylate (DEAD, 2.0 g, 11.6 mmol). Stir the mixture at ambient temperature for 15 hrs. Add water (100 mL), then extract the mixture with ethyl acetate (100 mL×3), combine the organic layers and dry over anhydrous sodium sulfate. Filter and concentrate the filtrate to get the crude product. Purify by flash chromatography (silica gel, DCM:MeOH=20:1) to afford the target product (1.5 g, 67%). MS: (M+1): 291.1.

Step 2: Synthesis of 3-(1-methylpyrrolidin-3-yloxy)-5-(trifluoromethyl)aniline

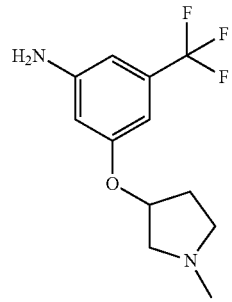 [SMILES: CN1CCC(Oc2cc(N)cc(C(F)(F)F)c2)C1]

Add Pd/C (10%, 400 mg) to the solution of 1-methyl-3-(3-nitro-5-(trifluoromethyl) phenoxy)pyrrolidine (1.54 g, 5.31 mmol) in methanol (10 mL). Stir the mixture under hydrogen atmosphere at room temperature for 15 hrs. Filter off the solid and concentrate the filtrate to give crude product. Purify by flash chromatography (silica gel, EtOAc:PE=1:1) to afford the target compound (900 mg, 65%). MS: (M+1): 261.1.

Intermediate C4 can be prepared with similar method (Table C1).

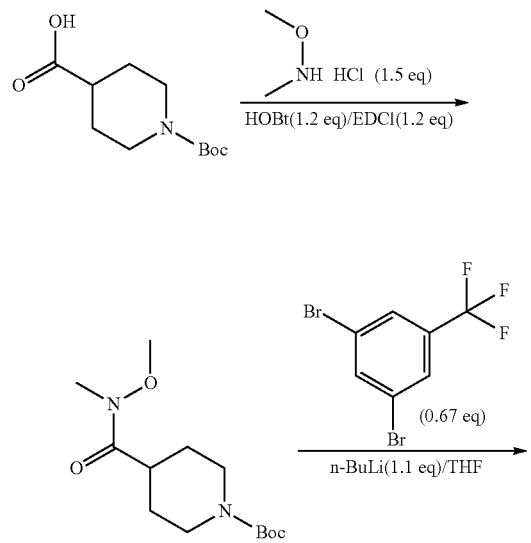

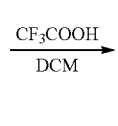

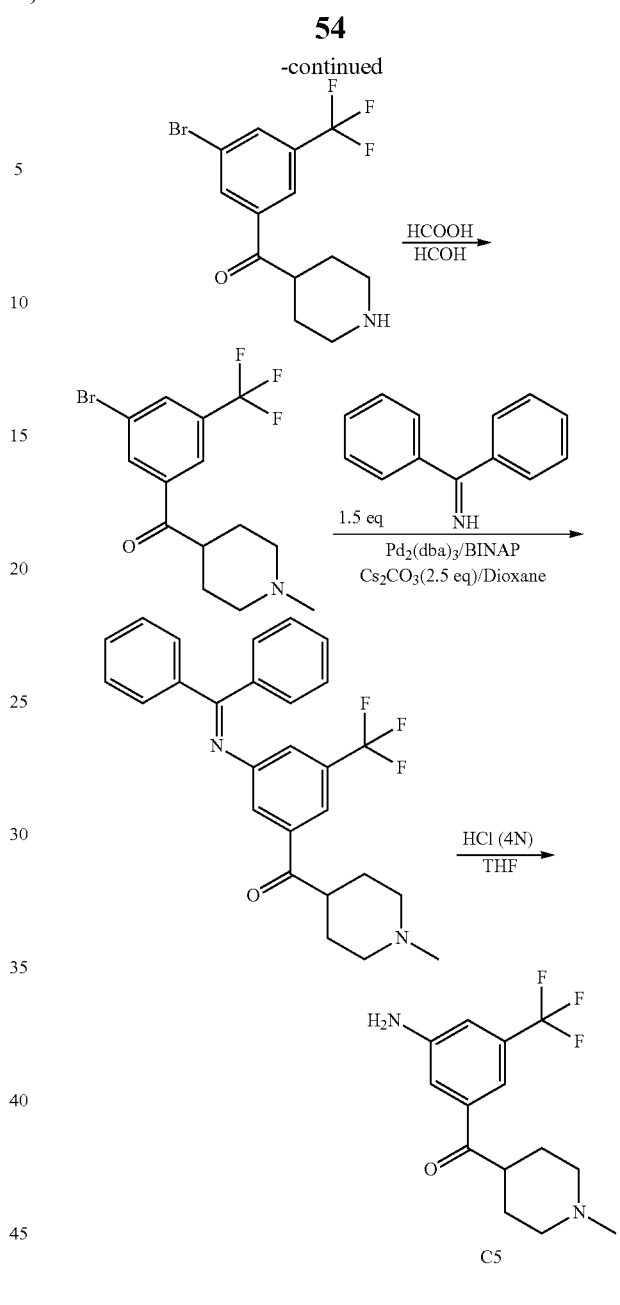

Step 1: Synthesis of tert-butyl 4-(methoxy(methyl)carbamoyl)piperidine-1-carboxylate

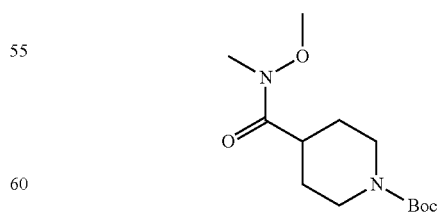

Add N,O-dimethylhydroxylamine hydrochloride (2.52 g, 26 mmol), 1-hydroxybenzotriazole (HOBt) (2.8 g, 20.8 mmol), 1-ethyl-3-(3-dimethylaminopropyl)carbodiimide hydrochloride (EDCI.HCl)(4 g, 20.8 mmol) and 4-methylmorpholine (5.28 g, 52 mmol) at 0° C. to the solution of N-Boc-piperidine-4-carboxylic acid (4 g, 17.4 mmol) in DMF (50 mL), stir the mixture overnight at room temperature. TLC (PE:EtOAc=1:1) shows the reaction is complete. Partition between ethyl acetate and water, collect the organic layer and wash with brine, dry over anhydrous sodium sulfate, filter and concentrate the filtrate under reduced pressure to give the crude product (4.5 g, 95%) which is used in next step without further purification.

Step 2: Synthesis of tert-butyl-4-(3-bromo-5-(trifluoromethyl)benzoyl)piperidine-1-carboxylate

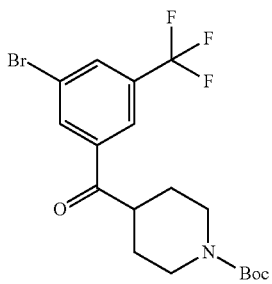 [SMILES: CC(C)(C)OC(=O)N1CCC(C(=O)c2cc(Br)cc(C(F)(F)F)c2)CC1]

Add n-butyllithium (2.5 N, 1.44 mL) to the solution of 1,3-dibromo-5-(trifluoromethyl)benzene (1 g, 3.28 mmol) in THF (15 mL) at −78° C. and stir the mixture at −78° C. for 1 hr. Then add tert-butyl 4-(methoxy(methyl)carbamoyl) piperidine-1-carboxylate (1.4 g, 4.92 mmol) obtained in Step 1 to the mixture and continue stirring. TLC (PE:EtOAc=5:1) shows the reaction is complete. Quench the reaction mixture with saturated ammonium chloride solution. Partition between EtOAc and water, separate the organic layer, and wash with brine, dry over anhydrous sodium sulfate, concentrate to give the crude product. Purify by flash chromatography (silica gel, DCM:MeOH=20:1) to afford the product (387 mg, 27%). MS: (M+1): 436.

Step 3: Synthesis of (3-bromo-5-(trifluoromethyl) phenyl)(piperidin-4-yl)methanone

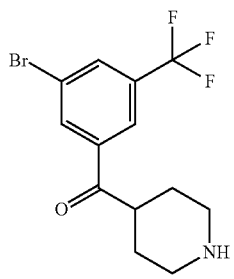 [SMILES: O=C(c1cc(Br)cc(C(F)(F)F)c1)C1CCNCC1]

Add trifluoroacetic acid in dichloromethane (20%, 5 mL) to the solution of tert-butyl-4-(3-bromo-5-(trifluoromethyl) benzoyl)piperidine-1-carboxylate (387 mg, 0.88 mmol) in dichloromethane (5 mL) at 0° C., stir the mixture. TLC (PE: EtOAc=5:1) shows the reaction is complete. Concentrate under reduced pressure to dryness to afford the crude product (400 mg, 100%) which is used directly in next step. MS: (M+1): 336.0.

Step 4: Synthesis of (3-bromo-5-(trifluoromethyl) phenyl)(1-methylpiperidin-4-yl)methanone

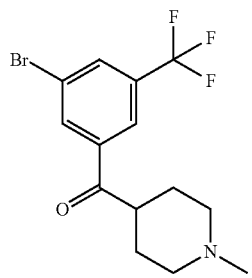 [SMILES: CN1CCC(C(=O)c2cc(Br)cc(C(F)(F)F)c2)CC1]

Stir the mixture of (3-bromo-5-(trifluoromethyl)phenyl) (piperidin-4-yl)methanone (400 mg, 0.96 mmol), formic acid (1 mL) and formaldehyde (1 mL) at 100° C. overnight. Upon the reaction completion, concentrate under reduced pressure to provide the crude product (250 mg, 77%) which is used in next step without further purification.

Step 5: Synthesis of (3-(diphenylmethyleneamino)-5-(trifluoromethyl)phenyl)(1-methylpiperidin-4-yl) methanone

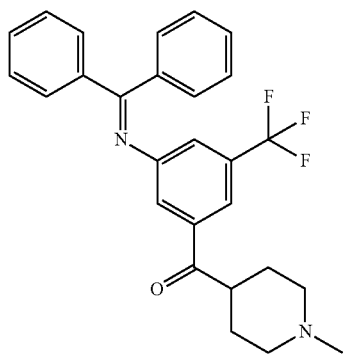 [SMILES: CN1CCC(C(=O)c2cc(N=C(c3ccccc3)c3ccccc3)cc(C(F)(F)F)c2)CC1]

Add benzophenone imine (195 mg, 1.07 mmol), (±)-2,2'-bis(diphenylphosphino)-1,1'-binaphthalene (BINAP, 37 mg, 0.059 mmol), tris(dibenzylideneacetone)dipalladium [$Pd_2$(dba)$_3$, 25 mg, 0.027 mmol] and cesium carbonate (585 mg, 1.79 mmol) to the solution of (3-bromo-5-(trifluoromethyl) phenyl)(1-methylpiperidin-4-yl)methanone (251 mg, 0.717 mmol) in dioxane (5 mL), then stir the reaction mixture overnight at 100° C. Upon reaction completion, filter the mixture and concentrate the filtrate under reduced pressure. Purify the residue with flash chromatography (silica gel, PE:EtOAc=1:1) to afford the product (210 mg, 65%). MS: (M+1): 451.2.

Step 6: Synthesis of (3-amino-5-(trifluoromethyl)phenyl)(1-methylpiperidin-4-yl)methanone

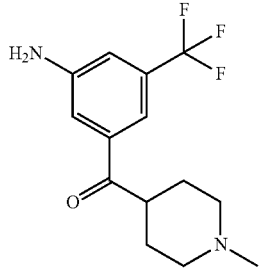 [SMILES: CN1CCC(C(=O)c2cc(N)cc(C(F)(F)F)c2)CC1]

Dissolve (3-(diphenylmethyleneamino)-5-(trifluoromethyl)phenyl)(1-methylpiperidin-4-yl)methanone (210 mg, 0.47 mmol) in THF (2 mL) in an ice-bath, add hydrochloric acid (4N, 0.5 mL), then stir it at room temperature for one hour. TLC (PE:EtOAc=1:1) shows the reaction is complete. Partition the mixture between EtOAc and water. Collect the aqueous layer, adjust pH=9 with sodium hydroxide solution, extract with ethyl acetate three times, combine the organic layers, dry over anhydrous sodium sulfate, concentrate to yield the crude product (78 mg, 59%). MS: (M+1): 287.1.

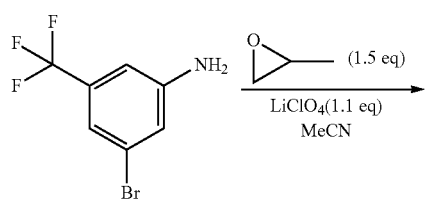

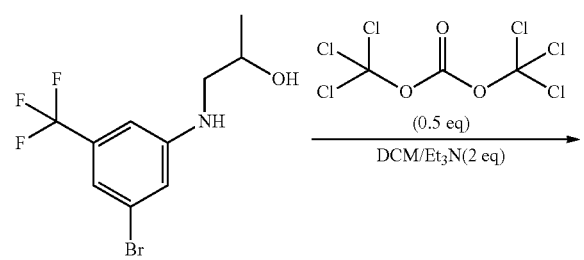

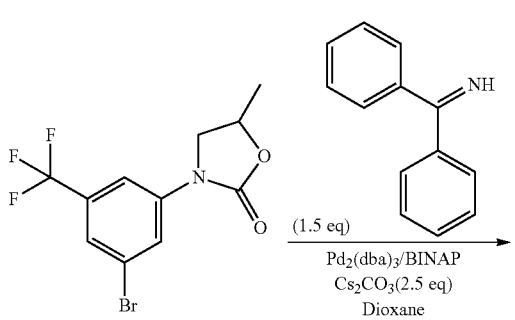

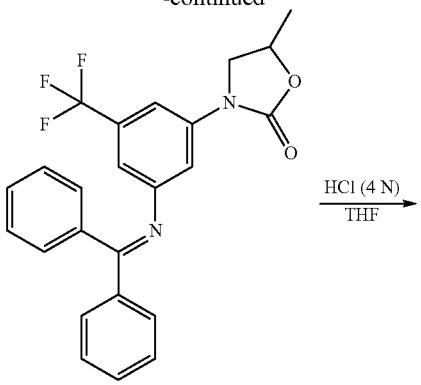

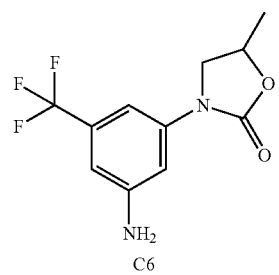

Step 1: Synthesis of 1-(3-bromo-5-(trifluoromethyl)phenylamino)propan-2-ol

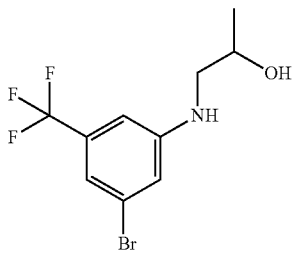 [SMILES: CC(O)CNc1cc(Br)cc(C(F)(F)F)c1]

Add propylene oxide (36 mg, 0.624 mmol) and lithium perchlorate (56 mg, 0.458 mmol) to the solution of 3-bromo-5-(trifluoromethyl)aniline (100 mg, 0.416 mmol) in acetonitrile (5 mL), stir the resulting mixture overnight at ambient temperature. Upon completion of the reaction, concentrate the mixture under reduced pressure. Purify the residue by flash chromatography (silica gel, PE:EtOAc=5:1) to afford the product (136 mg, 100%).

Step 2: Synthesis of 3-(3-bromo-5-(trifluoromethyl)phenyl)-5-methyloxazolidin-2-one

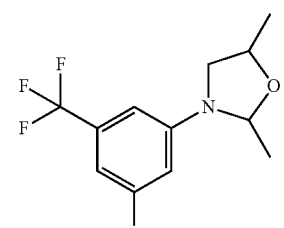

Add triethylamine (339 mg, 3.35 mmol) and triphosgene (250 mg, 0.838 mmol) to the solution of 1-(3-bromo-5-(trifluoromethyl)phenylamino)propan-2-ol (500 mg, 1.68 mmol) in dichloromethane (8 mL), stir the resulting mixture overnight at ambient temperature. Partition the reaction mixture between dichloromethane and water, separate the organic layer, dry over anhydrous sodium sulfate, and concentrate under reduced pressure to give the crude product. Purify with flash chromatography (silica gel, PE:EtOAc=1:1) to afford the product (530 mg, 97%). MS: (M+1): 324.0.

Step 3: Synthesis of 3-(3-(diphenylmethylene-amino)-5-(trifluoromethyl)phenyl)-5-methyloxazolidin-2-one

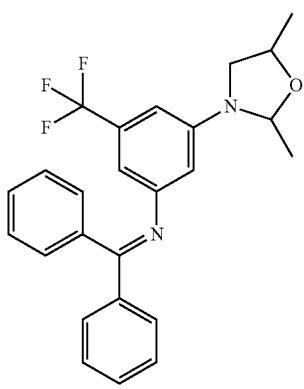 [SMILES: CC1CN(c2cc(N=C(c3ccccc3)c3ccccc3)cc(C(F)(F)F)c2)C(C)O1]

Add benzophenone imine (3.56 g, 2 mmol), (±)-2,2'-bis (diphenylphosphino)-1,1'-binaphthalene (BINAP, 43 mg, 0.069 mmol), tris(dibenzylideneacetone)dipalladium [Pd$_2$(dba)$_3$, 90 mg, 0.098 mmol] and cesium carbonate (858 mg, 2.63 mmol) to the solution of 3-(3-bromo-5-(trifluoromethyl) phenyl)-5-methyloxazolidin-2-one (430 mg, 1.32 mmol) in dioxane (5 mL). Stir the mixture under nitrogen atmosphere at 100° C. overnight. TLC (PE:EtOAc=1:1) shows the reaction is complete. Filter the mixture and concentrate the filtrate to yield the crude product. Purify by flash chromatography (silica gel, PE:EtOAc=1:1) to afford the product (500 mg, 89%).

Step 4: Synthesis of 3-(3-amino-5-(trifluoromethyl) phenyl)-5-methyloxazolidin-2-one

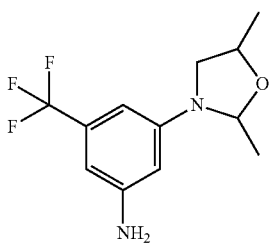 [SMILES: CC1CN(c2cc(N)cc(C(F)(F)F)c2)C(C)O1]

Add hydrochloric acid (4 N, 1 mL) to the solution of the above imine (310 mg, 0.731 mmol) in THF (5 mL) in an ice-bath. Then stir the reaction for half hour at ambient temperature. TLC (PE:EtOAc=1:1) shows the reaction is complete. Partition the mixture between water and ethyl acetate, collect the aqueous layer, adjust pH=9 with sodium hydroxide solution, extract the aqueous layer with ethyl acetate three times, combine the organic layers, dry over anhydrous sodium sulfate, concentrate under reduced pressure to get the crude product (170 mg, 89%). MS: (M+1): 261.0.

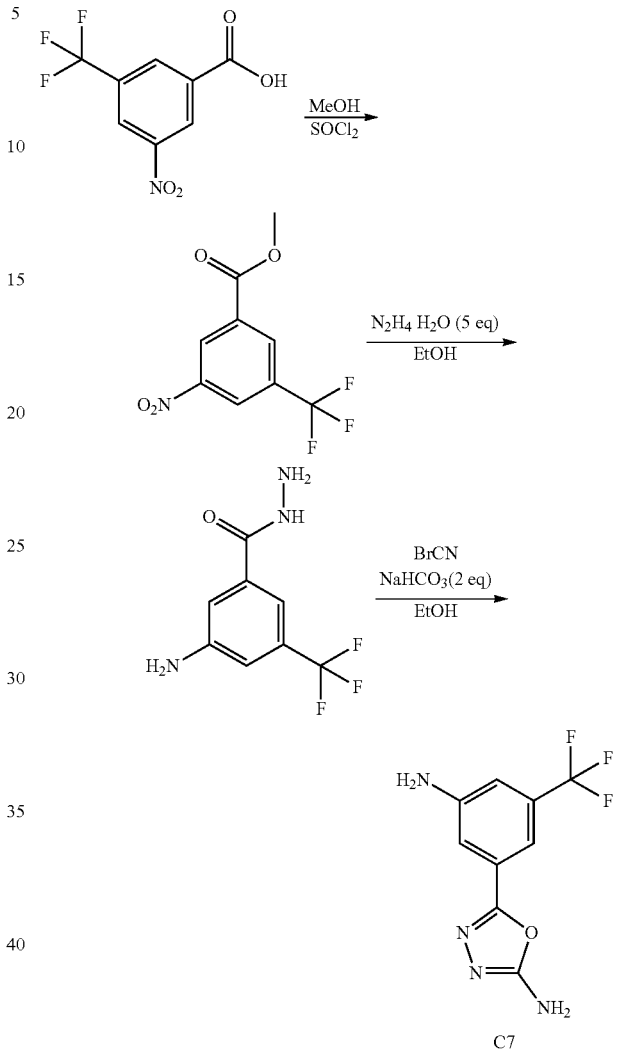

Step 1: Synthesis of methyl 3-nitro-5-(trifluoromethyl)benzoate

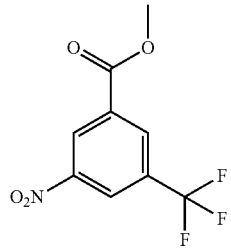 [SMILES: COC(=O)c1cc([N+](=O)[O-])cc(C(F)(F)F)c1]

Add thionyl chloride (2 mL) dropwise to the solution of 3-nitro-5-(trifluoromethyl)benzoic acid (1.5 g, 6.4 mmol) in methanol (20 mL), reflux for 5 hrs. TLC (PE:EtOAc=1:1) shows the reaction is complete. Concentrate under reduced Step 2: Synthesis of
3-amino-5-(trifluoromethyl)benzohydrazide

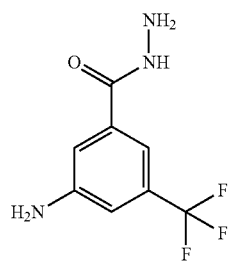 [SMILES: NNC(=O)c1cc(N)cc(C(F)(F)F)c1]

Mix methyl 3-nitro-5-(trifluoromethyl)benzoate (1.8 g, 12 mmol), ethanol (6 mL) and 80% (w/w) hydrazine (10 mL), reflux overnight. Concentrate the mixture, partition the resulting residue between ethyl acetate and water, collect the organic layer, wash with sodium bicarbonate, dry over anhydrous sodium sulfate, and concentrate under reduced pressure to give the crude product (1.23 g, 77%) which is used in next step without further purification.

Step 3: Synthesis of 5-(3-amino-5-(trifluoromethyl)phenyl)-1,3,4-oxadiazol-2-amine

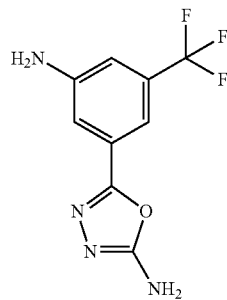 [SMILES: Nc1cc(-c2nnc(N)o2)cc(C(F)(F)F)c1]

Add sodium bicarbonate (270 mg, 3.21 mmol) and cyanogen bromide (187 mg, 1.76 mmol) to the solution of 3-amino-5-(trifluoromethyl)benzohydrazide (400 mg, 1.6 mmol) in ethanol (5 mL), reflux for 5 hrs. TLC (PE:EtOAc=1:1) shows the reaction is complete. Concentrate the mixture, partition the residue between EtOAc and water, collect the organic layer, wash with saturated sodium bicarbonate solution, dry over anhydrous sodium sulfate, and concentrate under reduced pressure to afford the crude product. Recrystallization in ethyl acetate yields the pure product (280 mg, 63%).

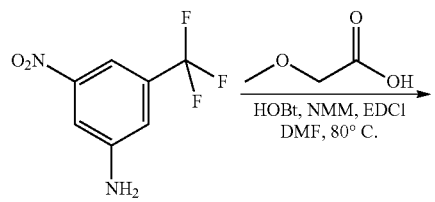

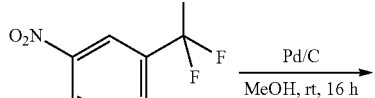

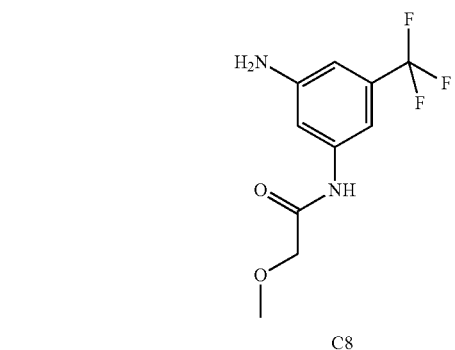

C8

Step 1: Synthesis of 2-methoxy-N-(3-nitro-5-(trifluoromethyl)phenyl)acetamide

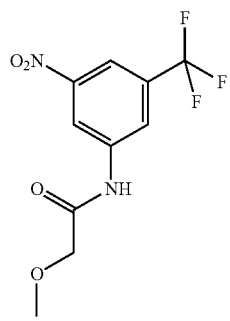

Stir the mixture of 3-nitro-5-(trifluoromethyl)aniline (500 mg, 2.4 mmol), 2-methoxyacetic acid (220 mg, 2.4 mmol), 1-hydroxybenzotriazole (HOBt, 324 mg, 2.4 mmol), N-methyl morpholine (NMM, 480 mg, 4.8 mmol), 1-ethyl-3-(3-dimethyllaminopropyl)carbodiimide hydrochloride (EDCI·HCl, 920 mg, 4.8 mmol) in DMF (8 mL) at 80° C. for 16 hrs. Cool the reaction mixture to room temperature, add water (100 mL), extract with ethyl acetate (30 mL×2), combine the organic layers, wash with brine, dry over anhydrous sodium sulfate, and concentrate under reduced pressure to give the crude product. Purify by flash chromatography (silica gel, EtOAc:PE=15:85) to yield the target compound (260 mg, 39%).

Step 2: Synthesis of N-(3-amino-5-(trifluoromethyl)phenyl)-2-methoxyacetamide

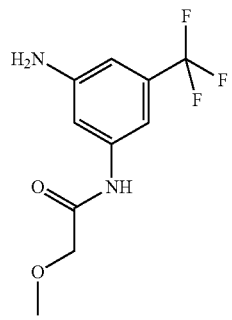 [SMILES: COCC(=O)Nc1cc([N+](=O)[O-])cc(C(F)(F)F)c1]

Add Pd/C (10%, 30 mg) to the solution of 2-methoxy-N-(3-nitro-5-(trifluoromethyl)phenyl)acetamide (100 mg, 0.36 mmol) in methanol (6 mL), stir the mixture under hydrogen atmosphere at room temperature for 16 hrs. Filter off the solid, concentrate the filtrate under reduced pressure to yield the crude product (89 mg, 100%) which is used without further purification.

Intermediate C9 can be synthesized with similar method (Table C1)

TABLE C1

Intermediates C1-C9

| Number | Starting material | Intermediate | MS [M + 1]+ |
|---|---|---|---|
| C1 | $O_2N$–(aryl with $CF_3$, Br) | $H_2N$–(aryl with $CF_3$, N-methylpiperidin-4-yl) | 259.2 |
| C2 | $O_2N$–(aryl with $CF_3$, Br) | $H_2N$–(aryl with $CF_3$, $SO_2Me$) | [M + 23] 262.0 |
| C3 | $O_2N$–(aryl with $CF_3$, OH) | $H_2N$–(aryl with $CF_3$, O-(N-methylpyrrolidin-3-yl)) | 261.1 |
| C4 | $O_2N$–(aryl with $CF_3$, OH) | $H_2N$–(aryl with $CF_3$, O-(tetrahydrofuran-3-yl)) | 248.1 |
| C5 | Br–(aryl with $CF_3$, Br) | $H_2N$–(aryl with $CF_3$, C(O)-(N-methylpiperidin-4-yl)) | 287.1 |

TABLE C1-continued
Intermediates C1-C9
| Number | Starting material | Intermediate | MS [M + 1]+ |
|---|---|---|---|
| C6 | 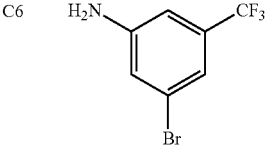 | 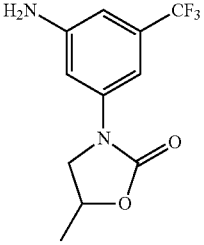 | NA |
| C7 | 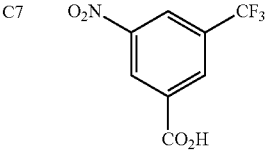 | 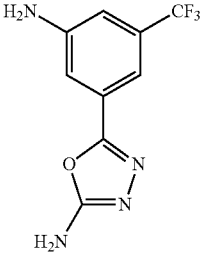 | NA |
| C8 | 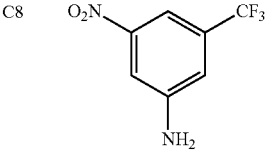 | 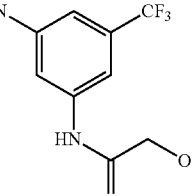 | 249.1 |
| C9 | 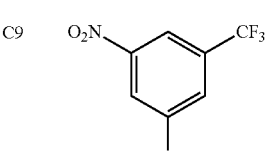 | 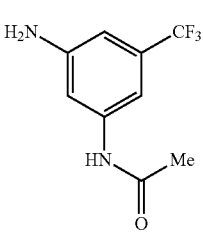 | 219.1 |
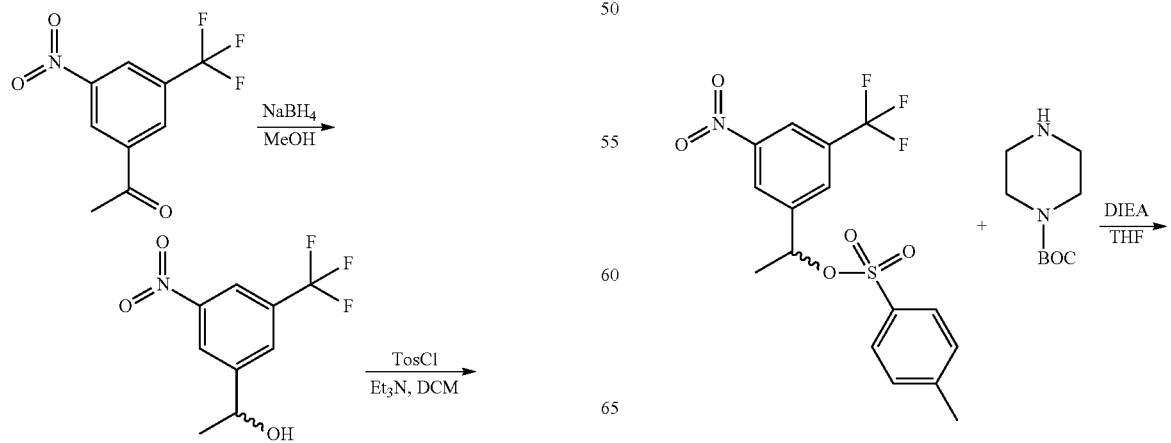

-continued

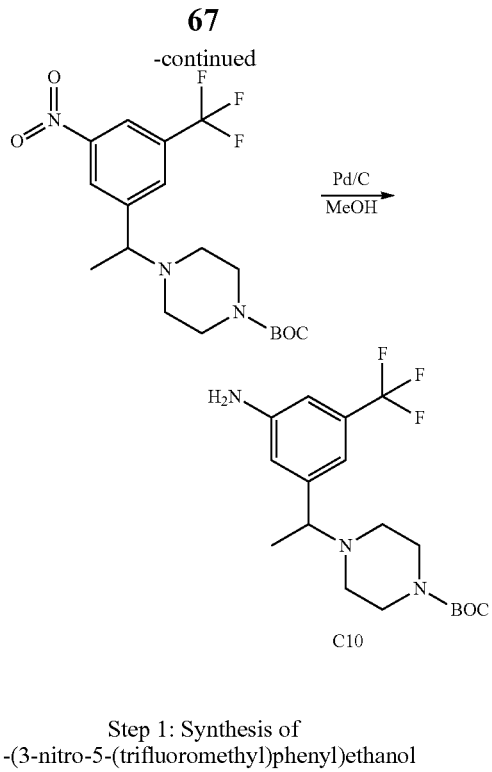

C10

Step 1: Synthesis of
1-(3-nitro-5-(trifluoromethyl)phenyl)ethanol

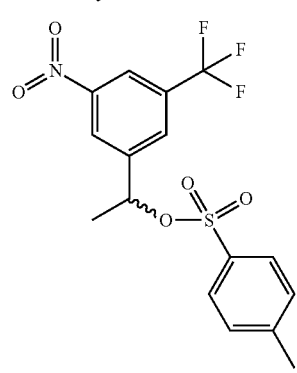

Add sodium borohydride (95 mg, 2.44 mmol) to a solution of 1-(3-nitro-5-(trifluoromethyl)phenyl)ethanone (570 mg, 2.44 mmol) in methanol (5 mL), stir the mixture for 15 min at ambient temperature. Quench the reaction with water, adjust pH=7 with 1N hydrochloric acid, extract with ethyl acetate (50 mL×3), combine the organic layers, wash with brine, dry over sodium sulfate. Concentrate under reduced pressure to provide the crude product. Purify by flash chromatography (silica gel, EtOAc:PE=1:10) to afford the title compound (520 mg, 91.2%).

Step 2: Synthesis of
1-(3-nitro-5-(trifluoromethyl)phenyl)ethyl
4-methylbenzenesulfonate Add p-toluenesulfonyl chloride (1.7 g, 8.9 mmol) dropwise at 0° C. to the mixture of 1-(3-nitro-5-(trifluoromethyl)phenyl)ethanol (520 mg, 2.23 mmol) and triethylamine (1.4 g, 13.4 mmol) in dichloromethane (20 mL), stir the resulting mixture for 12 hrs at ambient temperature. Concentrate the mixture under reduced pressure to get a residue, purify the residue by chromatography (silica gel, EtOAc:PE=1:10) to afford the title compound (700 mg, 80.6%).

Step 3: Synthesis of tert-butyl 4-(1-(3-nitro-5-(trifluoromethyl)phenyl)ethyl)piperazine-1-carboxylate

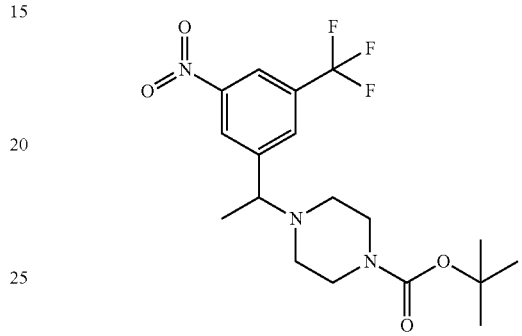

Stir the mixture of 1-(3-nitro-5-(trifluoromethyl)phenyl)ethyl 4-methylbenzenesulfonate (350 mg, 0.90 mmol), 1-piperazinecarboxylic acid tert-butyl ester (335 mg, 1.8 mmol) and diisopropylethylamine (232 mg, 1.8 mmol) in THF (10 mL) for 12 hrs at 80° C. Concentrate the reaction mixture to obtain the crude product, purify by flash chromatography (silica gel, EtOAc:PE=1:10) to afford the title compound (280 mg, 77.1%). MS: (M+1): 404.2.

Step 4: Synthesis of tert-butyl 4-(1-(3-amino-5-(trifluoromethyl)phenyl)ethyl) piperazine-1-carboxylate

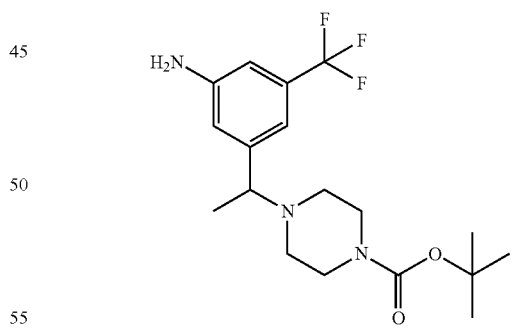

Add Pd/C (10%, 75 mg) to the solution of tert-butyl 4-(1-(3-nitro-5-(trifluoromethyl)-phenyl)ethyl)piperazine-1-carboxylate (280 mg, 0.69 mmol) in methanol (20 mL), stir the resulting mixture under hydrogen atmosphere for 2 hrs at room temperature. Filter and concentrate the filtrate to afford the crude product. Purify by flash chromatography (silica gel, EtOAc:PE=1:1) to afford the title compound (165 mg, 63.7%). MS: (M+1): 374.1.

Intermediates C11-C12 can be synthesized with similar method (Table C2).

TABLE C2

Intermediates C10-C12

| Number | Starting material | Intermediate | MS [M + 1]+ |
|---|---|---|---|
| C10 | O2N-C6H3(CF3)-C(O)CH3 | H2N-C6H3(CF3)-CH(CH3)-N(piperazine)-Boc | 374.2 |
| C11 | O2N-C6H3(CF3)-C(O)CH3 | H2N-C6H3(CF3)-CH(CH3)-N(piperazine)-Me | 288.2 |
| C12 | O2N-C6H3(CF3)-C(O)CH3 | H2N-C6H3(CF3)-CH(CH3)-NH-Boc | NA |

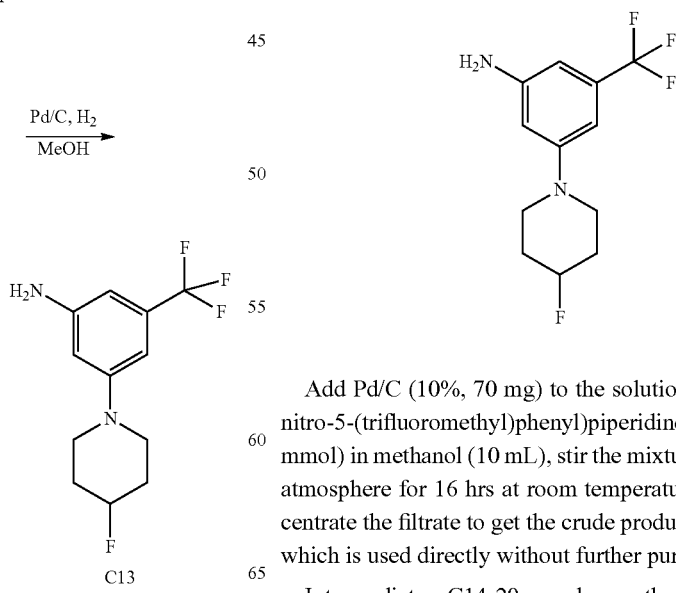

C13

Step 1: Synthesis of 4-fluoro-1-(3-nitro-5-(trifluoromethyl)phenyl)piperidine

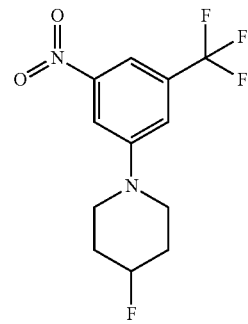 [SMILES: O=[N+]([O-])c1cc(N2CCC(F)CC2)cc(C(F)(F)F)c1]

Mix 1-bromo-3-nitro-5-(trifluoromethyl)benzene (700 mg, 2.59 mmol), 4-fluoropiperidine hydrochloride (544 mg, 3.89 mmol), cesium carbonate (2.5 g, 7.77 mmol), (±)-2,2'-bis(diphenylphosphino)-1,1'-binaphthalene (BINAP, 48 mg, 0.077 mmol), tris(dibenzylideneacetone)dipalladium [Pd$_2$(dba)$_3$, 47 mg, 0.052 mmol] in dioxane (10 mL), Stir the mixture under nitrogen atmosphere at 100° C. for 16 hrs. Cool the reaction mixture to room temperature, dilute it with water (10 mL), extract with ethyl acetate (10 mL×2), combine the organic layers, wash with brine (15 mL) and dry over anhydrous sodium sulfate. Concentrate the filtrate to get the crude product. Purify by flash chromatography (silica gel, 100% PE) to yield the target compound (480 mg, 63%).

Step 2: Synthesis of 3-(4-fluoropiperidin-1-yl)-5-(trifluoromethyl)aniline

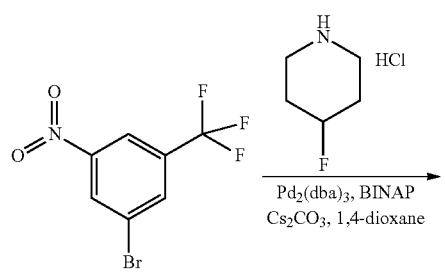

Add Pd/C (10%, 70 mg) to the solution of 4-fluoro-1-(3-nitro-5-(trifluoromethyl)phenyl)piperidine (300 mg, 1.0 mmol) in methanol (10 mL), stir the mixture under hydrogen atmosphere for 16 hrs at room temperature. Filter and concentrate the filtrate to get the crude product (270 mg, 100%) which is used directly without further purification.

Intermediates C14-20 can be synthesized with similar method (Table C3).

TABLE C3

Intermediates C13-C20

| Number | Starting material | Intermediate | MS [M + 1]+ |
|---|---|---|---|
| C13 | 1-bromo-3-nitro-5-(trifluoromethyl)benzene | 3-(4-fluoropiperidin-1-yl)-5-(trifluoromethyl)aniline | 263.1 |
| C14 | 1-bromo-3-nitro-5-(trifluoromethyl)benzene | tert-butyl 4-((3-amino-5-(trifluoromethyl)phenyl)amino)piperidine-1-carboxylate | [M + 23] 382.2 |
| C15 | 1-bromo-3-nitro-5-(trifluoromethyl)benzene | 3-(2,6-dimethylmorpholino)-5-(trifluoromethyl)aniline | 275.2 |
| C16 | 1-bromo-3-nitro-5-(trifluoromethyl)benzene | 3-(3-(dimethylamino)pyrrolidin-1-yl)-5-(trifluoromethyl)aniline | 274.2 |
| C17 | 1-bromo-3-nitro-5-(trifluoromethyl)benzene | N1-isopropyl-5-(trifluoromethyl)benzene-1,3-diamine | 219.2 |
| C18 | 1-bromo-3-nitro-5-(trifluoromethyl)benzene | N1-cyclopropyl-5-(trifluoromethyl)benzene-1,3-diamine | NA |

TABLE C3-continued

Intermediates C13-C20

| Number | Starting material | Intermediate | MS [M + 1]+ |
|---|---|---|---|
| C19 | 1-bromo-3-nitro-5-(trifluoromethyl)benzene | 3-amino-5-(trifluoromethyl)phenyl piperidin-4-ol | NA |
| C20 | 1-bromo-3-nitro-5-(trifluoromethyl)benzene | ethyl 3-((3-amino-5-(trifluoromethyl)phenyl)amino)-2,2-dimethylpropanoate | NA |

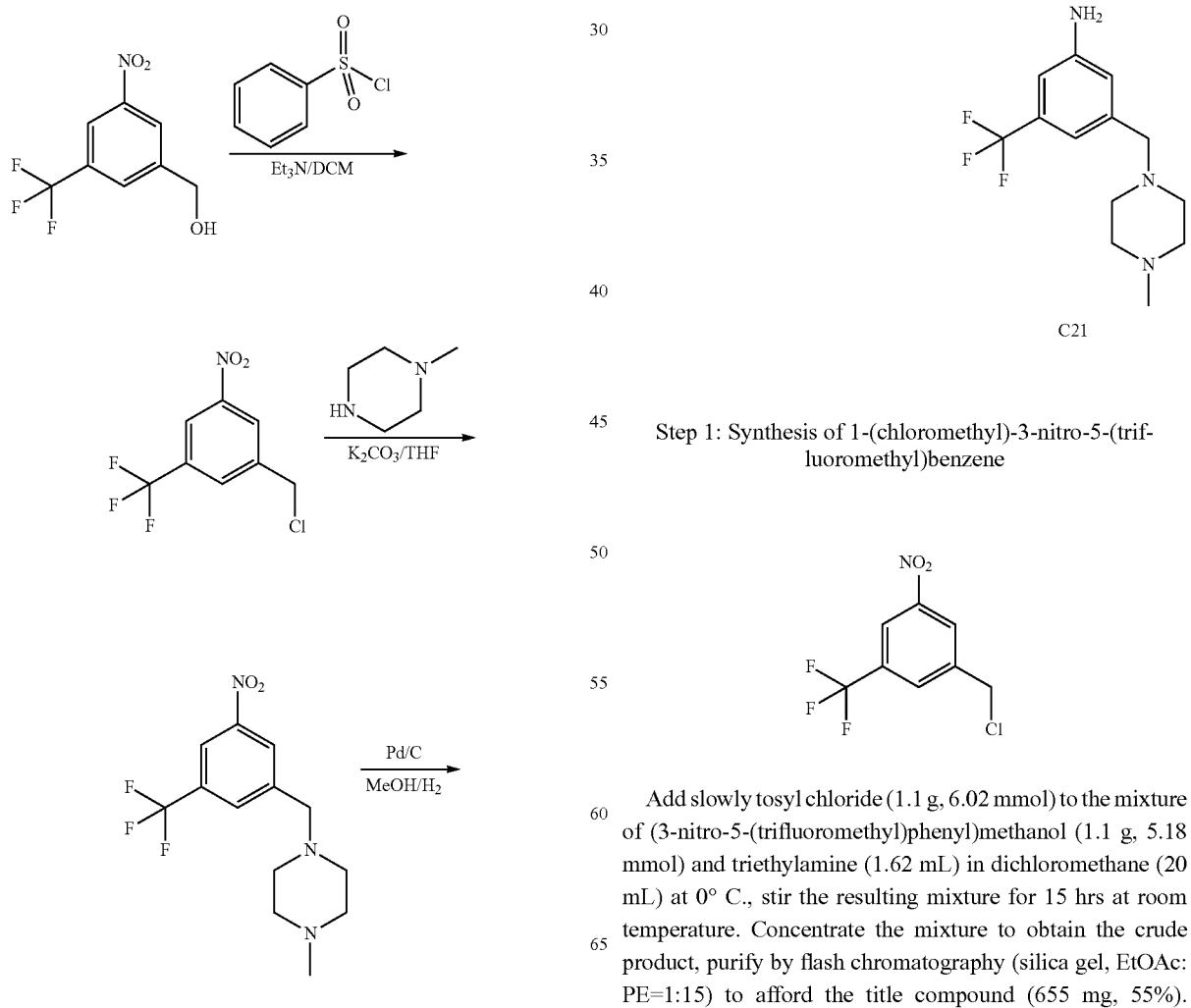

Step 1: Synthesis of 1-(chloromethyl)-3-nitro-5-(trifluoromethyl)benzene

Add slowly tosyl chloride (1.1 g, 6.02 mmol) to the mixture of (3-nitro-5-(trifluoromethyl)phenyl)methanol (1.1 g, 5.18 mmol) and triethylamine (1.62 mL) in dichloromethane (20 mL) at 0° C., stir the resulting mixture for 15 hrs at room temperature. Concentrate the mixture to obtain the crude product, purify by flash chromatography (silica gel, EtOAc:PE=1:15) to afford the title compound (655 mg, 55%).

Step 2: Synthesis of 1-methyl-4-(3-nitro-5-(trifluoromethyl)benzyl)piperazine

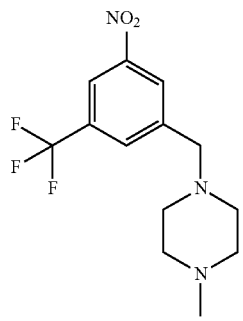 [SMILES: CN1CCN(Cc2cc([N+](=O)[O-])cc(C(F)(F)F)c2)CC1]

Stir the mixture of 1-(chloromethyl)-3-nitro-5-(trifluoromethyl)benzene (640 mg, 2.68 mmol) and N-methylpiperazine (536 mg, 5.36 mmol) in THF (8 mL) for 2 hrs at 60° C. TLC (EtOAc:PE=1:1) shows the reaction is complete. Concentrate the reaction mixture under reduced pressure to obtain the crude product (812 mg, 100%). MS: (M+1): 303.1.

Step 3: Synthesis of 3-((4-methylpiperazin-1-yl)methyl)-5-(trifluoromethyl)aniline

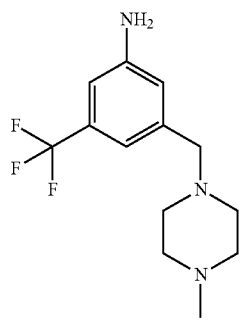 [SMILES: CN1CCN(Cc2cc(N)cc(C(F)(F)F)c2)CC1]

Add Pd/C (10%, 200 mg) to the solution of 1-methyl-4-(3-nitro-5-(trifluoromethyl)benzyl)piperazine (812 mg, 2.68 mmol) in methanol (15 mL), flush with $H_2$, stir under hydrogen atmosphere for 16 hrs at room temperature. Filter and concentrate the filtrate to give the crude product (732 mg, 100%). MS: (M+1): 273.0.

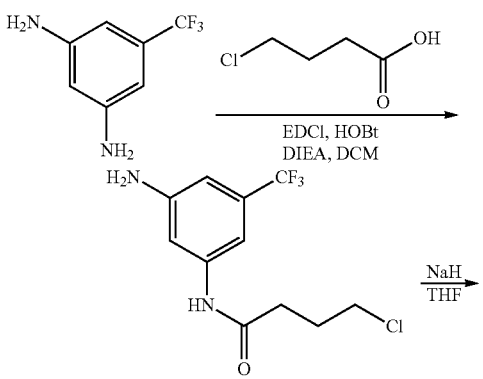

-continued

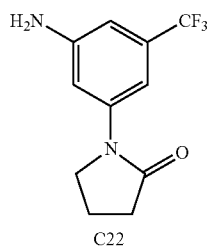

C22

Step 1: Synthesis of N-(3-amino-5-(trifluoromethyl)phenyl)-4-chlorobutanamide

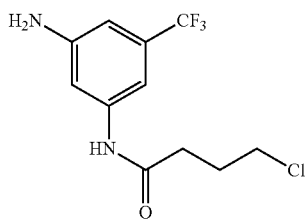 [SMILES: Nc1cc(NC(=O)CCCCl)cc(C(F)(F)F)c1]

Mix 5-(trifluoromethyl)benzene-1,3-diamine (300 mg, 1.70 mmol), 4-chlorobutanoic acid (230 mg, 1.87 mmol), 1-ethyl-3-(3-dimethyllaminopropyl)carbodiimide hydrochloride (EDCI.HCl, 650 mg, 3.40 mmol), 1-hydroxybenzotriazole (HOBt, 230 mg, 1.70 mmol) and diisopropylethylamine (450 mg, 3.40 mmol) in dichloromethane (10 mL), stir overnight at room temperature. Concentrate the reaction mixture under reduced pressure to obtain the crude product. Purify by flash chromatography (silica gel, PE:EtOAc=1:10) to yield the product (250 mg, 52%). MS: (M+1): 281.2.

Step 2: Synthesis of 1-(3-amino-5-(trifluoromethyl)phenyl)pyrrolidin-2-one

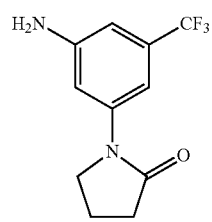

Add sodium hydride (60%, 65 mg, 1.64 mmol) portionwise to the solution of N-(3-amino-5-(trifluoromethyl)phenyl)-4-chlorobutanamide (230 mg, 0.82 mmol) in THF (5 mL), stir the resulting mixture for 2 hrs at ambient temperature. Quench the reaction with water, extract the mixture with ethyl acetate, wash the organic layer with water and brine sequentially, and dry over anhydrous sodium sulfate, concentrate to give brownish oil. Purify by flash chromatography (silica gel, PE:EtOAc=1:1) to yield white solid as the title compound (180 mg, 90%). MS: (M+1): 245.1.

77

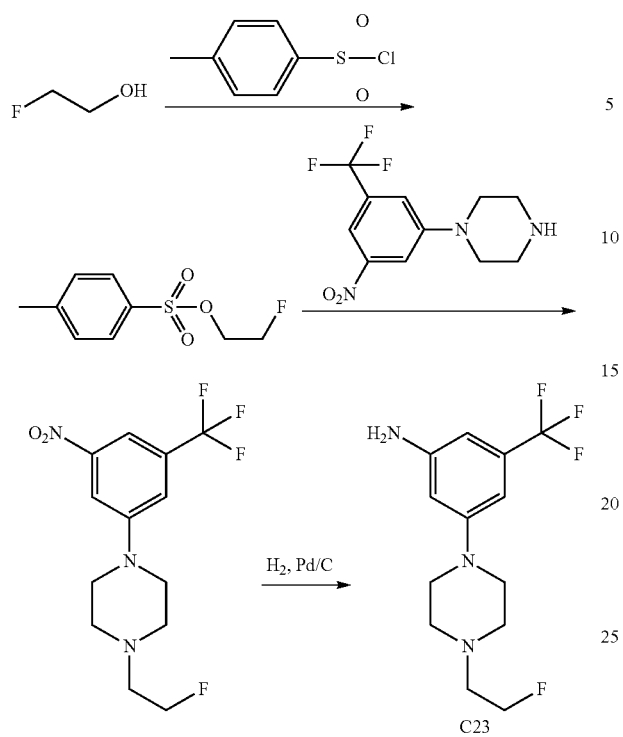

Step 1: Synthesis of 2-fluoroethyl 4-methylbenzenesulfonate

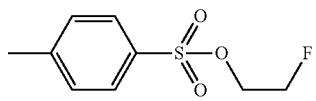

Add toluenesulfonyl chloride (1.8 g, 9.4 mmol) to the mixture of 2-fluoroethanol (500 mg, 7.8 mmol) and triethylamine (1.6 g, 15.6 mmol) in dichloromethane (30 mL) at 0-5° C. Stir the reaction at ambient temperature for 5 hrs. Remove the volatiles under reduced pressure to yield the crude product. Purify by flash chromatography (silica gel, PE:EtOAc=2:1) to afford a white solid as the title compound (1.3 g, 77%).

78

Step 2: Synthesis of 1-(2-fluoroethyl)-4-(3-nitro-5-(trifluoromethyl)phenyl)piperazine

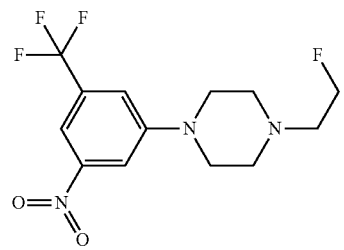 [SMILES: O=[N+]([O-])c1cc(N2CCN(CCF)CC2)cc(C(F)(F)F)c1]

Mix (3-nitro-5-(trifluoromethyl)phenyl)piperazine (200 mg, 0.73 mmol), 2-fluoroethyl 4-methylbenzenesulfonate (320 mg, 1.46 mmol) and 4-dimethylaminopyridine (50 mg, 0.37 mmol) in THF (15 mL), stir at 90° C. overnight. TLC (EtOAc:PE=1:1) shows the reaction is complete. Concentrate under reduced pressure to give a residue, purify the residue by flash chromatography (silica gel, PE:EtOAc=1:1) to yield a white solid as the target compound (120 mg, 51%).

Step 3: Synthesis of 3-(4-(2-fluoroethyl)piperazin-1-yl)-5-(trifluoromethyl)aniline

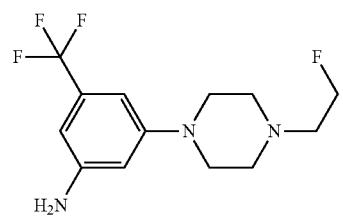 [SMILES: Nc1cc(N2CCN(CCF)CC2)cc(C(F)(F)F)c1]

Stir the mixture of 1-(2-fluoroethyl)-4-(3-nitro-5-(trifluoromethyl)phenyl)piperazine (120 mg, 0.50 mol) and Pd/C (10%, 30 mg) in methanol (5 mL) under hydrogen atmosphere for 2 hrs at room temperature. Filter and concentrate the filtrate under reduced pressure to afford the white solid as the target compound (90 mg, 84%).

Intermediates C24-C25 can be synthesized with similar method (Table C4)

TABLE C4

| | Intermediates C21-C25 | | |
|---|---|---|---|
| Number | Starting material | Intermediate | MS [M + 1]$^+$ |
| C21 | O$_2$N—⟨phenyl(CF$_3$)⟩—CH$_2$OH | H$_2$N—⟨phenyl(CF$_3$)⟩—CH$_2$-N(piperazine)NMe | 274.2 |

TABLE C4-continued

Intermediates C21-C25

| Number | Starting material | Intermediate | MS [M + 1]+ |
|---|---|---|---|
| C22 | 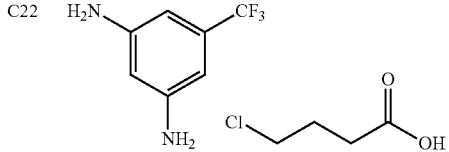 | 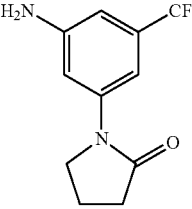 | 245.1 |
| C23 | 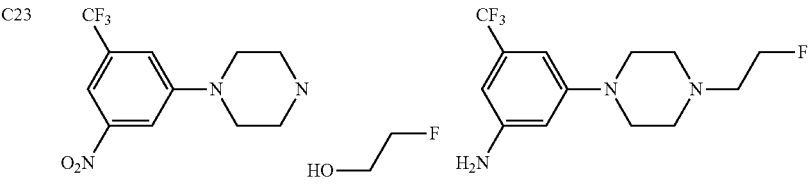 | 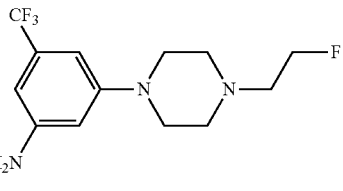 | NA |
| C24 | 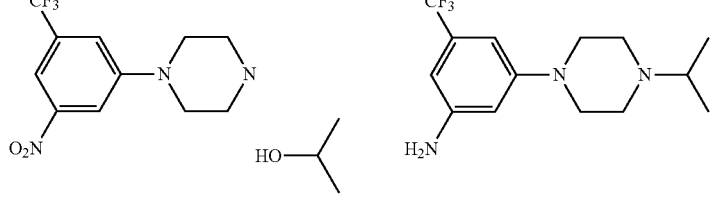 | 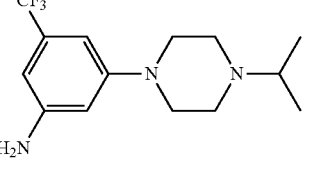 | NA |
| C25 | 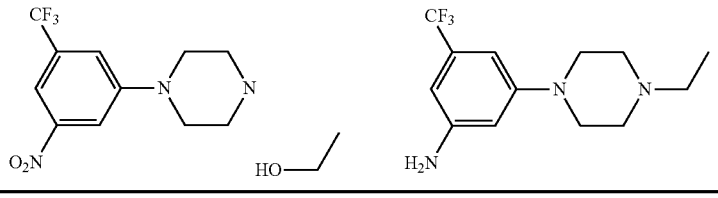 | 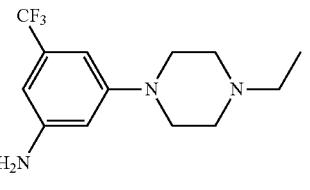 | NA |

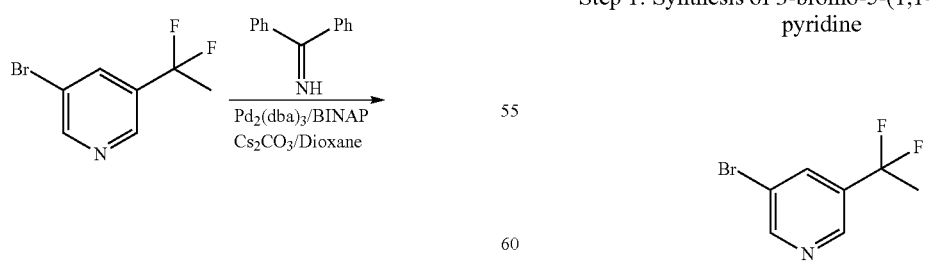

Step 1: Synthesis of 3-bromo-5-(1,1-difluoroethyl) pyridine

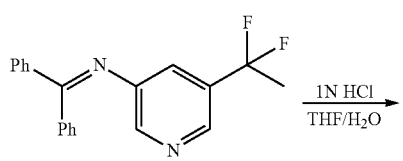

Heat the mixture of 1-(5-bromopyridin-3-yl)ethanone (500 mg, 2.5 mmol), bis-(2-methoxyethyl)aminosulfur trifluoride (BAST, 2.2 g, 10 mmol) in dichloromethane (8 mL) in a sealed tube at 60° C. overnight. TLC (PE:EtOAc=1:1) shows the reaction is complete. Concentrate the mixture, purify the residue by flash chromatography (silica gel, PE:EtOAc=1:1) to afford the title compound (200 mg, 36%). MS: (M+1): 222/224.

Step 2: Synthesis of 5-(1,1-difluoroethyl)-N-(diphenylmethylene)pyridin-3-amine

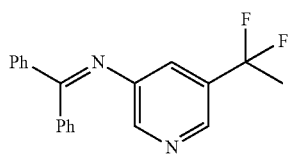 [SMILES: CC(F)(F)c1cncc(N=C(c2ccccc2)c2ccccc2)c1]

Add benzophenone imine (215 mg, 1.19 mmol), cesium carbonate (640 mg, 1.96 mmol), (±)-2,2'-bis(diphenylphosphino)-1,1'-binaphthalene (BINAP, 98 mg, 0.16 mmol), tris(dibenzylideneacetone)dipalladium [Pd₂(dba)₃, 90 mg, 0.098 mmol] to the solution of 3-bromo-5-(1,1-difluoroethyl)pyridine (200 mg, 0.9 mmol) in dioxane (10 mL), stir the resulting mixture under nitrogen atmosphere at 100° C. for 16 hrs. Cool the reaction mixture to room temperature, filter off the solid, concentrate the filtrate under reduced pressure, purify by flash chromatography (silica gel, EtOAc:PE=2:1) to yield the title compound (296 mg, 92%). MS: (M+1): 323.

Step 3: Synthesis of 5-(1,1-difluoroethyl)pyridin-3-amine

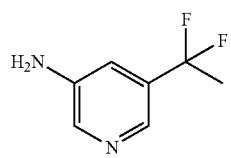

Add 5-(1,1-difluoroethyl)-N-(diphenylmethylene)pyridin-3-amine (296 mg, 0.92 mmol), water (1 mL) and hydrochloric acid (1N, 4 mL) to THF (10 mL), stir at room temperature for 3 hrs. TLC (PE:EtOAc=2:1) shows the reaction is complete. Extract the mixture with ethyl acetate, wash the organic layer with saturated sodium bicarbonate solution and brine sequentially, and dry over anhydrous sodium sulfate. Concentrate under reduced pressure to give the crude product. Purification by flash chromatography (silica gel, EtOAc:PE=1:1) yields the title compound (140 mg, 96.5%). MS: (M+1): 159.2.

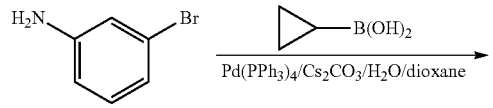

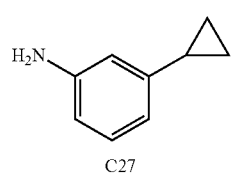

Synthesis of 3-cyclopropylaniline

Stir the mixture of 3-bromoaniline (400 mg, 2.35 mmol), cyclopropylboronic acid (240 mg, 2.79 mmol), tetrakis(triphenylphosphine)palladium(0) (140 mg, 0.12 mmol), cesium carbonate (1.5 g, 4.60 mmol) in dioxane (5 mL) and water (0.3 mL) under nitrogen atmosphere for 17 hrs at 100° C. Cool the reaction to room temperature, filter and concentrate the filtrate under reduced pressure. Purify by flash chromatography (silica gel, EtOAc:PE=3:7) to afford the title compound (120 mg, 38.8%). MS: (M+1): 134.0.

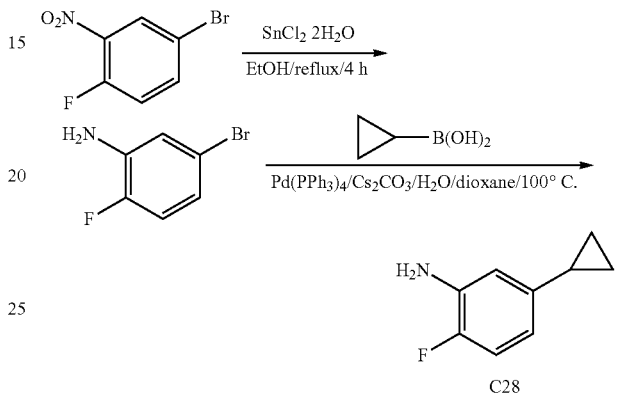

Step 1: Synthesis of 5-bromo-2-fluoroaniline

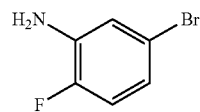

Mix 4-bromo-1-fluoro-2-nitrobenzene (2 g, 9.17 mmol) and stannous chloride dihydrate (8 g, 35 mmol) in ethanol (20 mL), heat the mixture to reflux for 4 hrs. Cool the reaction to room temperature, dilute with water and adjust pH=12 with sodium hydroxide solution, filter off the solid. Partition the filtrate in water and dichloromethane, collect the organic layer, dry over anhydrous sodium sulfate, and concentrate under reduced pressure to give crude product (800 mg, 46.5%). MS: (M+1): 190/192.

Step 2: Synthesis of 5-cyclopropyl-2-fluoroaniline

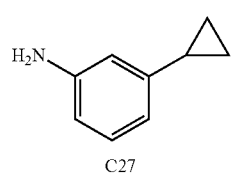

Stir the mixture of 5-bromo-2-fluoroaniline (800 mg, 4.26 mmol), cyclopropylboronic acid (434 mg, 5.05 mmol), tetrakis(triphenylphosphine)palladium(0) (242 mg, 0.21 mmol), cesium carbonate (2.7 g, 8.28 mmol) in dioxane (5 mL) and water (0.3 mL) under N₂ atmosphere at 100° C. for 17 hrs. TLC (EtOAc:PE=1:3) shows the reaction is complete. Filter off the solid, concentrate the filtrate. Purify by flash chromatography (silica gel, EtOAc:PE=3:7) to afford the title compound (350 mg, 55%). MS: (M+1): 152.1.

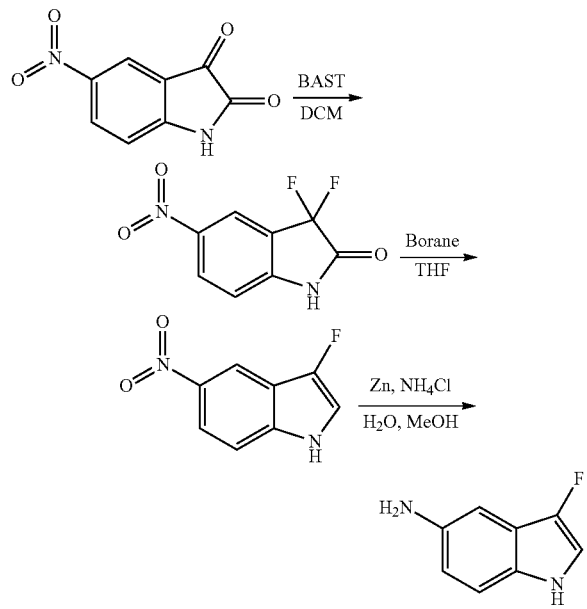

Step 1: Synthesis of 3,3-difluoro-5-nitroindolin-2-one

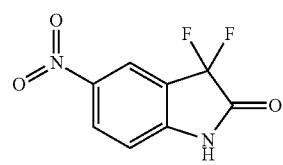 [SMILES: O=C1Nc2ccc([N+](=O)[O-])cc2C1(F)F]

Add 5-nitro-indoline-2,3-dione (5 g, 15.7 mmol) and bis-(2-methoxyethyl)aminosulfur trifluoride (20 mL) in dichloromethane (100 mL), stir at room temperature for 12 hrs. Quench the reaction with methanol (10 mL), pour the mixture into ice water (50 mL), extract with dichloromethane, combine the organic layers, wash with brine, dry over anhydrous sodium sulfate, concentrate under reduced pressure, purify by flash chromatography (silica gel, EtOAc:PE=1:4) to afford the title compound (3.5 g, 62.8%).

Step 2: Synthesis of 3-fluoro-5-nitro-1H-indole

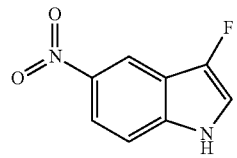 [SMILES: O=[N+]([O-])c1ccc2[nH]cc(F)c2c1]

Add borane-tetrahydrofuran complex (1M, 15 mL) dropwise to the solution of 3,3-difluoro-5-nitroindolin-2-one (650 mg, 3 mmol) in THF (10 mL) at 0° C. After addition, stir the reaction at 70° C. for 5 hrs. Concentrate under reduced pressure, add ethyl acetate to the residue, wash the organic layer with saturated sodium bicarbonate solution twice and then with brine twice, dry over anhydrous sodium sulfate. Concentrate under reduced pressure to obtain the crude product. Purify by flash chromatography (silica gel, EtOAc:PE=1:3) to yield the title compound (500 mg, 91.5%).

Step 3: Synthesis of 3-fluoro-1H-indol-5-amine

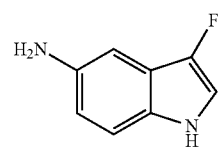 [SMILES: Nc1ccc2[nH]cc(F)c2c1]

Add zinc powder (387 mg, 5 mmol) portionwise to a solution of 3-fluoro-5-nitro-1H-indole (360 mg, 2 mmol) in methanol (10 mL). Then add dropwise 15.5% ammonium chloride solution (10 mL, 20 mmol), stir the reaction at ambient temperature for 5 hrs. Filter, dilute the filtrate with water (50 mL), extract with ethyl acetate (50 mL×2), wash with brine (50 mL×2), dry over anhydrous sodium sulfate. Concentrate under reduced pressure to give the crude product. Purify by flash chromatography (silica gel, EtOAc:PE=1:3) to yield the title compound (150 mg, 50%). MS: (M+1): 151.2.

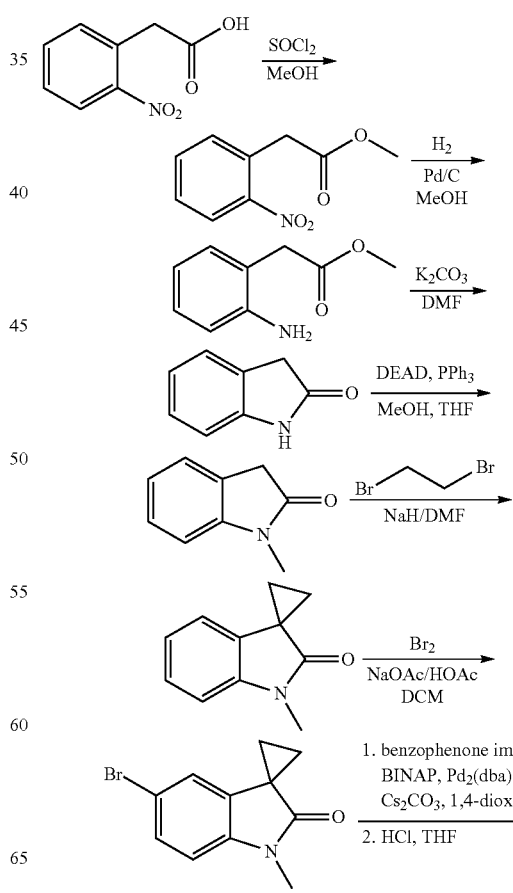

-continued

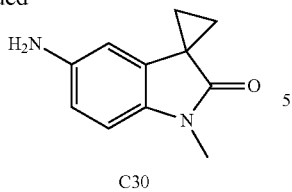

C30

Step 1: Synthesis of methyl 2-(2-nitrophenyl)acetate

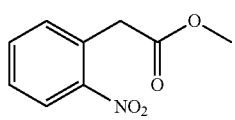

Add sulfonyl chloride (3 mL) dropwise to a solution of 2-nitrophenylacetic acid (7.0 g, 38.6 mmol) in methanol (20 mL) at 0° C., reflux the resulting mixture overnight. TLC (PE:EtOAc=3:1) shows the reaction is complete. Concentrate the reaction mixture under reduced pressure, add water, extract with ethyl acetate twice, and wash the combined organic layers with brine, dry over anhydrous sodium sulfate. Concentrate under reduced pressure to yield the crude product (7.5 g, 94.7%) which is used directly without further purification. MS: (M+1): 196.1.

Step 2: Synthesis of methyl 2-(2-aminophenyl)acetate

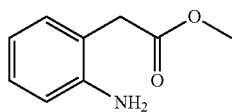

Add Pd/C (10%, 800 mg) to a solution of methyl 2-(2-nitrophenyl)acetate (7.5 g, 38.5 mmol) in methanol (50 mL) under $N_2$, then flush with $H_2$, stir the reaction under $H_2$ atmosphere at room temperature overnight. Remove the hydrogen; filter off the solid, concentrate the filtrate under reduced pressure to obtain the crude product (4.8 g, 76.2%) which is used directly without further purification. MS: (M+1):166.

Step 3: Synthesis of indolin-2-one

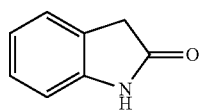

Stir the mixture of methyl 2-(2-aminophenyl)acetate (4.8 g, 29.1 mmol) and potassium carbonate (8.0 g, 58.2 mmol) in DMF (15 mL) at room temperature overnight. TLC (PE: EtOAc=2:1) shows the reaction is complete. Concentrate the reaction mixture under reduced pressure to give the crude product. Purify by chromatography (silica gel, EtOAc:PE=1:2) to afford the title compound (4.0 g, 95%). MS: (M+1): 134.2.

Step 4: Synthesis of 1-methylindolin-2-one

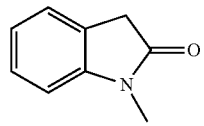

Add diethyl azodicarboxylate (DEAD, 8.0 g, 44.9 mmol) dropwise to a solution of indolin-2-one (4.0 g, 30.0 mmol), methanol (1.4 g, 44.9 mmol) and triphenylphosphine (12.0 g, 44.9 mmol) in THF (40 mL) at 0° C., stir the reaction at room temperature overnight. Concentrate under reduced pressure, purify the resulting residue with flash chromatography (silica gel, EtOAc:PE=1:3) to afford the title compound (2.6 g, 59.1%). MS: (M+1): 148.2.

Step 5: Synthesis of 1'-methylspiro[cyclopropane-1, 3'-indolin]-2'-one

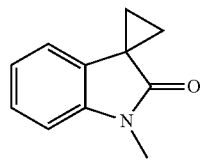

Add sodium hydride (60%, 1.4 g, 35.4 mmol) portionwise to the solution of 1-methylindolin-2-one (2.6 g, 17.7 mmol) in DMF (10 mL) at 0° C., stir for 30 min. Then add 1,2-dibromoethane (3.31 g, 17.7 mmol) to the mixture, stir the resulting mixture at room temperature overnight. Pour the reaction mixture to ice water, extract with ethyl acetate (100 mL×2), and wash the combined organic layers with brine (50 mL), dry over anhydrous sodium sulfate. Concentrate under reduced pressure, purify the residue by chromatography (silica gel, EtOAc:PE=1:3) to provide the title compound (1.5 g, 50.0%). MS: (M+1): 174.

Step 6: Synthesis of 5'-bromo-1'-methylspiro[cyclopropane-1,3'-indolin]-2'-one

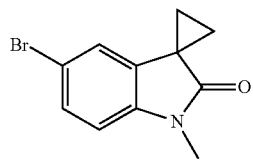

Add bromine (1.4 g, 8.7 mmol) dropwise to the mixture of 1'-methylspiro[cyclopropane-1,3'-indolin]-2'-one (1.5 g, 8.7 mmol), sodium acetate (0.7 g, 8.7 mmol) and acetic acid (0.52 g, 8.7 mmol) in dichloromethane (15 mL) at 0° C. After addition, stir the resulting mixture at room temperature overnight. Pour the reaction mixture to the cold sodium thiosulfate solution, extract with ethyl acetate (100 mL×2), combine the organic layers, and wash with brine (20 mL), dry over anhydrous sodium sulfate. Concentrate the solution under reduced pressure to give the crude product, purify by flash chromatography (silica gel, EtOAc:PE=1:5) to afford the title compound (1.0 g, 47.6%). MS: (M+1): 254.

Step 7: Synthesis of 5'-amino-1'-methylspiro[cyclopropane-1,3'-indolin]-2'-one

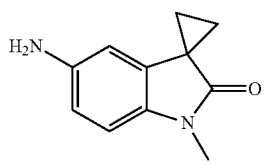

Add 5'-bromo-1'-methylspiro[cyclopropane-1,3'-indolin]-2'-one (1.0 g, 4.0 mmol), benzophenone imine (1.4 g, 8.0 mmol), cesium carbonate (3.2 g, 10.0 mmol), (±)-2,2'-bis (diphenylphosphino)-1,1'-binaphthalene (BINAP, 500 mg, 0.80 mmol), tris(dibenzylideneacetone)dipalladium(0) [$Pd_2(dba)_3$, 500 mg, 0.55 mmol] to dioxane (20 mL), stir the reaction under nitrogen atmosphere at 110° C. overnight. Cool to room temperature; filter off the solid, concentrate the filtrate under reduced pressure to give a residue. Add hydrochloric acid (1N, 2 mL) and THF (15 mL) to the residue; stir the mixture for 30 mins at room temperature. TLC (PE:EtOAc=1:1) shows the reaction is almost complete. Concentrate the mixture under reduce pressure to give the crude product, purify by flash chromatography (silica gel, EtOAc: PE=1:1) to afford the title compound as a yellow solid (0.7 g, 93.3%). MS: (M+1): 189.1.

Data of intermediate C26-30 are summarized in Table C5 below.

TABLE C5

Intermediates C26-C30

| Number | Starting material | Intermediate | MS [M + 1]⁺ |
|---|---|---|---|
| C26 | | | 159.1 |
| C27 | | | 134.1 |
| C28 | | | 152.1 |
| C29 | | | 151.1 |
| C30 | | | 189.1 |

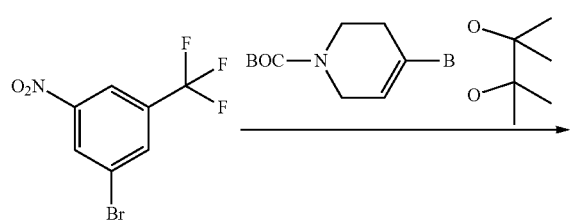

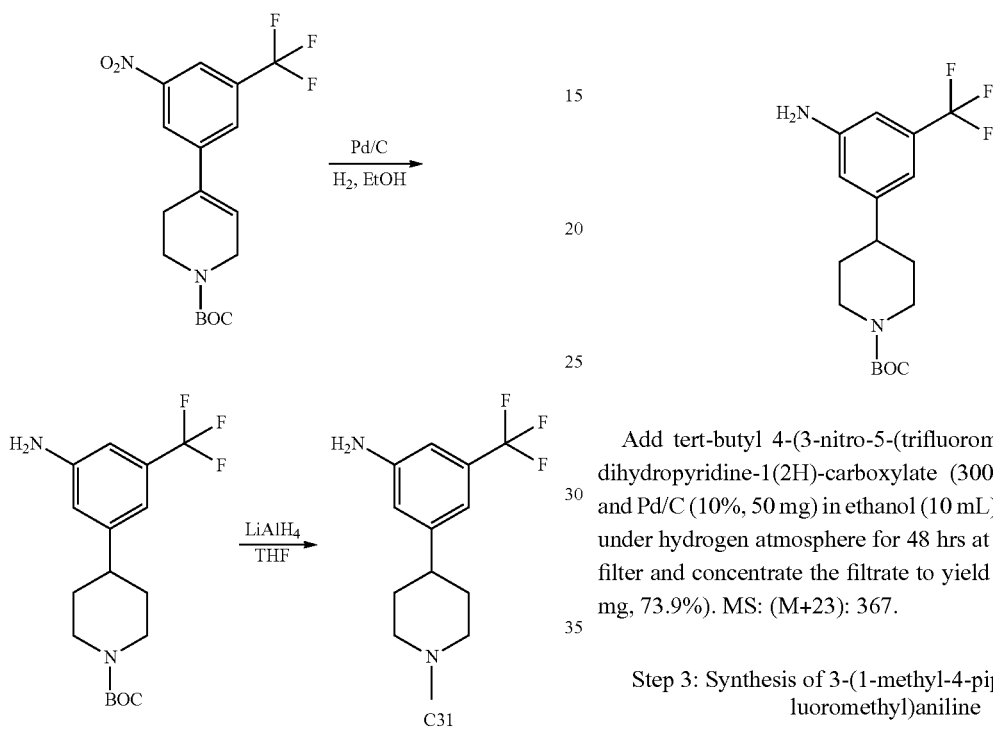

Step 1: Synthesis of tert-butyl 4-(3-nitro-5-(trifluoromethyl)phenyl)-5,6-dihydropyridine-1(2H)-carboxylate

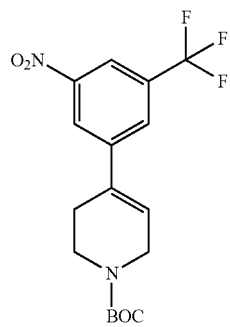 [SMILES: CC(C)(C)OC(=O)N1CC=C(c2cc([N+](=O)[O-])cc(C(F)(F)F)c2)CC1]

Mix 1-bromo-3-nitro-5-(trifluoromethyl)benzene (200 mg, 0.65 mmol), tert-butyl 4-(4,4,5,5-tetramethyl-1,3,2-dioxaborolan-2-yl)-5,6-dihydropyridine-1 (2H)-carboxylate (175 mg, 0.65 mmol), tetrakis(triphenylphosphine)palladium (0) (35 mg, 0.03 mmol) in dioxane and saturated sodium bicarbonate solution (3:1, 10 mL), stir the mixture at 120° C. for 1.5 hrs. Cool to room temperature; concentrate under reduced pressure to give the crude product. Purify by flash chromatography (silica gel, EtOAc:PE=20:1) to afford the product as a yellow solid (310 mg, 82.8%). MS: (M+23): 395.2.

Step 2: Synthesis of tert-butyl 4-[3-amino-5-(trifluoromethyl)phenyl]piperidine-1-carboxylate Add tert-butyl 4-(3-nitro-5-(trifluoromethyl)phenyl)-5,6-dihydropyridine-1(2H)-carboxylate (300 mg, 1.87 mmol) and Pd/C (10%, 50 mg) in ethanol (10 mL), flush with $H_2$, stir under hydrogen atmosphere for 48 hrs at room temperature, filter and concentrate the filtrate to yield a white solid (220 mg, 73.9%). MS: (M+23): 367.

Step 3: Synthesis of 3-(1-methyl-4-piperidyl)-5-(trifluoromethyl)aniline

Add lithium aluminum hydride (120 mg, 3.2 mmol) to a solution of the compound prepared in Step 2 (220 mg, 0.64 mmol) in THF (20 mL), stir the mixture at 90° C. for 12 hrs, TLC (MeOH:DCM=1:1) shows the reaction is complete, quench the reaction with water (2 mL), extract with ethyl acetate (20 mL), wash the organic layer with water and brine sequentially, dry over anhydrous sodium sulfate. Concentrate under reduced pressure to give the crude product, purify by flash chromatography (silica gel, MeOH:DCM=1:10) to afford the product as a yellow oil (110 mg, 48.3%).

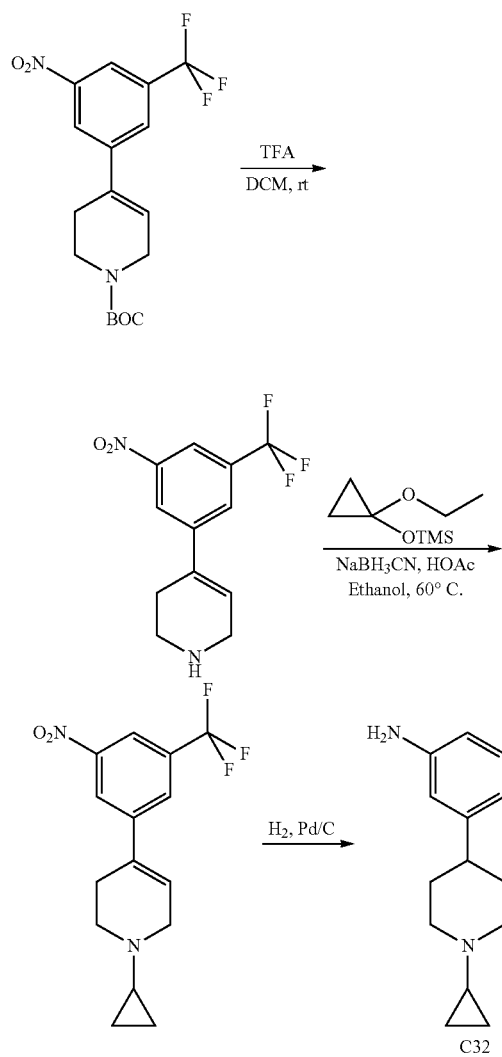

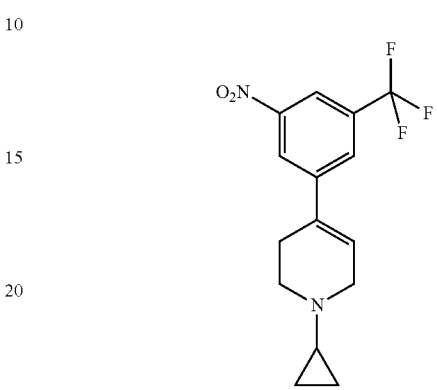

anhydrous sodium sulfate. Concentrate under reduced pressure to provide yellow oil (220 mg, 100%) which is used directly in next step.

Step 2: Synthesis of 1-cyclopropyl-4-(3-nitro-5-(trifluoromethyl)phenyl)-1,2,3,6-tetrahydropyridine Stir the mixture of 4-(3-nitro-5-(trifluoromethyl)phenyl)-1,2,3,6-tetrahydropyridine (150 mg, 0.55 mmol), (1-ethoxycyclopropoxy)trimethylsilane (700 mg, 2.4 mmol), sodium cyanoborohydride (200 mg, 3.3 mmol) and acetic acid (240 mg, 4.0 mmol) in ethanol (10 mL) at 60° C. overnight. Concentrate the mixture to get a residue, partition between EtOAc and water, collect the organic layer, wash with water and brine sequentially, and dry over anhydrous sodium sulfate. Concentrate under reduced pressure to give the product as a yellow solid (135 mg, 79%). MS: (M+1): 313.1.

Step 3: Synthesis of 3-(1-cyclopropylpiperidin-4-yl)-5-(trifluoromethyl)aniline

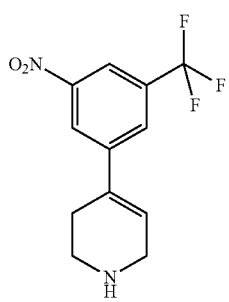 [SMILES: O=[N+]([O-])c1cc(C2=CCNCC2)cc(C(F)(F)F)c1]

Step 1: Synthesis of 4-(3-nitro-5-(trifluoromethyl)phenyl)-1,2,3,6-tetrahydropyridine Dissolve tert-butyl 4-(3-nitro-5-(trifluoromethyl)phenyl)-5,6-dihydropyridine-1(2H)-carboxylate (300 mg, 0.81 mmol) in dichloromethane (10 mL), add trifluoroacetic acid (3 mL), stir at room temperature overnight. Adjust pH=8 with saturated NaHCO₃ solution, extract with ethyl acetate, wash the organic extract with water and brine sequentially, dry over Stir the mixture of Pd/C (10%, 30 mg), 1-cyclopropyl-4-(3-nitro-5-(trifluoromethyl)phenyl)-1,2,3,6-tetrahydropyridine (120 mg 0.32 mmol) in methanol (10 mL) under hydrogen atmosphere at room temperature for 18 hrs. Remove hydrogen atmosphere, filter off the solid, concentrate the filtrate to yield the product as a white solid (85 mg, 94%). MS: (M+1): 285.1.

Data of intermediates C31-C32 are summarized in Table C6 below.

TABLE C6

Intermediates C31-C32

| Number | Starting material | Intermediate | MS [M + 1]+ |
|---|---|---|---|
| C31 | O2N—C6H3(CF3)—Br | CF3-C6H3(NH2)—piperidine-N-Me | NA |
| C32 | O2N—C6H3(CF3)—Br | CF3-C6H3(NH2)—piperidine-N-cyclopropyl | 285.2 |

Data of other commercially available intermediates C33-C37 are summarized in Table C7 below.

TABLE C7

Other intermediates C33-C37

| Number | Intermediate | MS [M + 1]+ |
|---|---|---|
| C33 | H2N-C6H4-CF3 (meta) | NA |
| C34 | H2N-C6H3(CF3)(CN) | NA |
| C35 | H2N-C6H4-OCF3 (meta) | NA |
| C36 | H2N-C6H3(OCF3)(Cl) | NA |
| C37 | H2N-C6H3(CF2F)(F) | 176.1 |

Preparation of Intermediate D

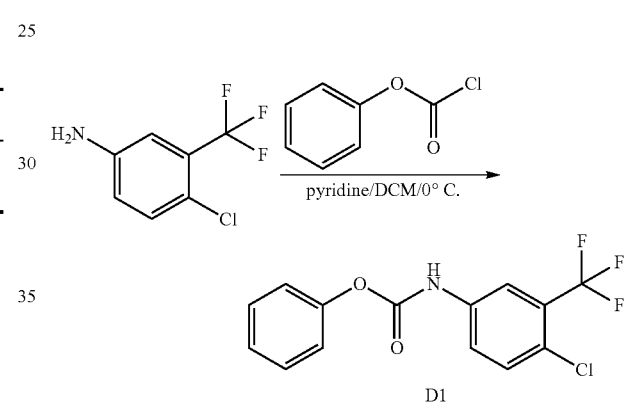

Step 1: Synthesis of phenyl N-[4-chloro-3-(trifluoromethyl)phenyl]carbamate

Add 4-chloro-3-(trifluoromethyl)aniline (1.0 g, 5.1 mmol) and pyridine (1.0 g, 12.8 mmol) in DCM (10 mL), stir well and cool to 0° C. Add phenyl chloroformate (1.04 g, 6.6 mmol) at 0° C. After addition, stir the reaction at room temperature for 1 hr. TLC (EtOAc:PE=1:2) shows the reaction is complete. Wash the organic layer with 1M HCl solution (20 mL) and brine (20 mL) respectively. Dry over anhydrous $Na_2SO_4$; concentrate under reduced pressure to give the target compound (1.16 g) which is used without further purification. MS: (M+1): 316.1.

Intermediates D2-D16 can be synthesized with similar method (Table D1).

TABLE D1
Intermediates D1-D16
| Number | Starting material | Intermediate | MS [M + 1]+ |
|---|---|---|---|
| D1 | 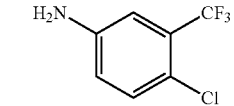 | 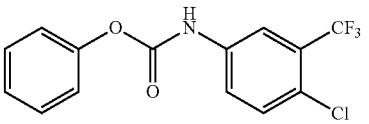 [SMILES: O=C(Nc1ccc(Cl)c(C(F)(F)F)c1)Oc1ccccc1] | 316.1 |
| D2 | 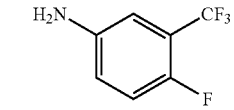 | 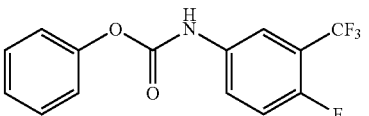 | 300.1 |
| D3 | 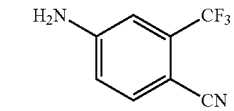 | 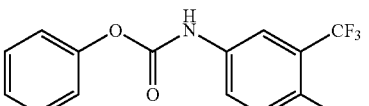 | NA |
| D4 | 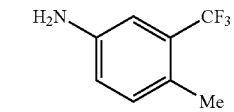 | 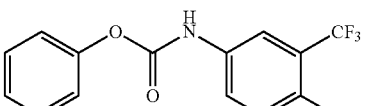 | 296.1 |
| D5 | 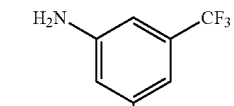 | 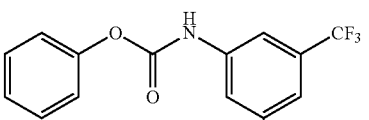 | NA |
| D6 | 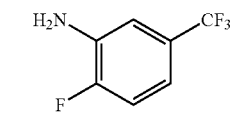 | 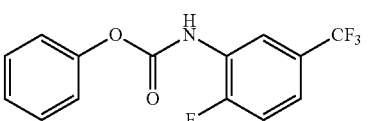 | NA |
| D7 | 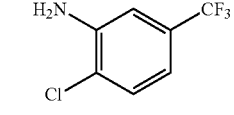 | 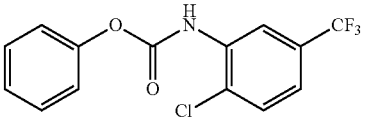 [SMILES: O=C(Nc1cc(C(F)(F)F)ccc1Cl)Oc1ccccc1] | NA |
| D8 | 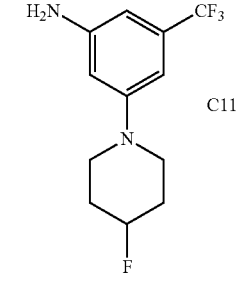 [SMILES: "C11" ; Nc1cc(N2CCC(F)CC2)cc(C(F)(F)F)c1] C11 | 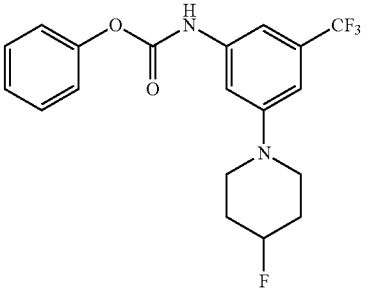 [SMILES: O=C(Nc1cc(N2CCC(F)CC2)cc(C(F)(F)F)c1)Oc1ccccc1] | NA |

TABLE D1-continued

Intermediates D1-D16

| Number | Starting material | Intermediate | MS [M + 1]+ |
|---|---|---|---|
| D9 | C31 | | NA |
| D10 | | | 282.1 |
| D11 | | | 283.2 |
| D12 | | | 316.1 |
| D13 | | | 296.2 |
| D14 | | | 359.1 |
| D15 | C2 | | 360.1 |
| D16 | | | NA |

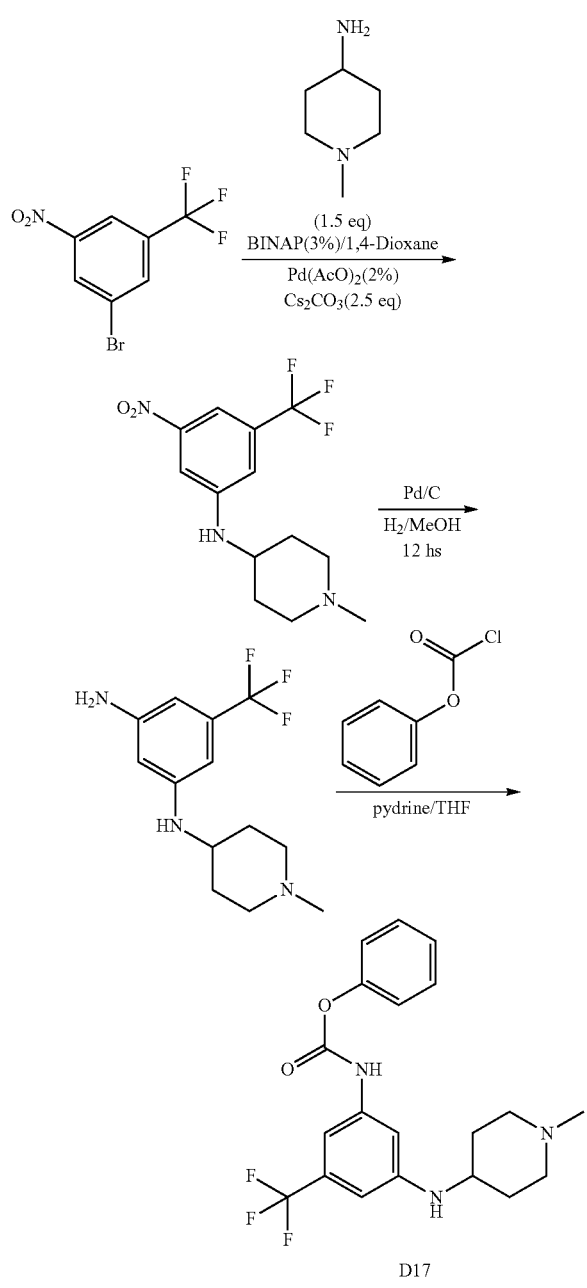

Step 1: Synthesis of 1-methyl-N-[3-nitro-5-(trifluoromethyl)phenyl]piperidin-4-amine

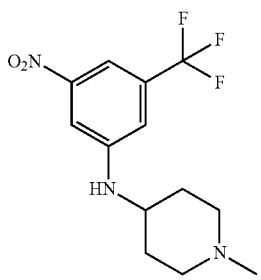 [SMILES: CN1CCC(Nc2cc([N+](=O)[O-])cc(C(F)(F)F)c2)CC1]

Add 1-bromo-3-nitro-5-(trifluoromethyl)benzene (3 g, 11.11 mmol), Cs₂CO₃ (9.5 g, 27.78 mmol), 1-methylpiperi- din-4-amine (1.9 g, 16.67 mmol) to 1,4-dioxane (25 mL), then under N₂, add Pd(OAc)₂ (50 mg, 0.22 mmol) and BINAP (207 mg, 0.33 mmol). Stir the reaction at 120° C. under N₂ overnight. TLC (DCM:MeOH=10:1) shows the reaction is complete. Cool to room temperature and filter off the solid. Concentrate the filtrate to get the crude product. Purification by chromatography (silica gel, DCM:MeOH-10:1) affords the title compound (3.44 g, 99%). MS: (M+1): 304.

Step 2: Synthesis of N1-(1-methyl-4-piperidyl)-5-(trifluoromethyl)benzene-1,3-diamine

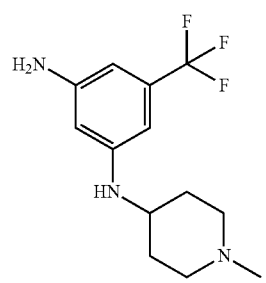

Dissolve the compound obtained in last step (3.44 g, 11.3 mmol) in methanol (30 mL), add Pd/C (10%, 0.6 g), flush with H₂. Stir the reaction at 30° C. under H₂ atmosphere overnight. TLC (DCM:MeOH=10:1) shows the reaction is complete. Filter, and concentrate the filtrate to get the crude product (2.9 g) which is used without further purification. MS: (M+1): 294.1.

Step 3: Synthesis of phenyl N-[3-[(1-methyl-4-piperidyl)amino]-5-(trifluoromethyl)phenyl]carbamate

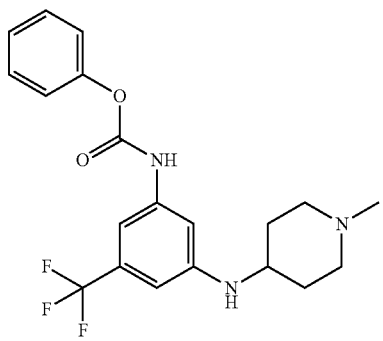 [SMILES: CN1CCC(Nc2cc(NC(=O)Oc3ccccc3)cc(C(F)(F)F)c2)CC1]

Dissolve the compound obtained in Step 2 (2.9 g, 10.61 mmol) in THF (30 mL), cool to −30° C., then add pyridine (1.68 g, 21.22 mmol) and phenyl chloroformate (1.83 g, 11.67 mmol). Stir at room temperature for 3 hrs. TLC (DCM: MeOH=10:1) shows the reaction is complete. Pour the solution to a mixture of EtOAc and water, separate the organic layer, and wash with brine, dry over anhydrous Na₂SO₄. Concentrate under reduced pressure to give the crude product (4.3 g). MS: (M+1): 394.1.

Intermediates D18-D20 can be synthesized with similar method (Table D2).

TABLE D2

Intermediates D17-D20

| Number | Starting material | Intermediate | MS [M + 1]⁺ |
|---|---|---|---|
| D17 | 1-bromo-3-nitro-5-(trifluoromethyl)benzene | phenyl (3-((1-methylpiperidin-4-yl)amino)-5-(trifluoromethyl)phenyl)carbamate | 394.1 |
| D18 | 1-bromo-3-nitro-5-(trifluoromethyl)benzene | phenyl (3-(3,3-difluoroazetidin-1-yl)-5-(trifluoromethyl)phenyl)carbamate | 373.1 |
| D19 | 1-bromo-3-nitro-5-(trifluoromethyl)benzene | phenyl (3-(pyrrolidin-1-yl)-5-(trifluoromethyl)phenyl)carbamate | NA |
| D20 | 1-bromo-3-nitro-5-(trifluoromethyl)benzene | phenyl (3-(2-methylmorpholino)-5-(trifluoromethyl)phenyl)carbamate | 381.1 |

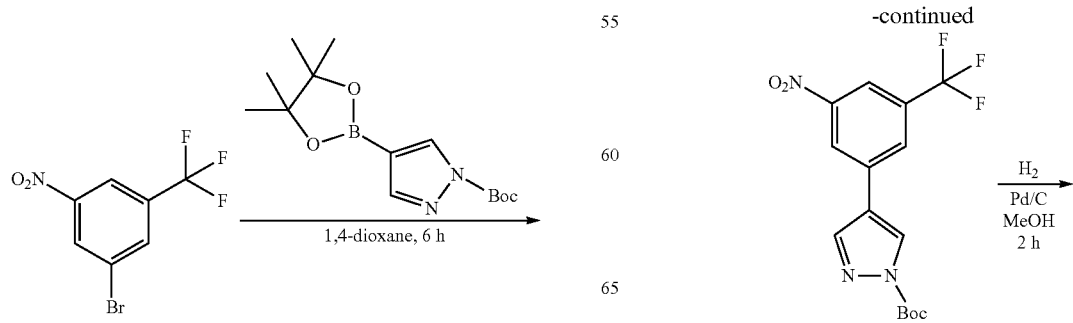

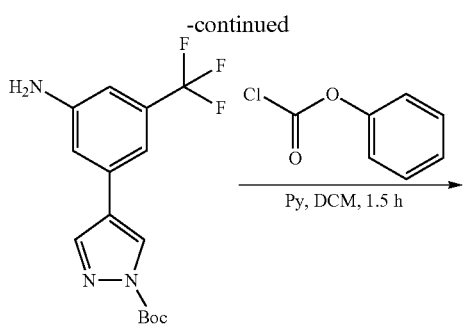

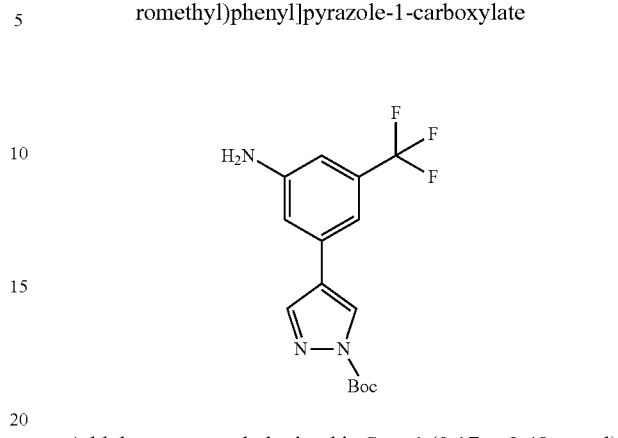

(silica gel, EtOAc:PE=1:1) affords the title compound (0.17 g, 80.9%). MS: (M+1): 358.2.

Step 2: Synthesis of tert-butyl 4-[3-amino-5-(trifluoromethyl)phenyl]pyrazole-1-carboxylate Add the compound obtained in Step 1 (0.17 g, 0.48 mmol) to methanol (15 mL), then add Pd/C (10%) under $N_2$. Flush with $H_2$, stir the reaction under $H_2$ atmosphere at room temperature for 2 hrs. Filter off the solid, concentrate the filtrate to give the crude product (0.08 g) which is used directly without further purification. MS: (M+1): 328.1.

Step 3: Synthesis of tert-butyl 4-[3-(phenoxycarbonylamino)-5-(trifluoromethyl)phenyl]pyrazole-1-carboxylate Step 1: Synthesis of tert-butyl 4-[3-nitro-5-(trifluoromethyl)phenyl]pyrazole-1-carboxylate

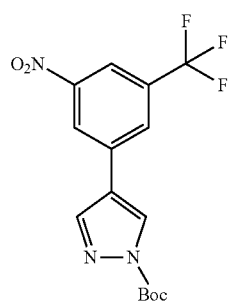 [SMILES: CC(C)(C)OC(=O)n1cc(-c2cc([N+](=O)[O-])cc(C(F)(F)F)c2)cn1]

Add 1-bromo-3-nitro-5-(trifluoromethyl)benzene (0.165 g, 0.61 mmol), tert-butyl 4-(4,4,5,5-tetramethyl-1,3,2-dioxaborolan-2-yl)pyrazole-1-carboxylate (0.18 g, 0.61 mmol), sodium acetate (0.1 g, 1.2 mmol), [1,1'-bis(diphenylphosphino)ferrocene]dichloropalladium (II) (22 mg, 0.03 mmol) to 1,4-dioxane (15 mL) and water (2 mL). Stir the mixture at 100° C. under $N_2$ for 6 hrs. TLC (EtOAc:PE=1:1) shows that the reaction is complete. Concentrate under reduced pressure to give the crude product. Purification by chromatography Mix the compound obtained in Step 2 (0.08 g, 0.24 mmol), pyridine (0.018 g, 0.24 mmol) and DCM (5 mL), add slowly phenyl chloroformate (0.042 g, 0.26 mmol) at 0° C. Stir the reaction at room temperature for one hour. Remove the solvent under reduced pressure to give a crude product. Purification by chromatography (silica gel, EtOAc:PE=1:1) affords the title compound (65 mg, 78.3%).

Intermediates D22 can be prepared with similar method (Table D3).

TABLE D3

| Intermediates D21-D22 | | | |
|---|---|---|---|
| Number | Starting material | Intermediate | MS [M + 1]+ |
| D21 | 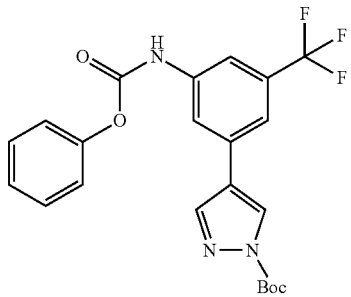 [SMILES: CC(C)(C)OC(=O)n1cc(-c2cc(NC(=O)Oc3ccccc3)cc(C(F)(F)F)c2)cn1] | | NA |

TABLE D3-continued

Intermediates D21-D22

| Number | Starting material | Intermediate | MS [M + 1]+ |
|---|---|---|---|
| D22 | 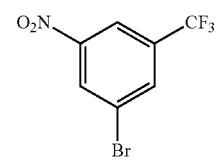 | 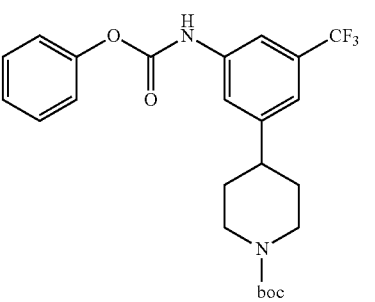 | [M + 23] 487.2 |

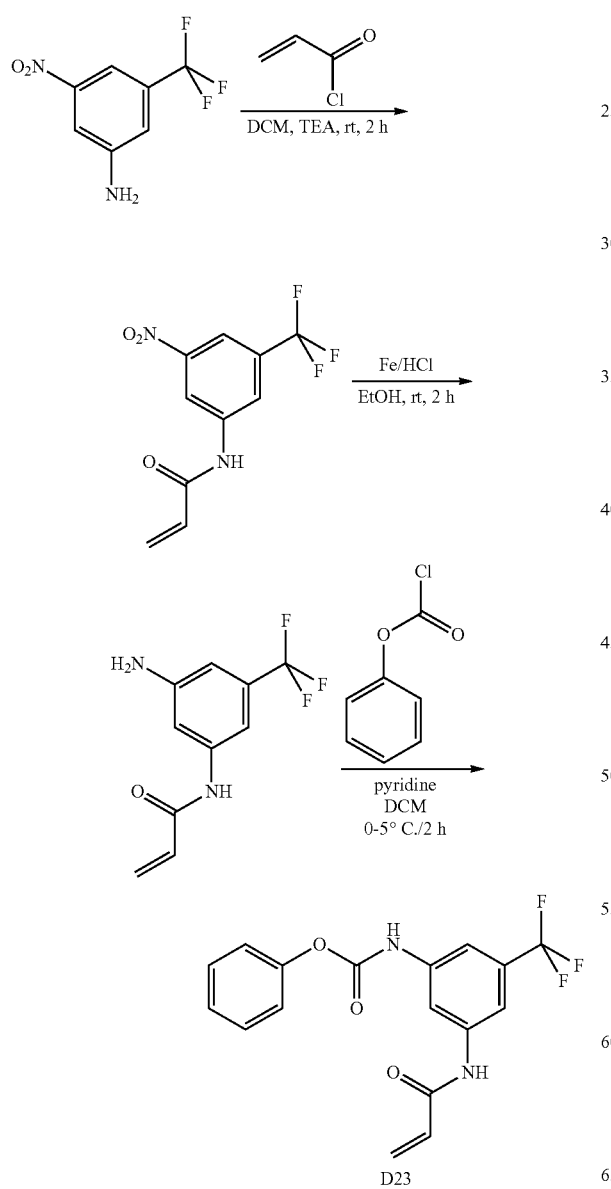

Step 1: Synthesis of N-[3-nitro-5-(trifluoromethyl) phenyl]prop-2-enamide

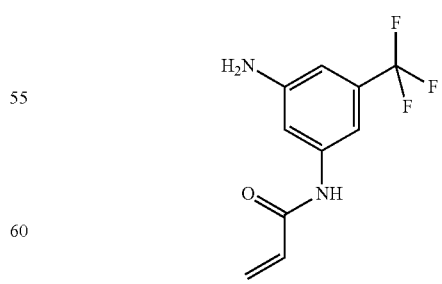

Dissolve 3-nitro-5-(trifluoromethyl)aniline (150 mg, 0.73 mmol), triethylamine (220 mg, 2.18 mmol) in DCM (8 mL), cool to 0° C. at ice bath, add slowly acryloyl chloride (198 mg, 2.18 mmol). After addition, stir the reaction at room temperature for 2 hrs. Pour the mixture into water (30 mL), extract with EtOAc (10 mL×3), combine the organic layers; wash with brine (50 mL), dry over anhydrous $Na_2SO_4$. Concentrate under reduced pressure to give the crude product (190 mg) which is used without further purification.

Step 2: Synthesis of N-[3-amino-5-(trifluoromethyl) phenyl]prop-2-enamide

Dissolve the product obtained in Step 1 (190 mg, 0.73 mmol) in ethanol (8 mL), add iron powder (204 mg, 3.65 mmol), concentrated HCl (0.43 mL). Stir the reaction at room temperature for 2 hrs. After the reaction is complete, adjust pH to neutral with sodium hydroxide solution. Filter off the solid, mix the filtrate with ice water (50 mL), extract with EtOAc (15 mL×3). Combine the organic layers, wash with brine (100 mL), dry over anhydrous Na₂SO₄, and concentrate under reduced pressure to give the crude product (168 mg) which is used without further purification.

Step 3: Synthesis of phenyl N-[3-(prop-2-enoylamino)-5-(trifluoromethyl)phenyl]carbamate Dissolve the product obtained in Step 2 (168 mg, 0.73 mmol) in DCM (6 mL), add pyridine (115 mg, 1.46 mmol) and then cool to 0° C. on ice bath. Add slowly phenyl chloroformate (125 mg, 0.8 mmol), stir at 0-5° C. for 2 hrs. Pour the mixture into water (50 mL), adjust pH to neutral with 1M HCl and extract with EtOAc (15 mL×3). Combine the organic layers, wash with brine (100 mL) and dry over anhydrous Na₂SO₄. Concentrate under reduced pressure to give the crude product (240 mg) which is used without further purification.

Intermediate D24 can be synthesized with similar method (Table D4).

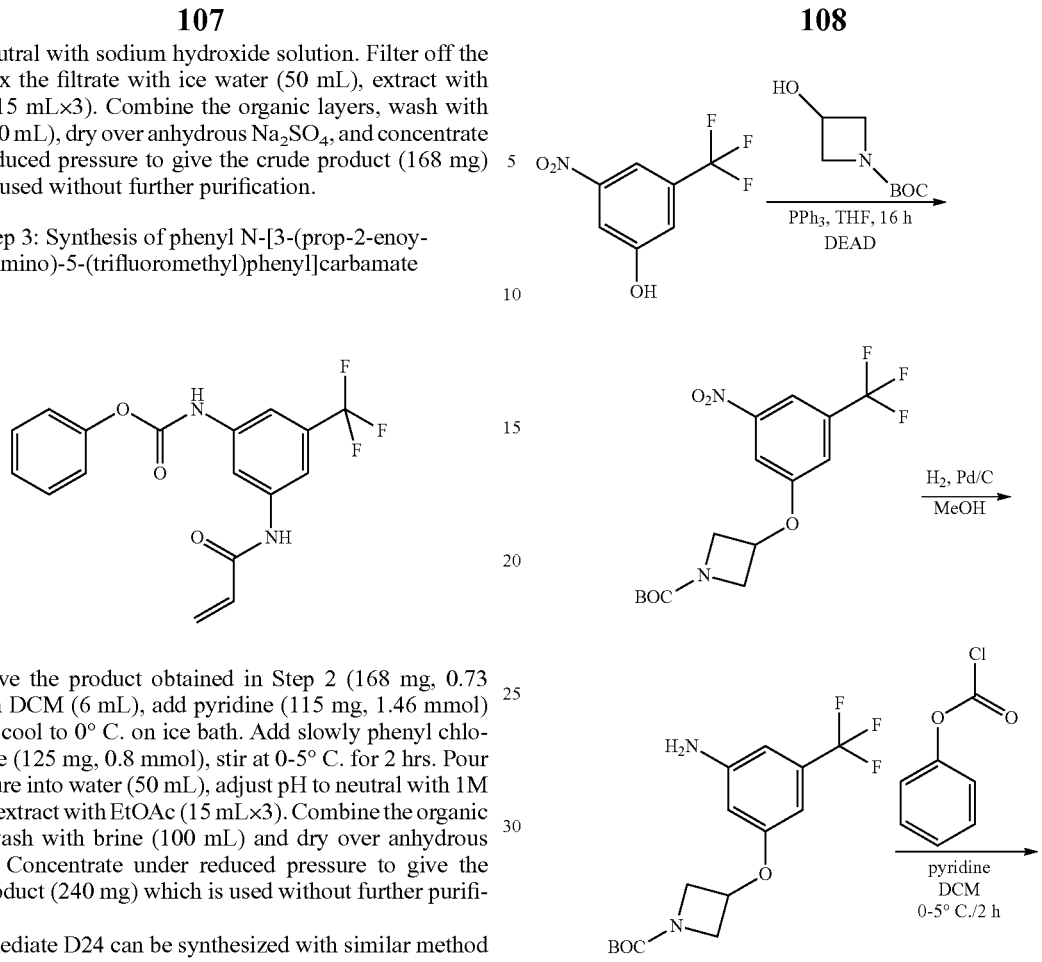

TABLE D4

| Intermediates D23-D24 | | | |
|---|---|---|---|
| Number | Starting material | Intermediate | MS [M + 1]⁺ |
| D23 | (structure) | (structure) | 351.1 |
| D24 | (structure) | (structure) | [M + 23] 487.2 |

-continued

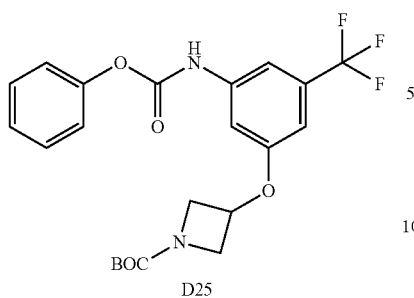

D25

Step 1: Synthesis of tert-butyl 3-[3-nitro-5-(trifluoromethyl)phenoxy]azetidine-1-carboxylate

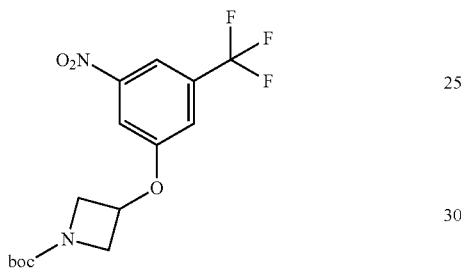

Dissolve 3-nitro-5-(trifluoromethyl)phenol (500 mg, 2.4 mmol), tert-butyl 3-hydroxyazetidine-1-carboxylate (500 mg, 2.9 mmol), PPh₃ (9.5 g, 3.6 mmol) in THF (8 mL) and cool to 0° C. on ice bath. Add slowly diethyl azodicarboxylate (630 mg, 3.6 mmol). Stir the mixture at 35° C. for 16 hrs. Pour the mixture into water (50 mL), adjust pH to neutral with saturated NaHCO₃ solution. Extract with EtOAc (15 mL×3), combine the organic layers; wash with brine (100 mL), dry over anhydrous Na₂SO₄. Concentrate under reduced pressure to give the crude product. Purification by chromatography (silica gel, EtOAc:PE=15:85) affords the target compound (760 mg, 87%).

Step 2: Synthesis of tert-butyl 3-[3-amino-5-(trifluoromethyl)phenoxy]azetidine-1-carboxylate

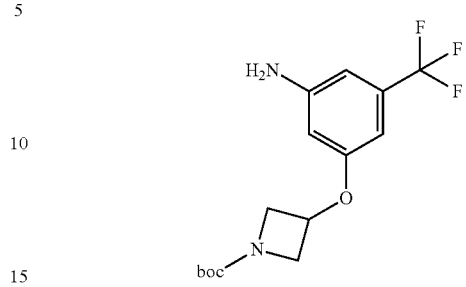

Dissolve the compound obtained in Step 1 (250 mg, 0.69 mmol) in methanol (10 mL), add wet Pd/C (10%, 70 mg), flush the system with H₂ and stir the reaction under H₂ atmosphere for 16 hrs at room temperature. After the reaction is complete, remove H₂, flush with N₂, filter and concentrate the filtrate to give the crude product (230 mg) which is used without further purification.

Step 3: Synthesis of tert-butyl 3-[3-(phenoxycarbonylamino)-5-(trifluoromethyl)phenoxy]azetidine-1-carboxylate

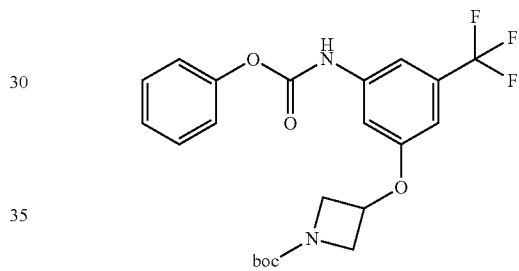

Dissolve the product obtained in Step 2 (230 mg, 0.39 mmol) in THF (10 mL), add pyridine (230 mg, 0.69 mmol) and cool to 0° C. on ice bath. Add slowly phenyl chloroformate (118 mg, 0.76 mmol), stir the reaction at 0-5° C. for 30 mins. Pour the reaction mixture into water (50 mL), adjust pH to neutral with 1M HCl solution. Extract with EtOAc (15 mL×3), combine the organic layers, wash with brine (100 mL) and dry over anhydrous Na₂SO₄. Concentrate under reduced pressure to give the crude product (312 mg) which is used without further purification.

Intermediates D26-D29 can be synthesized with similar method (Table D5).

TABLE D5

Intermediates D25-D29

| Number | Starting material | Intermediate | MS [M + 1]⁺ |
|---|---|---|---|
| D25 | 3-nitro-5-(trifluoromethyl)phenol (O₂N, CF₃, OH) | phenyl carbamate with azetidine-Nboc and CF₃ | [M + 23] 475.2 |

TABLE D5-continued
Intermediates D25-D29
| Number | Starting material | Intermediate | MS [M + 1]+ |
|---|---|---|---|
| D26 | 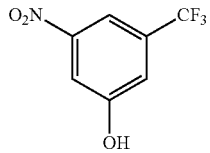 | 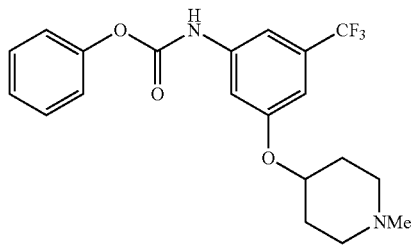 [SMILES: CN1CCC(Oc2cc(NC(=O)Oc3ccccc3)cc(C(F)(F)F)c2)CC1] | 395.2 |
| D27 | 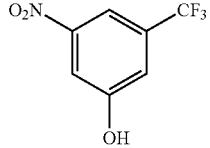 | 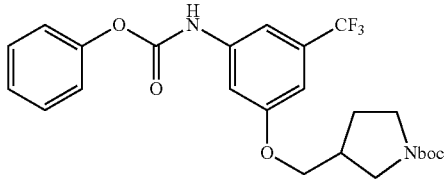 | NA |
| D28 | 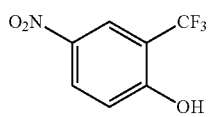 | 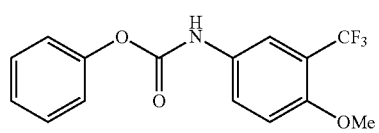 [SMILES: COc1ccc(NC(=O)Oc2ccccc2)cc1C(F)(F)F] | 312.1 |
| D29 | 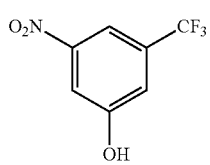 | 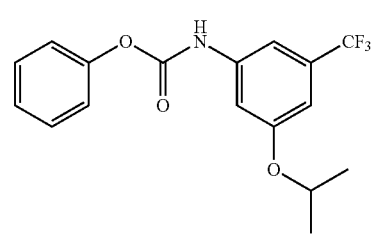 [SMILES: CC(C)Oc1cc(NC(=O)Oc2ccccc2)cc(C(F)(F)F)c1] | NA |

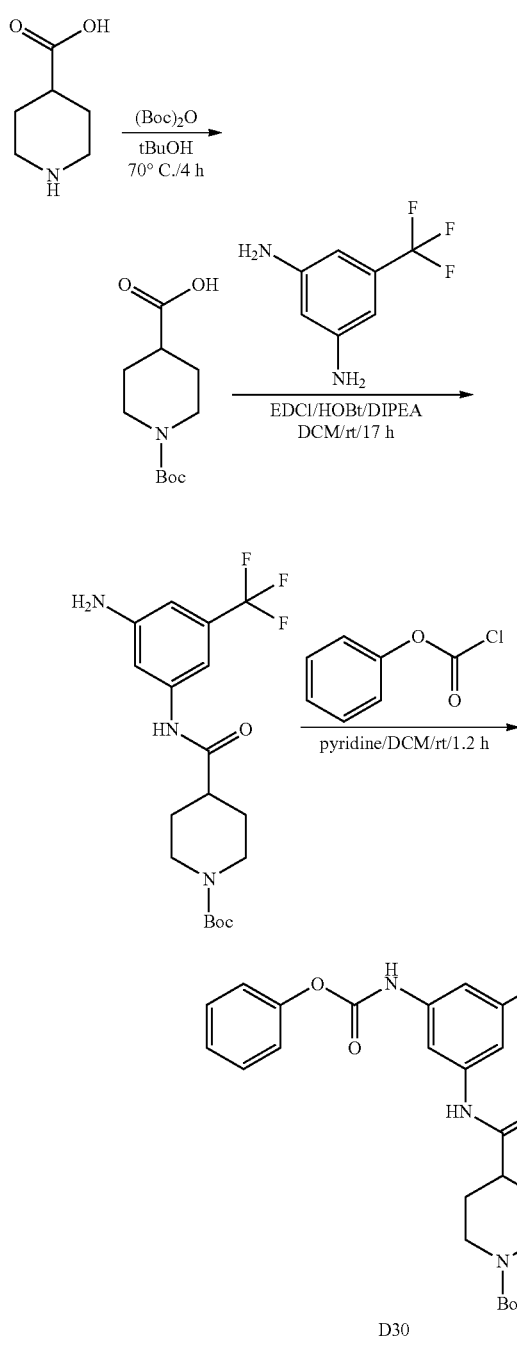

D30

Step 1: Synthesis of 1-tert-butoxycarbonylpiperidine-4-carboxylic acid

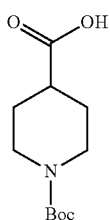

Mix piperidine-4-carboxylic acid (0.5 g, 3.9 mmol) and Boc₂O (1 g, 4.6 mmol) in t-BuOH (10 mL) and stir at 70° C. for 4 hrs. TLC (PE:EtOAc=1:1) shows the reaction is complete. Remove the volatiles under reduced pressure to get white solid as the crude product (1.1 g) which is used without further purification.

Step 2: Synthesis of tert-butyl 4-[[3-amino-5-(trifluoromethyl)phenyl]carbamoyl]piperidine-1-carboxylate

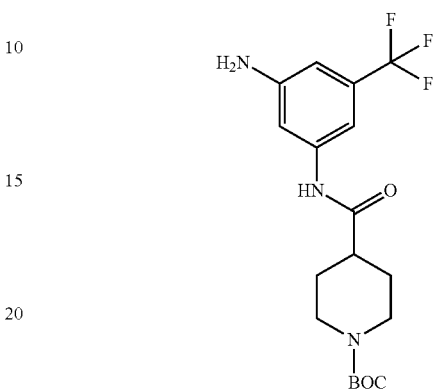

Mix the compound obtained in Step 1 (1.1 g, crude), HOBt (1.6 g, 12 mmol), 5-(trifluoromethyl)benzene-1,3-diamine (845 mg, 4.8 mmol) in DCM (16 mL), add diisopropylethylamine (1.55 g, 12 mmol), 1-ethyl-3-(3-dimethyllaminopropyl)carbodiimide hydrochloride (2.3 g, 12 mmol) and stir at room temperature for 17 hrs. TLC (PE:EtOAc=1:1) shows the reaction is complete. Remove the volatiles under reduced pressure, purify the residue by chromatography (silica gel, EOAc:PE=4:6) to give the title compound (600 mg, 40% two-step yield).

Step 3: Synthesis of tert-butyl 4-[[3-(phenoxycarbonylamino)-5-(trifluoromethyl)phenyl]carbamoyl]piperidine-1-carboxylate

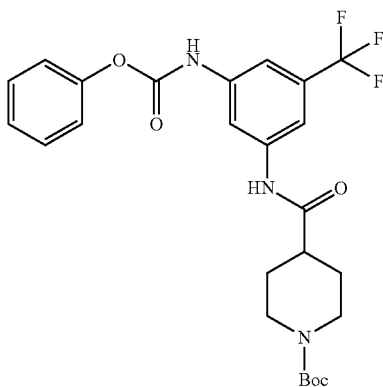 [SMILES: CC(C)(C)OC(=O)N1CCC(C(=O)Nc2cc(NC(=O)Oc3ccccc3)cc(C(F)(F)F)c2)CC1]

Mix the compound obtained in Step 2 (600 mg, 1.55 mmol), pyridine (306 mg, 3.9 mmol) in DCM (10 mL), cool to 0-5° C. Add the solution of phenyl chloroformate (315 mg, 2 mmol) in DCM (1 mL). Stir the reaction at room temperature for 1.5 hrs. TLC (PE:EtOAc=1:1) shows the reaction is complete. Quench the reaction with water (5 mL), wash the organic layer with 1N HCl solution, saturated NaHCO₃ solution and brine sequentially, dry over anhydrous Na₂SO₄. Concentrate under reduced pressure to give the crude product. Purification by chromatography (silica gel, EtOAc:PE=1:1) affords the title compound (400 mg, 51%). MS: (M+1): 508.1.

Intermediate D31 can be synthesized with similar method (Table D6).

TABLE D6

Intermediates D30-D31

| Number | Starting material | Intermediate | MS [M + 1]+ |
|---|---|---|---|
| D30 | 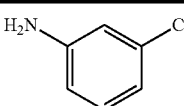 | 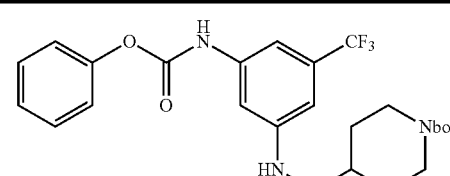 | [M + 23] 530.2 |
| D31 | 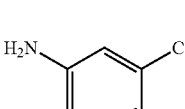 | 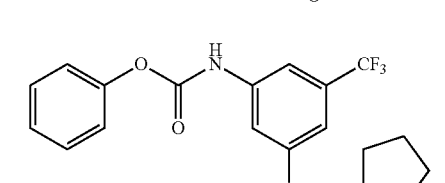 | NA |

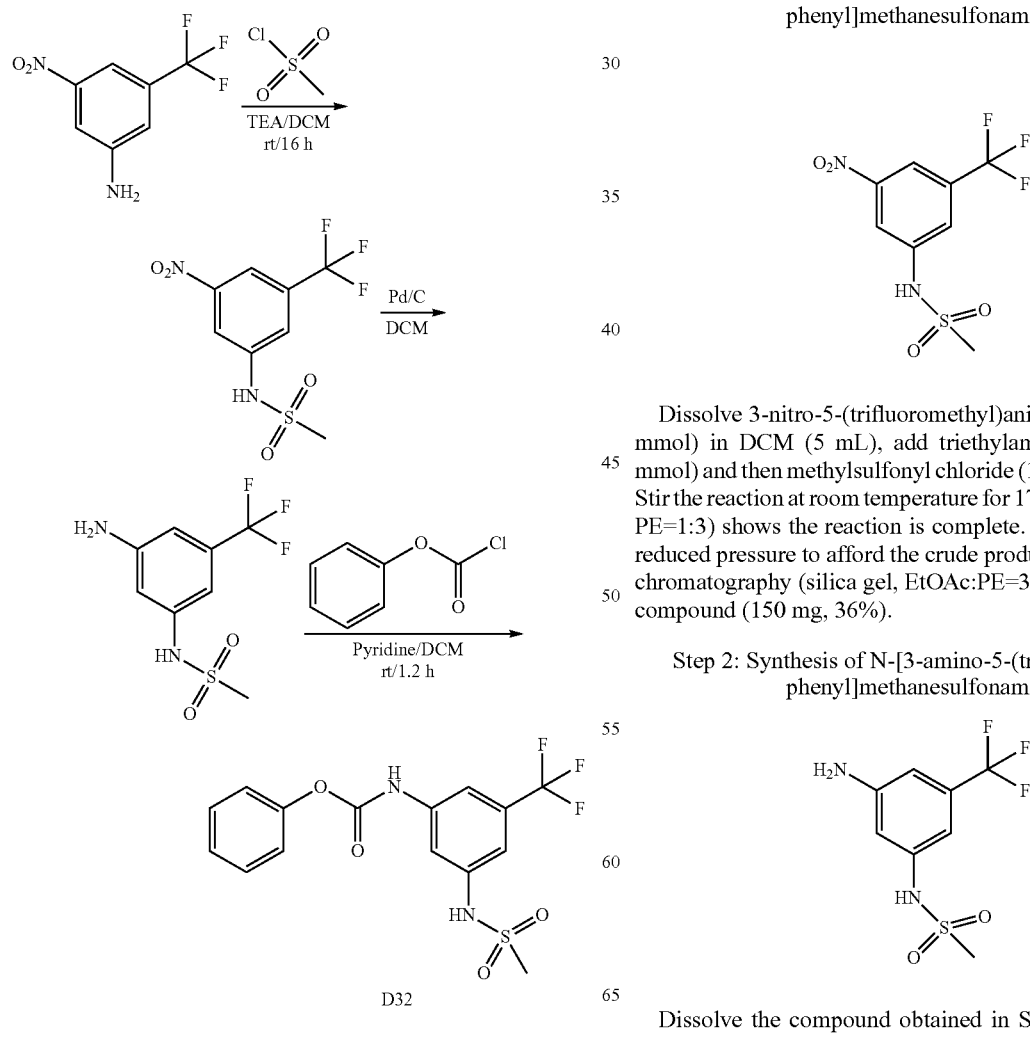

Step 1: Synthesis of N-[3-nitro-5-(trifluoromethyl)phenyl]methanesulfonamide

Dissolve 3-nitro-5-(trifluoromethyl)aniline (300 mg, 1.45 mmol) in DCM (5 mL), add triethylamine (294 mg, 2.9 mmol) and then methylsulfonyl chloride (182 mg, 1.6 mmol). Stir the reaction at room temperature for 17 hrs. TLC (EtOAc:PE=1:3) shows the reaction is complete. Concentrate under reduced pressure to afford the crude product. Purification by chromatography (silica gel, EtOAc:PE=3:7) affords the title compound (150 mg, 36%).

Step 2: Synthesis of N-[3-amino-5-(trifluoromethyl)phenyl]methanesulfonamide

Dissolve the compound obtained in Step 1 (150 mg) in DCM (5 mL), add Pd/C (20%, 50 mg). Flush the system with H₂ and then stir the reaction under H₂ atmosphere at room temperature for 2 hrs. TLC (EtOAc:PE=1:2) shows the reaction is complete. Remove the H₂, filter and concentrate the filtrate to give the product (110 mg, 82%). MS: (M+1): 255.1.

Step 3: Synthesis of phenyl N-[3-(methanesulfonamido)-5-(trifluoromethyl)phenyl]carbamate

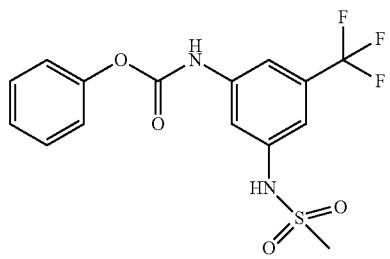 [SMILES: CS(=O)(=O)Nc1cc(NC(=O)Oc2ccccc2)cc(C(F)(F)F)c1]

Use similar procedure used in the preparation of D1.

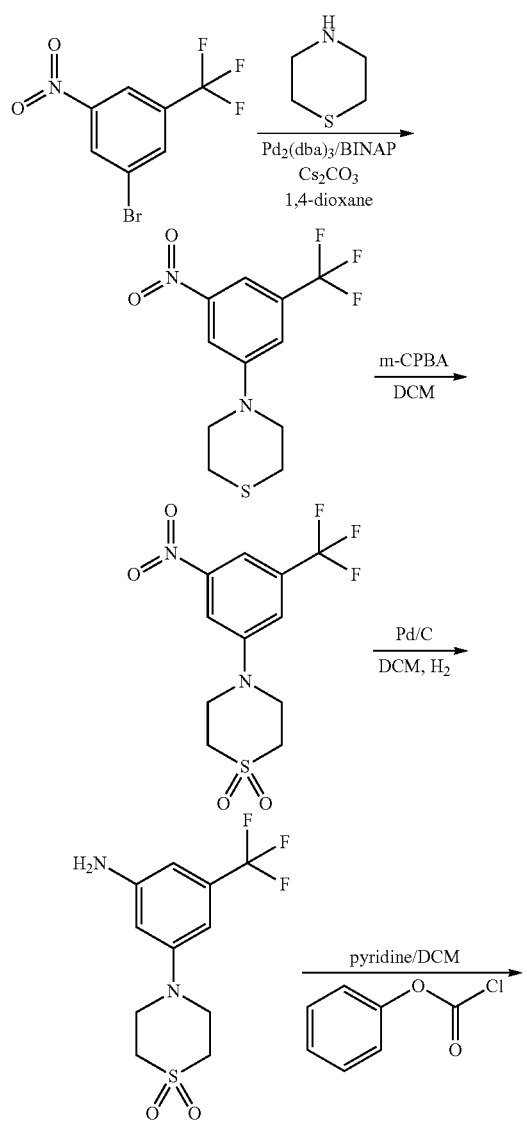

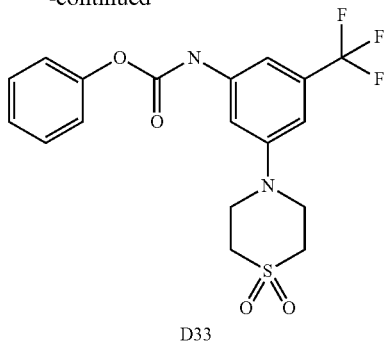

D33

Step 1: Synthesis of 4-[3-nitro-5-(trifluoromethyl)phenyl]thiomorpholine

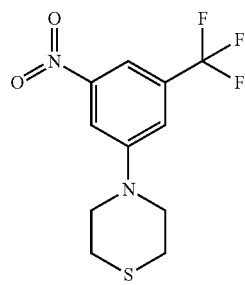 [SMILES: O=[N+]([O-])c1cc(N2CCSCC2)cc(C(F)(F)F)c1]

Add 1-bromo-3-nitro-5-(trifluoromethyl)benzene (500 mg, 2.9 mmol), thiomorpholine (455 mg, 4.4 mmol), Cs₂CO₃ (2.86 g, 8.8 mmol), BINAP (55 mg, 0.09 mmol) and Pd₂(dba)₃ (54 mg, 0.06 mmol) under N₂ to 1,4-dioxane (10 mL), stir the reaction under N₂ at 100° C. for 16 hrs. TLC (100% PE) shows the reaction is complete. Cool the reaction to room temperature, filter and concentrate the filtrate under reduced pressure to get crude product. Purification by chromatography (silica gel, 100% PE) affords the target compound (475 mg, 55%). MS: (M+1): 293.1.

Step 2: Synthesis of 4-[3-nitro-5-(trifluoromethyl)phenyl]-1,4-thiazinane 1,1-dioxide

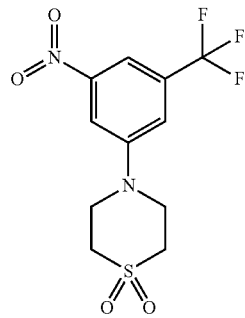 [SMILES: O=[N+]([O-])c1cc(N2CCS(=O)(=O)CC2)cc(C(F)(F)F)c1]

Dissolve the compound obtained in Step 1 (370 mg, 1.3 mmol) in DCM (30 mL), add mCPBA (655 mg, 3.8 mmol), stir the mixture at room temperature for 1 hr. Add water (20 mL), extract with DCM (20 mL×2), combine the organic layers, wash sequentially with saturated Na₂SO₃ solution (50 mL), saturated NaHCO₃ solution, brine (50 mL), dry over anhydrous Na₂SO₄. Concentrate under reduced pressure to give the crude product. Purification by chromatography (silica gel, EtOAc:PE=1:1) affords the title compound (400 mg, 97.5%). MS: (M+1): 325.2.

Step 3: Synthesis of 3-(1,1-dioxo-1,4-thiazinan-4-yl)-5-(trifluoromethyl)aniline

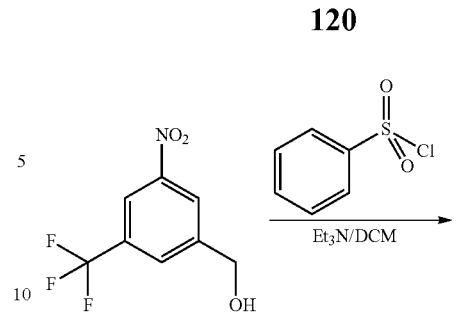

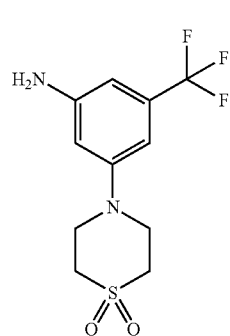 [SMILES: Nc1cc(N2CCS(=O)(=O)CC2)cc(C(F)(F)F)c1]

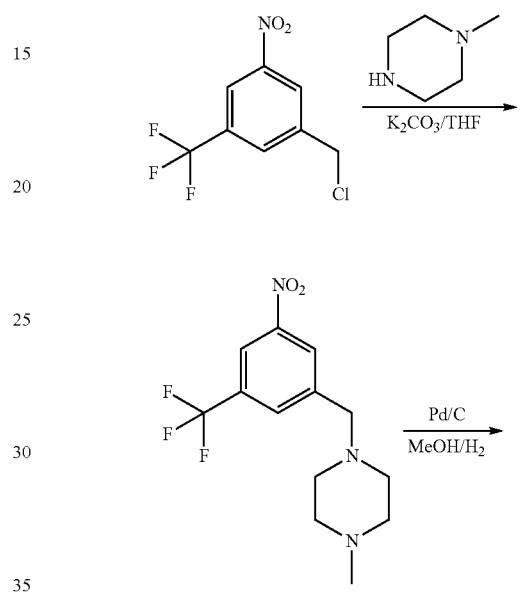

Dissolve the compound obtained in Step 2 (510 mg, 1.57 mmol) in DCM (30 mL), add Pd/C (10%, 100 mg) under N₂ atmosphere, then flush the system with H₂ and stir the reaction under H₂ atmosphere at room temperature for 15 hrs. Remove the H₂, filter the reaction mixture, and concentrate the filtrate to give the crude product (390 mg) which is used directly without further purification. MS: (M+1): 295.1.

Step 4: Synthesis of phenyl N-[3-(1,1-dioxo-1,4-thiazinan-4-yl)-5-(trifluoromethyl)phenyl]carbamate

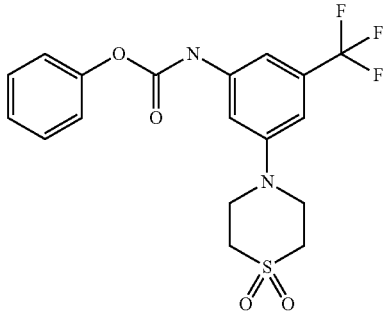 [SMILES: O=C(Nc1cc(N2CCS(=O)(=O)CC2)cc(C(F)(F)F)c1)Oc1ccccc1]

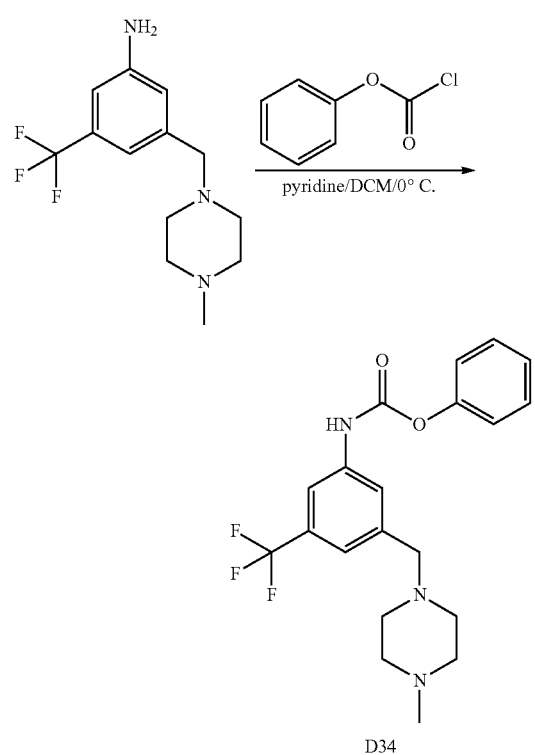

D34

Mix the compound obtained in Step 3 (390 mg, 1.33 mmol) and pyridine (262 mg, 3.31 mmol) in DCM (10 mL), cool to 0° C., add slowly phenyl chloroformate (270 mg, 1.72 mmol). After addition, stir the reaction at room temperature for 1 hr. TLC (EtOAc:PE=1:1) shows the reaction is complete. Wash the reaction mixture sequentially with 1M HCl solution (20 mL), brine (20 mL), and dry over anhydrous Na₂SO₄. Concentrate under reduced pressure to give the target product (600 mg) which is used directly without further purification. MS: (M+1): 415.1.

Step 1: Synthesis of 1-(chloromethyl)-3-nitro-5-(trifluoromethyl)benzene

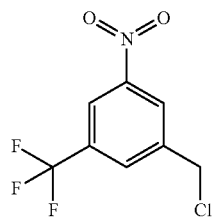 [SMILES: O=[N+]([O-])c1cc(CCl)cc(C(F)(F)F)c1]

Dissolve [3-nitro-5-(trifluoromethyl)phenyl]methanol (1.1 g, 5.18 mmol) and triethylamine (1.62 mL) in DCM (20 mL), cool to 0° C., add slowly p-toluenesulfonyl chloride (1.1 g, 6.02 mmol). After the addition, stir the reaction at room temperature for 15 hrs. TLC (EtOAc:PE=1:15) shows the reaction is complete. Concentrate under reduced pressure to get the crude product. Purification by chromatography (silica gel, EtOAc:PE=1:15) affords the title compound (655 mg, 55%).

Step 2: Synthesis of 1-methyl-4-[[3-nitro-5-(trifluoromethyl)phenyl]methyl]piperazine

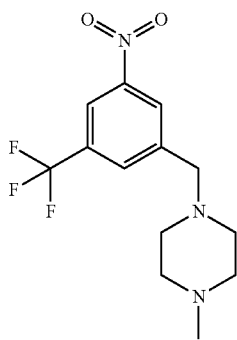 [SMILES: CN1CCN(Cc2cc([N+](=O)[O-])cc(C(F)(F)F)c2)CC1]

Mix the compound obtained in Step 1 (640 mg, 2.68 mmol) and 1-methylpiperazine (536 mg, 5.36 mmol) in THF (8 mL). Stir the reaction at 60° C. for 2 hrs. TLC (EtOAc:PE=1:10 shows the reaction is complete. Concentrate under reduced pressure to get the title compound (812 mg, 100%). MS: (M+1): 303.1.

Step 3: Synthesis of 3-[(4-methylpinerazin-1-yl)methyl]-5-(trifluoromethyl)aniline

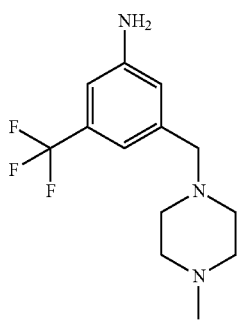 [SMILES: CN1CCN(Cc2cc(N)cc(C(F)(F)F)c2)CC1]

Dissolve the nitro compound obtained in Step 2 (812 mg, 2.68 mmol) in methanol (15 mL), add Pd/C (10%, 200 mg) under $N_2$ atmosphere. Flush the system with $H_2$ and stir the action under $H_2$ atmosphere at room temperature for 16 hrs. Remove the $H_2$, filter off the solid, concentrate the filtrate to get the crude product (732 mg, 100%). MS: (M+1): 273.1.

Step 4: Synthesis of phenyl N-[3-[(4-methylpiperazin-1-yl)methyl]-5-(trifluoromethyl)phenyl]carbamate

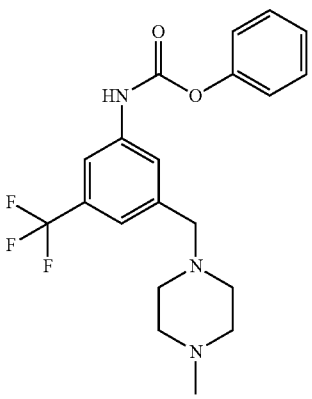 [SMILES: CN1CCN(Cc2cc(NC(=O)Oc3ccccc3)cc(C(F)(F)F)c2)CC1]

Dissolve the amine obtained in Step 3 (732 mg, 2.68 mmol) and pyridine (423 mg, 3.52 mmol) in DCM (10 mL), cool to 0° C., add slowly phenyl chloroformate (460 mg, 2.9 mmol). After addition, stir the reaction at room temperature for 2 hrs. TLC (EtOAc:PE=4:1) shows the reaction is complete. Add water, separate the organic layer, and extract the aqueous layer with DCM. Combine the organic layers, wash sequentially with 1M HCl solution, brine, dry over anhydrous $Na_2SO_4$. Concentrate under reduced pressure to give the crude product. Purification by chromatography (silica gel, EtOAc:PE=4;1) affords the target compound (380 mg, 36%). MS: (M+1): 393.

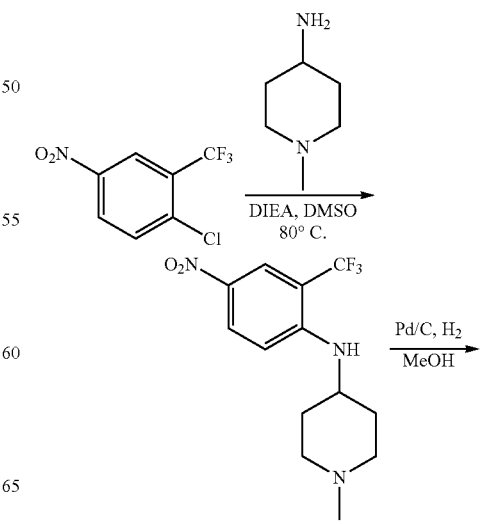

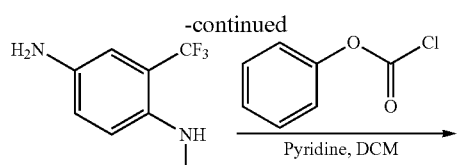

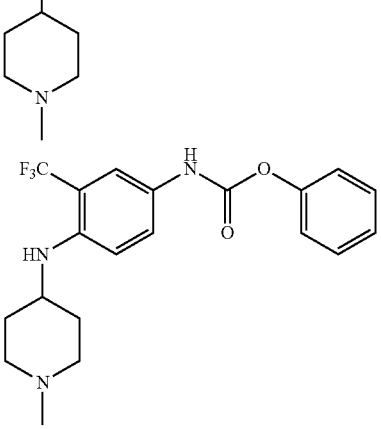

D35

Step 1: Synthesis of 1-methyl-N-[4-nitro-2-(trifluoromethyl)phenyl]piperidin-4-amine

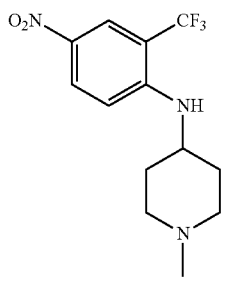 [SMILES: CN1CCC(Nc2ccc([N+](=O)[O-])cc2C(F)(F)F)CC1]

Dissolve 1-chloro-4-nitro-2-(trifluoromethyl)benzene (1.0 g, 4.44 mmol) in DMSO (5 mL), add 1-methylpiperidin-4-amine (0.56 g, 4.89 mmol) and DIEA (1.72 g, 13.3 mmol) and stir the reaction at 80° C. overnight. TLC (DCM:MeOH=10:1) shows the reaction is complete. Add water, extract with EtOAc (10 mL×3), combine the organic layers, wash with water and brine sequentially, and dry over anhydrous Na$_2$SO$_4$. Concentrate under reduced pressure to get the crude product. Purification by chromatography (silica gel, MeOH:DCM=1:15) affords the title compound (587 mg, 44%). MS: (M+1): 304.2.

Step 2: Synthesis of N1-(1-methyl-4-piperidyl)-2-(trifluoromethyl)benzene-1,4-diamine

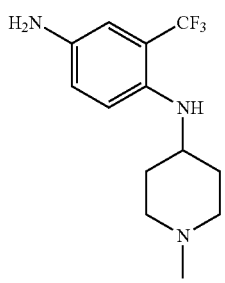

Dissolve the nitro compound obtained in Step 1 (587 mg, 1.94 mmol) in methanol (10 mL), add Pd/C (10%, 176 mg).

Flush the system with H$_2$. Stir the reaction under H$_2$ atmosphere at room temperature overnight. TLC (DCM:MeOH=5:1) shows the reaction is complete. Filter off the solid, concentrate the filtrate under reduced pressure to give a crude residue. Purification by chromatography (silica gel, MeOH:DCM=1:10) affords the product (300 mg, 57%). MS: (M+1) 274.2.

Step 3: Use the same procedure used for D1 to get the product: MS: (M+1): 394.2.

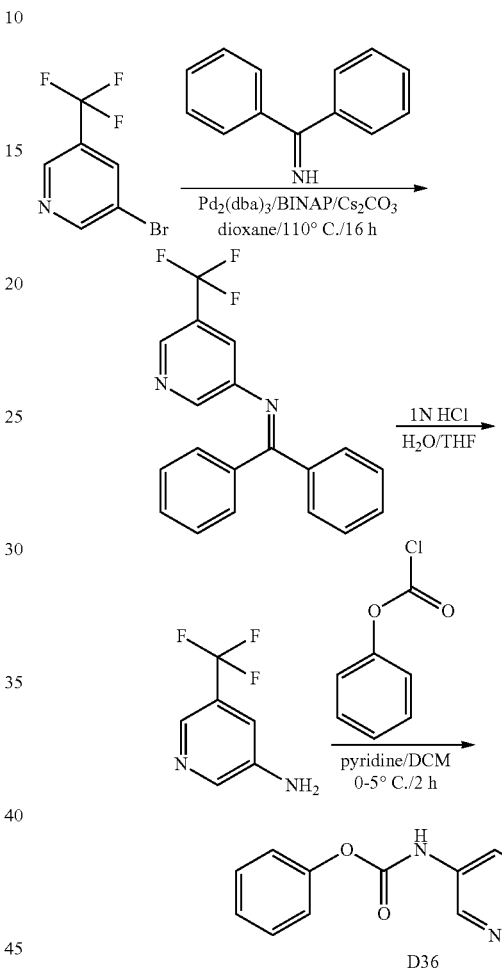

D36

Step 1: Synthesis of 1,1-diphenyl-N-[5-(trifluoromethyl)-3-pyridyl]methanimine

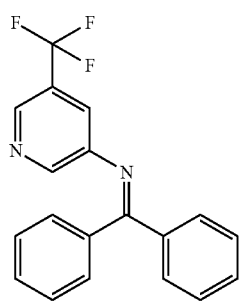 [SMILES: FC(F)(F)c1cncc(N=C(c2ccccc2)c2ccccc2)c1]

Add 3-bromo-5-(trifluoromethyl)pyridine (600 mg, 2.67 mmol), benzophenone imine (701 mg, 4.0 mmol), Cs$_2$CO$_3$ (2.17 g, 6.68 mmol), BINAP (25 mg, 0.040 mmol), Pd$_2$(dba)$_3$ (24 mg, 0.027 mmol) in 1,4-dioxane (10 mL), stir at 110° C. for 16 hrs. Cool to room temperature, add water (100 mL), extract with EtOAc (15 mL×3), wash the combined organic layers with brine, dry over anhydrous Na$_2$SO$_4$, concentrate under reduced pressure to give the crude product. Purification by chromatography (silica gel, EtOAc:PE=6:94) affords the target compound (850 mg, 98%).

Step 2: Synthesis of
5-(trifluoromethyl)pyridin-3-amine

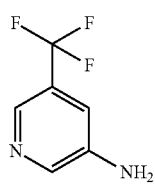

Dissolve the imine obtained in Step 1 (850 mg, 2.6 mmol) in THF (10 mL), add water (2 mL), 1N HCl solution (5 mL), stir the reaction at room temperature for 2 hrs. After the reaction, extract with EtOAc, wash the organic layer with saturated NaHCO$_3$ solution and brine sequentially, dry over anhydrous Na$_2$SO$_4$, and concentrate under reduced pressure to give the crude product. Purification by chromatography (silica gel, EtOAc:PE=1:1) affords the target compound (380 mg, 90%).

Step 3: Synthesis of phenyl
N-[5-(trifluoromethyl)-3-pyridyl]carbamate

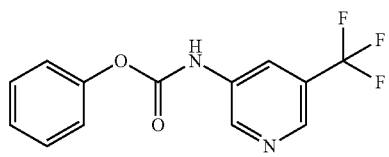 [SMILES: O=C(Nc1cncc(C(F)(F)F)c1)Oc1ccccc1]

Dissolve the amine obtained in Step 2 (380 mg, 2.35 mmol), pyridine (371 mg, 4.7 mmol) in DCM (8 mL), cool to 0° C. in ice bath. Add slowly phenyl chloroformate (403 mg, 2.35 mmol). After addition, stir the reaction at 0-5° C. for 2 hrs. Pour the mixture into water (50 mL), adjust pH to neutral with 1M HCl solution, extract with EtOAc (15 mL×3). Combine the organic layers; wash with brine (100 mL), dry over anhydrous Na$_2$SO$_4$, and concentrate under reduced pressure to get the crude product. Purification by chromatography (silica gel, EtOAc:PE=15:85) affords the target compound (390 mg, 59%).

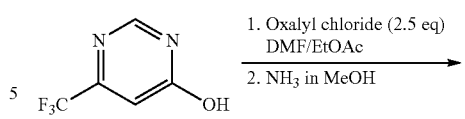

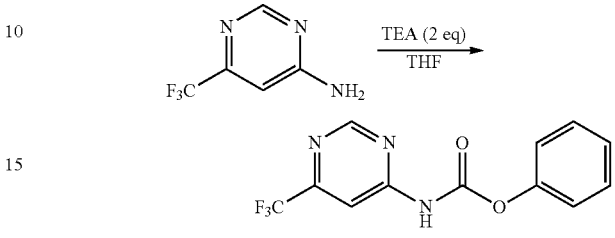

D37

Step 1: Synthesis of
6-(trifluoromethyl)pyrimidin-4-amine

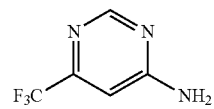

Add 6-(trifluoromethyl)pyrimidin-4-ol (1.5 g, 9.15 mmol) and oxalyl chloride (2.3 mL, 22.9 mmol) to EtOAc (15 mL), then add 5 drops of DMF. Heat the mixture to reflux for 2 hrs. After reaction, partition between EtOAc and brine, separate the organic layer; dry the organic layer over anhydrous Na$_2$SO$_4$. Transfer the organic solution to a sealed tube, add a solution of NH$_3$ in methanol (7M, 10 mL), seal the tube, heat at 70° C. for 15 hrs. Cool to room temperature; concentrate under reduced pressure to get the crude product. Purification by chromatography (silica gel, EtOAc:PE=2:1) affords the target compound (920 mg, 61.3%).

Step 2: Synthesis of phenyl
N-[6-(trifluoromethyl)pyrimidin-4-yl]carbamate

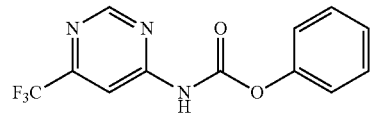 [SMILES: O=C(Nc1cc(C(F)(F)F)ncn1)Oc1ccccc1]

Add the amine obtained in Step 1 (550 mg, 3.37 mmol), Et$_3$N (680 mg, 6.74 mmol) to THF (10 mL), cool to 0° C. on ice bath. Add slowly a solution of phenyl chloroformate (789 mg, 5.06 mmol) in THF. After addition, stir the reaction on ice bath for 20 hrs. Remove the volatiles under reduced pressure. Purification by chromatography (silica gel, EtOAc:PE=1:3) affords the target compound (160 mg, 17%). MS: (M+1): 284.1.

Data on intermediates D32-37 are summarized in Table D7.

TABLE D7
Intermediates D31-D37
| Number | Starting material | Intermediate | MS [M + 1]+ |
|---|---|---|---|
| D32 | 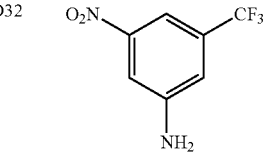 | 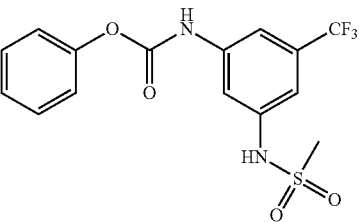 [SMILES: CS(=O)(=O)Nc1cc(NC(=O)Oc2ccccc2)cc(C(F)(F)F)c1] | NA |
| D33 | 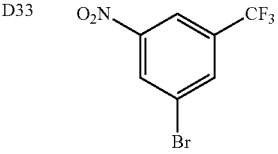 | 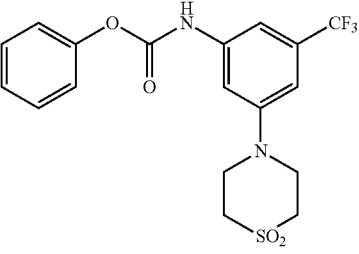 [SMILES: O=C(Nc1cc(N2CCS(=O)(=O)CC2)cc(C(F)(F)F)c1)Oc1ccccc1] | 415.1 |
| D34 | 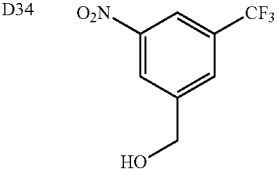 | 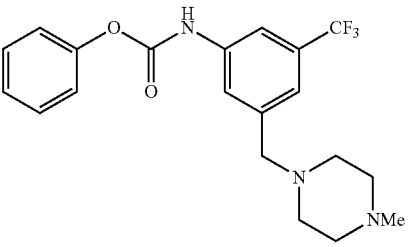 [SMILES: CN1CCN(Cc2cc(NC(=O)Oc3ccccc3)cc(C(F)(F)F)c2)CC1] | 394.2 |
| D35 | 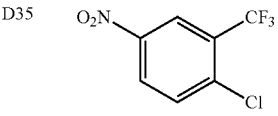 | 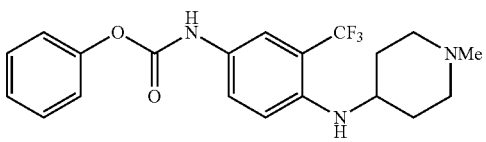 [SMILES: CN1CCC(Nc2ccc(NC(=O)Oc3ccccc3)cc2C(F)(F)F)CC1] | 394.2 |
| D36 | 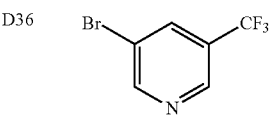 | 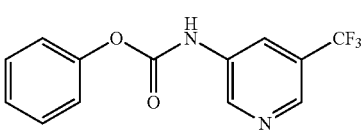 [SMILES: O=C(Nc1cncc(C(F)(F)F)c1)Oc1ccccc1] | 283.1 |
| D37 | 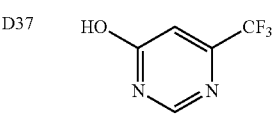 | 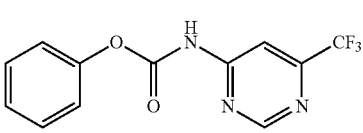 [SMILES: O=C(Nc1cc(C(F)(F)F)ncn1)Oc1ccccc1] | 284.1 |

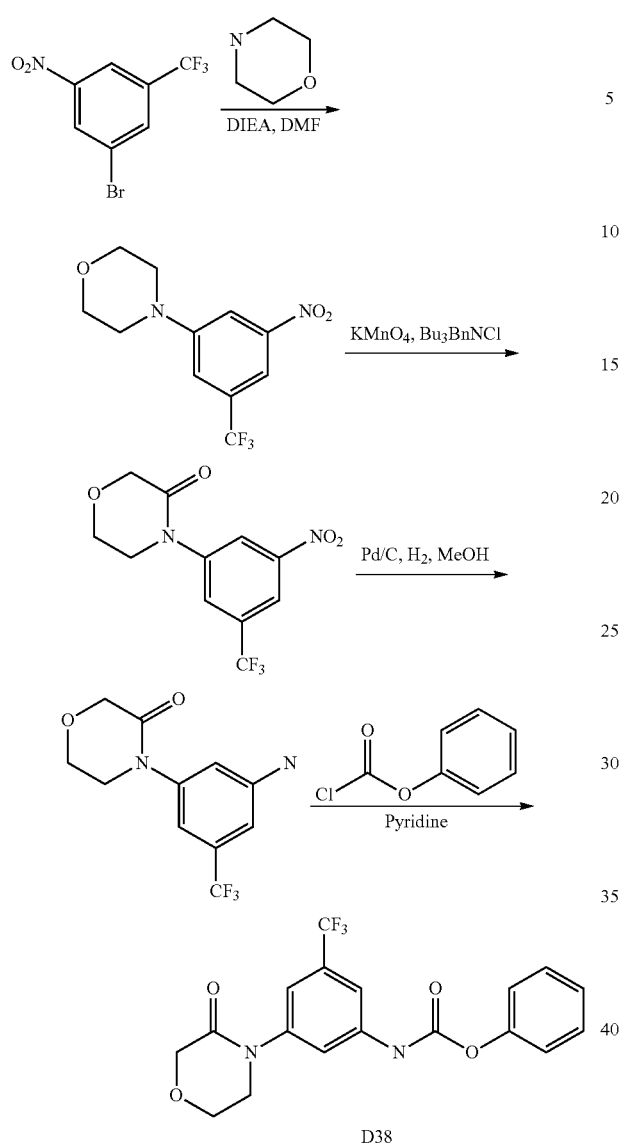

Step 1: Synthesis of
4-[3-nitro-5-(trifluoromethyl)phenyl]morpholine

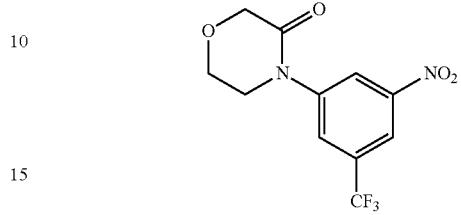

Dissolve 1-bromo-3-nitro-5-(trifluoromethyl)benzene (270 mg, 1 mmol) and DIEA (258 mg, 2 mmol) in DMF (5 mL), add morpholine (174 mg, 2 mmol). Stir the reaction at 120° C. overnight. Cool to room temperature; remove the volatiles under reduced pressure to give a crude residue. Purification of the residue by chromatography (silica gel, EtOAc: PE=1:5) affords the product (138 mg, 50%).

Step 2: Synthesis of 4-[3-nitro-5-(trifluoromethyl) phenyl]morpholin-3-one

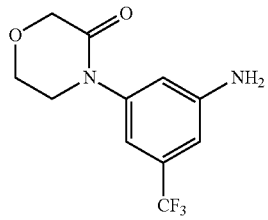 [SMILES: O=C1COCCN1c1cc([N+](=O)[O-])cc(C(F)(F)F)c1]

Dissolve the nitro compound obtained in Step 1 (276 mg, 1 mmol) and $Bu_3BnNCl$ (1.67 g, 6 mmol) in DCM (20 mL). Add $KMnO_4$ portionwise (948 mg, 6 mmol). Stir the mixture at 70° C. overnight. Cool to room temperature; remove the volatiles under reduced pressure to give a residue. Purification of the residue by chromatography (silica gel, EtOAc: PE=1:5) affords the product (64 mg, 22%).

Step 3: Synthesis of 4-[3-amino-5-(trifluoromethyl) phenyl]morpholin-3-one

Dissolve the nitro compound obtained in Step 2 (290 mg, 1 mmol) in methanol (5 mL), add Pd/C (10%, 29 mg), flush with $H_2$, and then stir at room temperature under 1 atm $H_2$ atmosphere for 12 hrs. After the reaction, remove the $H_2$, filter off the solid, concentrate the filtrate to give the crude product. Purification by chromatography (silica gel, EtOAc:PE=1:3) affords the product (221 mg, 85%). MS: (M+1): 261.

Step 4: Synthesis of phenyl N-[3-(3-oxomorpholin-4-yl)-5-(trifluoromethyl)phenyl]carbamate

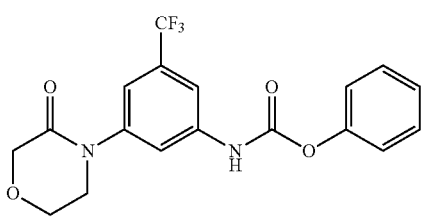 [SMILES: O=C(Nc1cc(N2CCOCC2=O)cc(C(F)(F)F)c1)Oc1ccccc1]

Dissolve the amine obtained in Step 3 (260 mg, 1 mmol) and pyridine (79 mg, 1 mmol) in DCM (2 mL), cool to 0° C. Add phenyl chloroformate (156 mg, 1 mmol), then stir at room temperature for 2 hrs. Concentrate under reduced pressure to give the crude product. Purification by chromatography (silica gel, EtOAc:PE=1:5) affords the product (300 mg, 79%). MS: (M+1): 381.1.

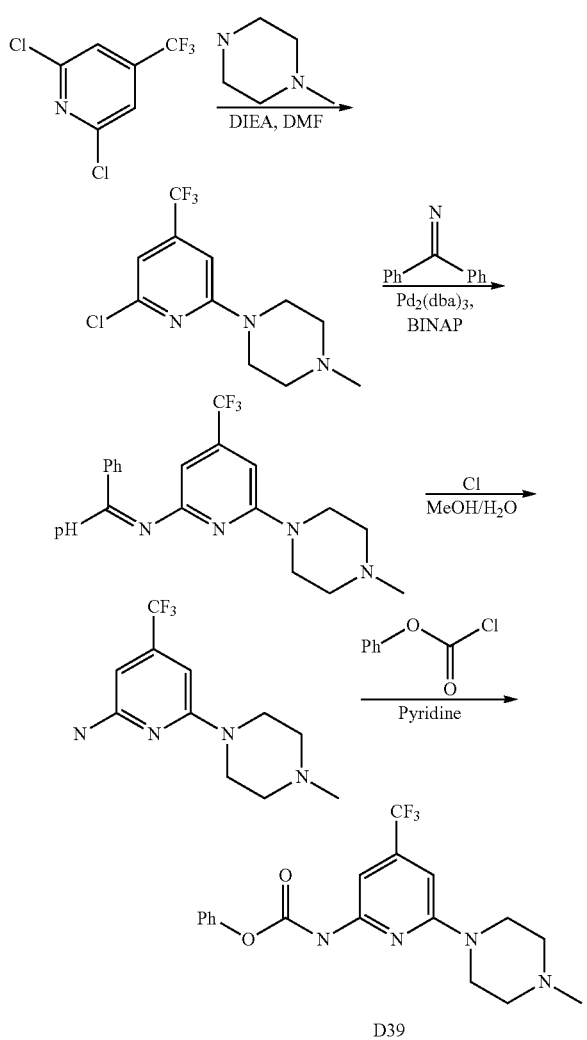

Step 1: Synthesis of 1-[6-chloro-4-(trifluoromethyl)-2-pyridyl]-4-methyl-piperazine

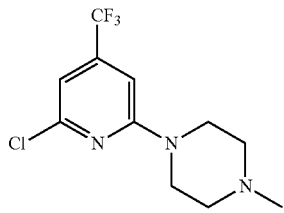 [SMILES: CN1CCN(c2cc(C(F)(F)F)cc(Cl)n2)CC1]

Dissolve 2,6-dichloro-4-(trifluoromethyl)pyridine (215 mg, 1 mmol) and DIEA (129 mg, 1 mmol) in DMF (2 mL), add 1-methyl piperazine (100 mg, 1 mmol). Stir the reaction at 120° C. overnight. Cool to room temperature; concentrate under reduced pressure to give the crude product. Purification by chromatography (silica gel, MeOH:DCM=1:10) affords the product (253 mg, 91%). MS: (M+1): 280.

Step 2: Synthesis of N-[6-(4-methylpiperazin-1-yl)-4-(trifluoromethyl)-2-pyridyl]-1,1-diphenyl-methanimine

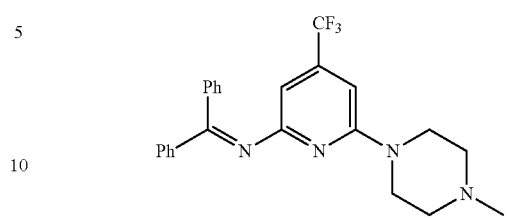

Dissolve the compound obtained in Step 1 (279 mg, 1 mmol) in 1,4-dioxane (4 mL), add benzophenone imine (181 mg, 1 mmol), DIEA (181 mg, 1 mmol), $Cs_2CO_3$ (650 mg, 2 mmol), $Pd_2(dba)_3$ (18 mg, 0.02 mmol) and BINAP (18 mg, 0.03 mmol). Stir the reaction at 100° C. overnight. Cool to room temperature; filter off the solid, concentrate the filtrate under reduced pressure to give a crude product. Purification by chromatography (silica gel, MeOH:DCM=1;10) affords the product (200 mg, 91%). MS: (M+1): 425.

Step 3: Synthesis of 6-(4-methylpiperazin-1-yl)-4-(trifluoromethyl)pyridin-2-amine

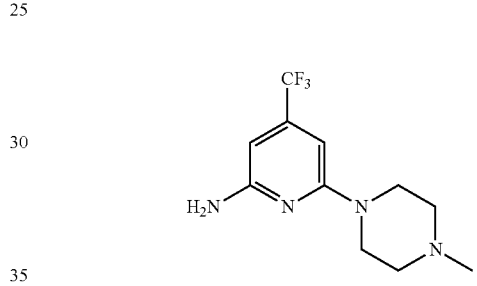

Suspend the imine obtained in Step 2 (424 mg, 1 mmol) in methanol and water (1:1, 2 mL), add aqueous HCl (1N, 2 mL), stir the reaction at room temperature for 1 hr. After the reaction, extract with EtOAc, discard the organic layer. Adjust the aqueous layer with NaOH solution to pH-10, extract with EtOAc, wash the organic layer with water, brine sequentially, and dry over anhydrous $Na_2SO_4$. Concentrate under reduced pressure to get the product (200 mg, 77%). MS: (M+1): 261.

Step 4: Synthesis of phenyl N-[6-(4-methylpiperazin-1-yl)-4-(trifluoromethyl)-2-pyridyl]carbamate

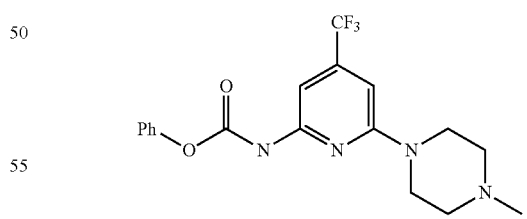

Dissolve the amine obtained in Step 3 (260 mg, 1 mmol) and pyridine (79 mg, 1 mmol) in DCM (2 mL), cool to 0° C. and add dropwise phenyl chloroformate (156 mg, 1 mmol). After addition, stir the reaction at room temperature for 2 hrs. Concentrate under reduced pressure to give a crude product. Purification by chromatography (silica gel, EtOAc:PE=1:1) affords the product (300 mg, 79%). MS: (M+1): 381.

Intermediates D38-D41 can be synthesized with similar method (Table D8).

TABLE D8

Intermediates D38-D41

| Number | Starting material | Intermediate | MS [M + 1]⁺ |
|---|---|---|---|
| D38 | 3-bromo-5-nitro-(trifluoromethyl)benzene | phenyl carbamate with morpholin-3-one | 381.1 |
| D39 | 2,6-dichloro-4-(trifluoromethyl)pyridine | phenyl carbamate with N-methylpiperazine | 381 |
| D40 | 2,6-dichloro-4-(trifluoromethyl)pyridine | phenyl carbamate with N-methylpiperidin-4-ylamine | 395.1 |
| D41 | 2,6-dichloro-4-(trifluoromethyl)pyridine | phenyl carbamate with morpholine | 368.1 |

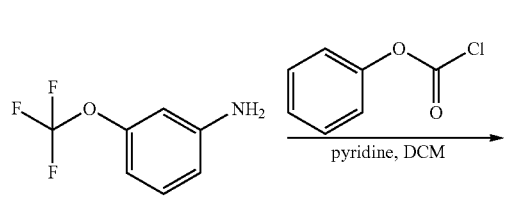

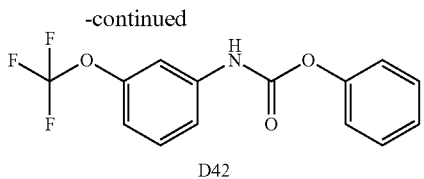

D42

Step 1: Synthesis of phenyl N-[3-(trifluoromethoxy)phenyl]carbamate

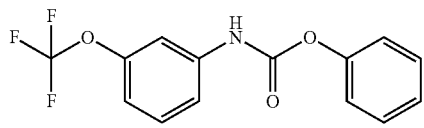 [SMILES: O=C(Nc1cccc(OC(F)(F)F)c1)Oc1ccccc1]

Add 3-(trifluoromethoxy)aniline (1.0 g, 5.65 mmol), pyridine (0.89 g, 11.3 mmol) to DCM (20 mL) and cool to 0° C. Add dropwise phenyl chloroformate (1.15 g, 7.34 mmol). After addition, stir for 1 hr. TLC (PE:EtOAc=3:1) shows the reaction is complete. Add water to the mixture, extract with DCM (10 mL×3), combine the organic layer, wash with 1N HCl solution, brine sequentially, and dry over anhydrous Na$_2$SO$_4$. Concentrate under reduced pressure to get the product (1.50 g, 89%).

Intermediates D42-D46 can be synthesized with similar method (Table D9)

-continued

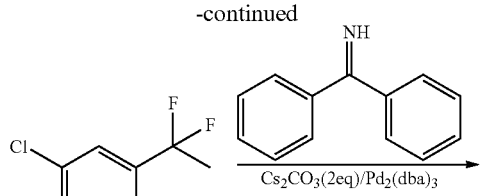

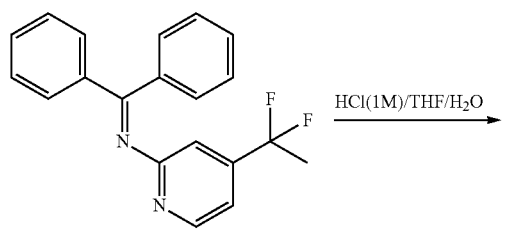

TABLE D9

Intermediates D42-D46

| Number | Starting material | Intermediate | MS [M + 1]$^+$ |
|---|---|---|---|
| D42 | H$_2$N–⌬–OCF$_3$ | PhO-C(O)-NH–⌬–OCF$_3$ | 298.1 |
| D43 | H$_2$N–⌬(F)–OCF$_3$ | PhO-C(O)-NH–⌬(F)–OCF$_3$ | 316.1 |
| D44 | H$_2$N–⌬–OCF$_3$, F | PhO-C(O)-NH–⌬–OCF$_3$, F | NA |
| D45 | H$_2$N–⌬–OCF$_3$, Cl | PhO-C(O)-NH–⌬–OCF$_3$, Cl | 332.1 |
| D46 | H$_2$N–⌬–OCF$_3$ | PhO-C(O)-NH–⌬–OCF$_3$ | NA |

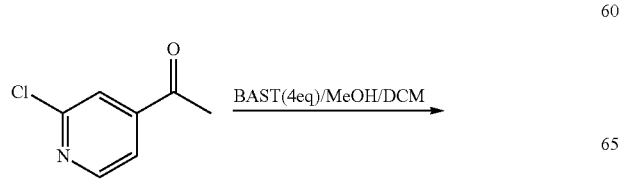

-continued

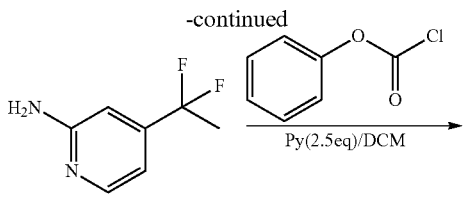

-continued

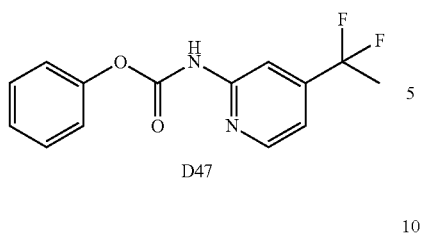

D47

Step 1: Synthesis of
2-chloro-4-(1,1-difluoroethyl)pyridine

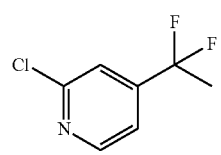

Mix 1-(2-chloro-4-pyridyl)ethanone (2 g, 12.90 mmol), DCM (2 mL) and bis-(2-methoxyethyl)aminosulfur trifluoride (BAST, 11.7 g, 51.6 mmol) in an unsealed tube, add 1 drop of methanol. Seal the tube and heat at 60° C. for 15 hrs. Cool to room temperature, add DCM to dilute the mixture, basicify with NaOH solution, pour into water (100 mL), extract with DCM (100 mL×2), combine the organic layers, dry over anhydrous $Na_2SO_4$. Concentrate under reduced pressure to get a crude residue. Purification by chromatography (silica gel, EtOAc:PE=1:3) affords the target compound (1.5 g, 65.7%).

Step 2: Synthesis of N-[4-(1,1-difluoroethyl)-2-pyridyl]-1,1-diphenyl-methanimine

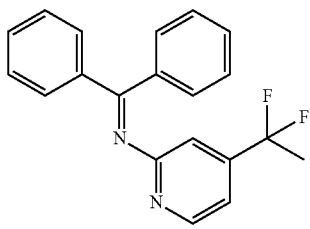 [SMILES: CC(F)(F)c1ccnc(N=C(c2ccccc2)c2ccccc2)c1]

Add the compound obtained in Step 1 (1.21 g, 6.81 mmol), benzophenone imine (1.83 g, 10.22 mmol), $Cs_2CO_3$ (4.43 g, 13.6 mmol) to 1,4-dioxane (15 mL), then under $N_2$, add BINAP (635 mg, 1.02 mmol), $Pd_2(dba)_3$ (623 mg, 0.68 mmol), stir the reaction at 120° C. under $N_2$ atmosphere for 15 hrs. Cool to room temperature; filter off the solid, concentrate the filtrate under reduced pressure to give a crude residue. Purification by chromatography (silica gel, EtOAc:PE=1:3) affords the target compound (1.68 g, 76.3%). MS: (M+1): 323.2.

Step 3: Synthesis of
4-(1,1-difluoroethyl)pyridin-2-amine

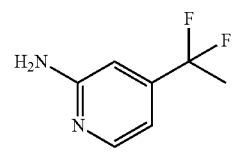

Dissolve the imine obtained in Step 2 (1.68 g, 5.22 mmol) in THF (10 mL), add 1M HCl solution (10 mL), stir the reaction at room temperature for 1 hr. Use saturated $NaHCO_3$ solution to adjust pH>7. Extract with EtOAc (50 mL×2), combine the organic layers, dry over anhydrous $Na_2SO_4$, concentrate to give the crude product. Purification by chromatography (silica gel, EtOAc:PE=1:3) affords the target compound (624 mg, 75.7%). MS: (M+1): 159.1.

Step 4: Synthesis of phenyl
N-[4-(1,1-difluoroethyl)-2-pyridyl]carbamate

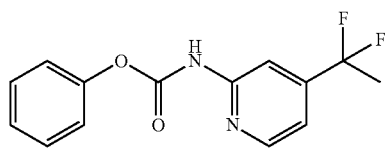 [SMILES: CC(F)(F)c1ccnc(NC(=O)Oc2ccccc2)c1]

Add the amine obtained in Step 3 (624 mg, 3.95 mmol), pyridine (780 mg, 9.85 mmol) in DCM (15 mL), cool to 0° C. on ice bath. Add slowly a solution of phenyl chloroformate (678 mg, 4.34 mmol) in DCM. After addition, stir on ice bath for 1 hr. Concentrate the mixture to get a crude residue. Purification by chromatography (silica gel, EtOAc:PE=1:3) affords the target compound (780 mg, 71%). MS: (M+1): 279.1.

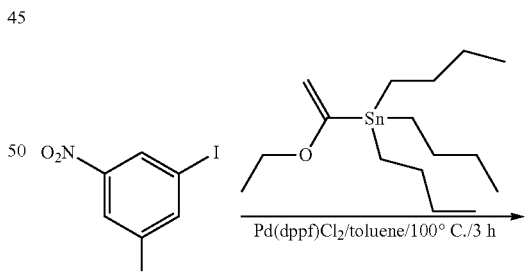

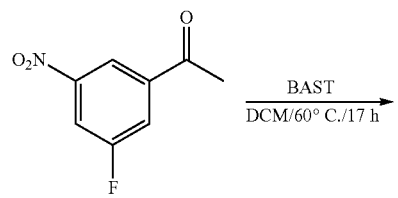

-continued

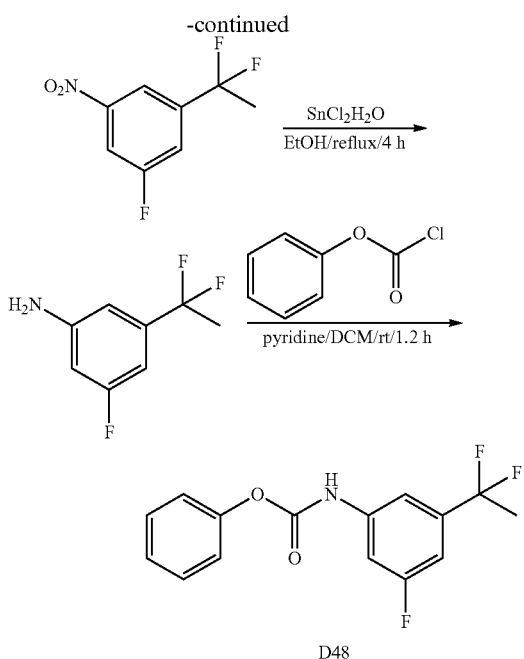

D48

Step 1: 1-(3-fluoro-5-nitro-phenyl)ethanone

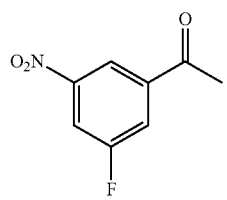

Mix 1-fluoro-3-iodo-5-nitro-benzene (1 g, 3.75 mmol), tributyl(1-ethoxyvinyl)stannane (1.5 g, 4.15 mmol) and Pd(dppf)Cl$_2$ (78 mg, 0.1 mmol) in toluene (5 mL) under N$_2$. Stir at 100° C. under N$_2$ atmosphere for 3 hrs. Cool to room temperature, add 1N HCl solution (5 mL) and stir for 20 min. Load directly onto silica gel column and purify by chromatography (EtOAc:PE=3:7) to give the title compound (660 mg, 96%).

Step 2: Synthesis of 1-(1,1-difluoroethyl)-3-fluoro-5-nitro-benzene

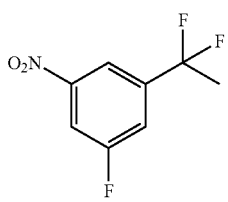

In an unsealed tube, add the compound obtained in Step 1 (660 mg, 3.6 mmol), bis-(2-methoxyethyl)aminosulfur trifluoride (BAST, 3.2 g, 14.5 mmol) and DCM (8 mL), seal the tube, heat at 60° C. with stirring overnight. Cool the reaction mixture, purify by chromatography (silica gel, 100% PE) to give the title compound (500 mg, 67.6%).

Step 3: Synthesis of 3-(1,1-difluoroethyl)-5-fluoro-aniline

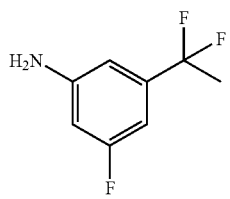

Add the nitro compound obtained in Step 2 (500 mg, 2.44 mmol) and SnCl$_2$.2H$_2$O (2.6 g, 11.5 mmol) in ethanol (20 mL), heat to reflux for 4 hrs. TLC (100% PE) shows the reaction is complete. Cool to room temperature, basicify to pH-10-12 with NaOH solution to get a suspension. Filter off the white solid, partition the filtrate between DCM and water. Collect the organic layer, dry over anhydrous Na$_2$SO$_4$, concentrate to get the crude product. Purification by chromatography (silica gel, PE:EtOAc=70:30) affords the title compound (350 mg, 82%). MS: (M+1): 176.

Step 4: Synthesis of phenyl N-[3-(1,1-difluoroethyl)-5-fluoro-phenyl]carbamate

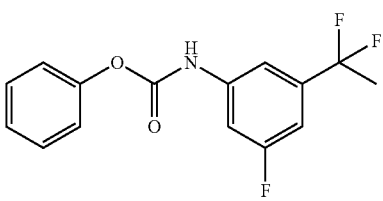 [SMILES: CC(F)(F)c1cc(F)cc(NC(=O)Oc2ccccc2)c1]

Dissolve the amine obtained in Step 3 (350 mg, 2.0 mmol) in DCM (8 mL), add pyridine (395 mg, 5 mmol), cool to 0-5° C. on ice bath. Add dropwise a solution of phenyl chloroformate (406.7 mg, 2.6 mmol) in DCM (1 mL). Stir the reaction at room temperature for 1.5 hrs. Quench the reaction with water (5 mL), collect the organic layer, wash the organic layer with 1N HCl solution, then saturated NaHCO$_3$ solution and brine sequentially. Dry the organic layer over anhydrous Na$_2$SO$_4$; concentrate under reduced pressure to give the crude product (400 mg, 80% pure) which is used without further purification. MS: (M+1): 296.

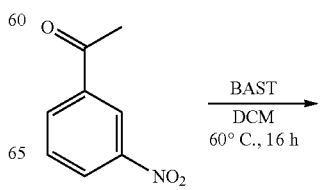

141

-continued

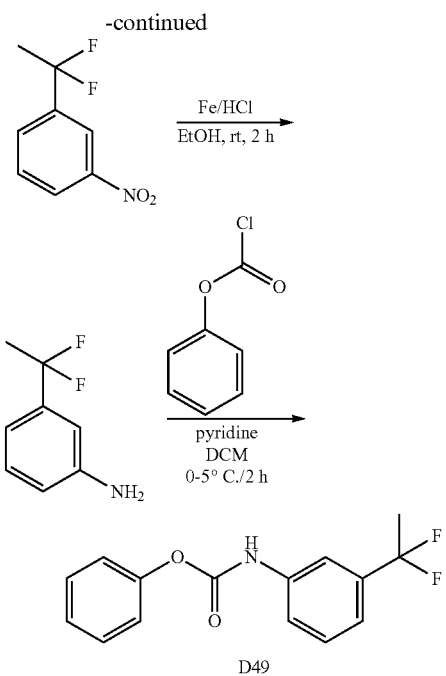

Step 1: Synthesis of
1-(1,1-difluoroethyl)-3-nitro-benzene

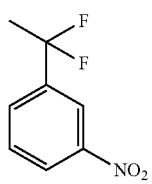

Dissolve 1-(3-nitrophenyl)ethanone (1 g, 6.1 mmol) in DCM (10 mL) in an unsealed tube, add dropwise bis-(2-methoxyethyl)aminosulfur trifluoride (BAST, 5.4 g, 24.2 mmol) and one drop of methanol, seal the tube and heat at 60° C. for 16 hrs. Cool to room temperature, pour the mixture to ice water (50 mL), neutralize with saturated NaHCO₃ solution. Extract with EtOAc (15 mL×3), combine the organic layers; wash with brine (100 mL), dry over anhydrous Na₂SO₄, concentrate to give a crude residue. Purification by chromatography (silica gel, PE:EtOAc=99:1) affords the target compound (970 mg, 85%).

Step 2: Synthesis of 3-(1,1-difluoroethyl)aniline

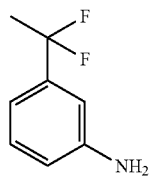

Dissolve the nitro compound obtained in Step 1 (870 mg, 4.8 mmol) in ethanol (10 mL), add iron powder (1.3 g, 23.3 mmol), concentrated aqueous HCl (37%, 2.7 mL), stir the reaction at room temperature for 2 hrs. After the reaction, carefully neutralize the mixture with NaOH solution. Filter off the solid, pour the filtrate to ice water (50 mL), extract with EtOAc (15 mL×3), combine the organic layers, wash with brine (100 mL) and dry over anhydrous Na₂SO₄. Concentrate under reduced pressure to get the crude product (760 mg) which is used without further purification.

Step 3: Synthesis of phenyl
N-[3-(1,1-difluoroethyl)phenyl]carbamate

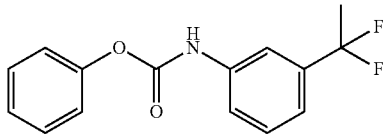 [SMILES: CC(F)(F)c1cccc(NC(=O)Oc2ccccc2)c1]

Dissolve the amine obtained in Step 2 (760 mg, 4.8 mmol) and pyridine (765 mg, 9.7 mmol) in DCM (15 mL) and cool to 0-5° C. on ice bath. Add dropwise phenyl chloroformate (831 mg, 5.3 mmol). After addition, stir the mixture at 0-5° C. for 2 hrs. Pour the mixture to water (50 mL), adjust pH to neutral with 1M HCl solution. Extract with EtOAc (15 mL×3), combine the organic layers and wash with brine (100 mL), dry over anhydrous Na₂SO₄. Concentrate under reduced pressure to give the crude product (1.15 g) which is used without further purification.

Intermediates D50-D52 can be synthesized with similar method (Table D10).

TABLE D10

| Intermediates D47-D52 | | | |
|---|---|---|---|
| Number | Starting Material | Intermediate | MS [M + 1]⁺ |
| D47 | | | 279.1 |

TABLE D10-continued

Intermediates D47-D52

| Number | Starting Material | Intermediate | MS [M + 1]+ |
|---|---|---|---|
| D48 | O₂N-C₆H₃(I)(F) | phenyl N-(3-fluoro-5-(trifluoromethyl)... carbamate analog | 296.2 |
| D49 | O₂N-C₆H₄-C(=O)CH₃ | phenyl carbamate with CF₂ group | 278.1 |
| D50 | O₂N-C₆H₃(F)-C(=O)CH₃ | phenyl carbamate, F-substituted | 296.1 |
| D51 | O₂N-C₆H₃(Cl)-C(=O)CH₃ | phenyl carbamate, Cl-substituted | 312.1 |
| D52 | O₂N-C₆H₃(F)-C(=O)CH₃ | phenyl carbamate, F-substituted | 296.1 |

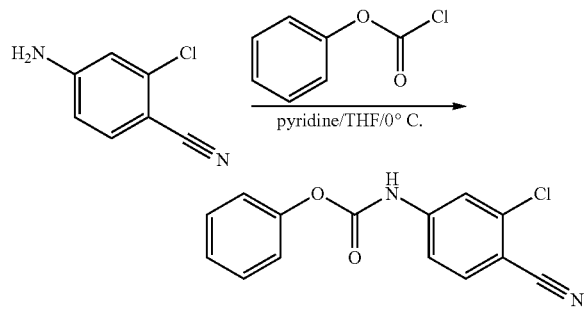

Step 1: Synthesis of phenyl N-(3-chloro-4-cyano-phenyl)carbamate

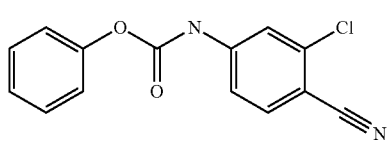 [SMILES: N#Cc1ccc(NC(=O)Oc2ccccc2)cc1Cl]

Dissolve 4-amino-2-chloro-benzonitrile (500 mg, 3.3 mmol) and pyridine (518 mg, 6.6 mmol) in THF (5 mL), cool to 0° C. and add slowly phenyl chloroformate (616 mg, 3.9 mmol). After addition, stir the reaction at room temperature for 2 hrs. TLC (EtOAc:PE=1:3) shows the reaction is complete. Add water, extract with DCM, separate the organic layer. Wash the organic layer with 1M HCl solution, brine sequentially, dry over anhydrous Na₂SO₄, and concentrate under reduced pressure to give the target compound (820 mg, 91.7%). MS: (M+1): 273.

Intermediate D54 can be synthesized with similar method (Table D11).

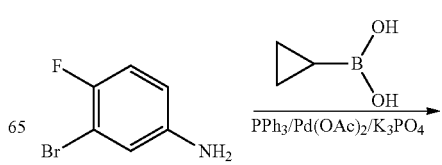

-continued

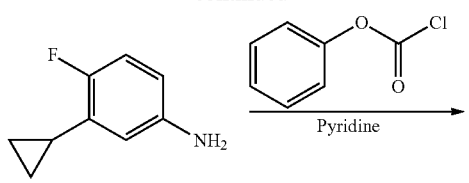

Step 1: Synthesis of 3-cyclopropyl-4-fluoro-aniline

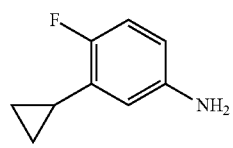 [SMILES: Nc1ccc(F)c(C2CC2)c1]

Mix 3-bromo-4-fluoro-aniline (415 mg, 2.18 mmol), cyclopropylboronic acid (244 mg, 2.84 mmol), $K_3PO_4$ (1.62 g, 7.64 mmol), triphenylphosphine (61 mg, 0.22 mmol), $Pd(OAc)_2$ (25 mg, 0.11 mmol), toluene (12 mL) and water (1 mL) under $N_2$, stir at 100° C. for 16 hrs. Cool the reaction to 25° C., add water (10 mL), extract with EtOAc (10 mL×2). Combine the organic layers; wash with brine (15 mL), dry over anhydrous $Na_2SO_4$. Concentrate under reduced pressure to give the crude product. Purification by chromatography (silica gel, PE:EtOAc=2:1) affords the target compound (200 mg, 61%).

Step 2: Synthesis of phenyl N-(3-cyclopropyl-4-fluoro-phenyl)carbamate

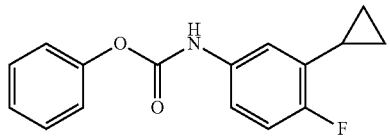 [SMILES: O=C(Nc1ccc(F)c(C2CC2)c1)Oc1ccccc1]

Add 3-cyclopropyl-4-fluoro-aniline (600 mg, 3.97 mmol), phenyl chloroformate (620 mg, 3.97 mmol) and pyridine (314 mg, 3.97 mmol) in DCM (30 mL), stir at room temperature (25° C.) for 4 hrs. After the reaction is complete, add water (15 mL), extract with EtOAc (15 mL×2), combine the organic layers, wash with 1M HCl solution (15 mL) and brine (15 mL) sequentially, dry over anhydrous $Na_2SO_4$. Concentrate under reduced pressure to give a crude product (350 mg) which is used directly without further purification.

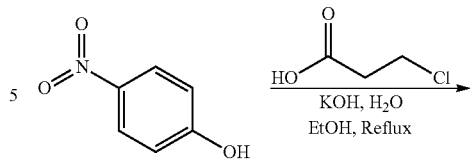

Step 1: Synthesis of 3-(4-nitrophenoxy)propanoic acid

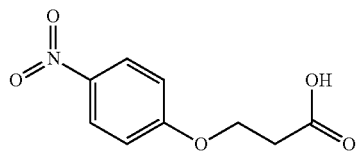 [SMILES: O=C(O)CCOc1ccc([N+](=O)[O-])cc1]

Dissolve p-nitrophenol (11 g, 100 mmol), 3-chloropropanoic acid (14 g, 100 mmol) in a mixture of ethanol (100 mL) and 20% aqueous KOH solution (100 mL). Heat to reflux for 2 hrs, then adjust pH=1-3, extract with EtOAc (300 mL×3), combine the organic layers and wash with brine (300 mL×2), dry over anhydrous $Na_2SO_4$. Concentrate under reduced pressure to give the crude product. Purification by chromatography (silica gel, EtOAc:PE=1:4) affords the title compound (7.5 g, 14.9%). MS: (M+1): 212.1.

Step 2: Synthesis of 6-nitrochroman-4-one

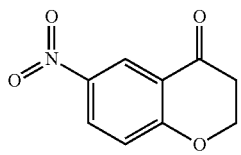 [SMILES: O=C1CCOc2ccc([N+](=O)[O-])cc21]

Mix 3-(4-nitrophenoxy)propanoic acid (6.5 g, 30 mmol) and concentrated $H_2SO_4$ (30 mL). Once dissolved, add $P_2O_5$, stir at 65° C. for 3 hrs. Cool to room temperature, pour slowly the reaction mixture to ice water (50 mL), stir for 15 min, and extract with EtOAc (100 mL×3). Combine the organic layers, wash with brine (100 mL×2), dry over anhydrous $Na_2SO_4$, concentrate to give the crude product. Purification by chromatography (silica gel, EtOAc:PE=1:1) affords the title compound (4.6 g, 77.8%). MS: (M−1): 192.2.

Step 3: Synthesis of 4,4-difluoro-6-nitro-chromane

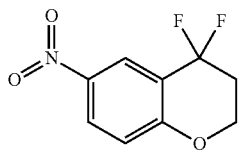 [SMILES: O=[N+]([O-])c1ccc2c(c1)C(F)(F)CCO2]

Add 6-nitrochroman-4-one (3 g, 15.7 mmol), bis-(2-methoxyethyl)aminosulfur trifluoride (Deoxo-Fluor®, BAST, 14 g, 62.8 mmol) and dry DCM (10 mL) in tube, seal the tube and heat at 50° C. for 12 hrs. Cool to room temperature, add dropwise methanol (5 mL), pour the mixture to ice water (50 mL), extract with DCM (100 mL×2), combine the organic layers, wash with brine (100 mL×2), dry over anhydrous $Na_2SO_4$. Concentrate under reduced pressure to give the crude product. Purification by chromatography (silica gel, EtOAc:PE=1:9) affords the title compound (2.6 g, 77.2%).

Step 4: Synthesis of 4,4-difluorochroman-6-amine

Dissolve 4,4-difluoro-6-nitro-chromane (2.5 g, 11.6 mmol) in methanol (100 mL), add zinc powder (2.5 g, 34.8 mmol), then add dropwise a 15.5% aqueous solution of ammonium chloride (40 mL, 139 mmol), stir at room temperature for 5 hrs. Filter off the solid, add water (50 mL) to the filtrate, extract with EtOAc (50 mL×2). Combine the organic layers, wash with brine (50 mL×2), dry over anhydrous $Na_2SO_4$. Concentrate under reduced pressure to get a crude residue. Purification by chromatography (silica gel, EtOAc:PE=1:3) affords the title compound (1.8 g, 83.7%). MS: (M+1): 186.2.

Data on Intermediates D53-56 are summarized in Table D11:

TABLE D11

Intermediates D53-D56

| Number | Starting material | Intermediate | MS [M + 1]+ |
|---|---|---|---|
| D53 | H₂N–(Cl, CN)-phenyl | phenyl O-C(=O)-NH-(Cl, CN)-phenyl | 273.1 |
| D54 | H₂N–(Cl, F)-phenyl | phenyl O-C(=O)-NH-(Cl, F)-phenyl | 266.1 |
| D55 | H₂N–(Br, F)-phenyl | phenyl O-C(=O)-NH-(cyclopropyl, F)-phenyl | 272.2 |
| D56 | O₂N–phenyl–OH | phenyl O-C(=O)-NH-(4,4-difluorochroman-6-yl) | 306.2 |

Intermediates D57-62 can be synthesized with similar method (Table D12)
TABLE D12
Intermediates D57-D62
| Number | Starting material | Intermediate | MS [M + 1]+ |
|---|---|---|---|
| D57 | 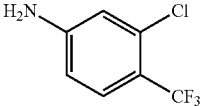 | 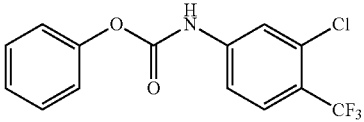 [SMILES: O=C(Nc1ccc(C(F)(F)F)c(Cl)c1)Oc1ccccc1] | 316.1 |
| D58 | 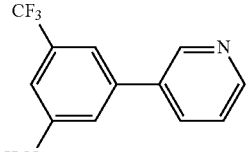 | 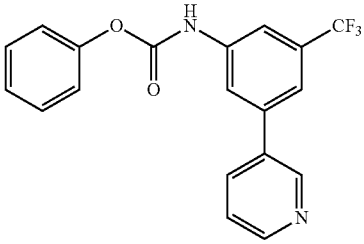 [SMILES: O=C(Nc1cc(-c2cccnc2)cc(C(F)(F)F)c1)Oc1ccccc1] | 359.1 |
| D59 | 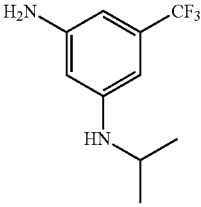
C17 | 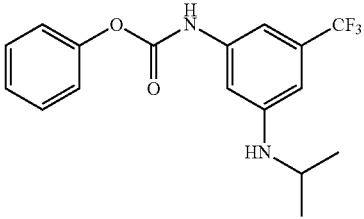 | NA |
| D60 | 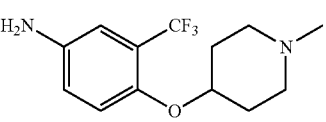 [SMILES: CN1CCC(Oc2ccc(N)cc2C(F)(F)F)CC1] | 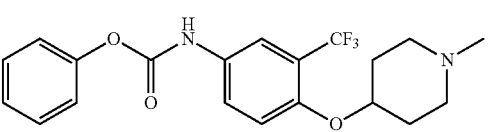 [SMILES: CN1CCC(Oc2ccc(NC(=O)Oc3ccccc3)cc2C(F)(F)F)CC1] | 395.2 |
| D61 | 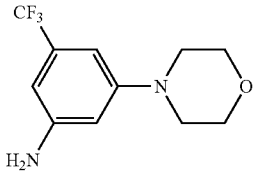 | 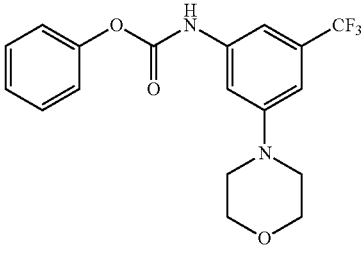 [SMILES: O=C(Nc1cc(N2CCOCC2)cc(C(F)(F)F)c1)Oc1ccccc1] | NA |
| D62 | 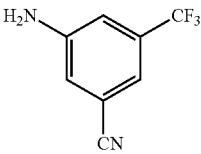 | 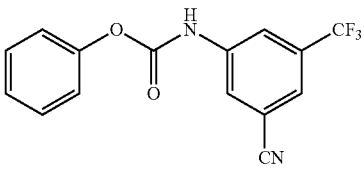 [SMILES: N#Cc1cc(NC(=O)Oc2ccccc2)cc(C(F)(F)F)c1] | NA |

EXAMPLES

Example 1

Synthesis of N-[6-[4-[[4-chloro-3-(trifluoromethyl) phenyl]carbamoylamino]-3-methyl-phenoxy]pyrimidin-4-yl]cyclopropanecarboxamide

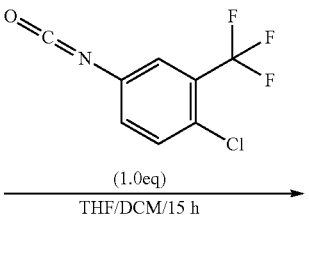

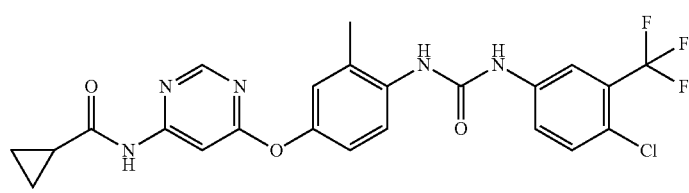

Dissolve N-[6-(4-amino-3-methyl-phenoxy)pyrimidin-4-yl]cyclopropanecarboxamide (1.8 g, 6.3 mmol) in tetrahydrofuran (50 mL) and dichloromethane (50 mL), add slowly 4-chloro-3-(trifluoromethyl)phenyl isocynate (1.4 g, 6.3 mmol), stir the reaction at room temperature for 15 hrs. Collect the white solid formed by filtration (2.0 g), recover from the mother liquor to give another 1.0 g (total 3.0 g, 93.7% yield). MS: (M+1): 506.2.

When the crude product contains a small amount of impurities, the product may be purified by recrystallization in ethanol/tetrahydrofuran as the following: add the crude product (8.2 g) to ethanol (120 mL) in a 250 mL flask, heat to reflux, add slowly tetrahydrofuran (about 50 mL) to dissolve the solid. Then cool slowly, filter and collect the white solid to give the pure product (6.2 g, 75.6% recovery yield).

Example 2

Synthesis of N-[6-[3-[[4-chloro-3-(trifluoromethyl) phenyl]carbamoyl-amino]-4-fluoro-phenoxy]pyrimidin-4-yl]cyclopropanecarboxamide

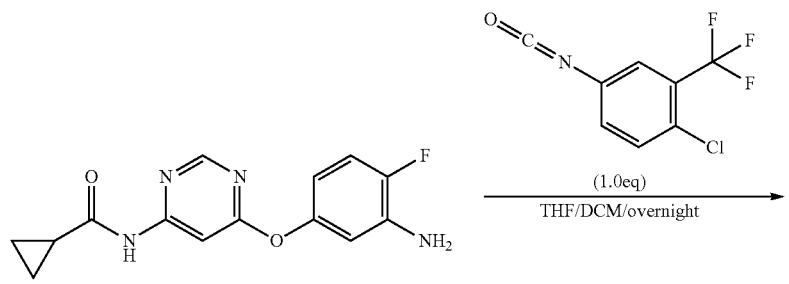

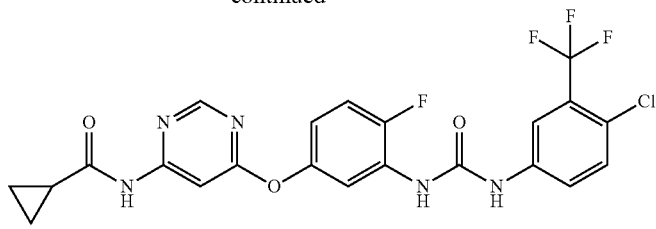

Dissolve N-[6-(3-amino-4-fluoro-phenoxy)pyrimidin-4-yl]cyclopropanecarboxamide (400 mg, 1.4 mmol) in THF (4 mL) and DCM (10 mL), add 4-chloro-3-(trifluoromethyl) phenyl isocynate (1.4 g, 6.3 mmol). Stir the reaction at room temperature overnight. Filter and collect the solid to get the title compound (545 mg, 77%). MS: (M+1): 510.2.

Examples 1-31 are prepared with similar method (Table 1).

TABLE 1

Examples 1-31

| Example Number | Structure | MS [M + 1]$^+$ |
|---|---|---|
| Example 1 | 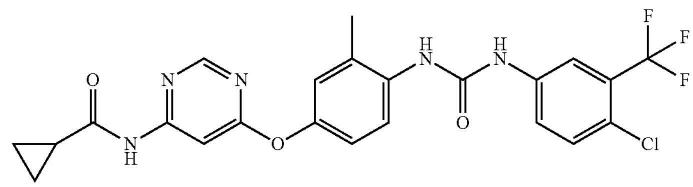 [SMILES: Cc1cc(Oc2cc(NC(=O)C3CC3)ncn2)ccc1NC(=O)Nc1ccc(Cl)c(C(F)(F)F)c1] | 506.2 |
| Example 2 | 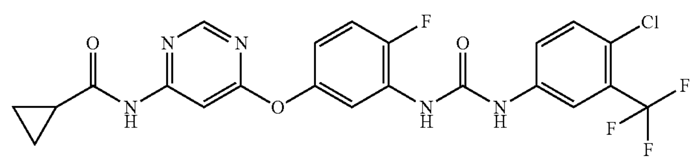 [SMILES: O=C(Nc1ccc(Cl)c(C(F)(F)F)c1)Nc1cc(Oc2cc(NC(=O)C3CC3)ncn2)ccc1F] | 510.2 |
| Example 3 | 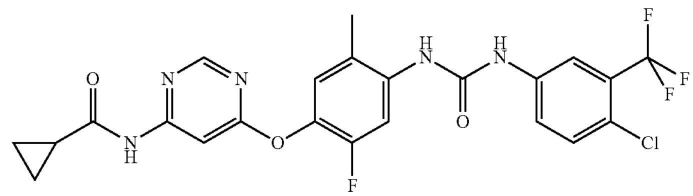 [SMILES: Cc1cc(Oc2cc(NC(=O)C3CC3)ncn2)c(F)cc1NC(=O)Nc1ccc(Cl)c(C(F)(F)F)c1] | 524.2 |
| Example 4 | 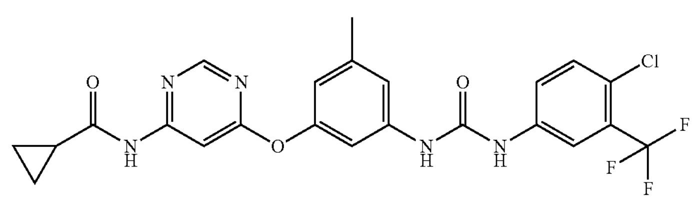 [SMILES: Cc1cc(NC(=O)Nc2ccc(Cl)c(C(F)(F)F)c2)cc(Oc2cc(NC(=O)C3CC3)ncn2)c1] | 502.3 |
| Example 5 | 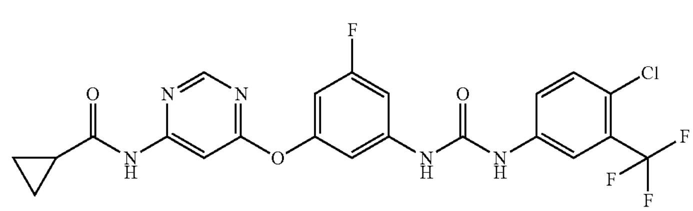 [SMILES: O=C(Nc1cc(F)cc(Oc2cc(NC(=O)C3CC3)ncn2)c1)Nc1ccc(Cl)c(C(F)(F)F)c1] | 510.2 |

TABLE 1-continued

Examples 1-31

| Example Number | Structure | MS [M + 1]+ |
|---|---|---|
| Example 6 | 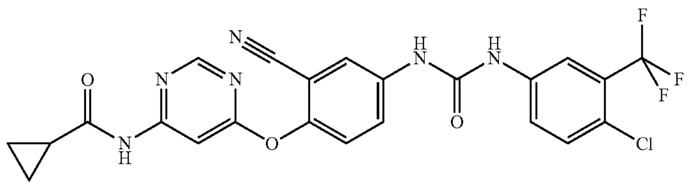 [SMILES: N#Cc1cc(NC(=O)Nc2ccc(Cl)c(C(F)(F)F)c2)ccc1Oc1cc(NC(=O)C2CC2)ncn1] | 517.2 |
| Example 7 | 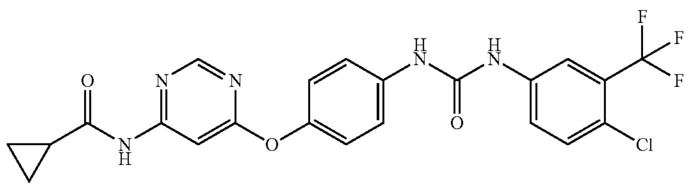 [SMILES: O=C(Nc1ccc(Oc2cc(NC(=O)C3CC3)ncn2)cc1)Nc1ccc(Cl)c(C(F)(F)F)c1] | 492.2 |
| Example 8 | 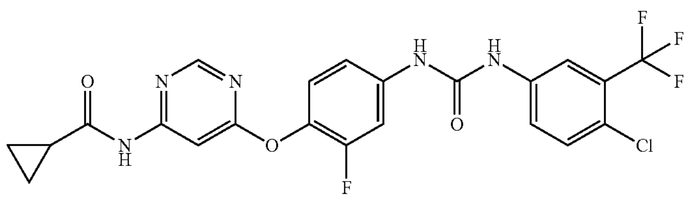 [SMILES: O=C(Nc1ccc(Oc2cc(NC(=O)C3CC3)ncn2)c(F)c1)Nc1ccc(Cl)c(C(F)(F)F)c1] | 510.1 |
| Example 9 | 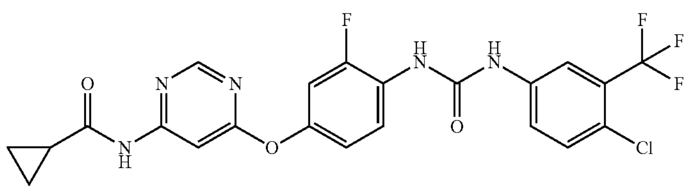 [SMILES: O=C(Nc1ccc(Cl)c(C(F)(F)F)c1)Nc1ccc(Oc2cc(NC(=O)C3CC3)ncn2)cc1F] | 510.2 |
| Example 10 | 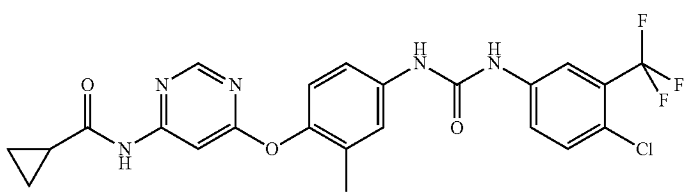 [SMILES: Cc1cc(NC(=O)Nc2ccc(Cl)c(C(F)(F)F)c2)ccc1Oc1cc(NC(=O)C2CC2)ncn1] | 506.2 |
| Example 11 | 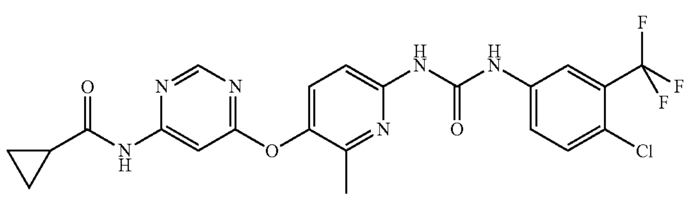 [SMILES: Cc1nc(NC(=O)Nc2ccc(Cl)c(C(F)(F)F)c2)ccc1Oc1cc(NC(=O)C2CC2)ncn1] | 507.2 |
| Example 12 | 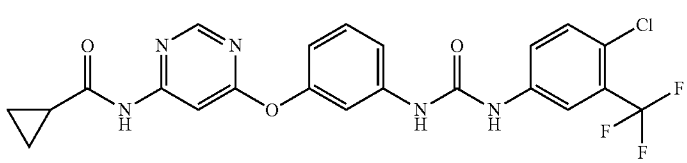 [SMILES: O=C(Nc1cccc(Oc2cc(NC(=O)C3CC3)ncn2)c1)Nc1ccc(Cl)c(C(F)(F)F)c1] | 492.2 |

TABLE 1-continued

Examples 1-31

| Example Number | Structure | MS [M + 1]⁺ |
|---|---|---|
| Example 13 | 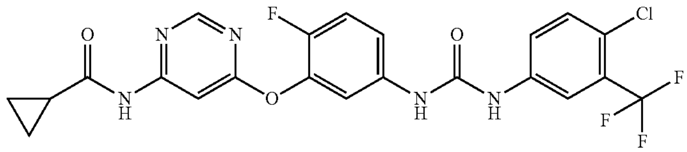 [SMILES: O=C(Nc1ccc(F)c(Oc2cc(NC(=O)C3CC3)ncn2)c1)Nc1ccc(Cl)c(C(F)(F)F)c1] | 510.2 |
| Example 14 | 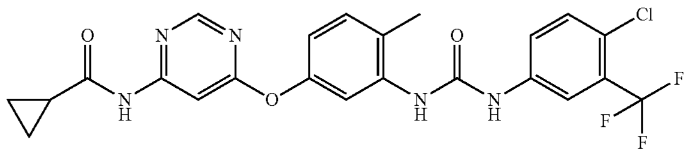 [SMILES: Cc1ccc(Oc2cc(NC(=O)C3CC3)ncn2)cc1NC(=O)Nc1ccc(Cl)c(C(F)(F)F)c1] | 506.2 |
| Example 15 | 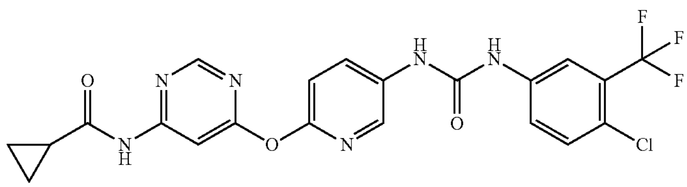 [SMILES: O=C(Nc1ccc(Oc2cc(NC(=O)C3CC3)ncn2)nc1)Nc1ccc(Cl)c(C(F)(F)F)c1] | 493.2 |
| Example 16 | 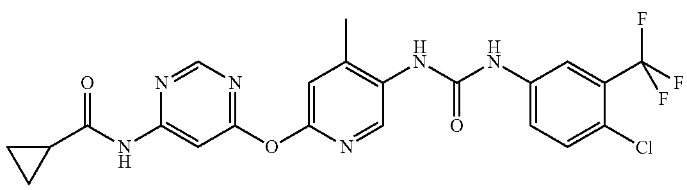 [SMILES: Cc1cc(Oc2cc(NC(=O)C3CC3)ncn2)ncc1NC(=O)Nc1ccc(Cl)c(C(F)(F)F)c1] | 507.2 |
| Example 17 | 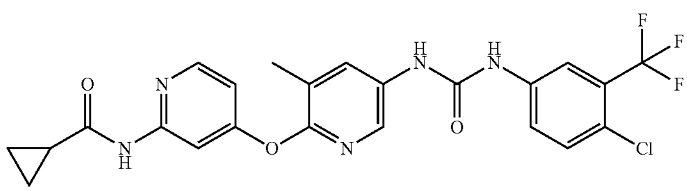 [SMILES: Cc1cc(NC(=O)Nc2ccc(Cl)c(C(F)(F)F)c2)cnc1Oc1ccnc(NC(=O)C2CC2)c1] | 506.2 |
| Example 18 | 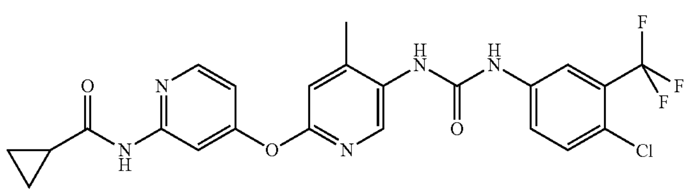 [SMILES: Cc1cc(Oc2ccnc(NC(=O)C3CC3)c2)ncc1NC(=O)Nc1ccc(Cl)c(C(F)(F)F)c1] | 506.2 |
| Example 19 | 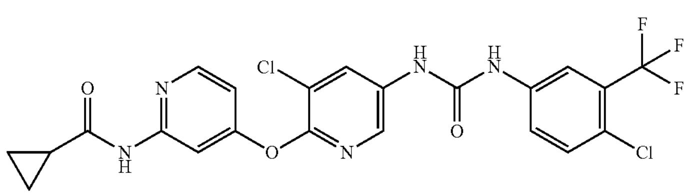 [SMILES: O=C(Nc1cnc(Oc2ccnc(NC(=O)C3CC3)c2)c(Cl)c1)Nc1ccc(Cl)c(C(F)(F)F)c1] | 526.1 |
| Example 20 | 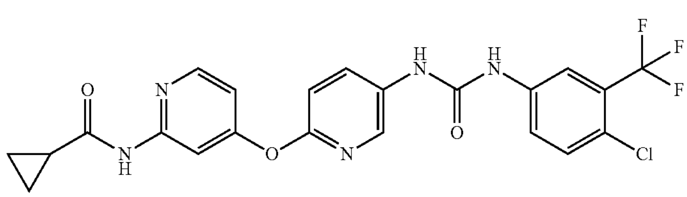 [SMILES: O=C(Nc1ccc(Oc2ccnc(NC(=O)C3CC3)c2)nc1)Nc1ccc(Cl)c(C(F)(F)F)c1] | 492.1 |

TABLE 1-continued

Examples 1-31

| Example Number | Structure | MS [M + 1]+ |
|---|---|---|
| Example 21 | 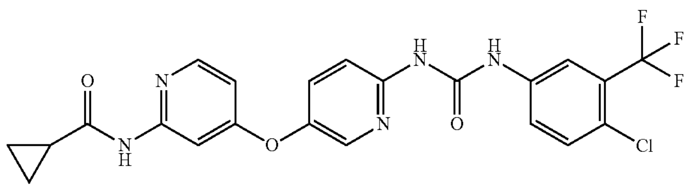 [SMILES: O=C(Nc1ccc(Cl)c(C(F)(F)F)c1)Nc1ccc(Oc2ccnc(NC(=O)C3CC3)c2)cn1] | 492.1 |
| Example 22 | 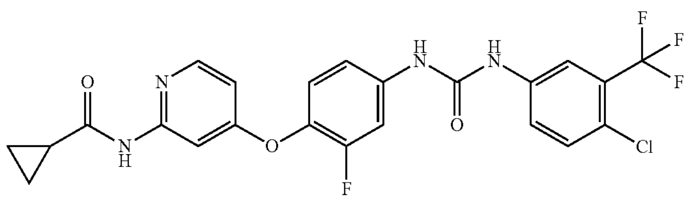 [SMILES: O=C(Nc1ccc(Oc2ccnc(NC(=O)C3CC3)c2)c(F)c1)Nc1ccc(Cl)c(C(F)(F)F)c1] | 509.2 |
| Example 23 | 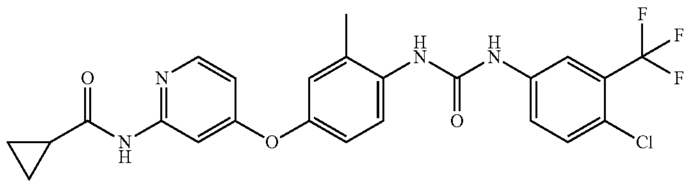 [SMILES: Cc1cc(Oc2ccnc(NC(=O)C3CC3)c2)ccc1NC(=O)Nc1ccc(Cl)c(C(F)(F)F)c1] | 505.2 |
| Example 24 | 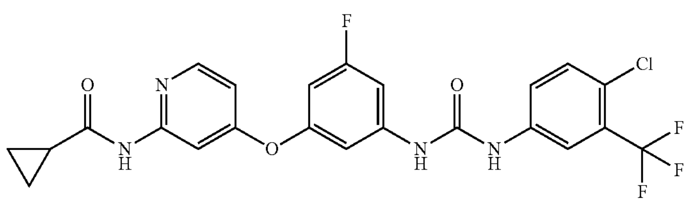 [SMILES: O=C(Nc1cc(F)cc(Oc2ccnc(NC(=O)C3CC3)c2)c1)Nc1ccc(Cl)c(C(F)(F)F)c1] | 509.1 |
| Example 25 | 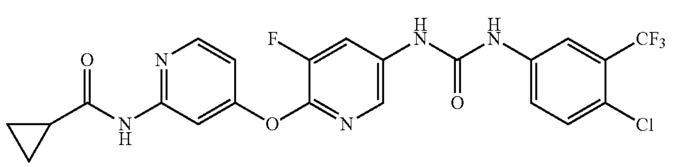 [SMILES: O=C(Nc1cnc(Oc2ccnc(NC(=O)C3CC3)c2)c(F)c1)Nc1ccc(Cl)c(C(F)(F)F)c1] | 510.1 |
| Example 26 | 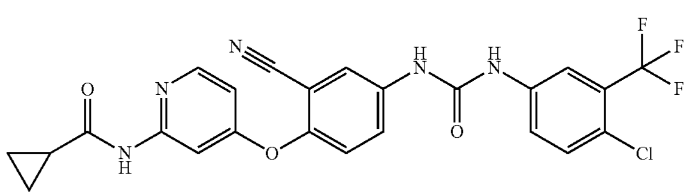 [SMILES: N#Cc1cc(NC(=O)Nc2ccc(Cl)c(C(F)(F)F)c2)ccc1Oc1ccnc(NC(=O)C2CC2)c1] | 516.2 |
| Example 27 | 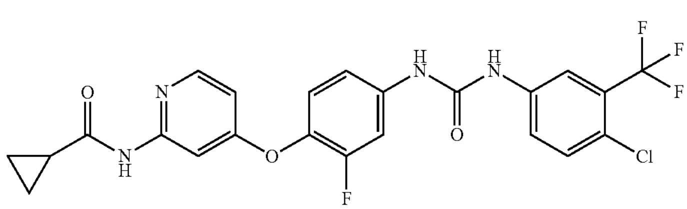 [SMILES: O=C(Nc1ccc(Oc2ccnc(NC(=O)C3CC3)c2)c(F)c1)Nc1ccc(Cl)c(C(F)(F)F)c1] | 508.2 |

TABLE 1-continued
Examples 1-31
| Example Number | Structure | MS [M + 1]+ |
|---|---|---|
| Example 28 | 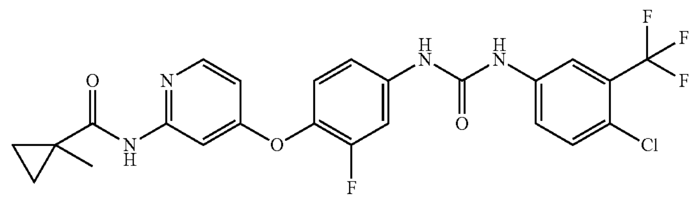 [SMILES: CC1(C(=O)Nc2cc(Oc3ccc(NC(=O)Nc4ccc(Cl)c(C(F)(F)F)c4)cc3F)ccn2)CC1] | 523.3 |
| Example 29 | 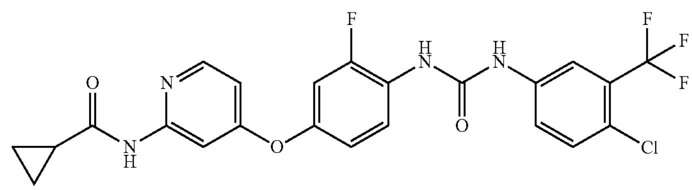 [SMILES: O=C(Nc1ccc(Cl)c(C(F)(F)F)c1)Nc1ccc(Oc2ccnc(NC(=O)C3CC3)c2)cc1F] | 509.2 |
| Example 30 | 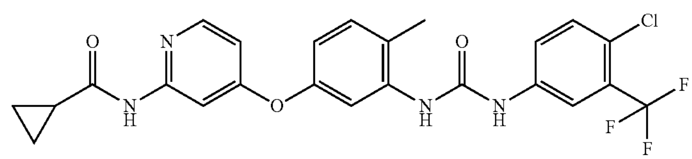 | 505.2 |
| Example 31 | 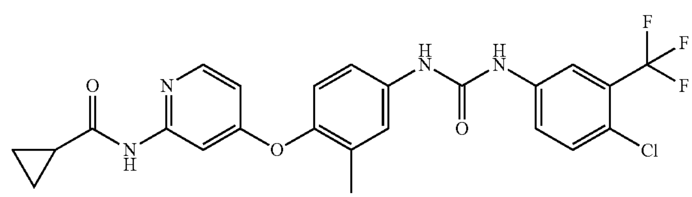 [SMILES: Cc1cc(NC(=O)Nc2ccc(Cl)c(C(F)(F)F)c2)ccc1Oc1ccnc(NC(=O)C2CC2)c1] | 505.3 |
Example 32
Synthesis of N-[6-[4-[[3-(isopropylamino)-5-(trifluoromethyl)phenyl]carbamoylamino]-3-methyl-phenoxy]pyrimidin-4-yl]cyclopropanecarboxamide
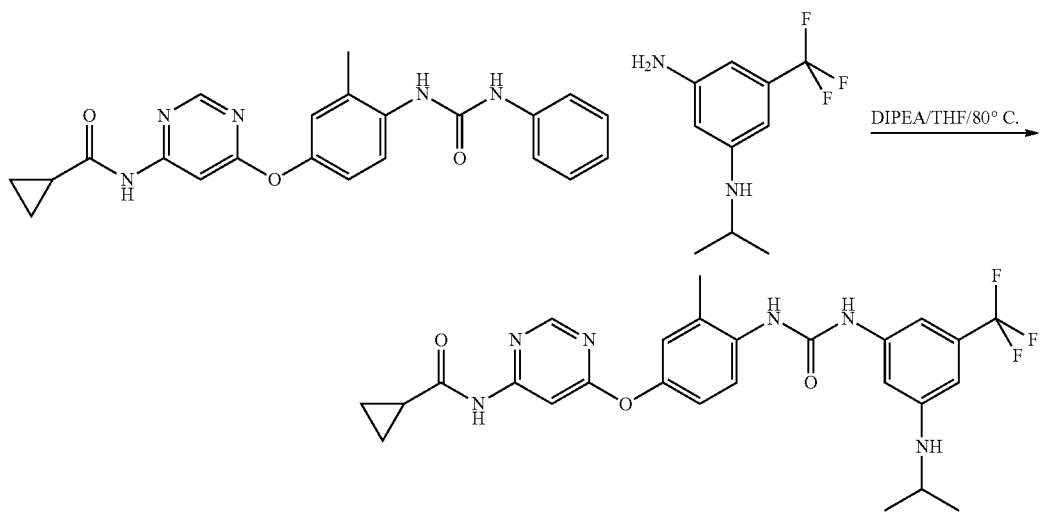

Dissolve phenyl N-[4-[6-(cyclopropanecarbonylamino)pyrimidin-4-yl]oxy-2-methyl-phenyl]carbamate (343 mg, 1.57 mmol), N1-isopropyl-5-(trifluoromethyl)benzene-1,3-diamine (700 mg, 1.73 mmol) and DIEA (608 mg, 4.72 mmol) in THF (4 mL), heat the reaction at 80° C. for 3 hrs. After the reaction is complete, remove the volatiles under reduced pressure. Purification by chromatography (silica gel, EtOAc:PE=1:1) affords the title compound (450 mg, 83%). MS: (M+1): 529.3.

Examples 33-66 are prepared with similar method (Table 2).

TABLE 2

Examples 32-66

| Example Number | Structure | MS [M + 1]+ |
| --- | --- | --- |
| Example 32 | 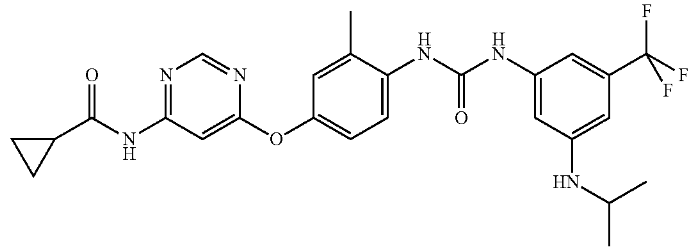 [SMILES: Cc1cc(Oc2cc(NC(=O)C3CC3)ncn2)ccc1NC(=O)Nc1cc(NC(C)C)cc(C(F)(F)F)c1] | 529.3 |
| Example 33 | 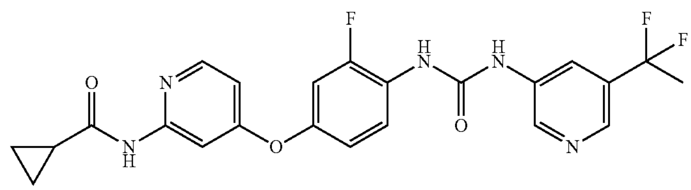 | 472.3 |
| Example 34 | 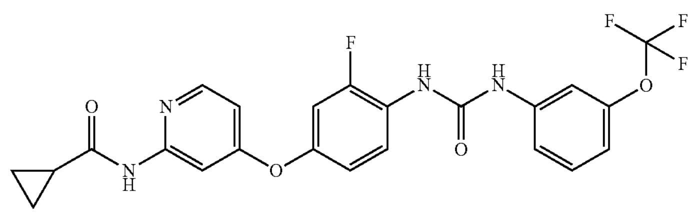 [SMILES: O=C(Nc1cccc(OC(F)(F)F)c1)Nc1ccc(Oc2ccnc(NC(=O)C3CC3)c2)cc1F] | 491.3 |
| Example 35 | 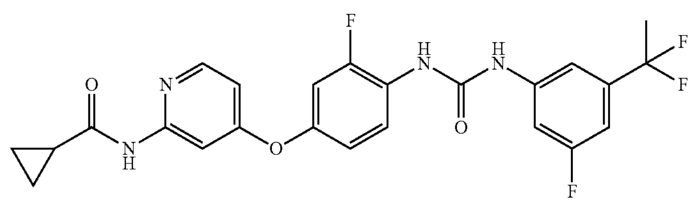 [SMILES: CC(F)(F)c1cc(F)cc(NC(=O)Nc2ccc(Oc3ccnc(NC(=O)C4CC4)c3)cc2F)c1] | 489.3 |
| Example 36 | 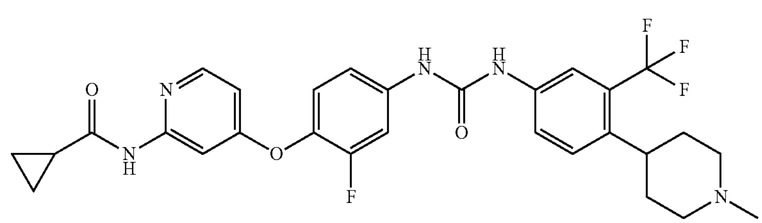 [SMILES: CN1CCC(c2ccc(NC(=O)Nc3ccc(Oc4ccnc(NC(=O)C5CC5)c4)c(F)c3)cc2C(F)(F)F)CC1] | 572.3 |
| Example 37 | 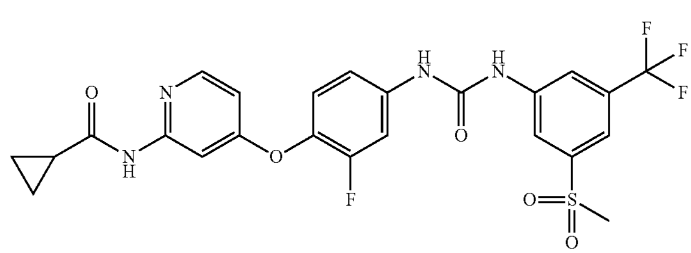 [SMILES: CS(=O)(=O)c1cc(NC(=O)Nc2ccc(Oc3ccnc(NC(=O)C4CC4)c3)c(F)c2)cc(C(F)(F)F)c1] | 553.2 |

TABLE 2-continued

Examples 32-66

| Example Number | Structure | MS [M + 1]+ |
|---|---|---|
| Example 38 | 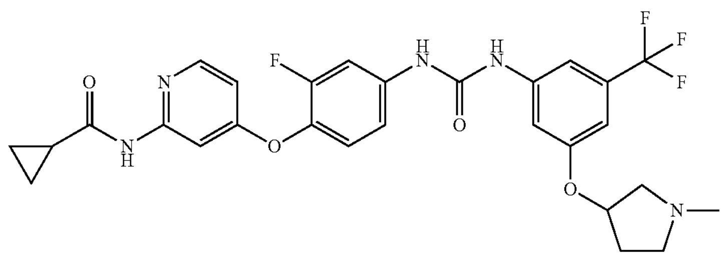 [SMILES: CN1CCC(Oc2cc(NC(=O)Nc3ccc(Oc4ccnc(NC(=O)C5CC5)c4)c(F)c3)cc(C(F)(F)F)c2)C1] | 574.3 |
| Example 39 | 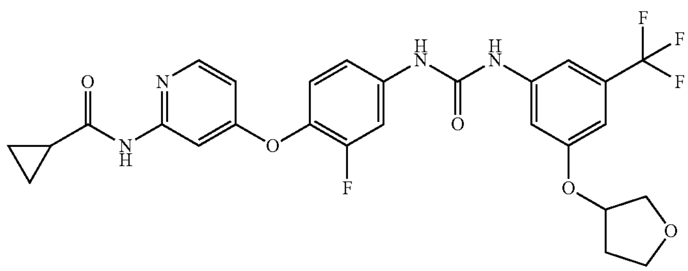 [SMILES: O=C(Nc1cc(OC2CCOC2)cc(C(F)(F)F)c1)Nc1ccc(Oc2ccnc(NC(=O)C3CC3)c2)c(F)c1] | 561.2 |
| Example 40 | 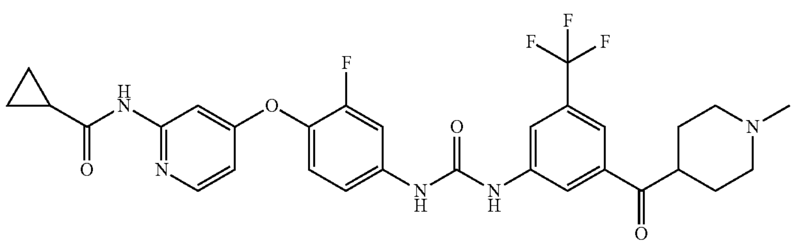 [SMILES: CN1CCC(C(=O)c2cc(NC(=O)Nc3ccc(Oc4ccnc(NC(=O)C5CC5)c4)c(F)c3)cc(C(F)(F)F)c2)CC1] | 600.3 |
| Example 41 | 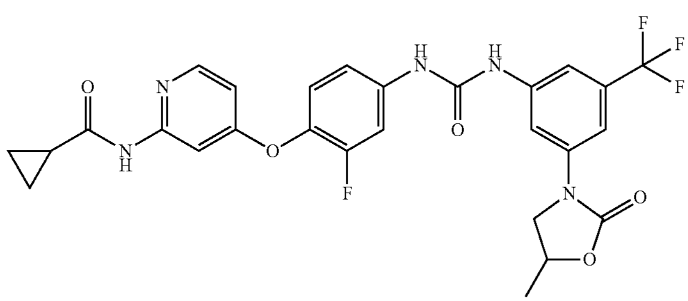 [SMILES: CC1CN(c2cc(NC(=O)Nc3ccc(Oc4ccnc(NC(=O)C5CC5)c4)c(F)c3)cc(C(F)(F)F)c2)C(=O)O1] | 574.2 |
| Example 42 | 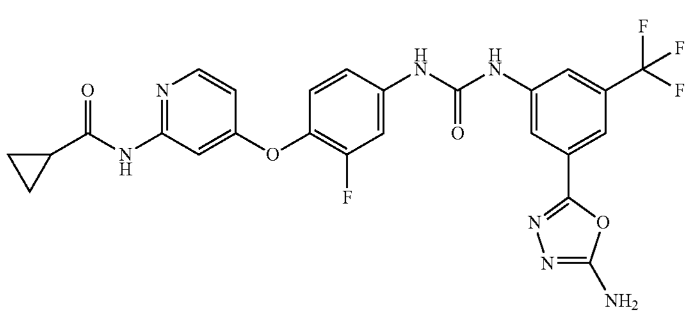 [SMILES: Nc1nnc(-c2cc(NC(=O)Nc3ccc(Oc4ccnc(NC(=O)C5CC5)c4)c(F)c3)cc(C(F)(F)F)c2)o1] | 558.2 |

TABLE 2-continued

Examples 32-66

| Example Number | Structure | MS [M + 1]+ |
|---|---|---|
| Example 43 | 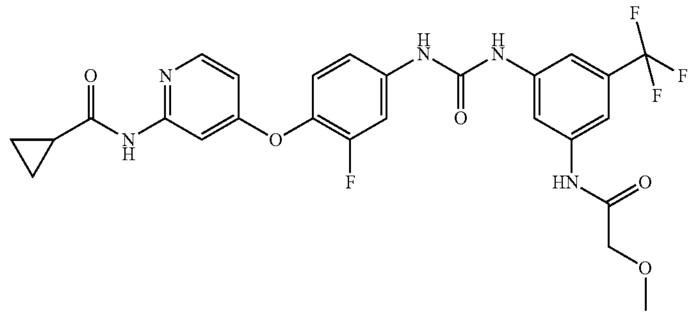 [SMILES: COCC(=O)Nc1cc(NC(=O)Nc2ccc(Oc3ccnc(NC(=O)C4CC4)c3)c(F)c2)cc(C(F)(F)F)c1] | 562.2 |
| Example 44 | 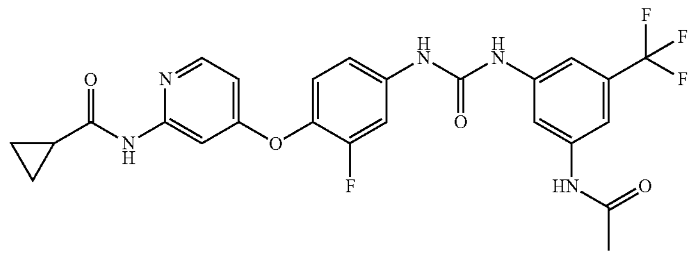 [SMILES: CC(=O)Nc1cc(NC(=O)Nc2ccc(Oc3ccnc(NC(=O)C4CC4)c3)c(F)c2)cc(C(F)(F)F)c1] | 532.2 |
| Example 45 | 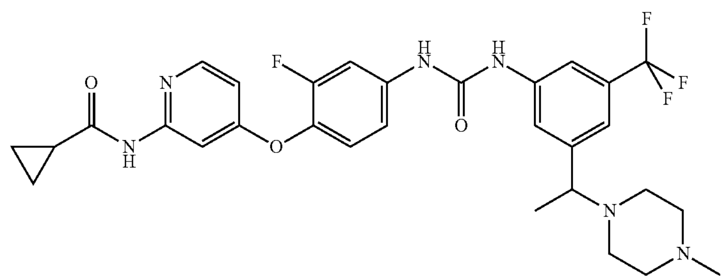 [SMILES: CC(c1cc(NC(=O)Nc2ccc(Oc3ccnc(NC(=O)C4CC4)c3)c(F)c2)cc(C(F)(F)F)c1)N1CCN(C)CC1] | 601.3 |
| Example 46 | 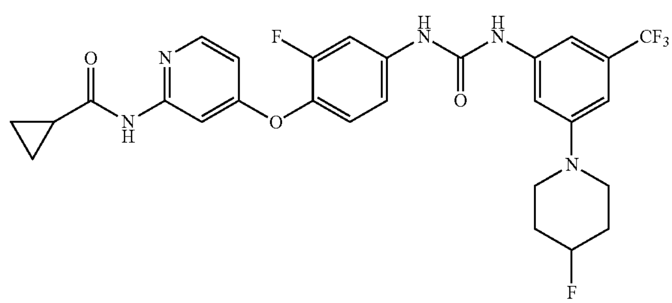 [SMILES: O=C(Nc1cc(N2CCC(F)CC2)cc(C(F)(F)F)c1)Nc1ccc(Oc2ccnc(NC(=O)C3CC3)c2)c(F)c1] | 576.3 |
| Example 47 | 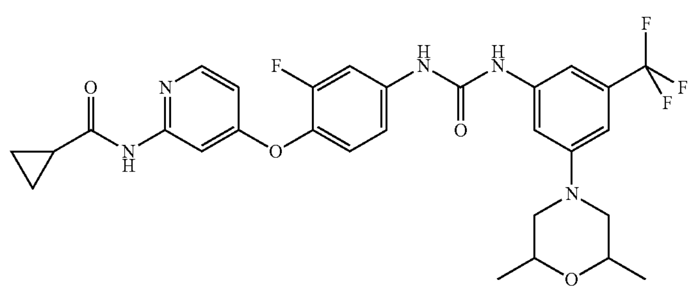 [SMILES: CC1CN(c2cc(NC(=O)Nc3ccc(Oc4ccnc(NC(=O)C5CC5)c4)c(F)c3)cc(C(F)(F)F)c2)CC(C)O1] | 588.3 |

TABLE 2-continued

Examples 32-66

| Example Number | Structure | MS [M + 1]+ |
|---|---|---|
| Example 48 | 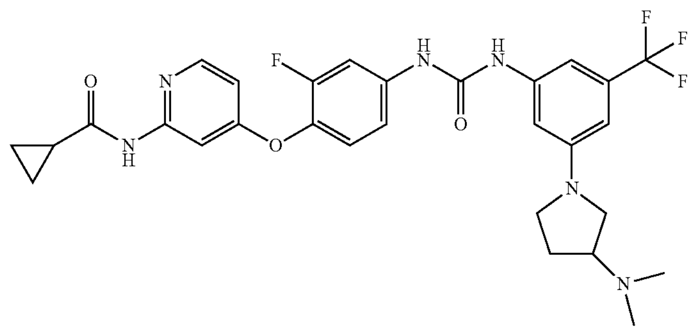 [SMILES: CN(C)C1CCN(c2cc(NC(=O)Nc3ccc(Oc4ccnc(NC(=O)C5CC5)c4)c(F)c3)cc(C(F)(F)F)c2)C1] | 587.3 |
| Example 49 | 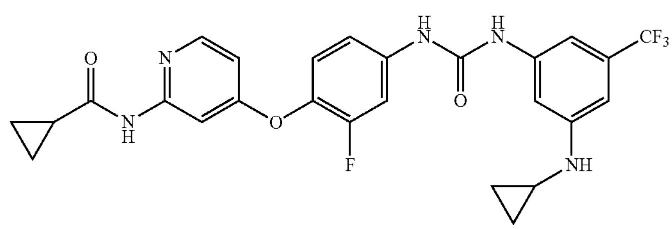 [SMILES: O=C(Nc1cc(NC2CC2)cc(C(F)(F)F)c1)Nc1ccc(Oc2ccnc(NC(=O)C3CC3)c2)c(F)c1] | 530.3 |
| Example 50 | 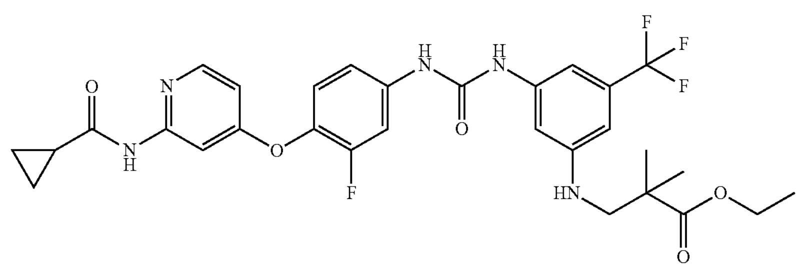 [SMILES: CCOC(=O)C(C)(C)CNc1cc(NC(=O)Nc2ccc(Oc3ccnc(NC(=O)C4CC4)c3)c(F)c2)cc(C(F)(F)F)c1] | 618.3 |
| Example 51 | 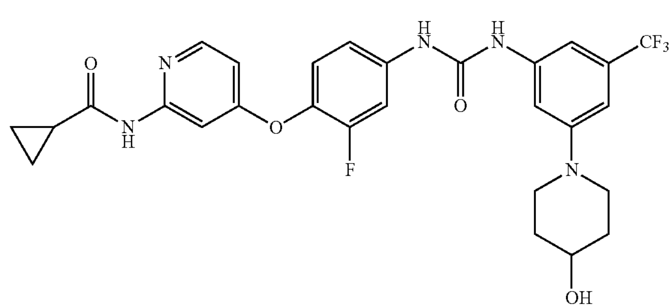 [SMILES: O=C(Nc1cc(N2CCC(O)CC2)cc(C(F)(F)F)c1)Nc1ccc(Oc2ccnc(NC(=O)C3CC3)c2)c(F)c1] | 574.3 |
| Example 52 | 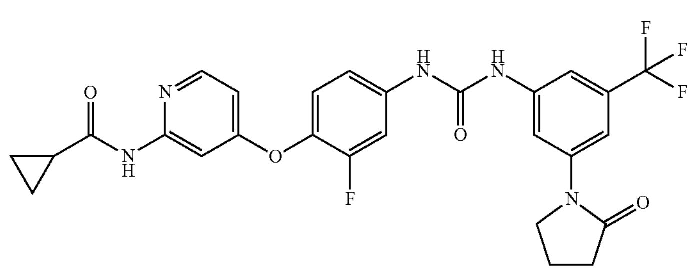 [SMILES: O=C(Nc1cc(N2CCCC2=O)cc(C(F)(F)F)c1)Nc1ccc(Oc2ccnc(NC(=O)C3CC3)c2)c(F)c1] | 558.2 |

TABLE 2-continued

Examples 32-66

| Example Number | Structure | MS [M + 1]+ |
|---|---|---|
| Example 53 | 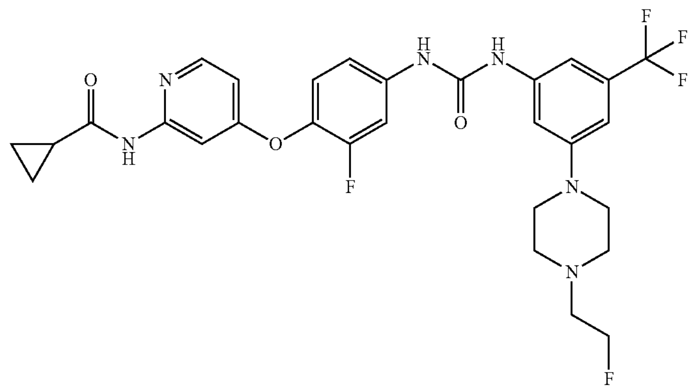 [SMILES: O=C(Nc1cc(N2CCN(CCF)CC2)cc(C(F)(F)F)c1)Nc1ccc(Oc2ccnc(NC(=O)C3CC3)c2)c(F)c1] | 605.3 |
| Example 54 | 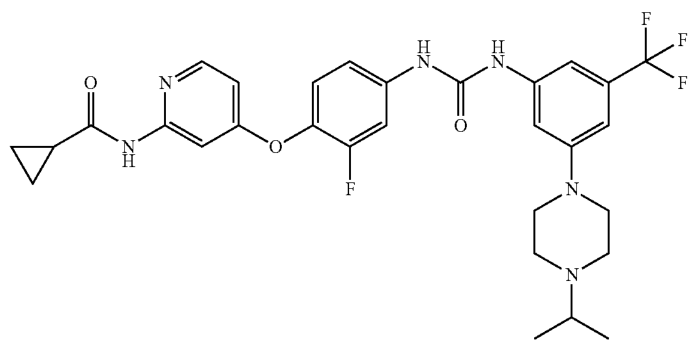 [SMILES: CC(C)N1CCN(c2cc(NC(=O)Nc3ccc(Oc4ccnc(NC(=O)C5CC5)c4)c(F)c3)cc(C(F)(F)F)c2)CC1] | 601.3 |
| Example 55 | 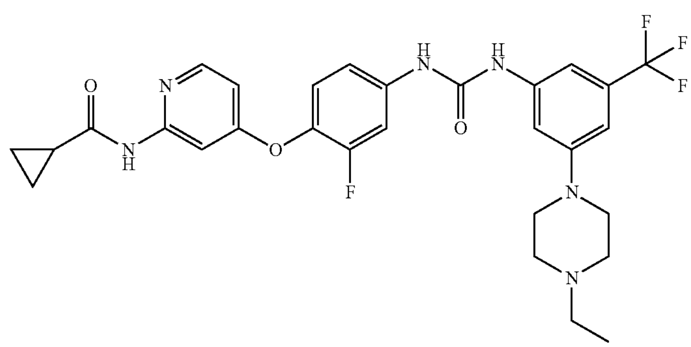 [SMILES: CCN1CCN(c2cc(NC(=O)Nc3ccc(Oc4ccnc(NC(=O)C5CC5)c4)c(F)c3)cc(C(F)(F)F)c2)CC1] | 587.3 |
| Example 56 | 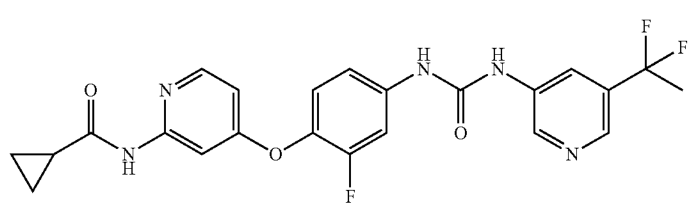 [SMILES: CC(F)(F)c1cncc(NC(=O)Nc2ccc(Oc3ccnc(NC(=O)C4CC4)c3)c(F)c2)c1] | 472.3 |
| Example 57 | 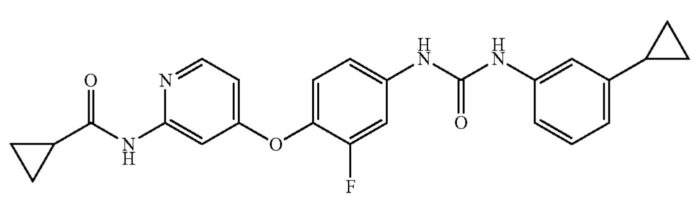 [SMILES: O=C(Nc1cccc(C2CC2)c1)Nc1ccc(Oc2ccnc(NC(=O)C3CC3)c2)c(F)c1] | 447.2 |

TABLE 2-continued

Examples 32-66

| Example Number | Structure | MS [M + 1]+ |
|---|---|---|
| Example 58 | 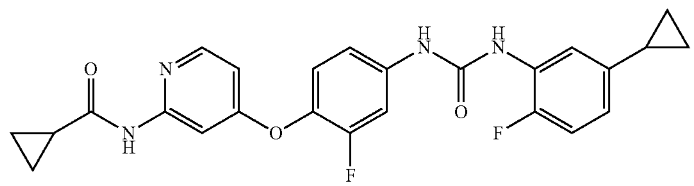 [SMILES: O=C(Nc1ccc(Oc2ccnc(NC(=O)C3CC3)c2)c(F)c1)Nc1cc(C2CC2)ccc1F] | 465.2 |
| Example 59 | 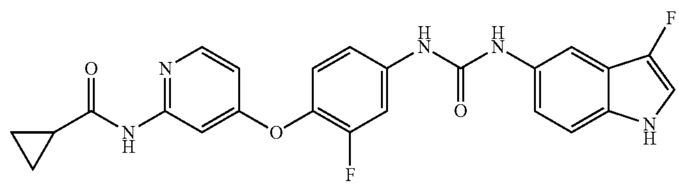 [SMILES: O=C(Nc1ccc(Oc2ccnc(NC(=O)C3CC3)c2)c(F)c1)Nc1ccc2[nH]cc(F)c2c1] | 464.3 |
| Example 60 | 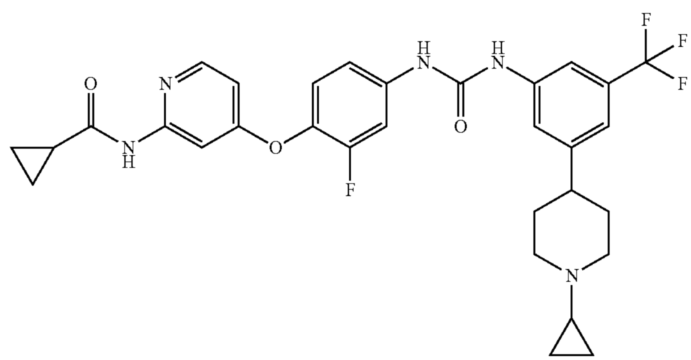 [SMILES: O=C(Nc1cc(C2CCN(C3CC3)CC2)cc(C(F)(F)F)c1)Nc1ccc(Oc2ccnc(NC(=O)C3CC3)c2)c(F)c1] | 598.3 |
| Example 61 | 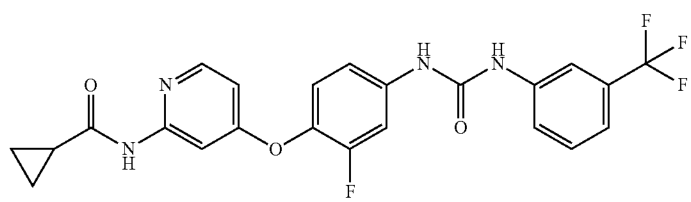 [SMILES: O=C(Nc1cccc(C(F)(F)F)c1)Nc1ccc(Oc2ccnc(NC(=O)C3CC3)c2)c(F)c1] | 475.2 |
| Example 62 | 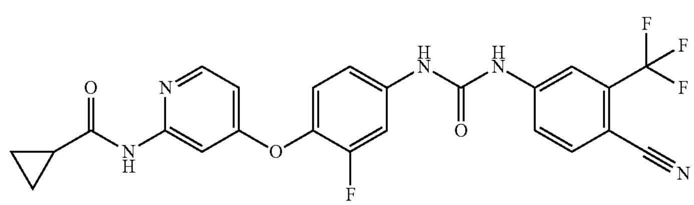 [SMILES: N#Cc1ccc(NC(=O)Nc2ccc(Oc3ccnc(NC(=O)C4CC4)c3)c(F)c2)cc1C(F)(F)F] | 500.2 |
| Example 63 | 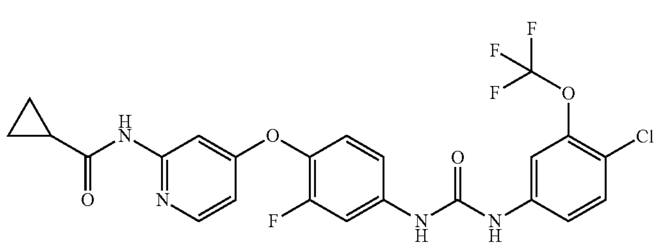 [SMILES: O=C(Nc1ccc(Oc2ccnc(NC(=O)C3CC3)c2)c(F)c1)Nc1ccc(Cl)c(OC(F)(F)F)c1] | 525.1 |

TABLE 2-continued
Examples 32-66
| Example Number | Structure | MS [M + 1]+ |
|---|---|---|
| Example 64 | 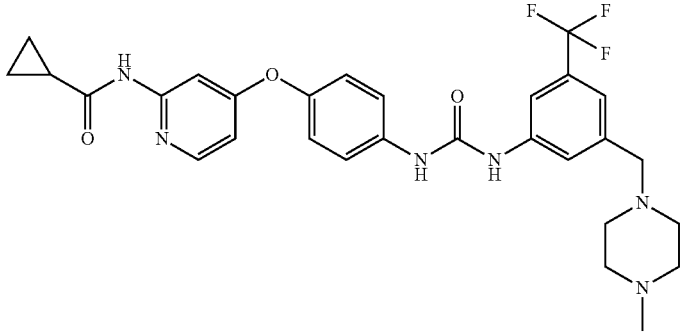 [SMILES: CN1CCN(Cc2cc(NC(=O)Nc3ccc(Oc4ccnc(NC(=O)C5CC5)c4)cc3)cc(C(F)(F)F)c2)CC1] | 569.2 |
| Example 65 | 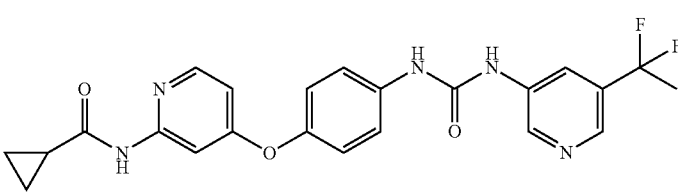 | 454.3 |
| Example 66 | 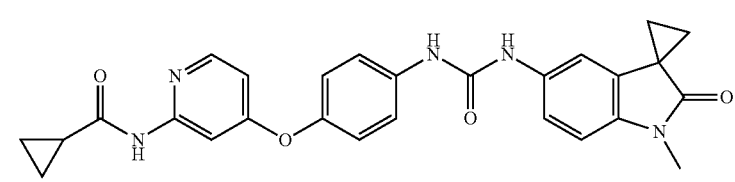 [SMILES: CN1C(=O)C2(CC2)c2cc(NC(=O)Nc3ccc(Oc4ccnc(NC(=O)C5CC5)c4)cc3)ccc21] | 484.3 |
Example 67
Synthesis of N-[4-[2-fluoro-4-[[3-(1-piperazin-1-ylethyl)-5-(trifluoromethyl)phenyl]carbamoylamino]phenoxy]-2-pyridyl]cyclopropanecarboxamide
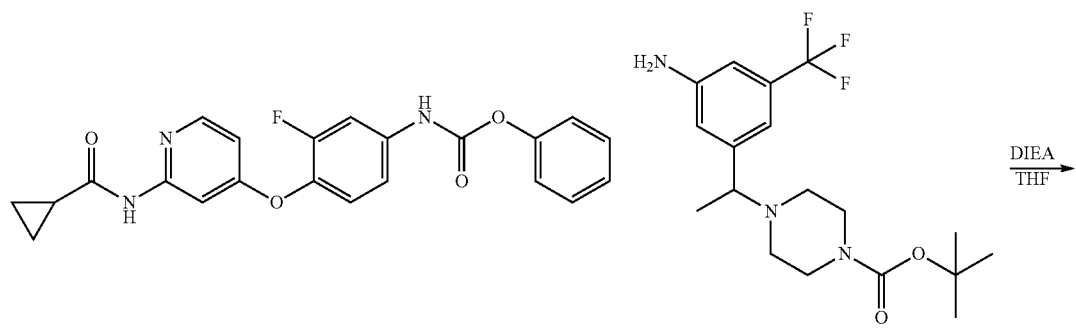

-continued

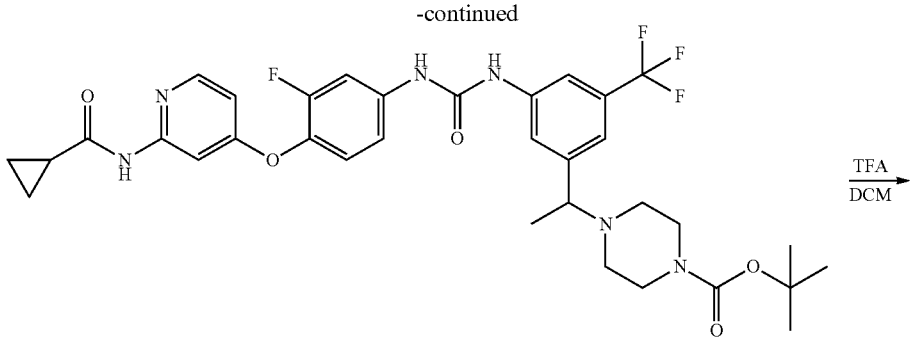

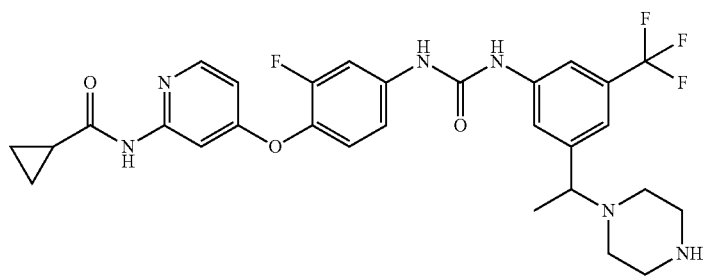

Step 1: Synthesis of tert-butyl 4-[1-[3-[[4-[[2-(cyclopropanecarbonylamino)-4-pyridyl]oxy]-3-fluoro-phenyl]carbamoyl amino]-5-(trifluoromethyl)phenyl]ethyl]piperazine-1-carboxylate

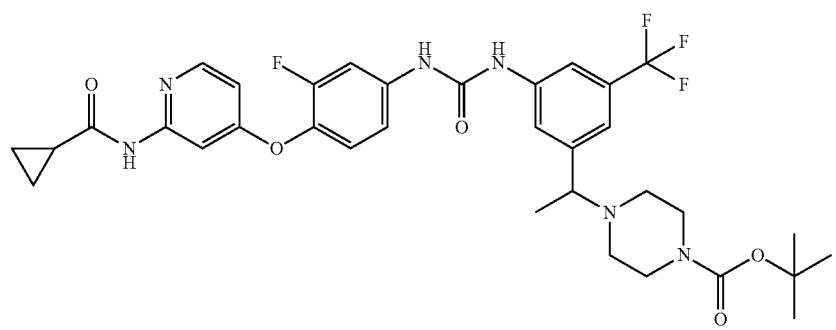 [SMILES: CC(c1cc(NC(=O)Nc2ccc(Oc3ccnc(NC(=O)C4CC4)c3)c(F)c2)cc(C(F)(F)F)c1)N1CCN(C(=O)OC(C)(C)C)CC1]

Add phenyl N-[4-[[2-(cyclopropanecarbonylamino)-4-pyridyl]oxy]-3-fluoro-phenyl]carbamate (220 mg, 0.53 mmol), tert-butyl 4-[1-[3-amino-5-(trifluoromethyl)phenyl]-ethyl] piperazine-1carboxylate (165 mg, 0.442 mmol) and DIEA (120 mg, 0.88 mmol) in THF (10 mL), stir the reaction under $N_2$ at 80° C. for 12 hrs. Concentrate under reduced pressure to give the crude product. Purification by chromatography (silica gel, EtOAc:PE=1:1) affords the title compound (230 mg, 75.6%).

Step 2: Synthesis of N-[4-[2-fluoro-4-[[3-(1-piper-azin-1-ylethyl)-5-(trifluoromethyl)phenyl]carbamoylamino]phenoxy]-2-pyridyl]cyclopropanecarboxamide

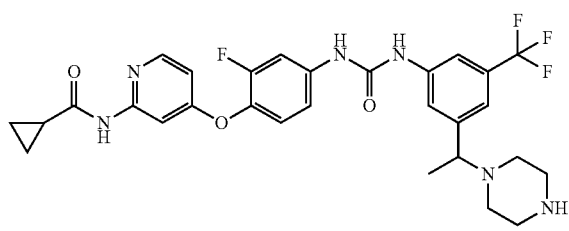 [SMILES: CC(c1cc(NC(=O)Nc2ccc(Oc3ccnc(NC(=O)C4CC4)c3)c(F)c2)cc(C(F)(F)F)c1)N1CCNCC1]

Dissolve the compound obtained in Step 1 (230 mg, 0.33 mmol) in DCM (15 mL), add trifluoroacetic acid (400 mg), stir at room temperature for 2 hrs. Remove the volatiles, partition the residue in EtOAc and saturated NaHCO₃ solution, and separate the organic layer, dry over anhydrous Na₂SO₄. Concentrate under reduced pressure to give the crude product. Purification by chromatography (silica gel, EtOAc:PE=3:1) affords the title compound (173 mg, 88.3%). MS: (M+1): 588.

Examples 68-69 are prepared with similar method (Table 3).

TABLE 3

Examples 67-69

| Example number | Structure | MS [M + 1]⁺ |
|---|---|---|
| Example 67 | 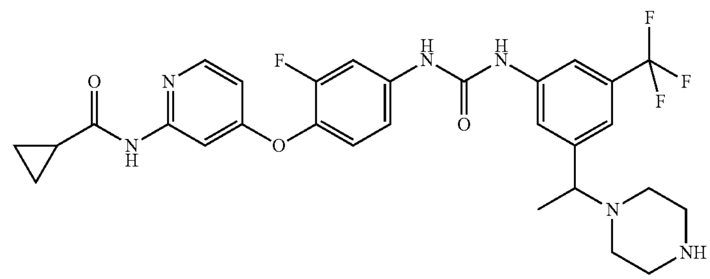 [SMILES: CC(c1cc(NC(=O)Nc2ccc(Oc3ccnc(NC(=O)C4CC4)c3)c(F)c2)cc(C(F)(F)F)c1)N1CCNCC1] | 588 |
| Example 68 | 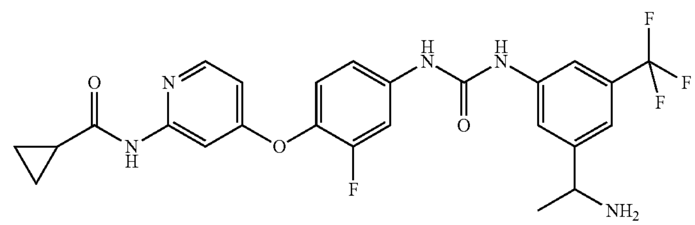 [SMILES: CC(N)c1cc(NC(=O)Nc2ccc(Oc3ccnc(NC(=O)C4CC4)c3)c(F)c2)cc(C(F)(F)F)c1] | 518.2 |
| Example 69 | 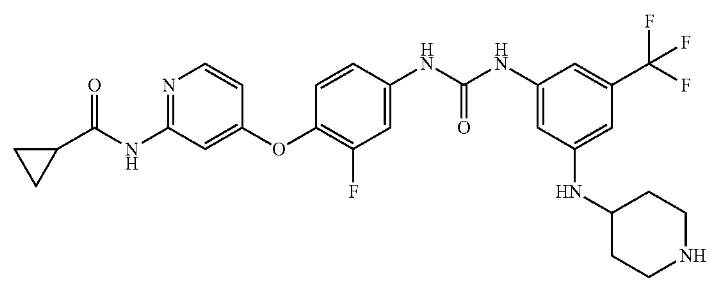 [SMILES: O=C(Nc1cc(NC2CCNCC2)cc(C(F)(F)F)c1)Nc1ccc(Oc2ccnc(NC(=O)C3CC3)c2)c(F)c1] | 573.3 |

Example 70

Synthesis of N-[6-[4-[[4-fluoro-3-(trifluoromethyl)phenyl]carbamoylamino]-3-methyl-phenoxy]pyrimidin-4-yl]cyclopropanecarboxamide

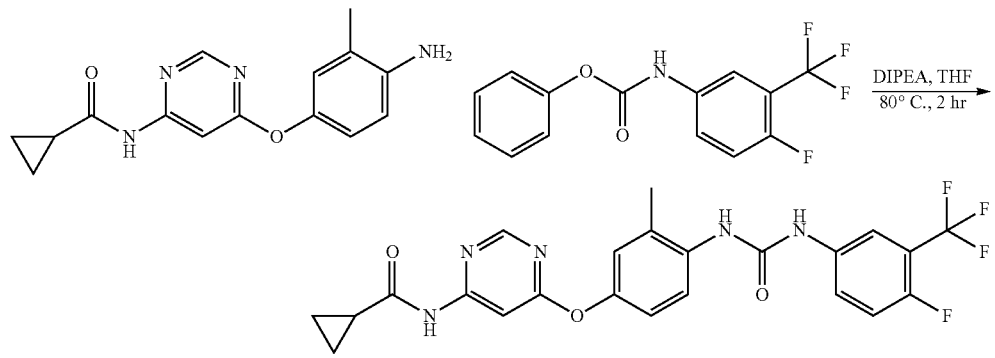

Add N-[6-(4-amino-3-methyl-phenoxy)pyrimidin-4-yl]cyclopropanecarboxamide (99 mg, 0.35 mmol), phenyl N-[4-fluoro-3-(trifluoromethyl)phenyl]carbamate (100 mg, 0.35 mmol) and DIEA (135 mg, 1.05 mmol) in THF (4 mL), stir at 80° C. for 2 hrs, Remove the volatiles, suspend the residue in DCM, filter and collect the solid to get the target compound (132 mg, 77%). MS: (M+1): 490.3.

Examples 71-236 are prepared with similar method (Table 4)

TABLE 4

| Example number | Structure | MS [M + 1]$^+$ |
|---|---|---|
| Example 70 | 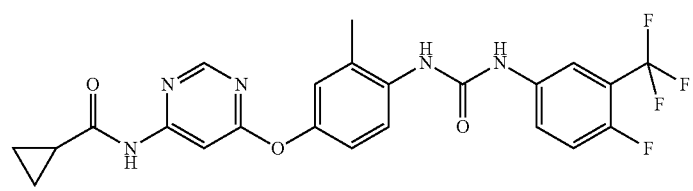 [SMILES: Cc1cc(Oc2cc(NC(=O)C3CC3)ncn2)ccc1NC(=O)Nc1ccc(F)c(C(F)(F)F)c1] | 490.3 |
| Example 71 | 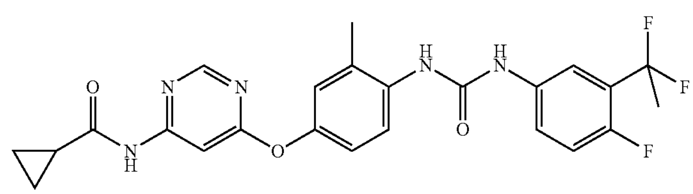 | 486.3 |
| Example 72 | 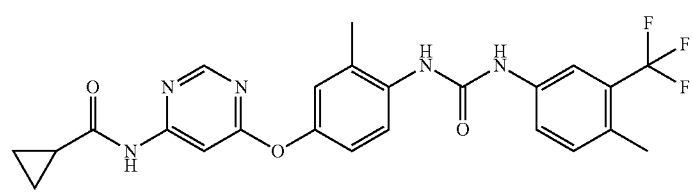 [SMILES: Cc1cc(Oc2cc(NC(=O)C3CC3)ncn2)ccc1NC(=O)Nc1ccc(C)c(C(F)(F)F)c1] | 486.3 |

TABLE 4-continued
Examples 70-236
| Example number | Structure | MS [M + 1]+ |
|---|---|---|
| Example 73 | 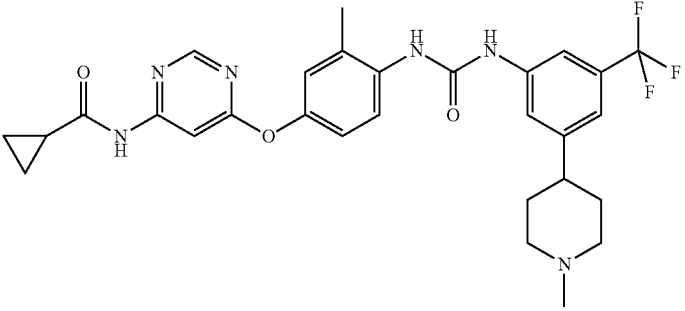 [SMILES: Cc1cc(Oc2cc(NC(=O)C3CC3)ncn2)ccc1NC(=O)Nc1cc(C2CCN(C)CC2)cc(C(F)(F)F)c1] | 569.4 |
| Example 74 | 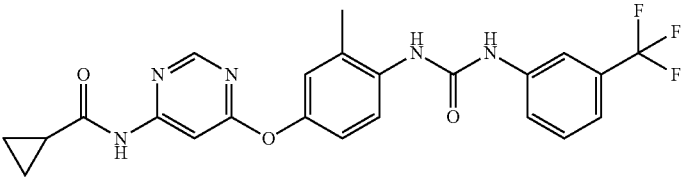 [SMILES: Cc1cc(Oc2cc(NC(=O)C3CC3)ncn2)ccc1NC(=O)Nc1cccc(C(F)(F)F)c1] | 472.3 |
| Example 75 | 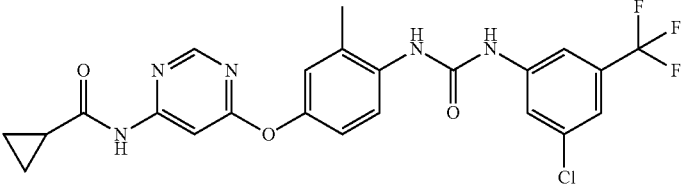 [SMILES: Cc1cc(Oc2cc(NC(=O)C3CC3)ncn2)ccc1NC(=O)Nc1cc(Cl)cc(C(F)(F)F)c1] | 506.2 |
| Example 76 | 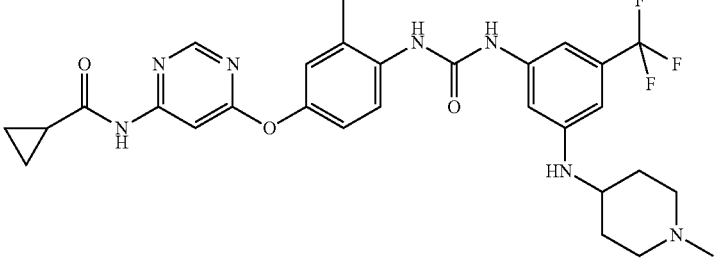 | 584.4 |
| Example 77 | 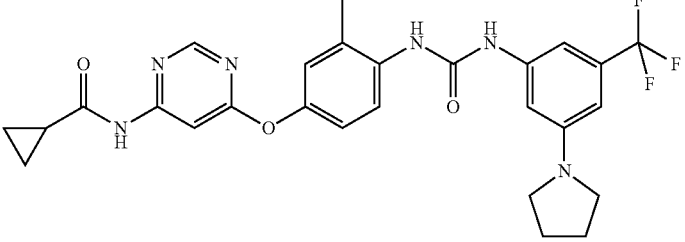 | 541.3 |

TABLE 4-continued

Examples 70-236

| Example number | Structure | MS [M + 1]+ |
|---|---|---|
| Example 78 | 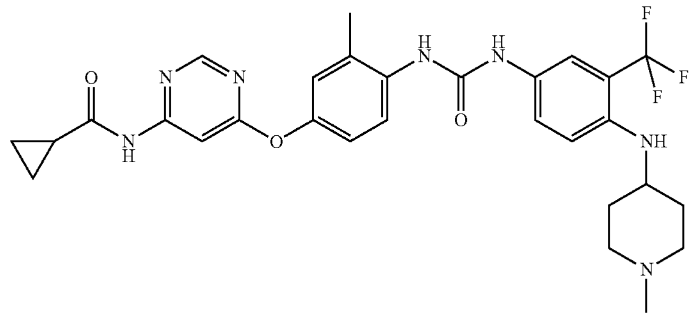 [SMILES: Cc1cc(Oc2cc(NC(=O)C3CC3)ncn2)ccc1NC(=O)Nc1ccc(NC2CCN(C)CC2)c(C(F)(F)F)c1] | 584.4 |
| Example 79 | 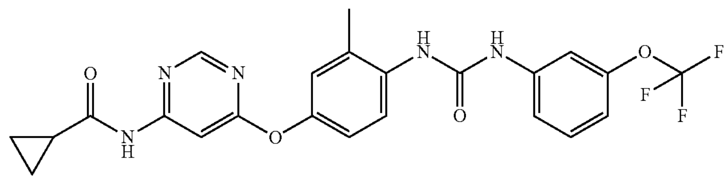 [SMILES: Cc1cc(Oc2cc(NC(=O)C3CC3)ncn2)ccc1NC(=O)Nc1cccc(OC(F)(F)F)c1] | 488.3 |
| Example 80 | 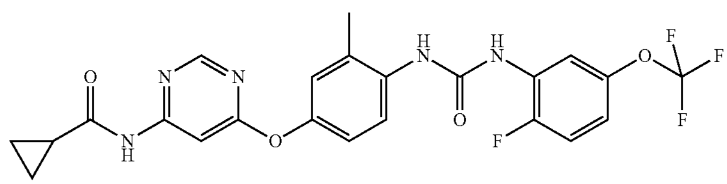 [SMILES: Cc1cc(Oc2cc(NC(=O)C3CC3)ncn2)ccc1NC(=O)Nc1cc(OC(F)(F)F)ccc1F] | 506.2 |
| Example 81 | 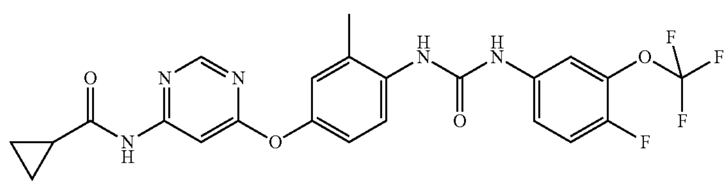 | 506.3 |
| Example 82 | 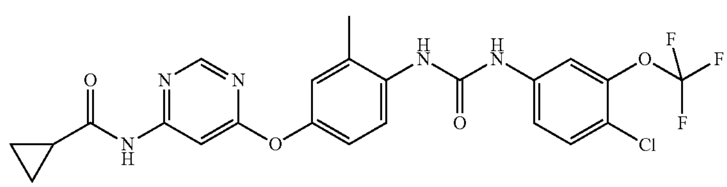 [SMILES: Cc1cc(Oc2cc(NC(=O)C3CC3)ncn2)ccc1NC(=O)Nc1ccc(Cl)c(OC(F)(F)F)c1] | 522.2 |
| Example 83 | 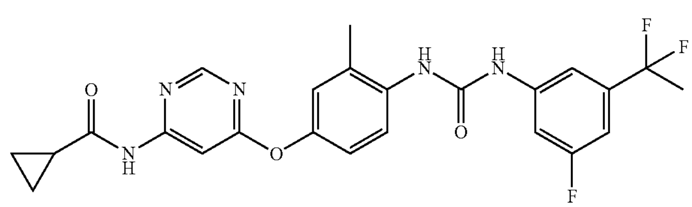 [SMILES: Cc1cc(Oc2cc(NC(=O)C3CC3)ncn2)ccc1NC(=O)Nc1cc(F)cc(C(C)(F)F)c1] | 486.3 |
| Example 84 | 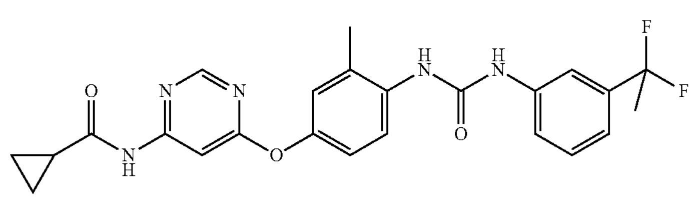 [SMILES: Cc1cc(Oc2cc(NC(=O)C3CC3)ncn2)ccc1NC(=O)Nc1cccc(C(C)(F)F)c1] | 468.3 |

TABLE 4-continued

Examples 70-236

| Example number | Structure | MS [M + 1]+ |
|---|---|---|
| Example 85 | 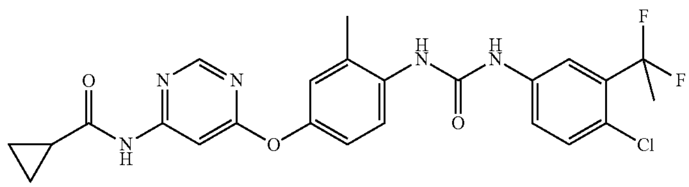 [SMILES: Cc1cc(Oc2cc(NC(=O)C3CC3)ncn2)ccc1NC(=O)Nc1ccc(Cl)c(C(C)(F)F)c1] | 502.3 |
| Example 86 | 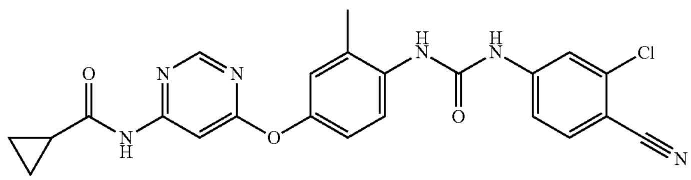 [SMILES: Cc1cc(Oc2cc(NC(=O)C3CC3)ncn2)ccc1NC(=O)Nc1ccc(C#N)c(Cl)c1] | 463.2 |
| Example 87 | 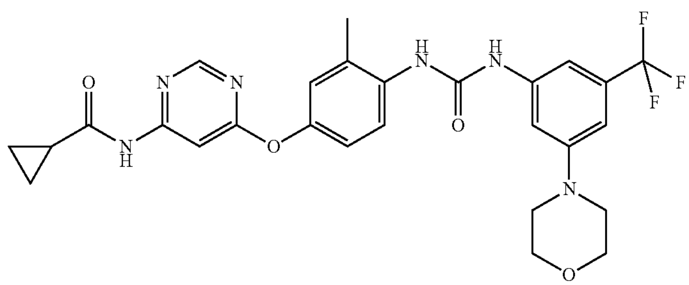 [SMILES: Cc1cc(Oc2cc(NC(=O)C3CC3)ncn2)ccc1NC(=O)Nc1cc(N2CCOCC2)cc(C(F)(F)F)c1] | 557.3 |
| Example 88 | 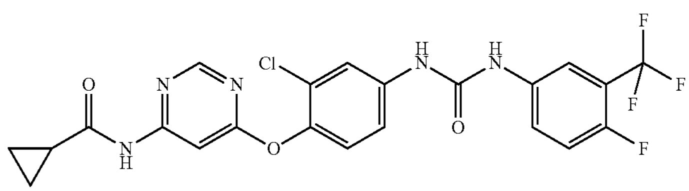 [SMILES: O=C(Nc1ccc(Oc2cc(NC(=O)C3CC3)ncn2)c(Cl)c1)Nc1ccc(F)c(C(F)(F)F)c1] | 510.2 |
| Example 89 | 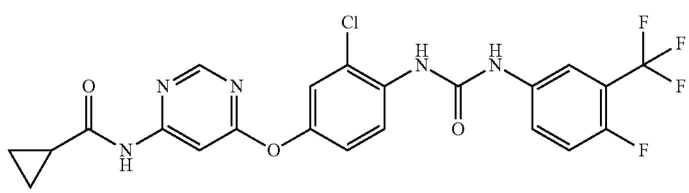 | 510.2 |
| Example 90 | 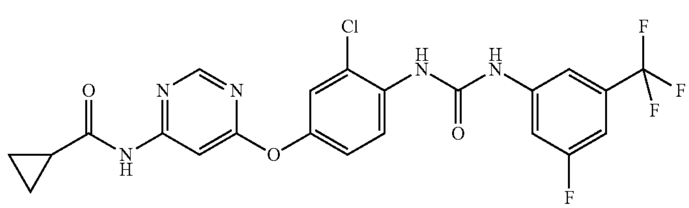 [SMILES: O=C(Nc1cc(F)cc(C(F)(F)F)c1)Nc1ccc(Oc2cc(NC(=O)C3CC3)ncn2)cc1Cl] | 510.2 |
| Example 91 | 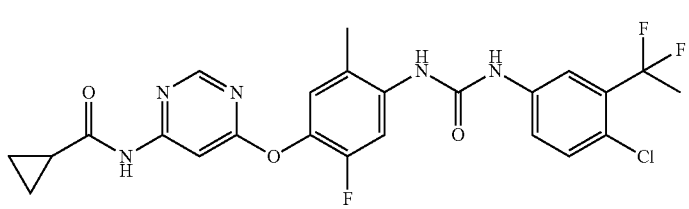 [SMILES: Cc1cc(Oc2cc(NC(=O)C3CC3)ncn2)c(F)cc1NC(=O)Nc1ccc(Cl)c(C(C)(F)F)c1] | 520.2 |

TABLE 4-continued

Examples 70-236

| Example number | Structure | MS [M + 1]+ |
|---|---|---|
| Example 92 | 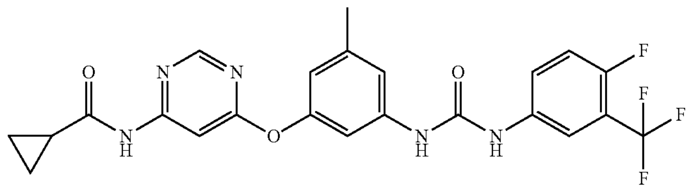 [SMILES: Cc1cc(NC(=O)Nc2ccc(F)c(C(F)(F)F)c2)cc(Oc2cc(NC(=O)C3CC3)ncn2)c1] | 490.3 |
| Example 93 | 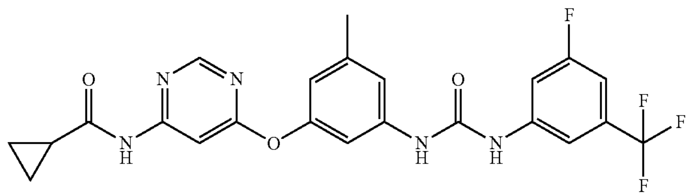 [SMILES: Cc1cc(NC(=O)Nc2cc(F)cc(C(F)(F)F)c2)cc(Oc2cc(NC(=O)C3CC3)ncn2)c1] | 502.2 |
| Example 94 | 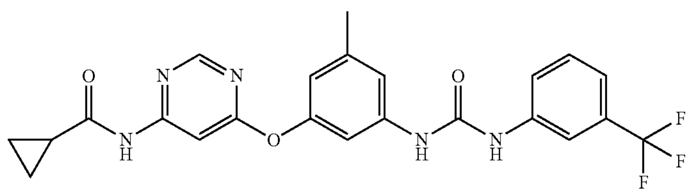 [SMILES: Cc1cc(NC(=O)Nc2cccc(C(F)(F)F)c2)cc(Oc2cc(NC(=O)C3CC3)ncn2)c1] | 472.3 |
| Example 95 | 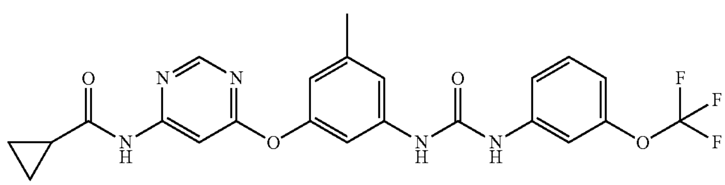 [SMILES: Cc1cc(NC(=O)Nc2cccc(OC(F)(F)F)c2)cc(Oc2cc(NC(=O)C3CC3)ncn2)c1] | 488.3 |
| Example 96 | 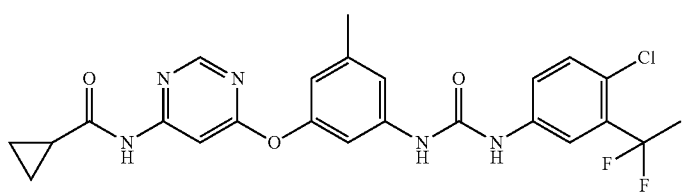 [SMILES: Cc1cc(NC(=O)Nc2ccc(Cl)c(C(C)(F)F)c2)cc(Oc2cc(NC(=O)C3CC3)ncn2)c1] | 502.3 |
| Example 97 | 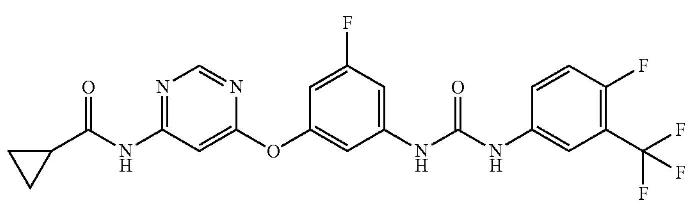 [SMILES: O=C(Nc1cc(F)cc(Oc2cc(NC(=O)C3CC3)ncn2)c1)Nc1ccc(F)c(C(F)(F)F)c1] | 494.2 |
| Example 98 | 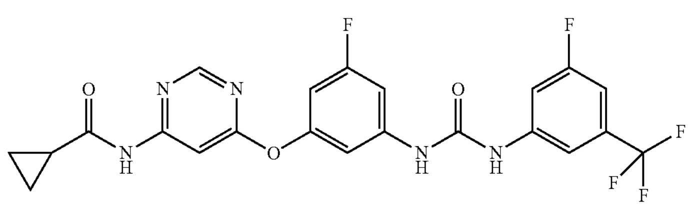 [SMILES: O=C(Nc1cc(F)cc(Oc2cc(NC(=O)C3CC3)ncn2)c1)Nc1cc(F)cc(C(F)(F)F)c1] | 494.2 |

TABLE 4-continued

Examples 70-236

| Example number | Structure | MS [M + 1]+ |
|---|---|---|
| Example 99 | 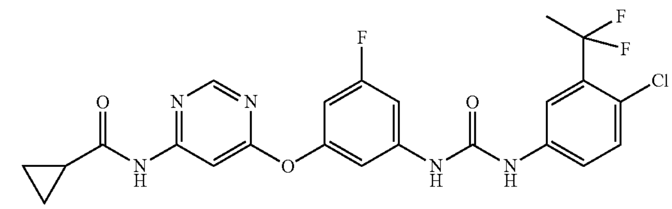 [SMILES: CC(F)(F)c1cc(NC(=O)Nc2cc(F)cc(Oc3cc(NC(=O)C4CC4)ncn3)c2)ccc1Cl] | 506.2 |
| Example 100 | 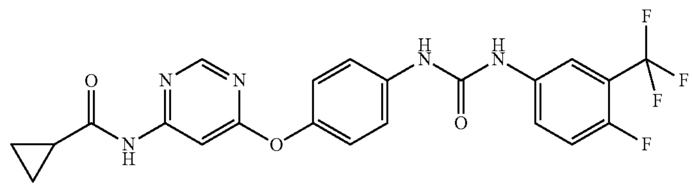 [SMILES: O=C(Nc1ccc(Oc2cc(NC(=O)C3CC3)ncn2)cc1)Nc1ccc(F)c(C(F)(F)F)c1] | 476.2 |
| Example 101 | 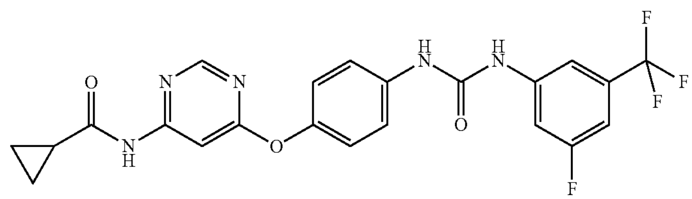 [SMILES: O=C(Nc1ccc(Oc2cc(NC(=O)C3CC3)ncn2)cc1)Nc1cc(F)cc(C(F)(F)F)c1] | 476.2 |
| Example 102 | 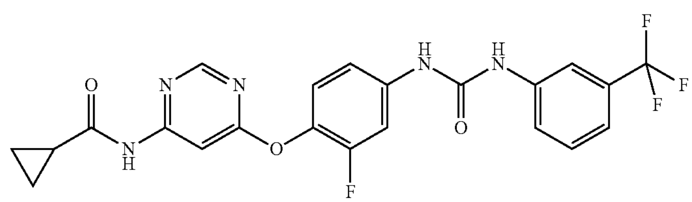 [SMILES: O=C(Nc1cccc(C(F)(F)F)c1)Nc1ccc(Oc2cc(NC(=O)C3CC3)ncn2)c(F)c1] | 476.2 |
| Example 103 | 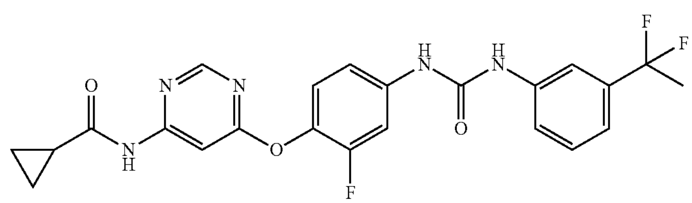 [SMILES: CC(F)(F)c1cccc(NC(=O)Nc2ccc(Oc3cc(NC(=O)C4CC4)ncn3)c(F)c2)c1] | 472.3 |
| Example 104 | 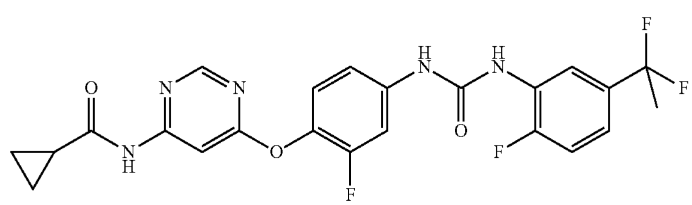 [SMILES: CC(F)(F)c1ccc(F)c(NC(=O)Nc2ccc(Oc3cc(NC(=O)C4CC4)ncn3)c(F)c2)c1] | 490.3 |
| Example 105 | 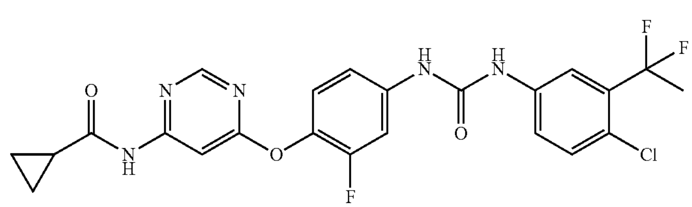 [SMILES: CC(F)(F)c1cc(NC(=O)Nc2ccc(Oc3cc(NC(=O)C4CC4)ncn3)c(F)c2)ccc1Cl] | 506.2 |

TABLE 4-continued

Examples 70-236

| Example number | Structure | MS [M + 1]+ |
|---|---|---|
| Example 106 | 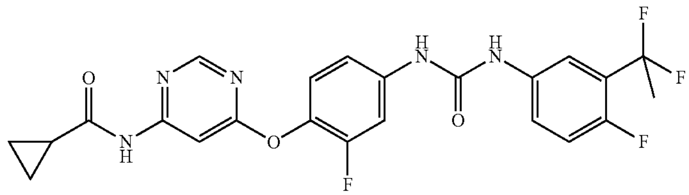 [SMILES: CC(F)(F)c1cc(NC(=O)Nc2ccc(Oc3cc(NC(=O)C4CC4)ncn3)c(F)c2)ccc1F] | 490.3 |
| Example 107 | 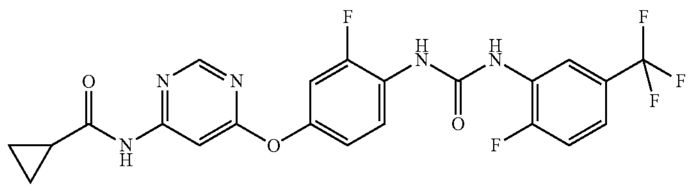 | 494.2 |
| Example 108 | 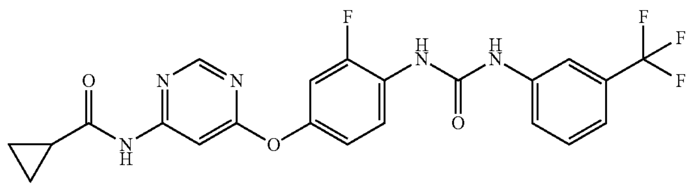 [SMILES: O=C(Nc1cccc(C(F)(F)F)c1)Nc1ccc(Oc2cc(NC(=O)C3CC3)ncn2)cc1F] | 476.2 |
| Example 109 | 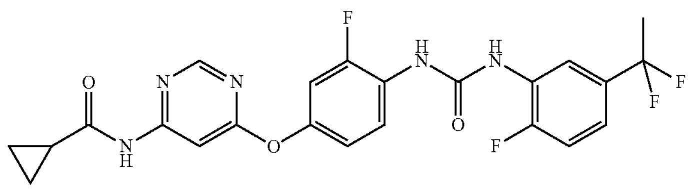 [SMILES: CC(F)(F)c1ccc(F)c(NC(=O)Nc2ccc(Oc3cc(NC(=O)C4CC4)ncn3)cc2F)c1] | 490.2 |
| Example 110 | 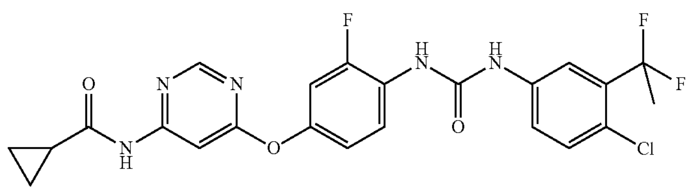 [SMILES: CC(F)(F)c1cc(NC(=O)Nc2ccc(Oc3cc(NC(=O)C4CC4)ncn3)cc2F)ccc1Cl] | 506.2 |
| Example 111 | 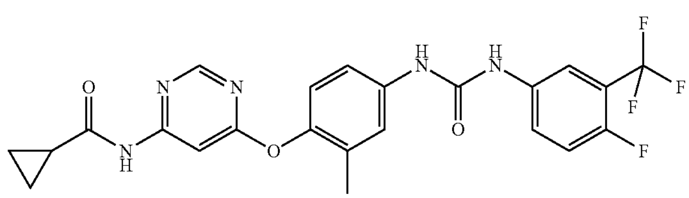 [SMILES: Cc1cc(NC(=O)Nc2ccc(F)c(C(F)(F)F)c2)ccc1Oc1cc(NC(=O)C2CC2)ncn1] | 490.3 |
| Example 112 | 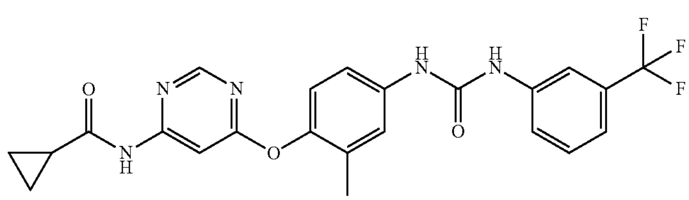 [SMILES: Cc1cc(NC(=O)Nc2cccc(C(F)(F)F)c2)ccc1Oc1cc(NC(=O)C2CC2)ncn1] | 472.3 |
| Example 113 | 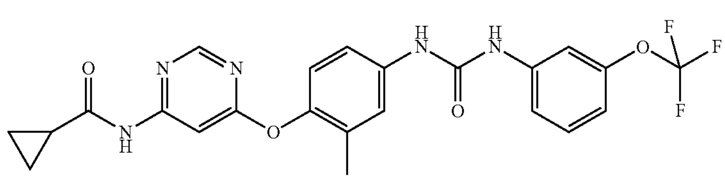 [SMILES: Cc1cc(NC(=O)Nc2cccc(OC(F)(F)F)c2)ccc1Oc1cc(NC(=O)C2CC2)ncn1] | 488.2 |

TABLE 4-continued

Examples 70-236

| Example number | Structure | MS [M + 1]+ |
|---|---|---|
| Example 114 | 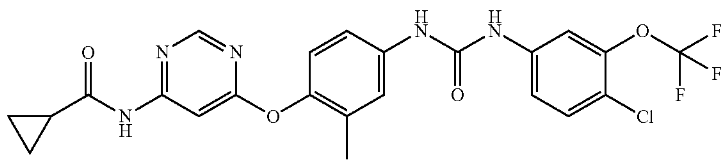 [SMILES: Cc1cc(NC(=O)Nc2ccc(Cl)c(OC(F)(F)F)c2)ccc1Oc1cc(NC(=O)C2CC2)ncn1] | 522.2 |
| Example 115 | 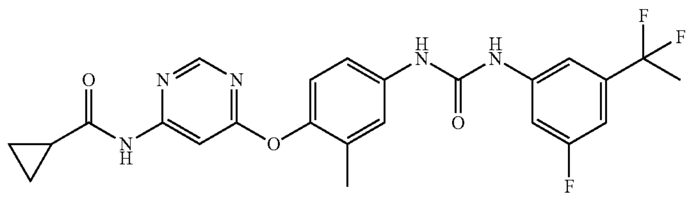 [SMILES: Cc1cc(NC(=O)Nc2cc(F)cc(C(C)(F)F)c2)ccc1Oc1cc(NC(=O)C2CC2)ncn1] | 486.2 |
| Example 116 | 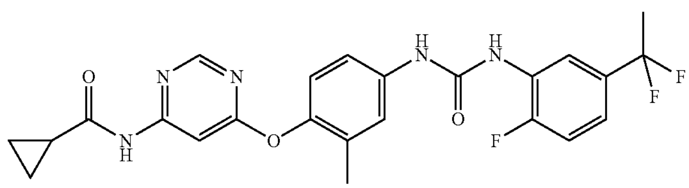 [SMILES: Cc1cc(NC(=O)Nc2cc(C(C)(F)F)ccc2F)ccc1Oc1cc(NC(=O)C2CC2)ncn1] | 486.3 |
| Example 117 | 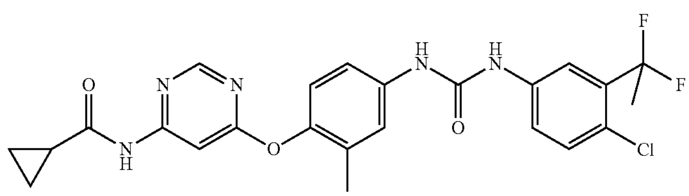 [SMILES: Cc1cc(NC(=O)Nc2ccc(Cl)c(C(C)(F)F)c2)ccc1Oc1cc(NC(=O)C2CC2)ncn1] | 502.2 |
| Example 118 | 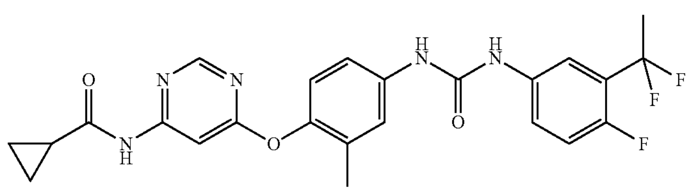 [SMILES: Cc1cc(NC(=O)Nc2ccc(F)c(C(C)(F)F)c2)ccc1Oc1cc(NC(=O)C2CC2)ncn1] | 486.3 |
| Example 119 | 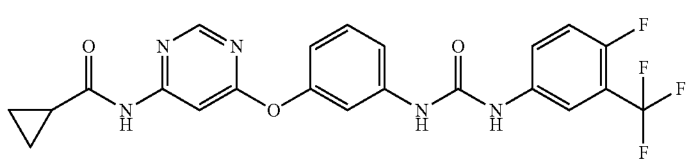 [SMILES: O=C(Nc1cccc(Oc2cc(NC(=O)C3CC3)ncn2)c1)Nc1ccc(F)c(C(F)(F)F)c1] | 476.2 |
| Example 120 | 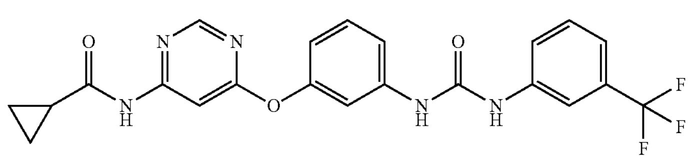 [SMILES: O=C(Nc1cccc(Oc2cc(NC(=O)C3CC3)ncn2)c1)Nc1cccc(C(F)(F)F)c1] | 458.2 |
| Example 121 | 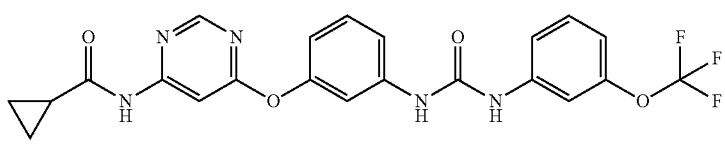 [SMILES: O=C(Nc1cccc(Oc2cc(NC(=O)C3CC3)ncn2)c1)Nc1cccc(OC(F)(F)F)c1] | 474.2 |

TABLE 4-continued

Examples 70-236

| Example number | Structure | MS [M + 1]+ |
|---|---|---|
| Example 122 | 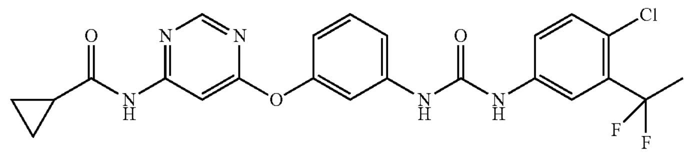 [SMILES: CC(F)(F)c1cc(NC(=O)Nc2cccc(Oc3cc(NC(=O)C4CC4)ncn3)c2)ccc1Cl] | 488.2 |
| Example 123 | 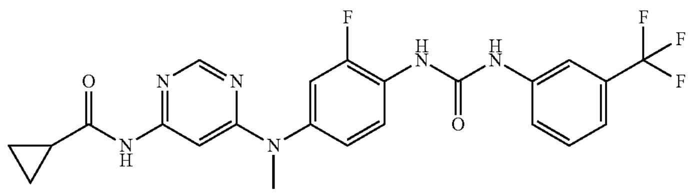 [SMILES: CN(c1ccc(NC(=O)Nc2cccc(C(F)(F)F)c2)c(F)c1)c1cc(NC(=O)C2CC2)ncn1] | 489.3 |
| Example 124 | 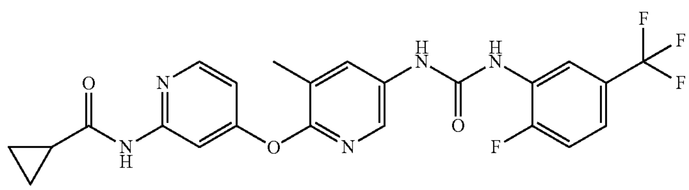 [SMILES: Cc1cc(NC(=O)Nc2cc(C(F)(F)F)ccc2F)cnc1Oc1ccnc(NC(=O)C2CC2)c1] | 490.2 |
| Example 125 | 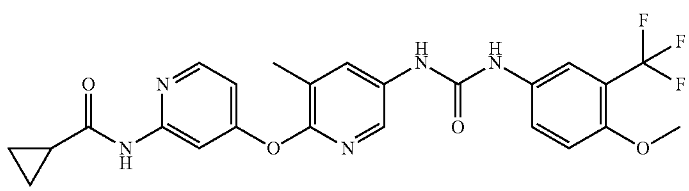 [SMILES: COc1ccc(NC(=O)Nc2cnc(Oc3ccnc(NC(=O)C4CC4)c3)c(C)c2)cc1C(F)(F)F] | 502.2 |
| Example 126 | 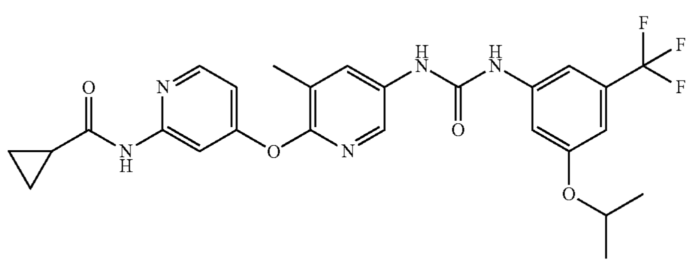 [SMILES: Cc1cc(NC(=O)Nc2cc(OC(C)C)cc(C(F)(F)F)c2)cnc1Oc1ccnc(NC(=O)C2CC2)c1] | 530.3 |
| Example 127 | 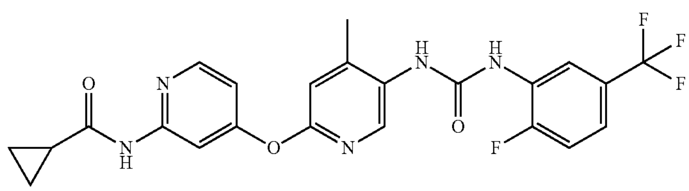 [SMILES: Cc1cc(Oc2ccnc(NC(=O)C3CC3)c2)ncc1NC(=O)Nc1cc(C(F)(F)F)ccc1F] | 490.2 |
| Example 128 | 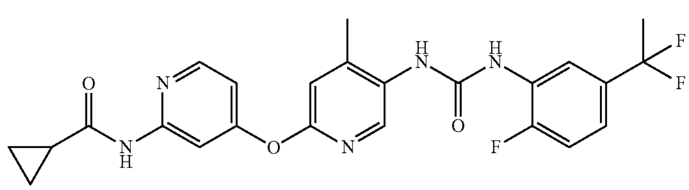 [SMILES: Cc1cc(Oc2ccnc(NC(=O)C3CC3)c2)ncc1NC(=O)Nc1cc(C(C)(F)F)ccc1F] | 486.2 |

TABLE 4-continued

Examples 70-236

| Example number | Structure | MS [M + 1]+ |
|---|---|---|
| Example 129 | 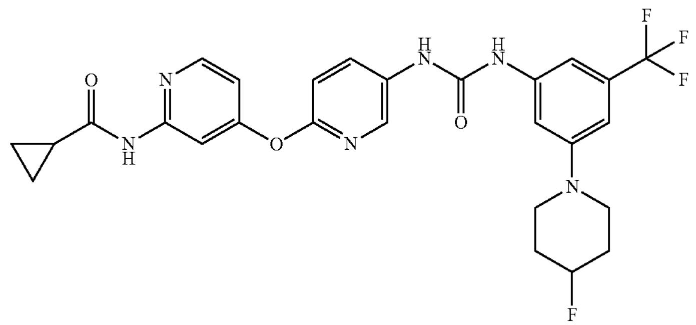 [SMILES: O=C(Nc1ccc(Oc2ccnc(NC(=O)C3CC3)c2)nc1)Nc1cc(N2CCC(F)CC2)cc(C(F)(F)F)c1] | 559.3 |
| Example 130 | 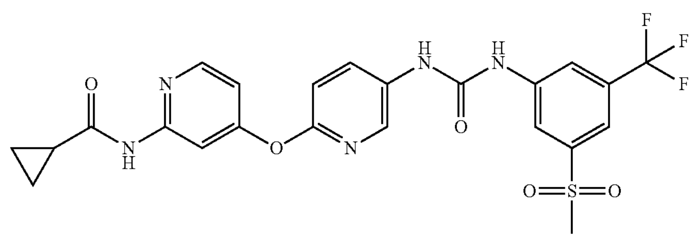 [SMILES: CS(=O)(=O)c1cc(NC(=O)Nc2ccc(Oc3ccnc(NC(=O)C4CC4)c3)nc2)cc(C(F)(F)F)c1] | 536.2 |
| Example 131 | 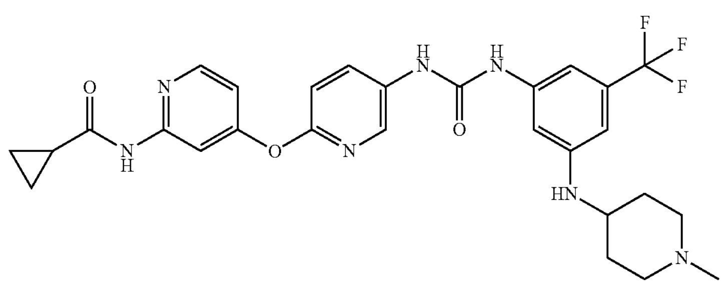 [SMILES: CN1CCC(Nc2cc(NC(=O)Nc3ccc(Oc4ccnc(NC(=O)C5CC5)c4)nc3)cc(C(F)(F)F)c2)CC1] | 570.3 |
| Example 132 | 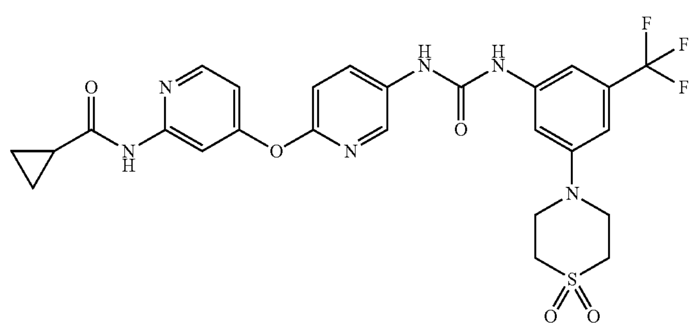 [SMILES: O=C(Nc1ccc(Oc2ccnc(NC(=O)C3CC3)c2)nc1)Nc1cc(N2CCS(=O)(=O)CC2)cc(C(F)(F)F)c1] | 591.2 |
| Example 133 | 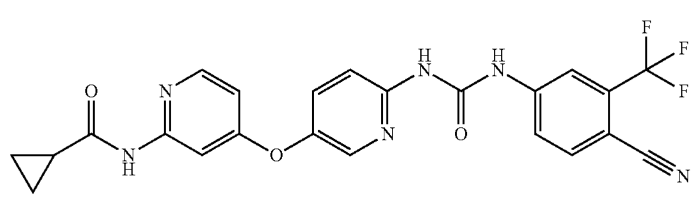 [SMILES: N#Cc1ccc(NC(=O)Nc2ccc(Oc3ccnc(NC(=O)C4CC4)c3)cn2)cc1C(F)(F)F] | 483.2 |

TABLE 4-continued

Examples 70-236

| Example number | Structure | MS [M + 1]+ |
|---|---|---|
| Example 134 | (structure) | 555.3 |
| Example 135 | (structure) | 458.2 |
| Example 136 | (structure) | 536.2 |
| Example 137 | (structure) | 491.2 |
| Example 138 | (structure) | 475.2 |
| Example 139 | (structure) | 482.2 |
| Example 140 | (structure) | 471.2 |

TABLE 4-continued

Examples 70-236

| Example number | Structure | MS [M + 1]+ |
|---|---|---|
| Example 141 | 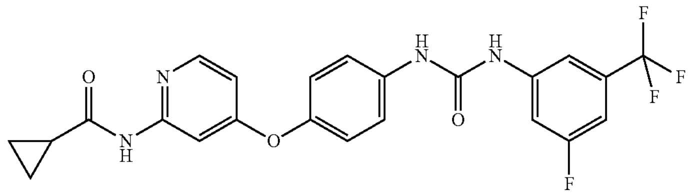 [SMILES: O=C(Nc1ccc(Oc2ccnc(NC(=O)C3CC3)c2)cc1)Nc1cc(F)cc(C(F)(F)F)c1] | 475.3 |
| Example 142 | 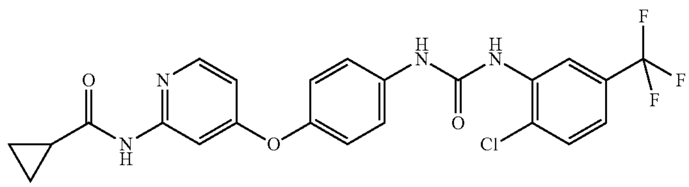 [SMILES: O=C(Nc1ccc(Oc2ccnc(NC(=O)C3CC3)c2)cc1)Nc1cc(C(F)(F)F)ccc1Cl] | 491.2 |
| Example 143 | 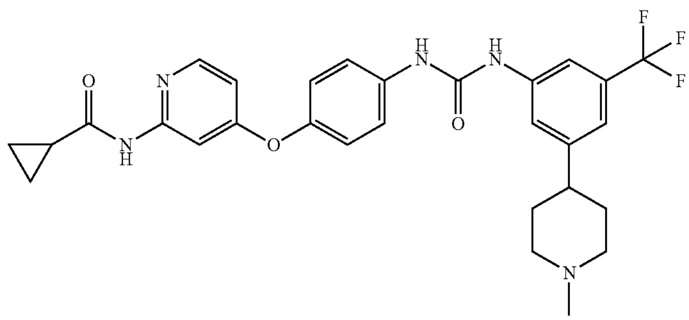 [SMILES: CN1CCC(c2cc(NC(=O)Nc3ccc(Oc4ccnc(NC(=O)C5CC5)c4)cc3)cc(C(F)(F)F)c2)CC1] | 554.3 |
| Example 144 | 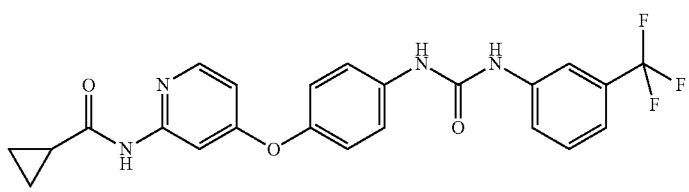 [SMILES: O=C(Nc1ccc(Oc2ccnc(NC(=O)C3CC3)c2)cc1)Nc1cccc(C(F)(F)F)c1] | 457.2 |
| Example 145 | 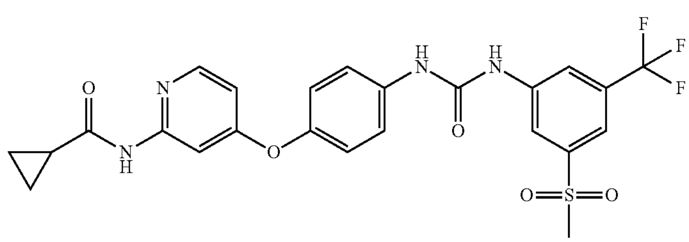 [SMILES: CS(=O)(=O)c1cc(NC(=O)Nc2ccc(Oc3ccnc(NC(=O)C4CC4)c3)cc2)cc(C(F)(F)F)c1] | 535.2 |
| Example 146 | 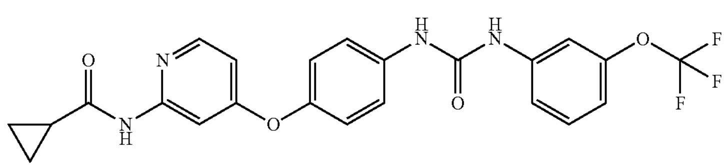 [SMILES: O=C(Nc1ccc(Oc2ccnc(NC(=O)C3CC3)c2)cc1)Nc1cccc(OC(F)(F)F)c1] | 473.3 |
| Example 147 | 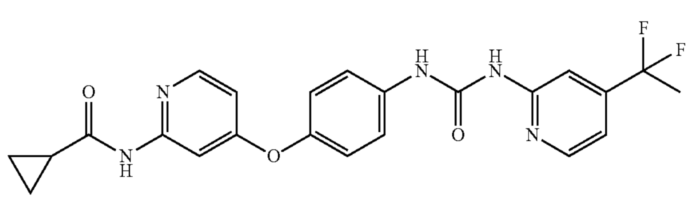 [SMILES: CC(F)(F)c1ccnc(NC(=O)Nc2ccc(Oc3ccnc(NC(=O)C4CC4)c3)cc2)c1] | 454.3 |

TABLE 4-continued

Examples 70-236

| Example number | Structure | MS [M + 1]+ |
|---|---|---|
| Example 148 | 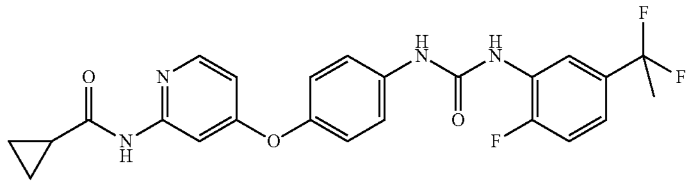 [SMILES: CC(F)(F)c1ccc(F)c(NC(=O)Nc2ccc(Oc3ccnc(NC(=O)C4CC4)c3)cc2)c1] | 471.3 |
| Example 149 | 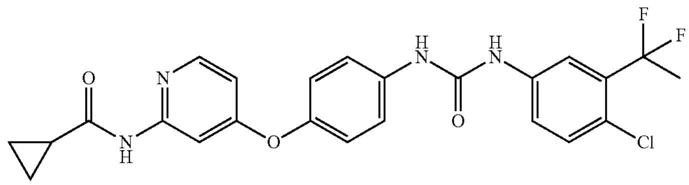 [SMILES: CC(F)(F)c1cc(NC(=O)Nc2ccc(Oc3ccnc(NC(=O)C4CC4)c3)cc2)ccc1Cl] | 487.2 |
| Example 150 | 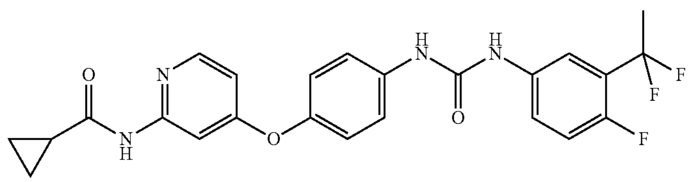 [SMILES: CC(F)(F)c1cc(NC(=O)Nc2ccc(Oc3ccnc(NC(=O)C4CC4)c3)cc2)ccc1F] | 471.2 |
| Example 151 | 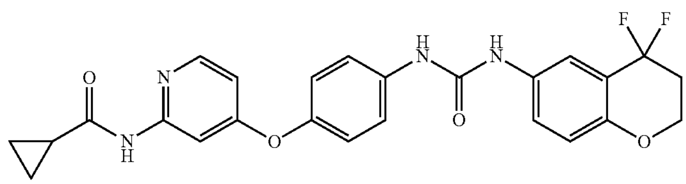 [SMILES: O=C(Nc1ccc(Oc2ccnc(NC(=O)C3CC3)c2)cc1)Nc1ccc2c(c1)C(F)(F)CCO2] | 481.3 |
| Example 152 | 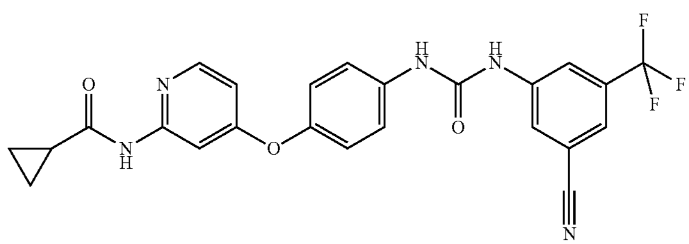 [SMILES: N#Cc1cc(NC(=O)Nc2ccc(Oc3ccnc(NC(=O)C4CC4)c3)cc2)cc(C(F)(F)F)c1] | 482.3 |
| Example 153 | 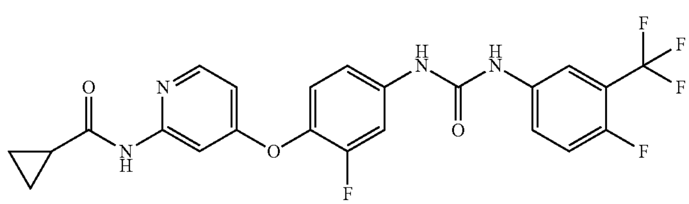 [SMILES: O=C(Nc1ccc(Oc2ccnc(NC(=O)C3CC3)c2)c(F)c1)Nc1ccc(F)c(C(F)(F)F)c1] | 493.2 |
| Example 154 | 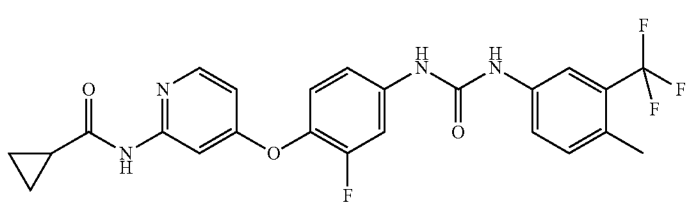 [SMILES: Cc1ccc(NC(=O)Nc2ccc(Oc3ccnc(NC(=O)C4CC4)c3)c(F)c2)cc1C(F)(F)F] | 489.2 |

TABLE 4-continued
Examples 70-236
| Example number | Structure | MS [M + 1]+ |
|---|---|---|
| Example 155 | 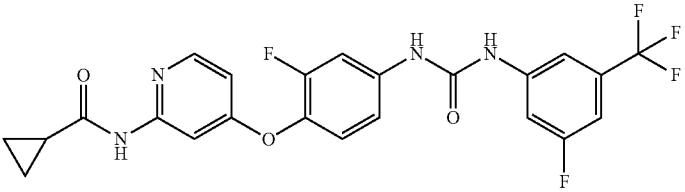 [SMILES: O=C(Nc1cc(F)cc(C(F)(F)F)c1)Nc1ccc(Oc2ccnc(NC(=O)C3CC3)c2)c(F)c1] | 493.1 |
| Example 156 | 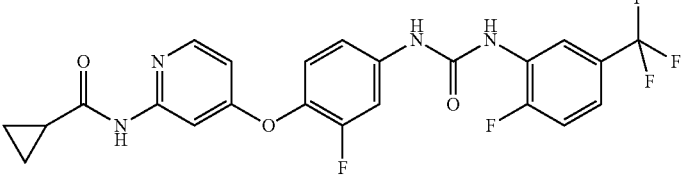 | 493.3 |
| Example 157 | 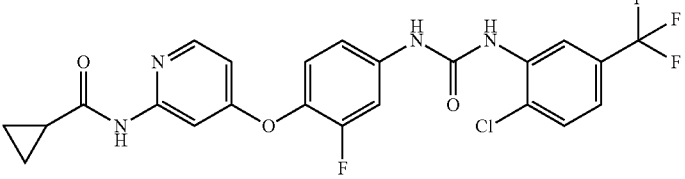 | 509.2 |
| Example 158 | 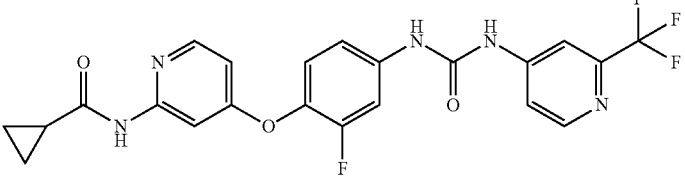 | 476.2 |
| Example 159 | 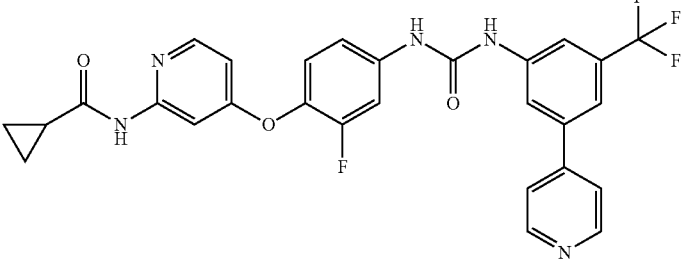 | 552.2 |
| Example 160 | 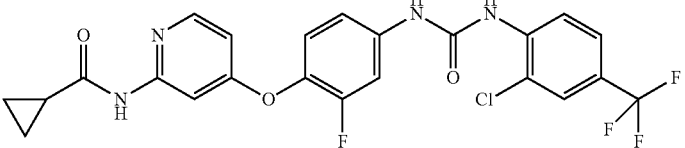 | 509.2 |
| Example 161 | 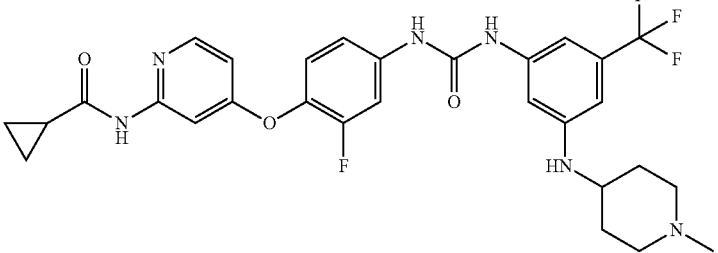 | 587.3 |

TABLE 4-continued

Examples 70-236

| Example number | Structure | MS [M + 1]+ |
|---|---|---|
| Example 162 | 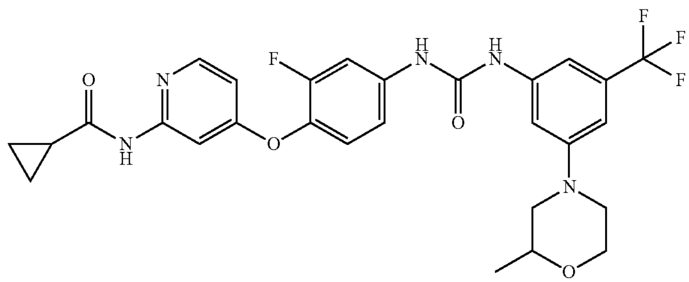 [SMILES: CC1CN(c2cc(NC(=O)Nc3ccc(Oc4ccnc(NC(=O)C5CC5)c4)c(F)c3)cc(C(F)(F)F)c2)CCO1] | 574.3 |
| Example 163 | 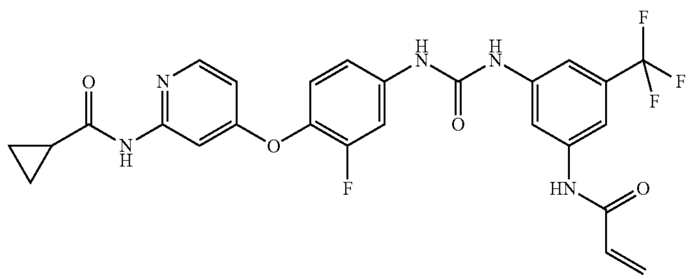 [SMILES: C=CC(=O)Nc1cc(NC(=O)Nc2ccc(Oc3ccnc(NC(=O)C4CC4)c3)c(F)c2)cc(C(F)(F)F)c1] | 544.2 |
| Example 164 | 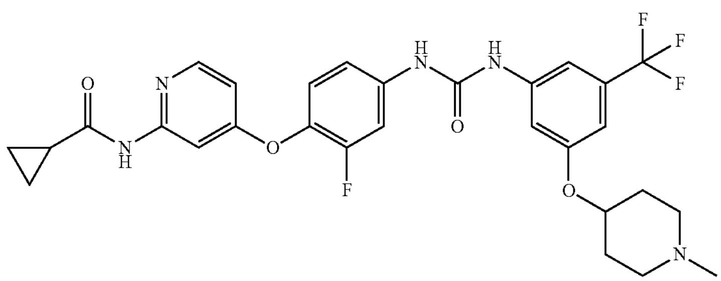 | 588.3 |
| Example 165 | 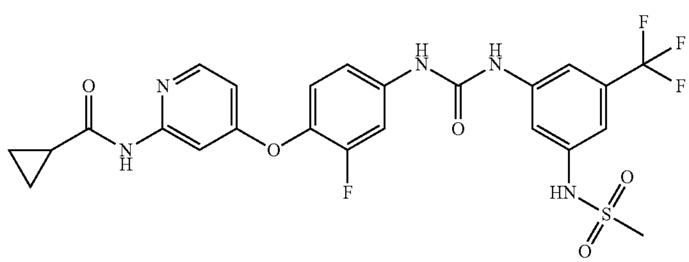 [SMILES: CS(=O)(=O)Nc1cc(NC(=O)Nc2ccc(Oc3ccnc(NC(=O)C4CC4)c3)c(F)c2)cc(C(F)(F)F)c1] | 568.2 |
| Example 166 | 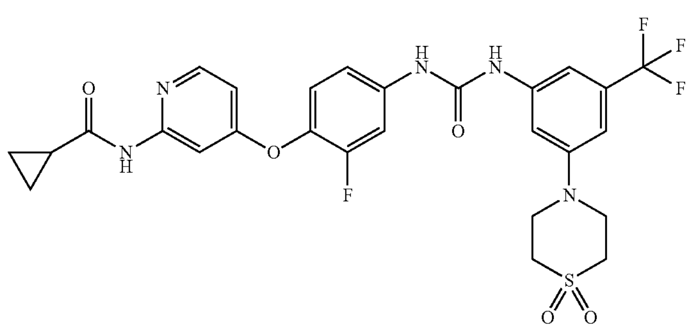 [SMILES: O=C(Nc1cc(N2CCS(=O)(=O)CC2)cc(C(F)(F)F)c1)Nc1ccc(Oc2ccnc(NC(=O)C3CC3)c2)c(F)c1] | 608.2 |

TABLE 4-continued

Examples 70-236

| Example number | Structure | MS [M + 1]⁺ |
|---|---|---|
| Example 167 | 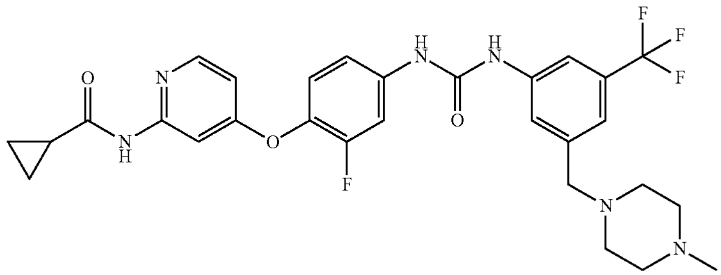 [SMILES: CN1CCN(Cc2cc(NC(=O)Nc3ccc(Oc4ccnc(NC(=O)C5CC5)c4)c(F)c3)cc(C(F)(F)F)c2)CC1] | 587.3 |
| Example 168 | 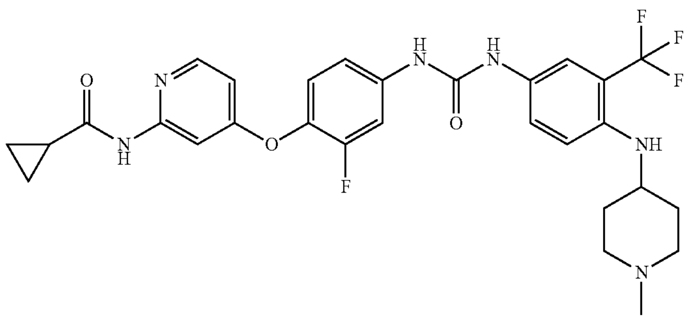 [SMILES: CN1CCC(Nc2ccc(NC(=O)Nc3ccc(Oc4ccnc(NC(=O)C5CC5)c4)c(F)c3)cc2C(F)(F)F)CC1] | 587.3 |
| Example 169 | 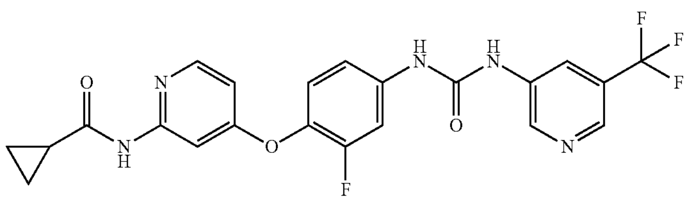 [SMILES: O=C(Nc1cncc(C(F)(F)F)c1)Nc1ccc(Oc2ccnc(NC(=O)C3CC3)c2)c(F)c1] | 476.2 |
| Example 170 | 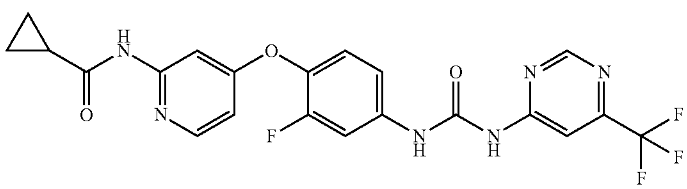 [SMILES: O=C(Nc1ccc(Oc2ccnc(NC(=O)C3CC3)c2)c(F)c1)Nc1cc(C(F)(F)F)ncn1] | 477.2 |
| Example 171 | 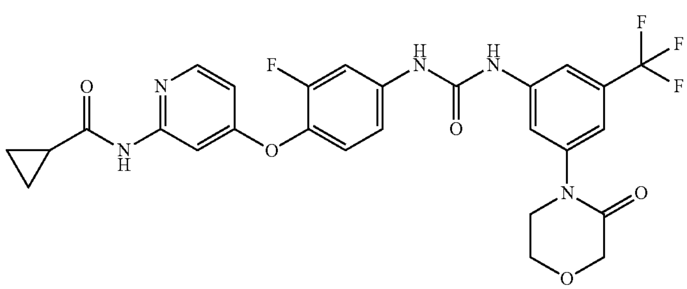 [SMILES: O=C(Nc1cc(N2CCOCC2=O)cc(C(F)(F)F)c1)Nc1ccc(Oc2ccnc(NC(=O)C3CC3)c2)c(F)c1] | 574.2 |
| Example 172 | 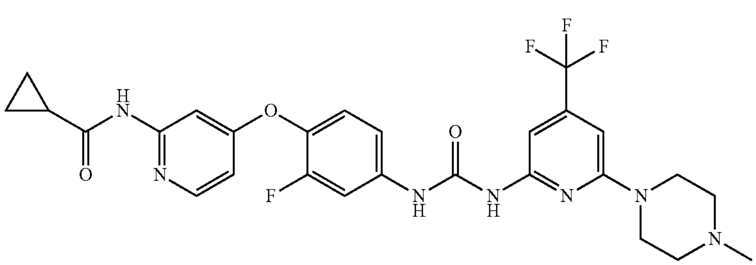 [SMILES: CN1CCN(c2cc(C(F)(F)F)cc(NC(=O)Nc3ccc(Oc4ccnc(NC(=O)C5CC5)c4)c(F)c3)n2)CC1] | 574.3 |

TABLE 4-continued

Examples 70-236

| Example number | Structure | MS [M + 1]+ |
|---|---|---|
| Example 173 | 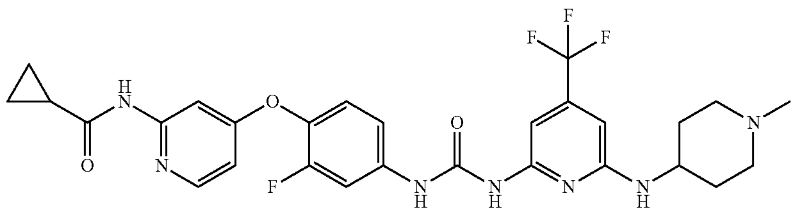 [SMILES: CN1CCC(Nc2cc(C(F)(F)F)cc(NC(=O)Nc3ccc(Oc4ccnc(NC(=O)C5CC5)c4)c(F)c3)n2)CC1] | 588.3 |
| Example 174 | 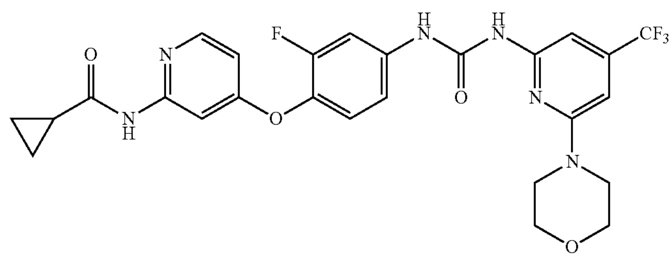 [SMILES: O=C(Nc1ccc(Oc2ccnc(NC(=O)C3CC3)c2)c(F)c1)Nc1cc(C(F)(F)F)cc(N2CCOCC2)n1] | 561.2 |
| Example 175 | 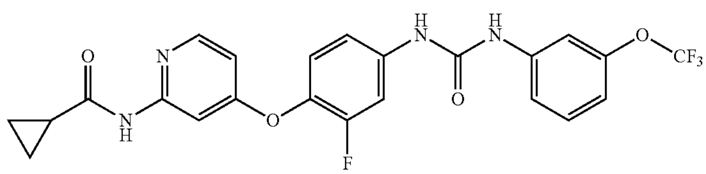 [SMILES: O=C(Nc1cccc(OC(F)(F)F)c1)Nc1ccc(Oc2ccnc(NC(=O)C3CC3)c2)c(F)c1] | 491.2 |
| Example 176 | 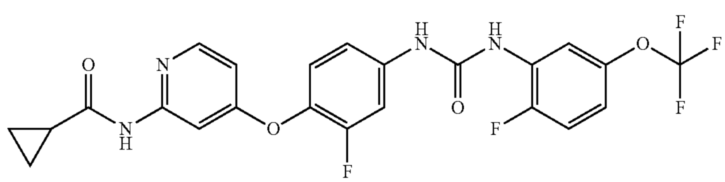 [SMILES: O=C(Nc1ccc(Oc2ccnc(NC(=O)C3CC3)c2)c(F)c1)Nc1cc(OC(F)(F)F)ccc1F] | 509.2 |
| Example 177 | 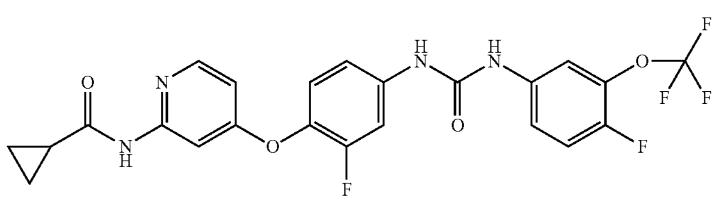 [SMILES: O=C(Nc1ccc(Oc2ccnc(NC(=O)C3CC3)c2)c(F)c1)Nc1ccc(F)c(OC(F)(F)F)c1] | 509.2 |
| Example 178 | 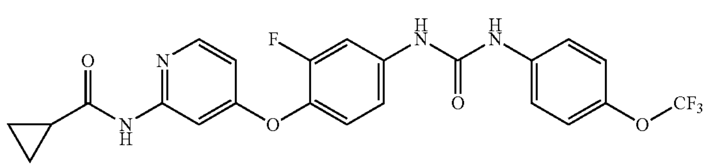 [SMILES: O=C(Nc1ccc(OC(F)(F)F)cc1)Nc1ccc(Oc2ccnc(NC(=O)C3CC3)c2)c(F)c1] | 491.2 |
| Example 179 | 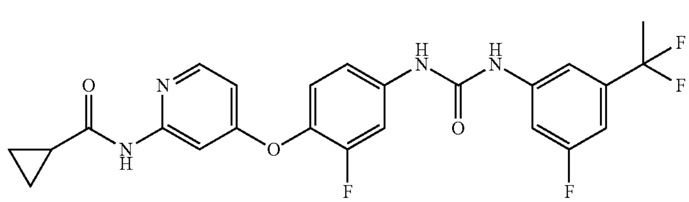 [SMILES: CC(F)(F)c1cc(F)cc(NC(=O)Nc2ccc(Oc3ccnc(NC(=O)C4CC4)c3)c(F)c2)c1] | 489.3 |

TABLE 4-continued

Examples 70-236

| Example number | Structure | MS [M + 1]+ |
|---|---|---|
| Example 180 | 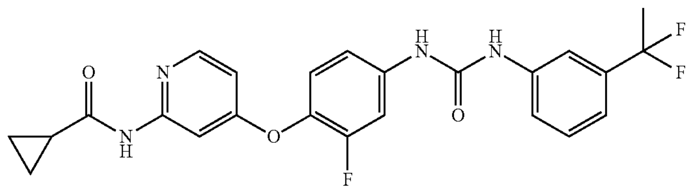 [SMILES: CC(F)(F)c1cccc(NC(=O)Nc2ccc(Oc3ccnc(NC(=O)C4CC4)c3)c(F)c2)c1] | 471.2 |
| Example 181 | 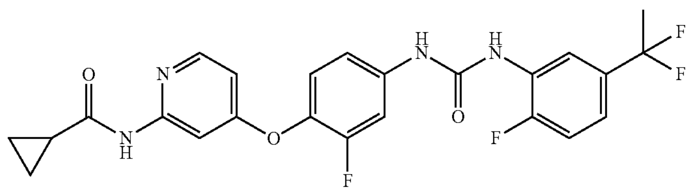 [SMILES: CC(F)(F)c1ccc(F)c(NC(=O)Nc2ccc(Oc3ccnc(NC(=O)C4CC4)c3)c(F)c2)c1] | 489.3 |
| Example 182 | 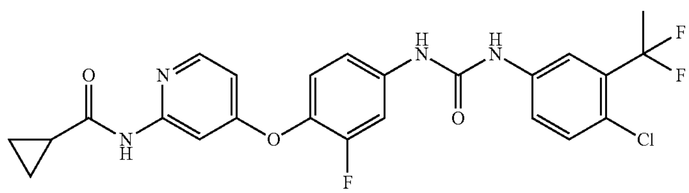 [SMILES: CC(F)(F)c1cc(NC(=O)Nc2ccc(Oc3ccnc(NC(=O)C4CC4)c3)c(F)c2)ccc1Cl] | 505.3 |
| Example 183 | 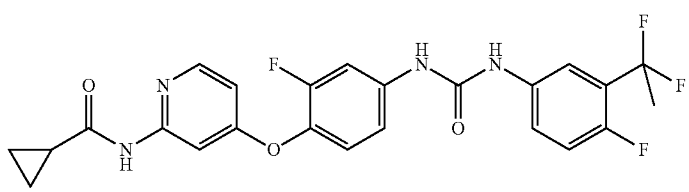 [SMILES: CC(F)(F)c1cc(NC(=O)Nc2ccc(Oc3ccnc(NC(=O)C4CC4)c3)c(F)c2)ccc1F] | 489.3 |
| Example 184 | 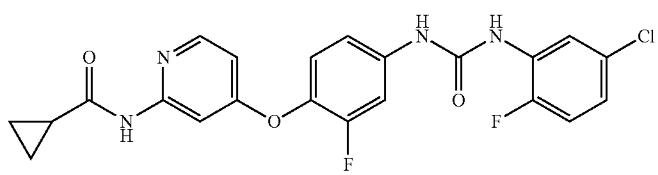 [SMILES: O=C(Nc1ccc(Oc2ccnc(NC(=O)C3CC3)c2)c(F)c1)Nc1cc(Cl)ccc1F] | 459.1 |
| Example 185 | 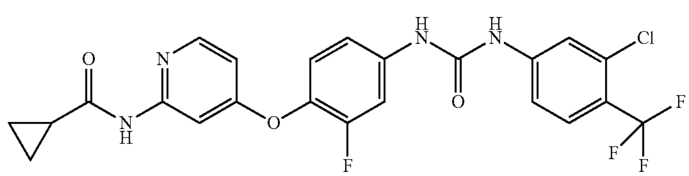 [SMILES: O=C(Nc1ccc(Oc2ccnc(NC(=O)C3CC3)c2)c(F)c1)Nc1ccc(C(F)(F)F)c(Cl)c1] | 509.2 |
| Example 186 | 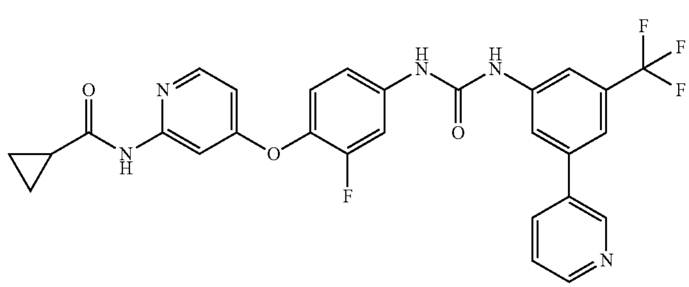 [SMILES: O=C(Nc1cc(-c2cccnc2)cc(C(F)(F)F)c1)Nc1ccc(Oc2ccnc(NC(=O)C3CC3)c2)c(F)c1] | 552.2 |

TABLE 4-continued

Examples 70-236

| Example number | Structure | MS [M + 1]+ |
|---|---|---|
| Example 187 | 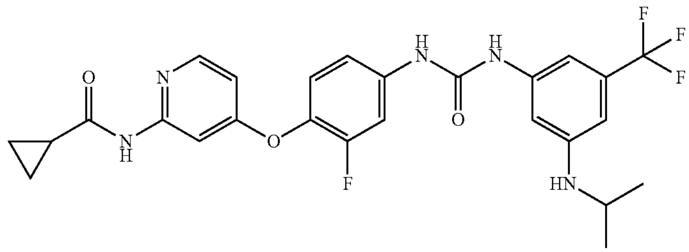 [SMILES: CC(C)Nc1cc(NC(=O)Nc2ccc(Oc3ccnc(NC(=O)C4CC4)c3)c(F)c2)cc(C(F)(F)F)c1] | 532.2 |
| Example 188 | 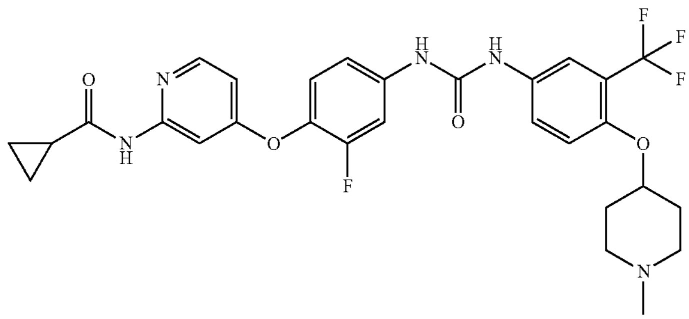 [SMILES: CN1CCC(Oc2ccc(NC(=O)Nc3ccc(Oc4ccnc(NC(=O)C5CC5)c4)c(F)c3)cc2C(F)(F)F)CC1] | 588.3 |
| Example 189 | 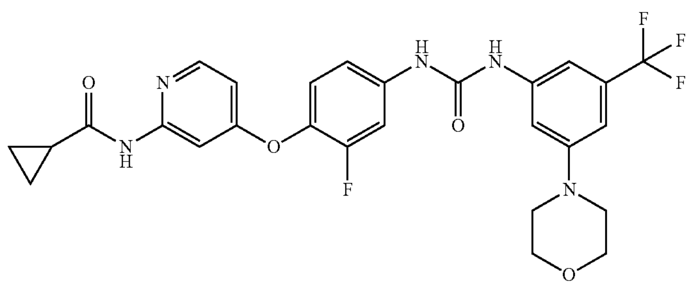 [SMILES: O=C(Nc1cc(N2CCOCC2)cc(C(F)(F)F)c1)Nc1ccc(Oc2ccnc(NC(=O)C3CC3)c2)c(F)c1] | 560.3 |
| Example 190 | 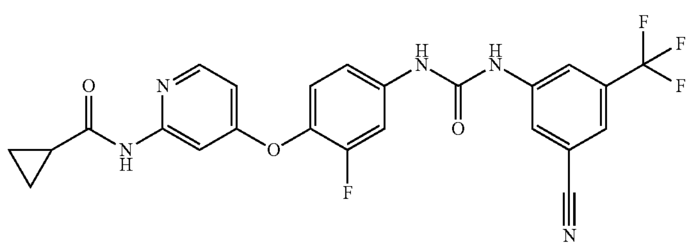 [SMILES: N#Cc1cc(NC(=O)Nc2ccc(Oc3ccnc(NC(=O)C4CC4)c3)c(F)c2)cc(C(F)(F)F)c1] | 500.2 |
| Example 191 | 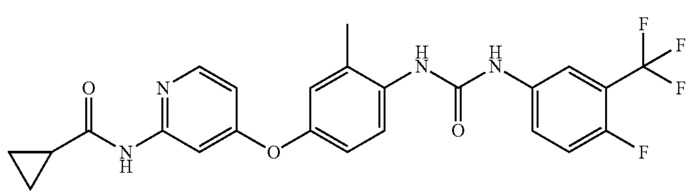 [SMILES: Cc1cc(Oc2ccnc(NC(=O)C3CC3)c2)ccc1NC(=O)Nc1ccc(F)c(C(F)(F)F)c1] | 489.3 |
| Example 192 | 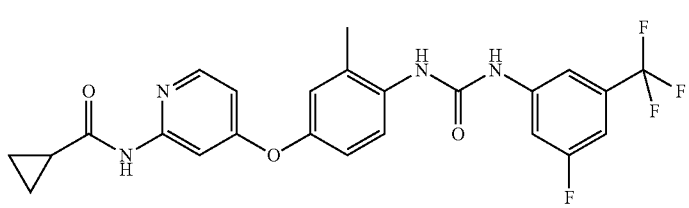 [SMILES: Cc1cc(Oc2ccnc(NC(=O)C3CC3)c2)ccc1NC(=O)Nc1cc(F)cc(C(F)(F)F)c1] | 489.3 |

TABLE 4-continued

Examples 70-236

| Example number | Structure | MS [M + 1]+ |
|---|---|---|
| Example 193 | cyclopropyl-C(O)NH-pyridine-O-(2-methylphenyl)-NHC(O)NH-(3-trifluoromethylphenyl) | 471.3 |
| Example 194 | cyclopropyl-C(O)NH-pyridine-O-(2-methylphenyl)-NHC(O)NH-(3-trifluoromethoxyphenyl) | 487.3 |
| Example 195 | cyclopropyl-C(O)NH-pyridine-O-(2-methylphenyl)-NHC(O)NH-(2-fluoro-5-trifluoromethoxyphenyl) | 505.3 |
| Example 196 | cyclopropyl-C(O)NH-pyridine-O-(2-methylphenyl)-NHC(O)NH-(4-fluoro-3-trifluoromethoxyphenyl) | 505.3 |
| Example 197 | cyclopropyl-C(O)NH-pyridine-O-(2-methylphenyl)-NHC(O)NH-(3-fluoro-5-(1,1-difluoroethyl)phenyl) | 485.2 |
| Example 198 | cyclopropyl-C(O)NH-pyridine-O-(2-methylphenyl)-NHC(O)NH-(2-fluoro-5-(1,1-difluoroethyl)phenyl) | 485.3 |
| Example 199 | cyclopropyl-C(O)NH-pyridine-O-(2-methylphenyl)-NHC(O)NH-(4-chloro-3-(1,1-difluoroethyl)phenyl) | 501.3 |
| Example 200 | cyclopropyl-C(O)NH-pyridine-O-(2-methylphenyl)-NHC(O)NH-(4-fluoro-3-trifluoromethylphenyl) | 485.3 |

TABLE 4-continued

Examples 70-236

| Example number | Structure | MS [M + 1]+ |
|---|---|---|
| Example 201 | 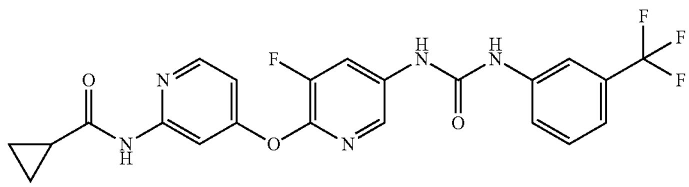 [SMILES: O=C(Nc1cccc(C(F)(F)F)c1)Nc1cnc(Oc2ccnc(NC(=O)C3CC3)c2)c(F)c1] | 476.1 |
| Example 202 | 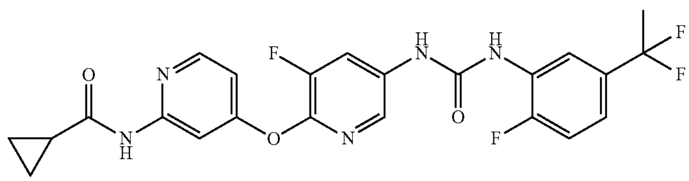 [SMILES: CC(F)(F)c1ccc(F)c(NC(=O)Nc2cnc(Oc3ccnc(NC(=O)C4CC4)c3)c(F)c2)c1] | 490.2 |
| Example 203 | 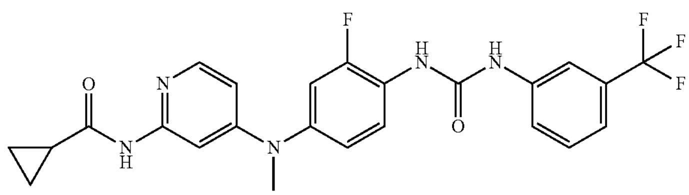 | 488.3 |
| Example 204 | 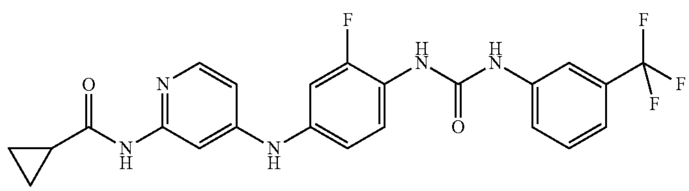 [SMILES: O=C(Nc1cccc(C(F)(F)F)c1)Nc1ccc(Nc2ccnc(NC(=O)C3CC3)c2)cc1F] | 474.3 |
| Example 205 | 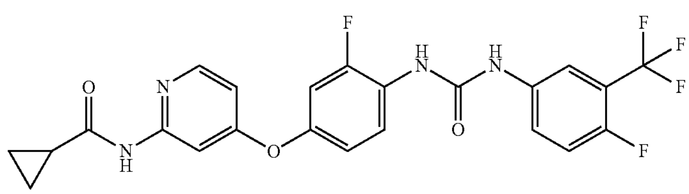 [SMILES: O=C(Nc1ccc(F)c(C(F)(F)F)c1)Nc1ccc(Oc2ccnc(NC(=O)C3CC3)c2)cc1F] | 493.2 |
| Example 206 | 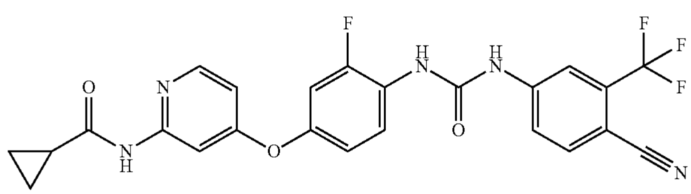 [SMILES: N#Cc1ccc(NC(=O)Nc2ccc(Oc3ccnc(NC(=O)C4CC4)c3)cc2F)cc1C(F)(F)F] | 500.2 |
| Example 207 | 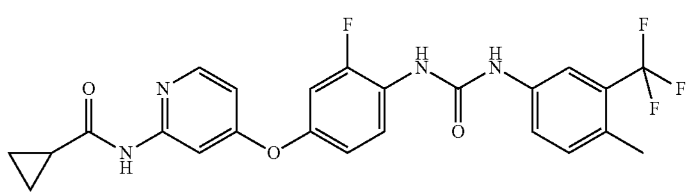 [SMILES: Cc1ccc(NC(=O)Nc2ccc(Oc3ccnc(NC(=O)C4CC4)c3)cc2F)cc1C(F)(F)F] | 489.2 |

TABLE 4-continued

Examples 70-236

| Example number | Structure | MS [M + 1]+ |
|---|---|---|
| Example 208 | 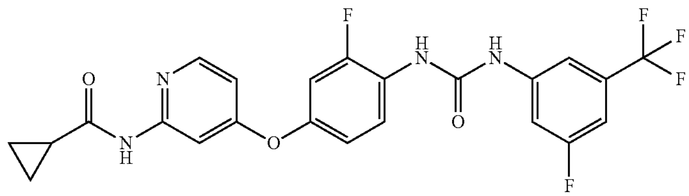 [SMILES: O=C(Nc1cc(F)cc(C(F)(F)F)c1)Nc1ccc(Oc2ccnc(NC(=O)C3CC3)c2)cc1F] | 493.3 |
| Example 209 | 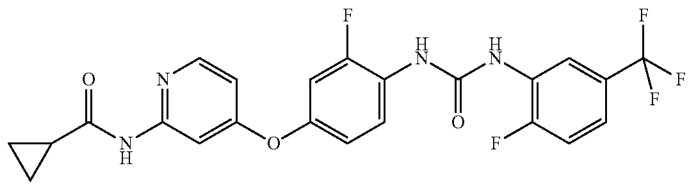 [SMILES: O=C(Nc1ccc(Oc2ccnc(NC(=O)C3CC3)c2)cc1F)Nc1cc(C(F)(F)F)ccc1F] | 493.2 |
| Example 210 | 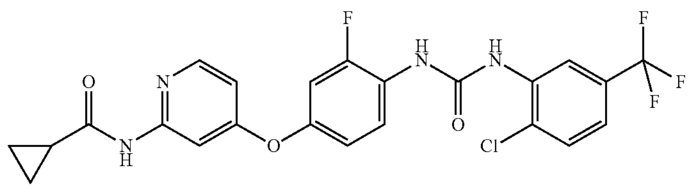 [SMILES: O=C(Nc1ccc(Oc2ccnc(NC(=O)C3CC3)c2)cc1F)Nc1cc(C(F)(F)F)ccc1Cl] | 509.2 |
| Example 211 | 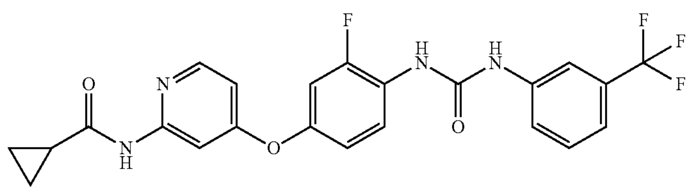 [SMILES: O=C(Nc1cccc(C(F)(F)F)c1)Nc1ccc(Oc2ccnc(NC(=O)C3CC3)c2)cc1F] | 475.2 |
| Example 212 | 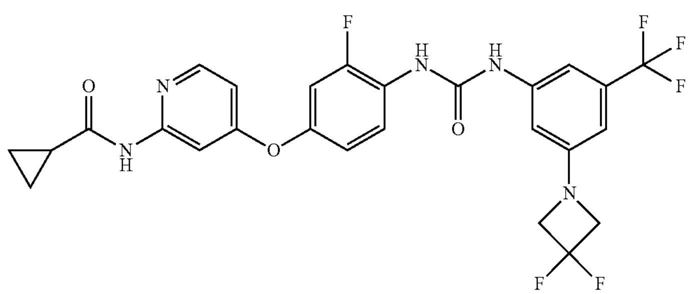 [SMILES: O=C(Nc1cc(N2CC(F)(F)C2)cc(C(F)(F)F)c1)Nc1ccc(Oc2ccnc(NC(=O)C3CC3)c2)cc1F] | 566.2 |
| Example 213 | 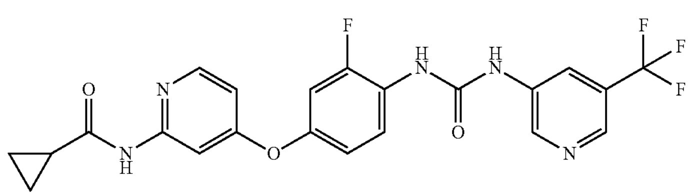 [SMILES: O=C(Nc1cncc(C(F)(F)F)c1)Nc1ccc(Oc2ccnc(NC(=O)C3CC3)c2)cc1F] | 476.2 |
| Example 214 | 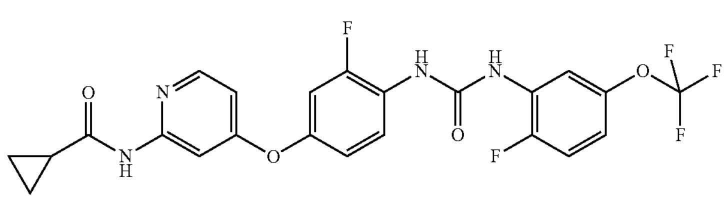 [SMILES: O=C(Nc1ccc(Oc2ccnc(NC(=O)C3CC3)c2)cc1F)Nc1cc(OC(F)(F)F)ccc1F] | 509.3 |

TABLE 4-continued

Examples 70-236

| Example number | Structure | MS [M + 1]+ |
|---|---|---|
| Example 215 | 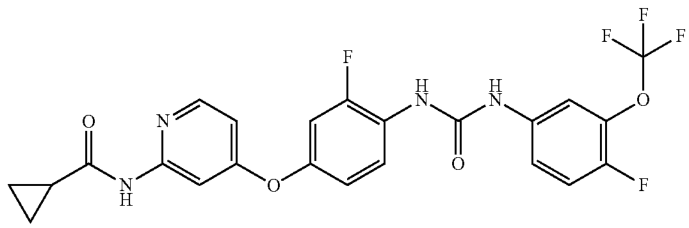 [SMILES: O=C(Nc1ccc(F)c(OC(F)(F)F)c1)Nc1ccc(Oc2ccnc(NC(=O)C3CC3)c2)cc1F] | 509.2 |
| Example 216 | 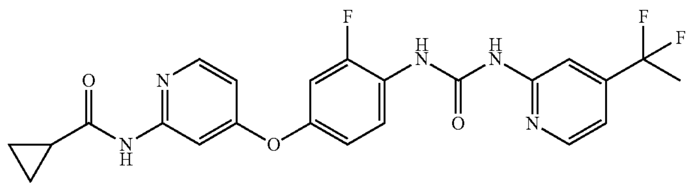 [SMILES: CC(F)(F)c1ccnc(NC(=O)Nc2ccc(Oc3ccnc(NC(=O)C4CC4)c3)cc2F)c1] | 472.3 |
| Example 217 | 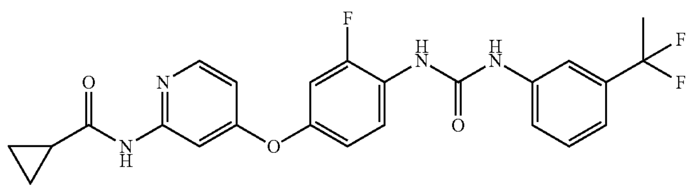 [SMILES: CC(F)(F)c1cccc(NC(=O)Nc2ccc(Oc3ccnc(NC(=O)C4CC4)c3)cc2F)c1] | 471.2 |
| Example 218 | 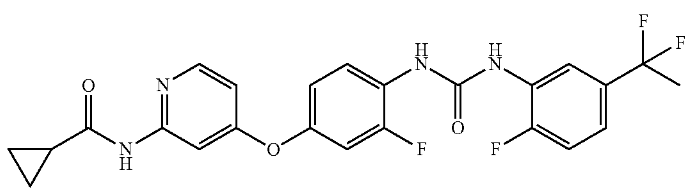 [SMILES: CC(F)(F)c1ccc(F)c(NC(=O)Nc2ccc(Oc3ccnc(NC(=O)C4CC4)c3)cc2F)c1] | 489.3 |
| Example 219 | 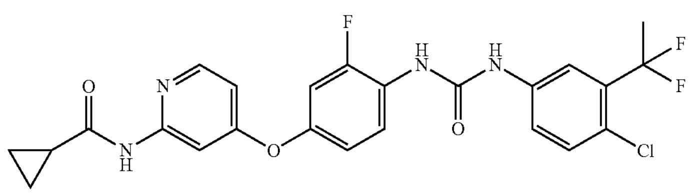 [SMILES: CC(F)(F)c1cc(NC(=O)Nc2ccc(Oc3ccnc(NC(=O)C4CC4)c3)cc2F)ccc1Cl] | 505.2 |
| Example 220 | 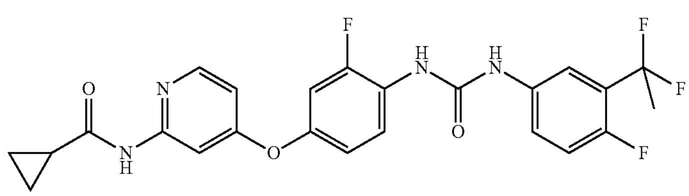 [SMILES: CC(F)(F)c1cc(NC(=O)Nc2ccc(Oc3ccnc(NC(=O)C4CC4)c3)cc2F)ccc1F] | 489.2 |
| Example 221 | 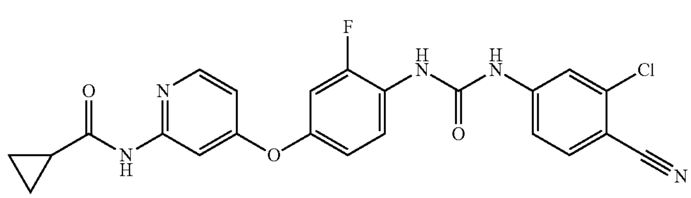 [SMILES: N#Cc1ccc(NC(=O)Nc2ccc(Oc3ccnc(NC(=O)C4CC4)c3)cc2F)cc1Cl] | 466.2 |

TABLE 4-continued
Examples 70-236
| Example number | Structure | MS [M + 1]+ |
|---|---|---|
| Example 222 | 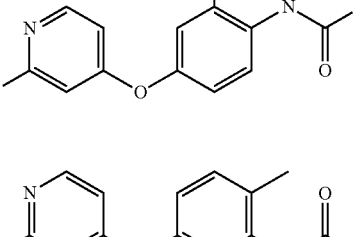 | 465.2 |
| Example 223 | 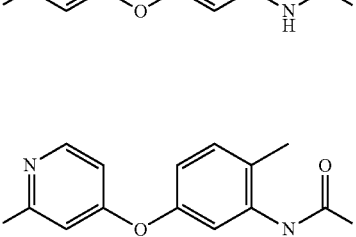 | 489.3 |
| Example 224 | 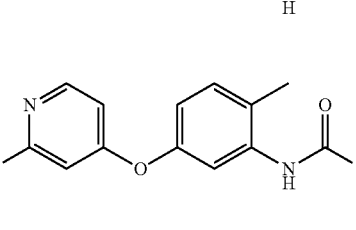 | 489.3 |
| Example 225 | 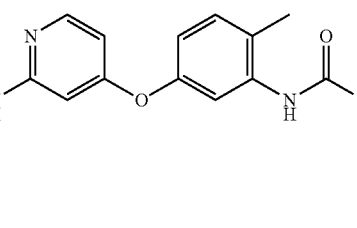 | 489.3 |
| Example 226 | 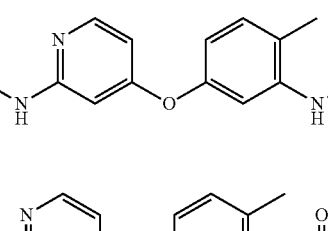 | 471.3 |
| Example 227 | 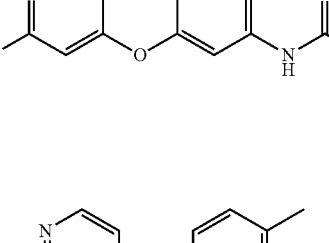 | 485.3 |
| Example 228 | 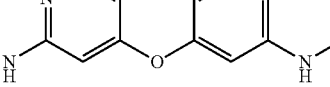 | 501.3 |
| Example 229 | 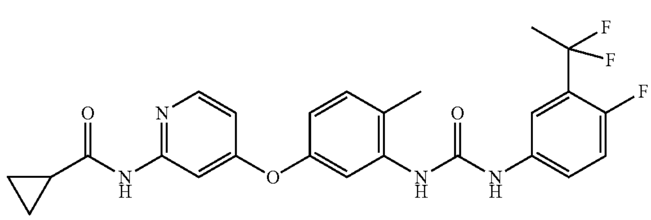 [SMILES: Cc1ccc(Oc2ccnc(NC(=O)C3CC3)c2)cc1NC(=O)Nc1ccc(F)c(C(C)(F)F)c1] | 485.3 |

TABLE 4-continued

Examples 70-236

| Example number | Structure | MS [M + 1]+ |
|---|---|---|
| Example 230 | 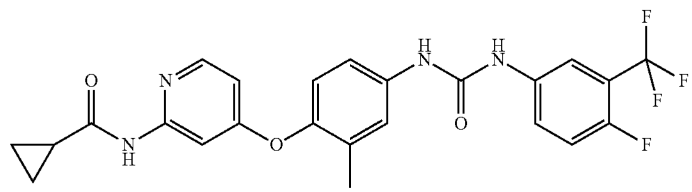 [SMILES: Cc1cc(NC(=O)Nc2ccc(F)c(C(F)(F)F)c2)ccc1Oc1ccnc(NC(=O)C2CC2)c1] | 489.3 |
| Example 231 | 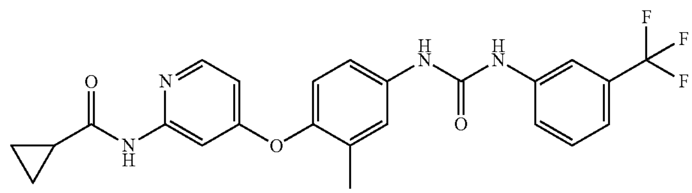 | 471.3 |
| Example 232 | 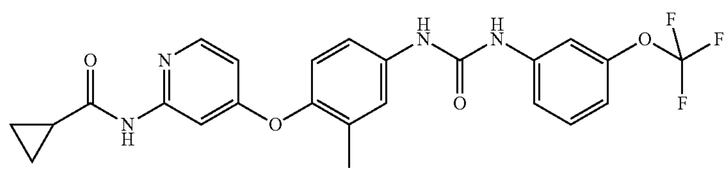 [SMILES: Cc1cc(NC(=O)Nc2cccc(OC(F)(F)F)c2)ccc1Oc1ccnc(NC(=O)C2CC2)c1] | 487.2 |
| Example 233 | 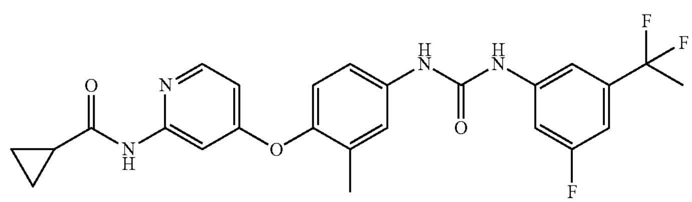 [SMILES: Cc1cc(NC(=O)Nc2cc(F)cc(C(C)(F)F)c2)ccc1Oc1ccnc(NC(=O)C2CC2)c1] | 485.2 |
| Example 234 | 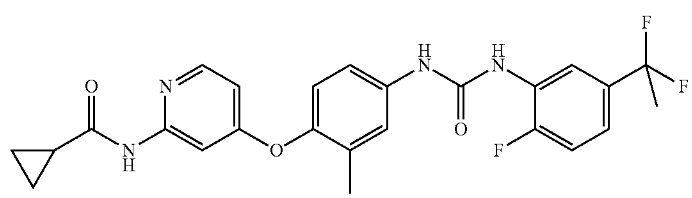 [SMILES: Cc1cc(NC(=O)Nc2cc(C(C)(F)F)ccc2F)ccc1Oc1ccnc(NC(=O)C2CC2)c1] | 485.3 |
| Example 235 | 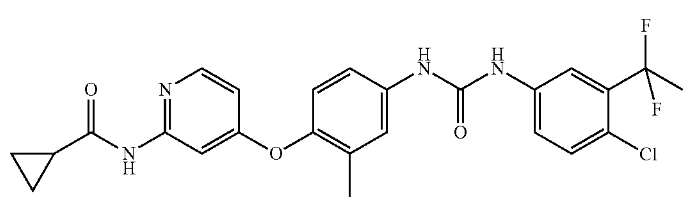 [SMILES: Cc1cc(NC(=O)Nc2ccc(Cl)c(C(C)(F)F)c2)ccc1Oc1ccnc(NC(=O)C2CC2)c1] | 501.3 |
| Example 236 | 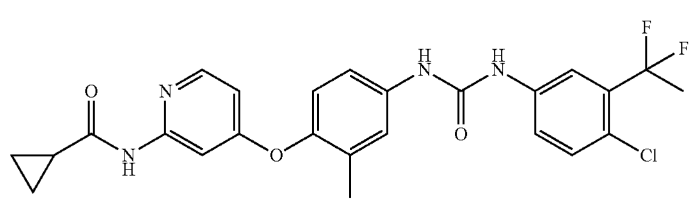 [SMILES: Cc1cc(NC(=O)Nc2ccc(Cl)c(C(C)(F)F)c2)ccc1Oc1ccnc(NC(=O)C2CC2)c1] | 485.3 |

Example 237

Synthesis of N-[4-[4-[[3-(azetidin-3-ylmethoxy)-5-(trifluoromethyl)phenyl]carbamoylamino]phenoxy]-2-pyridyl]cyclopropanecarboxamide

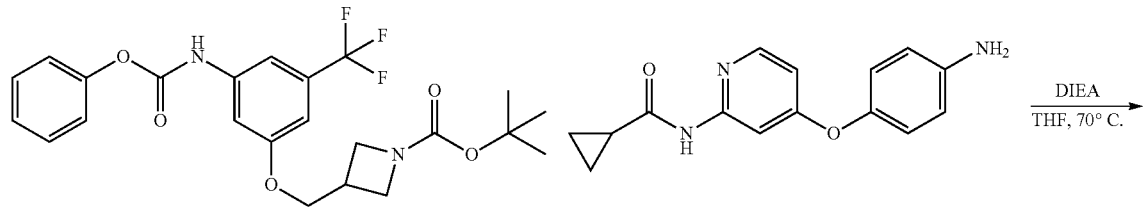

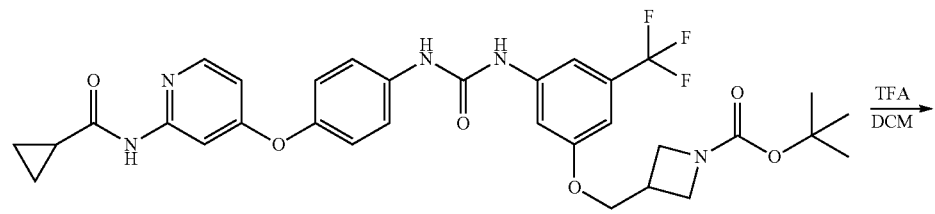

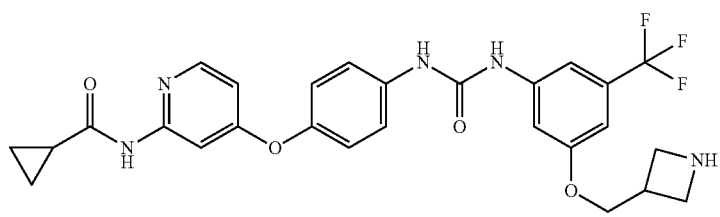

Step 1: Synthesis of tert-butyl 3-[[3-[[4-[[2-(cyclopropanecarbonylamino)-4-pyridyl]oxy]phenyl]carbamoylamino]-5-(trifluoromethyl)phenoxy]methyl]azetidine-1-carboxylate

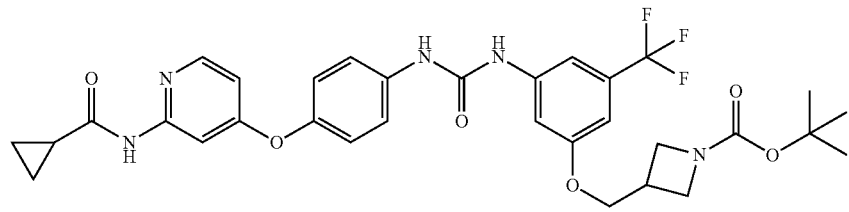 [SMILES: CC(C)(C)OC(=O)N1CC(COc2cc(NC(=O)Nc3ccc(Oc4ccnc(NC(=O)C5CC5)c4)cc3)cc(C(F)(F)F)c2)C1]

Dissolve N-[4-(4-aminophenoxy)-2-pyridyl]cyclopropanecarboxamide (200 mg, 0.74 mmol) and tert-butyl 3-[[3-(phenoxycarbonylamino)-5-(trifluoromethyl)phenoxy]methyl]-azetidine-1-carboxylate (415 mg, 0.89 mmol) in THF (10 mL), add DIEA (200 mg, 1.48 mmol), stir under $N_2$ at 70° C. for 12 hrs. Concentrate under reduced pressure to give the crude product. Purification by chromatography (silica gel, EtOAc:PE=2:1) affords the title compound (250 mg, 52.4%). MS: (M+1): 642.3.

Step 2: Synthesis of N-[4-[4-[[3-(azetidin-3-yl-methoxy)-5-(trifluoromethyl)phenyl]carbamoy-lamino]phenoxy]-2-pyridyl]cyclopropanecarboxamide

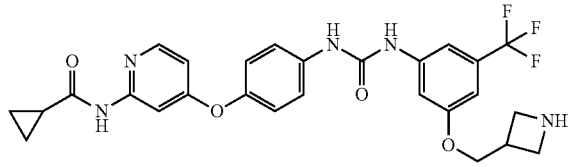 [SMILES: O=C(Nc1ccc(Oc2ccnc(NC(=O)C3CC3)c2)cc1)Nc1cc(OCC2CNC2)cc(C(F)(F)F)c1]

Dissolve the compound obtained in last step (250 mg, 0.39 mmol) in DCM (15 mL), add trifluoroacetic acid (6 mL), stir at room temperature for 2 hrs. Remove the volatiles, partition between EtOAc and saturated $NaHCO_3$ solution. Separate the organic layer, dry over anhydrous $Na_2SO_4$, concentrate under reduced pressure to give the crude product. Purification by chromatography (silica gel, EtOAc:PE=3:1) affords the title compound (150 mg, 71%). MS: (M+1): 542.1.

Examples 238-240 are prepared with the above method (Table 5).

TABLE 5

| Examples 237-240 | | |
|---|---|---|
| Example number | Structure | MS [M + 1]⁺ |
| Example 237 | | 542.1 |
| Example 238 | | 541.2 |
| Example 239 | | 490.2 |
| Example 240 | | 587.3 |

Example 241

Synthesis of N-[4-[4-[[3-(1-methylazetidin-3-yl)oxy-5-(trifluoromethyl)phenyl]carbamoylamino]phenoxy]-2-pyridyl]cyclopropanecarboxamide

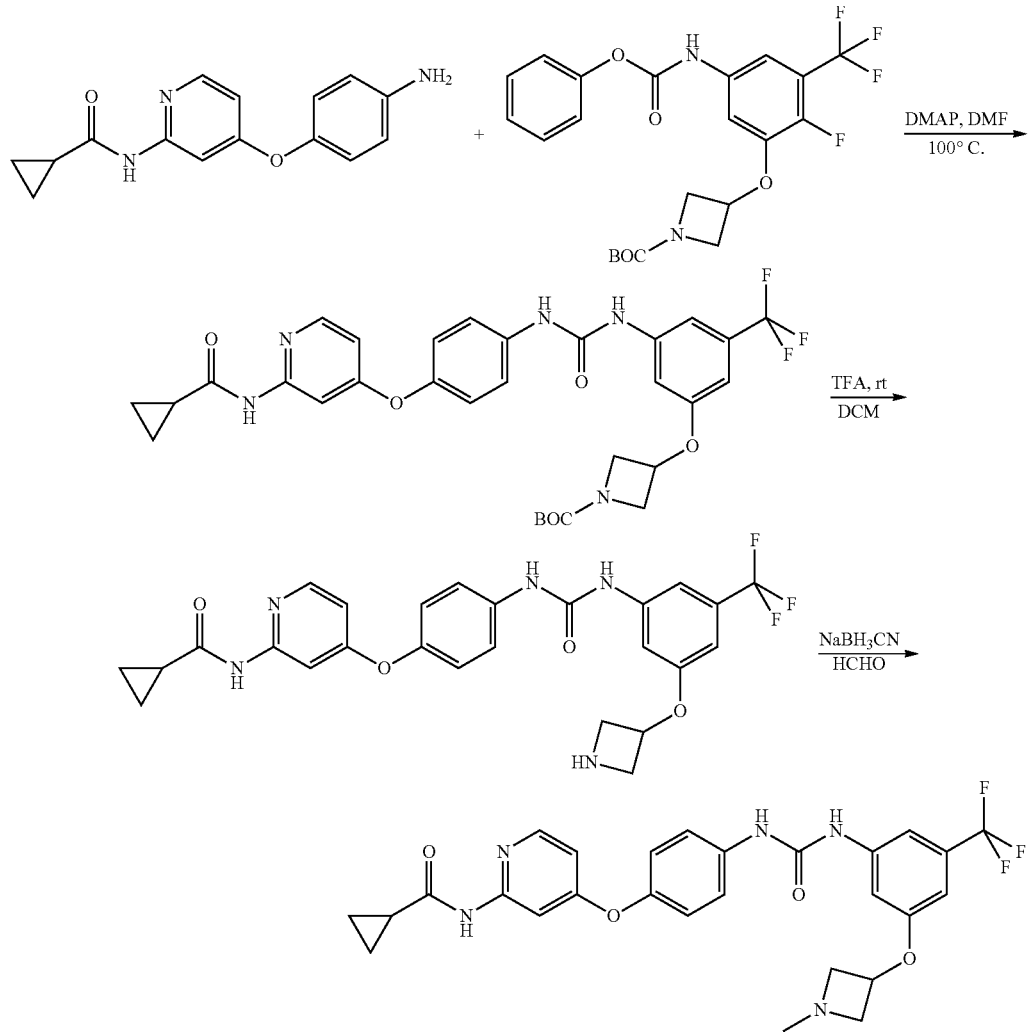

Step 1: Synthesis of tert-butyl 3-[3-[[4-[[2-(cyclopropanecarbonylamino)-4-pyridyl]oxy]phenyl]carbamoylamino]-5-(trifluoromethyl)phenoxy]azetidine-1-carboxylate

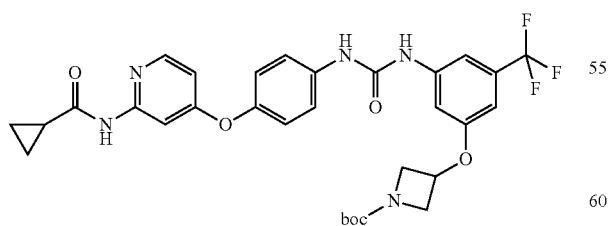

Dissolve N-[4-(4-aminophenoxy)-2-pyridyl]cyclopropanecarboxamide (186 mg, 0.69 mmol), tert-butyl 3-[3-(phenoxycarbonylamino)-5-(trifluoromethyl)phenoxy]azetidine-1-carboxylate (312 mg, 0.69 mmol) and DMAP (17 mg, 0.14 mmol) in DMF (10 mL), stir at 100° C. for 16 hrs. Cool the reaction, pour the mixture to water (50 mL), adjust pH=7 with saturated NaHCO₃ solution, extract with EtOAc (15 mL×3). Combine the organic layers, wash with brine (100 mL), dry over anhydrous Na₂SO₄. Concentrate under reduced pressure to give the crude product. Purification by chromatography (silica gel, EtOAc:PE=1:1) affords the target compound (300 mg, 69%). MS: (M+1): 628.3.

Step 2: Synthesis of N-[4-[4-[[3-(azetidin-3-yloxy)-5-(trifluoromethyl)phenyl]carbamoylamino]phenoxy]-2-pyridyl]cyclopropanecarboxamide

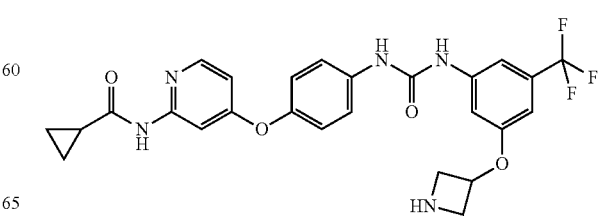

Dissolve tert-butyl 3-[3-[[4-[[2-(cyclopropanecarbonylamino)-4-pyridyl]oxy]phenyl]-carbamoylamino]-5-(trifluoromethyl)phenoxy]azetidine-1-carboxylate (300 mg, 0.48 mmol) in DCM (4 mL), add slowly trifluoroacetic acid (2 mL), stir the reaction at room temperature for 2 hrs. After reaction, pour the mixture to water (50 mL), adjust pH=7 with saturated NaHCO₃ solution, extract with EtOAc (15 mL×3). Combine the organic layers, wash with brine (100 mL), dry over anhydrous Na₂SO₄. Concentrate under reduced pressure to give the crude product (240 mg) which is used without further purification. MS: (M+1): 528.2.

Step 3: Synthesis of N-[4-[4-[[3-(1-methylazetidin-3-yl)oxy-5-(trifluoromethyl)phenyl]carbamoylamino]phenoxy]-2-pyridyl]cyclopropanecarboxamide

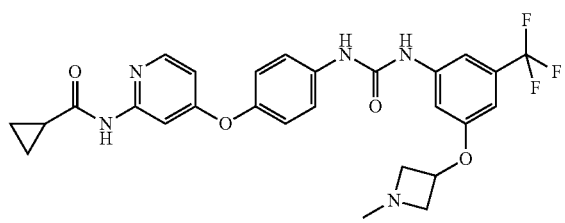 [SMILES: CN1CC(Oc2cc(NC(=O)Nc3ccc(Oc4ccnc(NC(=O)C5CC5)c4)cc3)cc(C(F)(F)F)c2)C1]

Dissolve N-[4-[4-[[3-(azetidin-3-yloxy)-5-(trifluoromethyl)phenyl]carbamoylamino]-phenoxy]-2-pyridyl]cyclopropanecarboxamide (210 mg, 0.4 mmol) in methanol (10 mL), add 35% aqueous formaldehyde solution (205 mg, 2.39 mmol), sitr for 1.5 hrs. Add Na(CN)BH₃ (150 mg, 2.39 mmol) and stir at room temperature for 3 hrs. After reaction, pour the reaction mixture to water (50 mL), adjust pH=7 with saturated NaHCO₃ solution, extract with EtOAc (15 mL×3), combine the organic layers, wash with brine (100 mL), dry over anhydrous Na₂SO₄. Concentrate under reduced pressure to give the crude product. Purification by chromatography (silica gel, DCM:MeOH=20:1) affords the target compound (16 mg, 7%). MS: (M+1): 542.3.

Example 242 is prepared with similar method (Table 7)

TABLE 6

Examples 241-242

| Example number | Structure | MS [M + 1]⁺ |
|---|---|---|
| Example 241 | 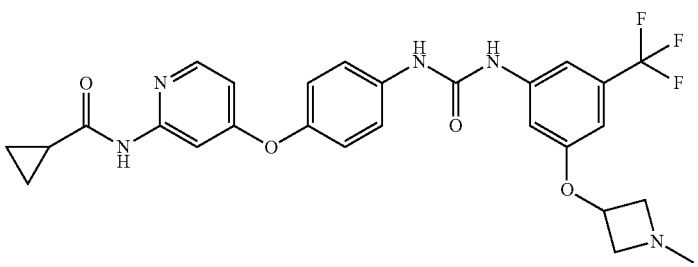 [SMILES: CN1CC(Oc2cc(NC(=O)Nc3ccc(Oc4ccnc(NC(=O)C5CC5)c4)cc3)cc(C(F)(F)F)c2)C1] | 542.3 |
| Example 242 | 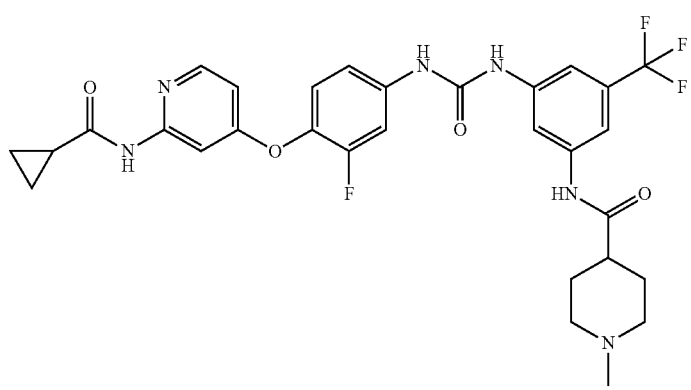 [SMILES: CN1CCC(C(=O)Nc2cc(NC(=O)Nc3ccc(Oc4ccnc(NC(=O)C5CC5)c4)c(F)c3)cc(C(F)(F)F)c2)CC1] | 615.3 |

EXAMPLES ON BIOLOGICAL ACTIVITIES

Biological Activity Example 1

Inhibitory Activity of Compounds at KDR Kinase

[Experimental method]: Use Lance@Ultra Ulight™-TK assay kit from PerKinElmer to evaluate the inhibitory activity of compounds at KDR kinase.
[Instrument]: PerKinElmer's ENVISION plate reader
[Materials]: Optiplate-384 well plate (PerKinElmer), kinase buffer (50 mM Hepes pH7.5, 0.25 mM EGTA, 2 mM DTT, 0.01% Tween 20, 10 mM Mg²⁺, 0.5 mM Mn²⁺), KDR kinase (790-1356 AA, Crown Bioscience), KDR kinase substrate (PerKinElmer catalogue # TRF0127-M), Lance@Eu-W1024-anti-phosphotyrosine (PT66) (PerKinElmer, catalogue #AD0068), ATP (Invitrogen), DMSO (Sigma, catalogue #34869), purified water (Millipore, type: Milli-Q).
[Study conditions]: Mix KDR (final concentration: 20 nM) and compound (final DMSO: 0.5%), pre-incubate for 20 min at 30° C.; then add ATP (final concentration: 90 μM) and the substrate (final concentration 50 μM). React for 2 hrs at 30° C. After the reaction, add antibody and reaction for 60 min at 30° C. Read the plate (615 nm, 665 nm), calculate the ratio of the value at 665 nm vs 615 nm and analyze the data.

[Samples]: Compounds in the examples and Sorafenib (positive control)

[Data Analysis]: Use CBIS data analysis software to calculate $IC_{50}$ values

Biological Activity Example 2

Inhibitory Activity of Compounds at B-Raf Kinase

[Experimental method]: Use ADP-GLO™ assay kit from Promega to evaluate the inhibitory activity of compounds at B-Raf

[Instrument]: PerKinElmer's ENVISION plate reader

[Material]: Optiplate-384 well plate (PerKinElmer), kinase buffer (50 mM Hepes pH7.5, 1 mM EGTA, 2 mM DTT, 10 mM $Mg^{2+}$, 0.05% BSA), B-Raf kinase (Millipore, catalogue #14-530-K), GST-MEK1 substrate (Carna, catalogue #07-141-10), Super pure ATP (Promega), ADP-GLO™ assay kit (Promega, catalogue # V9102), DMSO (Sigma, catalogue #34869), purified water (Millipore, type: Milli-Q).

[Study conditions]: Mix B-Raf kinase (final concentration: 5 nM) and compound (DMSO final concentration: 0.25%) and preincubate at 30° C. for 20 min, then add ATP (final concentration: 6 µM) and reaction substrate (final concentration: 30 nM), React for 2 hrs at 30° C. After reaction, add ADP-GLO™ reagent, react for 40 min at room temperature, then add ADP-GLO™ detecting agent, react for 30 min at room temperature. After that, use ENVSION to measure the fluorescence.

[Samples]: Compounds in the examples and Sorafenib (positive control)

[Data analysis]: Use CBIS data analysis software to calculate $IC_{50}$ values

Biological Activity Example 3

Inhibitory Activity of Compounds at pERK

[Experimental method]: Use Acumen (TPP) to measure In Cell Western Blot results

[Instrument]: Acumen (TPP), Centrifuge (Thermo Scientific, Sorvall ST16R)

[Material]: MDA-MB-231 cells (ATCC), 96 well plate (BD, #356640), DMEM medium (Gibco, #11965-092), PBS (Invitrogen, #10010023), fetal bovine serum (Gibco, #16000044), BSA (Sigma, #A7030), DMSO (Sigma, #D2650); formaldehyde (Sinopharm), methanol (Sinopharm), $1^{St}$ antibody (anti-pERK antibody, Cell Signaling, #CST 4307s), $2^{nd}$ antibody (FITC Donkey anti-rabbit IgG, Biolegend, #406403), Propidium Iodide (Invitrogen, #P3566), purified water (Millipore, type: Milli-Q).

[Protocol]: Grow MDA-MB-231 cells in DMEM medium (contains 10% FBS). When the cells reach 80% confluency, collect cells by trypsinization and centrifugation at 800 rpm for 3 minutes. Resuspend cells with appropriate volume of medium and count cell numbers. Adjust cell concentration to 70000 cells/mL, and split 100 µL cell suspension per well into 96-well plates. Transfer the plates into cell culture incubator (37° C., 5% $CO_2$) and incubate cells overnight. Discard the medium, wash with PBS once, Prepare compound serial dilutions in culture medium with total 8 compound concentrations at 3-fold serial dilutions (the final top concentration starts from 30 µM). Dispense 75 µL DMEM medium (with 0.1% BSA) and 25 µL of each test compound dilution into corresponding wells with DMSO at 0.3% final concentration. Continue incubating cells in cell culture incubator for additional 2 hrs at 37° C., 5% $CO_2$. Discard culture medium, and wash cells once with PBS. Add 100 µL of 4% formaldehyde solution to each well and fix for 20 min. Discard the formaldehyde, then add 100 µL ice-cold 100% methanol at 4° C. for 20 min. Discard methanol, wash with PBS three times. Add to each well 100 µL of 2% BSA solution, seal for 30 min at room temperature. Discard the BSA solution, add to each well 50 µL of the $1^{st}$ antibody solution (prepared with 2% BSA, 1:250 dilution), incubate at 4° C. overnight. Discard the $1^{St}$ antibody solution, wash with PBS four times. Add to each well 50 pit the $2^{nd}$ antibody solution (prepared with 1% BSA, 1:1000 dilution), incubate at room temperature for 1 hr. Discard the $2^{nd}$ antibody solution, wash with PBS four times, add to each well 100 µL PI solution (1.5 µM), incubate at room temperature for 30 min. Use Acumen (TPP) to measure the fluorescence.

[Samples]: Compounds in the examples and sorafenib (positive control)

[Data Analysis]: Use CBIS data analysis software to calculate $IC_{50}$ values

Biological Activity Example 4

Inhibitory Activity of Compounds to the Proliferation of PLC-PRF-5 Cells

[experimental Method]: Use PerKinElmer's ATPlite™ Luminescence ATP Detection Assay System to evaluate the inhibitory activity of compounds to the proliferation of PLC-PRF-5 cells.

[Instruments]: ENVISION plate reader (PerKinElmer) and centrifuge (Thermo Scientific, Sorvall ST16R)

[material]: PLC-PRF-5 cells (ATCC), 96-well plate (Nunc, #165305), DMEM medium (Gibco, #11965-092), PBS (Invitrogen, #10010023), fetal bovine serum (Gibco, #16000044), DMSO (Sigma, #D2650), ATPlite™ Luminescence ATP Detection Assay System (PerkinElmer, #6016949), purified water (Millipore, type: Milli-Q).

[Protocol]: Grow PLC-PRF-5 cells in DMEM supplemented with 10% FBS. When the cells reach 80% confluency, collect cells by trypsinization and centrifugation at 800 rpm for 3 min. Resuspend cells with appropriate volume of medium and count cell numbers. Adjust cell concentration to 50000 cells/mL, and split 160 µL cell suspension per well into 96-well plates. Transfer the plates into cell culture incubator (37° C., 5% $CO_2$) and incubate cells for 2 hrs. Prepare compound serial dilutions in culture medium with total 8 compound concentrations at 3-fold serial dilutions (the final top concentration starts from 30 µM). Dispense 40 µL of each test compound dilution into corresponding wells with DMSO at 0.3% final concentration. Continue incubating cells in cell culture incubator for additional 96 hrs at 37° C., 5% $CO_2$. Discard culture medium, and wash cells once with PBS. Add 50 µL cell lysis buffer per well and shake plates for 5 min at room temperature to ensure complete lysis of cells. Then add 50 µL of substrate solution and shake plates for 1 min at room temperature. Allow the plates to incubate at room temperature for 5 min, followed by recording the luminescence signals using Envision, and subsequent data analysis.

[Samples]: Compounds in the examples and Sorafenib (positive control)

[Data analysis]: Use CBIS data analysis software to calculate $IC_{50}$ values

In vitro activity summary for example 1-242 ($IC_{50}$, nM)

| Example Number | KDR | B-Raf | MDA-MB-231 pERK | PLC-PRF-5 cell proliferation |
|---|---|---|---|---|
| Exe. 001 | 10.9 | 39 | 31 | 6900 |
| Exe. 002 | 5.4 | | 15.5 | 3400 |
| Exe. 003 | 16.7 | | 87 | 11500 |
| Exe. 004 | 292 | | 74 | 21900 |
| Exe. 005 | 27 | | 40.6 | 6000 |
| Exe. 006 | 25 | | 281 | 5380 |
| Exe. 007 | 5.7 | 24.8 | 46 | 7240 |
| Exe. 008 | 5.7 | 24.9 | 124 | 4550 |
| Exe. 009 | 8.9 | 26 | 20.5 | 3650 |
| Exe. 010 | 13.7 | 97 | 43.1 | 4350 |
| Exe. 011 | 13.4 | | 261 | 19500 |
| Exe. 012 | 9.9 | | 71 | 10300 |
| Exe. 013 | 14.2 | | 50 | 16100 |
| Exe. 014 | 7 | | 48.5 | 8700 |
| Exe. 015 | 4.2 | | 94 | 6500 |
| Exe. 016 | 9.4 | | 55 | 20100 |
| Exe. 017 | 29.2 | 15.7 | 18.8 | 2820 |
| Exe. 018 | 9.4 | | 4.6 | 4040 |
| Exe. 019 | 22.3 | 18.1 | 172 | 840 |
| Exe. 020 | 5.8 | 19.7 | 290.6 | 1990 |
| Exe. 021 | 7.5 | 24.7 | 10.2 | 600 |
| Exe. 022 | 4.3 | 3.6 | 19.5 | 1710 |
| Exe. 023 | 10.5 | 15 | 6.9 | 4170 |
| Exe. 024 | 33.8 | 5.1 | 19.5 | 4240 |
| Exe. 025 | 14.9 | 9.1 | 71.6 | 371 |
| Exe. 026 | 18.2 | | 39 | 900 |
| Exe. 027 | 11.5 | | 66.5 | 2390 |
| Exe. 028 | 12.7 | 21 | 391 | 2490 |
| Exe. 029 | 3.9 | 7.3 | 10.1 | 790 |
| Exe. 030 | 12.4 | 18 | 23.2 | 2800 |
| Exe. 031 | 14.5 | 25 | 33.8 | 1300 |
| Exe. 032 | 26 | | 115 | 20000 |
| Exe. 033 | 5.6 | | 5.0 | 35 |
| Exe. 034 | 10.2 | 9.4 | 4.7 | 219 |
| Exe. 035 | 7.8 | 8.9 | 9.3 | 259 |
| Exe. 036 | 15.6 | | 290 | 2400 |
| Exe. 037 | 13.5 | 26 | 33.9 | 768 |
| Exe. 038 | 8.2 | 5.3 | 23.5 | 130 |
| Exe. 039 | 14.2 | | 54.4 | 500 |
| Exe. 040 | 15.2 | | 134 | 640 |
| Exe. 041 | 4.2 | 37.5 | 18.1 | 358 |
| Exe. 042 | 11.5 | | 94 | 3560 |
| Exe. 043 | 18.1 | | 30 | 604 |
| Exe. 044 | 14.2 | 13 | 29.8 | 752 |
| Exe. 045 | 15.4 | | 40 | 108 |
| Exe. 046 | 16.6 | | 58.2 | 640 |
| Exe. 047 | 6.2 | 73.6 | 53.3 | 682 |
| Exe. 048 | 7.3 | 11.0 | 25 | 233 |
| Exe. 049 | 9.9 | | 51.3 | 642 |
| Exe. 050 | 12.8 | | 110 | 2230 |
| Exe. 051 | 5.2 | 23.6 | 33.9 | 749 |
| Exe. 052 | 15.5 | 13 | 22 | 360 |
| Exe. 053 | 13 | | 65.1 | 686 |
| Exe. 054 | 15.3 | | 97.6 | 340 |
| Exe. 055 | 14.5 | | 284 | 420 |
| Exe. 056 | 17.5 | 65 | 39.7 | 110 |
| Exe. 057 | 12.0 | | 85 | 250 |
| Exe. 058 | 13.7 | 116 | 30 | 43 |
| Exe. 059 | 8.2 | 90 | 19.4 | 643 |
| Exe. 060 | 34.3 | | 324 | 1510 |
| Exe. 061 | 3.73 | 6.3 | 26.3 | 211 |
| Exe. 062 | 7.18 | 7.0 | 29.4 | 3050 |
| Exe. 063 | 5.5 | 14.9 | 29.1 | 2330 |
| Exe. 064 | 11.9 | 4.6 | | 610 |
| Exe. 065 | 6.5 | 25 | 46.5 | 162 |
| Exe. 066 | 8.0 | | 16 | 2500 |
| Exe. 067 | 26.6 | | 75.9 | 235 |
| Exe. 068 | 15.7 | | 8.4 | 325 |
| Exe. 069 | 17.1 | | 337 | 10500 |
| Exe. 070 | 11.0 | 145 | 63.5 | 9300 |
| Exe. 071 | 13.3 | | 100 | 20500 |
| Exe. 072 | 8.9 | | 12 | 7000 |
| Exe. 073 | 14 | | 14 | 2970 |
| Exe. 074 | 10.5 | 146 | 77.5 | 6070 |
| Exe. 075 | 13.1 | | 420 | 20000 |
| Exe. 076 | 12.5 | | 83 | 5600 |
| Exe. 077 | 14.3 | | 169 | 16500 |
| Exe. 078 | 13.3 | | 28 | 879 |
| Exe. 079 | 14 | | 80 | 6000 |
| Exe. 080 | 8.1 | | 29 | 3040 |
| Exe. 081 | 13.3 | | 104 | 16000 |
| Exe. 082 | 6.8 | | 36 | 22500 |
| Exe. 083 | 14.3 | | 609 | 20400 |
| Exe. 084 | 12.2 | | 122 | 5860 |
| Exe. 085 | 10.7 | 45 | 19.3 | 11000 |
| Exe. 086 | 8.3 | | 226 | 19300 |
| Exe. 087 | 12.9 | | 36 | 5050 |
| Exe. 088 | 11.4 | | 106 | 2050 |
| Exe. 089 | 15.2 | | 19 | 6870 |
| Exe. 090 | 12.2 | | 42 | 2800 |
| Exe. 091 | 12.8 | | 53 | 7600 |
| Exe. 092 | 192 | | 57 | 17200 |
| Exe. 093 | 200 | | 244 | 17300 |
| Exe. 094 | 200 | | 163 | 19000 |
| Exe. 095 | 434 | | 82 | 19200 |
| Exe. 096 | 624 | | 28 | 21000 |
| Exe. 097 | 62.8 | | 137 | 9100 |
| Exe. 098 | 105 | | 752 | 8400 |
| Exe. 099 | 41 | | 37 | 15000 |
| Exe. 100 | 9 | | 300 | 2420 |
| Exe. 101 | 12.5 | | 682 | 2600 |
| Exe. 102 | 15 | | 294 | 936 |
| Exe. 103 | 12.4 | | 300 | 373 |
| Exe. 104 | 10.2 | | 252 | 100 |
| Exe. 105 | 11.3 | 153 | 85.5 | 1900 |
| Exe. 106 | 10.4 | | 465 | 850 |
| Exe. 107 | 13.4 | 31 | 20.2 | 324 |
| Exe. 108 | 8.6 | 41 | 20 | 1610 |
| Exe. 109 | 10.9 | 32 | 9.8 | 274 |
| Exe. 110 | 7.3 | 24 | 13.4 | 1580 |
| Exe. 111 | 7 | | 41 | 2630 |
| Exe. 112 | 14.5 | | 85 | 2000 |
| Exe. 113 | 8.1 | | 54 | 781 |
| Exe. 114 | 9.8 | | 37 | 4600 |
| Exe. 115 | 9.5 | | 300 | 1310 |
| Exe. 116 | 7.9 | 111 | 30.4 | 125 |
| Exe. 117 | 12 | | 27 | 2930 |
| Exe. 118 | 7.4 | 293 | 55.3 | 706 |
| Exe. 119 | 14.9 | | 184 | 18800 |
| Exe. 120 | 12 | | 617 | >30000 |
| Exe. 121 | 11.5 | | 252 | >30000 |
| Exe. 122 | 8.7 | | 133 | 22000 |
| Exe. 123 | 7.4 | | 703 | 8380 |
| Exe. 124 | 13.8 | 10.4 | 19.4 | 160 |
| Exe. 125 | 8.7 | 8.6 | 4.7 | 1720 |
| Exe. 126 | 30.2 | 61.4 | 24.3 | 2440 |
| Exe. 127 | 11.8 | 7.2 | 11.6 | 642 |
| Exe. 128 | 9.8 | 6.2 | 38.0 | 819 |
| Exe. 129 | 14.2 | | 105 | 2260 |
| Exe. 130 | 4.6 | 29.7 | 725 | 4990 |
| Exe. 131 | 6.1 | 12.5 | >1000 | 10500 |
| Exe. 132 | 10 | 39 | 341 | 5910 |
| Exe. 133 | 9.1 | 25 | 23.6 | 1020 |
| Exe. 134 | 7.8 | | 33 | 199 |
| Exe. 135 | 5.8 | | 208 | 100 |
| Exe. 136 | 6.6 | 29 | 46 | 470 |
| Exe. 137 | 10.2 | 11.3 | 7.8 | 5960 |
| Exe. 138 | 10.5 | 26 | 9.1 | 1510 |
| Exe. 139 | 10 | 13 | 10.9 | 654 |

In vitro activity summary for example 1-242 (IC$_{50}$, nM)

| Example Number | KDR | B-Raf | MDA-MB-231 pERK | PLC-PRF-5 cell proliferation |
|---|---|---|---|---|
| Exe. 140 | 10.0 | | 10.6 | 230 |
| Exe. 141 | 7.1 | 125 | 40.4 | 642 |
| Exe. 142 | 10.4 | 39 | 13.9 | 642 |
| Exe. 143 | 9.5 | 5.5 | 13.4 | 892 |
| Exe. 144 | 11.4 | 30 | 6.0 | 403 |
| Exe. 145 | 7.6 | 5.1 | 20.7 | 1670 |
| Exe. 146 | 7.8 | 14 | 11.4 | 689 |
| Exe. 147 | 11.1 | 15 | 23.8 | 1160 |
| Exe. 148 | 6.2 | 16 | 7.7 | 240 |
| Exe. 149 | 25.4 | 38 | 25.4 | 800 |
| Exe. 150 | 11.5 | | 20.4 | 737 |
| Exe. 151 | 4.5 | 3.3 | 3.6 | 608 |
| Exe. 152 | 7.1 | 72 | 33 | 390 |
| Exe. 153 | 15.2 | 32 | 23 | 735 |
| Exe. 154 | 11.3 | | 14.9 | 130 |
| Exe. 155 | 12.1 | | 195 | 571 |
| Exe. 156 | 8.3 | 37 | 37.7 | 52 |
| Exe. 157 | 5.9 | 43 | 34.7 | 156 |
| Exe. 158 | 8.3 | | 81.9 | 1040 |
| Exe. 159 | 8.0 | 35.4 | 44.3 | 642 |
| Exe. 160 | 7.8 | | 186 | 4100 |
| Exe. 161 | 12.2 | 7.9 | 86.9 | 1340 |
| Exe. 162 | 6.8 | 22.5 | 30.6 | 330 |
| Exe. 163 | 11.6 | 24 | 32.9 | 998 |
| Exe. 164 | 30.7 | 71.5 | 198 | 2950 |
| Exe. 165 | 5.5 | 6.6 | 41.0 | 1070 |
| Exe. 166 | 11.5 | 27 | 45.5 | 1640 |
| Exe. 167 | 16.1 | 23.8 | 262 | 1230 |
| Exe. 168 | 12.0 | 7.9 | 11.6 | 31 |
| Exe. 169 | 14.6 | | 43 | 340 |
| Exe. 170 | 5.6 | 96 | 31.6 | 230 |
| Exe. 171 | 12.4 | | 30.2 | 1980 |
| Exe. 172 | 14.8 | | 74 | 197 |
| Exe. 173 | 22.5 | | 80 | 254 |
| Exe. 174 | 5.4 | | 60.6 | 240 |
| Exe. 175 | 4.9 | 9.8 | 30.5 | 270 |
| Exe. 176 | 5.7 | | 40 | 60 |
| Exe. 177 | 9.5 | | 37 | 690 |
| Exe. 178 | 5.3 | 34.7 | 159 | 4880 |
| Exe. 179 | 10.5 | | 51.5 | 206 |
| Exe. 180 | 9.8 | | 31.7 | 152 |
| Exe. 181 | 7.1 | 4.8 | 25.7 | 23 |
| Exe. 182 | 14.7 | 32 | 17.0 | 752 |
| Exe. 183 | 13.6 | 56 | 15.7 | 230 |
| Exe. 184 | 7.6 | 73.4 | 310 | 610 |
| Exe. 185 | 12.3 | | 46.4 | 1480 |
| Exe. 186 | 5.0 | 27.5 | 53.3 | 640 |
| Exe. 187 | 6.8 | 34.3 | 63.8 | 638 |
| Exe. 188 | 17.2 | 19 | 23.5 | 34 |
| Exe. 189 | 10.7 | 29.8 | 19.3 | 260 |
| Exe. 190 | 11.9 | 87 | 74.3 | 875 |
| Exe. 191 | 11.8 | 10 | 9.4 | 2530 |
| Exe. 192 | 17.5 | | 20 | 2910 |
| Exe. 193 | 10.9 | 6.8 | 7.4 | 2300 |
| Exe. 194 | 10.5 | 8.8 | 9.5 | 2320 |
| Exe. 195 | 6.1 | 13 | 10.1 | 790 |
| Exe. 196 | 11.8 | 13 | 14.6 | 2500 |
| Exe. 197 | 5.7 | | 14.2 | 3290 |
| Exe. 198 | 8.3 | | 5.7 | 740 |
| Exe. 199 | 14 | 11.7 | 11 | 3700 |
| Exe. 200 | 10 | | 5.5 | 3180 |
| Exe. 201 | 11.4 | | 326 | 239 |
| Exe. 202 | 12.7 | | 246 | 66 |
| Exe. 203 | 16.2 | | 61 | 539 |
| Exe. 204 | 9.3 | | 72 | 1850 |
| Exe. 205 | 25.1 | 13 | 9.2 | 1090 |
| Exe. 206 | 14.6 | | 8.2 | 1650 |
| Exe. 207 | 10.2 | | 8.3 | 71 |
| Exe. 208 | 14.9 | 37 | 9.8 | 640 |
| Exe. 209 | 8.4 | 9.0 | 5.9 | 51 |
| Exe. 210 | 11.8 | 19 | 17 | 636 |
| Exe. 211 | 7.8 | 6.4 | 2.3 | 190 |
| Exe. 212 | 5.5 | 20.1 | 21.1 | 177 |
| Exe. 213 | 10.7 | | 7.2 | 79 |
| Exe. 214 | 9.4 | | 11.5 | 180 |
| Exe. 215 | 13.2 | 19 | 14.5 | 618 |
| Exe. 216 | 10.6 | 10 | 11.8 | 536 |
| Exe. 217 | 9.9 | 8.9 | 2.3 | 178 |
| Exe. 218 | 9.1 | 7.8 | 3.1 | 21 |
| Exe. 219 | 11 | 8.3 | 8.8 | 632 |
| Exe. 220 | 14.9 | 7.1 | 4.6 | 240 |
| Exe. 221 | 6.7 | 11 | 7.8 | 1270 |
| Exe. 222 | 8.7 | | 17.3 | 490 |
| Exe. 223 | 6.9 | | 9.0 | 3430 |
| Exe. 224 | 9.5 | 29 | 22.4 | 4700 |
| Exe. 225 | 10.7 | 11 | 12 | 5720 |
| Exe. 226 | 9.1 | | 11 | 3530 |
| Exe. 227 | 17.2 | 27 | 34.4 | 17800 |
| Exe. 228 | 14.7 | | 12 | 3330 |
| Exe. 229 | 13.4 | | 6.9 | 3170 |
| Exe. 230 | 11.7 | 20.7 | 12 | 830 |
| Exe. 231 | 11.6 | 12.5 | 7.1 | 310 |
| Exe. 232 | 11 | 14 | 10.9 | 418 |
| Exe. 233 | 8.1 | | 18.5 | 559 |
| Exe. 234 | 9.9 | 16 | 6.8 | 63 |
| Exe. 235 | 13.4 | 22 | 12.2 | 1290 |
| Exe. 236 | 9.5 | 21 | 7.1 | 404 |
| Exe. 237 | 13.9 | 3.7 | 730 | 14900 |
| Exe. 238 | 15.6 | | 57.3 | 2220 |
| Exe. 239 | 9.7 | 7.0 | 27.2 | 930 |
| Exe. 240 | 19.1 | | 27.2 | 1040 |
| Exe. 241 | 17.9 | 9.1 | 61.5 | 1770 |
| Exe. 242 | 16.7 | | 372 | 4630 |

We claim:

1. A compound of formula (I) or a pharmaceutically acceptable salt thereof

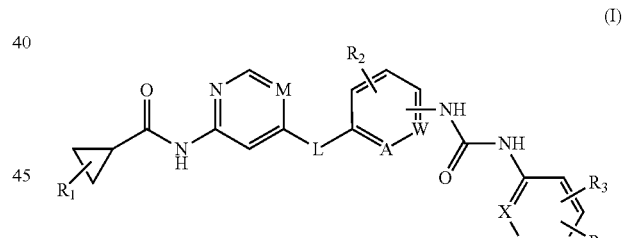

wherein:
R$_1$ is hydrogen, C$_{1-6}$ alkyl, C$_{1-6}$ haloalkyl, halo or cyano;
M is CH or N;
L is O, NH or N(CH$_3$);
A is CR$_5$ or N;
W is CR$_6$ or N;
R$_2$, R$_5$ and R$_6$ are independently hydrogen, C$_{1-6}$ alkyl, C$_{1-6}$ haloalkyl, halo, C$_{3-7}$ cycloalkyl or cyano;
X, Y, and Z are independently CH or N; and
R$_3$ and R$_4$ are independently hydrogen, halo, cyano, C$_{1-6}$ alkyl, C$_{1-6}$ haloalkyl, C$_{2-6}$ alkenyl, hydroxyl-C$_{1-6}$ alkyl, di-(C$_{1-6}$ alkylamino)-C$_{1-6}$ alkyl, amino, C$_{1-6}$ alkylamino, C$_{3-7}$ cycloalkylamino, di-(C$_{1-6}$ alkyl)amino, amino-C$_{1-6}$ alkylamino, C$_{1-6}$ alkoxy-C$_{1-6}$ alkylamino, C$_{1-6}$ alkoxycarbonyl-C$_{1-6}$ alkylamino, di-(C$_{1-6}$ alkoxy-C$_{1-6}$ alkyl)amino, aminocarbonyl, C$_{1-6}$ alkylaminocarbonyl, di-(C$_{1-6}$ alkyl)aminocarbonyl, C$_{3-7}$ cycloalkylaminocarbonyl, C$_{1-6}$ alkoxy, C$_{3-7}$ cycloalkoxy, hydroxyl-$C_{1-6}$ alkoxy, $C_{1-6}$ haloalkoxy, amino-$C_{1-6}$ alkyl, amino-$C_{1-6}$ alkoxy, $C_{1-6}$ alkylsulfonyl, $C_{2-6}$ alkenylsulfonyl, $C_{3-7}$ cycloalkylsulfonyl, heterocyclyl optionally substituted by B, aryl optionally substituted by B, heteroaryl optionally substituted by B, $C_{1-6}$ alkylsulfonylamino, $C_{2-6}$ alkenylsulfonylamino, $C_{3-7}$ cyclooalkylsulfonylamino, amido, $C_{1-6}$ alkylcarbonylamino, $C_{2-6}$ alkenylcarbonylamino, $C_{3-7}$ cyclooalkylcarbonylamino, $C_{1-6}$ alkoxycarbonylamino, $C_{3-7}$ cycloalkoxycarbonylamino, ureido, $C_{3-7}$ cycloalkyl, $C_{3-7}$ halocycloalkyl, heterocyclyl-oxy, piperidinylamino, N-methyl-piperidinyl-4-carbonyl, piperazinyl-$C_{1-6}$ alkyl, pyrrolylcarbonylamino, N-methyl-piperidinylcarbonylamino or heterocyclyl-$C_{1-6}$ alkoxy; or $R_3$ and $R_4$ together form a 3 to 8-membered ring with the atoms in the aromatic ring to which they are attached; and B is hydrogen, $C_{1-6}$ alkyl, $C_{1-6}$ haloalkyl, halo, hydroxyl, aryl, amino, $C_{1-6}$ alkylamino, $C_{3-7}$ cycloalkylamino, di-($C_{1-6}$ alkyl)amino, cyano, or $C_{3-7}$ cycloalkyl.

2. The compound of claim 1, wherein the NHCONH and L substituents on the central aromatic ring are in a 1,3-configuration.

3. The compound of claim 1, wherein the NHCONH and L substituents on the central aromatic ring are in a 1,4-configuration.

4. The compound according to claim 1, wherein L is O.

5. The compound according to claim 1, wherein L is NH or N(CH$_3$).

6. The compound according to claim 1, wherein X, Y, and Z are all CH.

7. The compound according to claim 1, wherein one of X, Y, or Z is N and the other two are CH.

8. The compound according to claim 1, wherein M is CH.

9. The compound according to claim 1, wherein M is N.

10. The compound according to claim 1, wherein A is CR$_5$.

11. The compound according to claim 1, wherein A is N.

12. The compound according to claim 1, wherein W is CR$_6$.

13. The compound according to claim 1, wherein W is N.

14. The compound according to claim 1, wherein $R_1$ is hydrogen or $C_{1-3}$ alkyl.

15. The compound according to claim 1, wherein $R_2$, $R_5$ and $R_6$ are independently hydrogen, $C_{1-3}$ alkyl, $C_{1-3}$ haloalkyl, halo, or cyano.

16. The compound according to claim 1, wherein $R_3$ and $R_4$ are independently hydrogen, halo, cyano, $C_{1-6}$ alkyl, $C_{1-6}$ haloalkyl, $C_{2-6}$ alkenyl, hydroxyl-$C_{1-6}$ alkyl, di-($C_{1-6}$ alkylamino)-$C_{1-6}$ alkyl, amino, $C_{1-6}$ alkylamino, $C_{3-7}$ cycloalkylamino, di-($C_{1-6}$ alkyl)amino, amino-$C_{1-6}$ alkylamino, $C_{1-6}$ alkoxy-$C_{1-6}$ alkylamino, $C_{1-6}$ alkoxycarbonyl-$C_{1-6}$ alkylamino, di-($C_{1-6}$ alkoxy-$C_{1-6}$ alkyl)amino, aminocarbonyl, $C_{1-6}$ alkylaminocarbonyl, di-($C_{1-6}$ alkyl)aminocarbonyl, $C_{3-7}$ cycloalkylaminocarbonyl, $C_{1-6}$ alkoxy, $C_{3-7}$ cycloalkoxy, hydroxyl-$C_{1-6}$ alkoxy, $C_{1-6}$ haloalkoxy, amino-$C_{1-6}$ alkyl, amino-$C_{1-6}$ alkoxy, $C_{1-6}$ alkylsulfonyl, $C_{2-6}$ alkenylsulfonyl, $C_{3-7}$ cycloalkylsulfonyl, heterocycle optionally substituted by B, aryl optionally substituted by B, heteroaryl optionally substituted by B, $C_{1-6}$ alkylsulfonylamino, $C_{2-6}$ alkenylsulfonylamino, $C_{3-7}$ clcyoalkylsulfonylamino, amido, $C_{1-6}$ alkylcarbonylamino, $C_{2-6}$ alkenylcarbonylamino, $C_{3-7}$ clcyoalkylcarbonylamino, $C_{1-6}$ alkoxycarbonylamino, $C_{3-7}$ cycloalkoxycarbonylamino, ureido, $C_{3-7}$ cycloalkyl, $C_{3-7}$ halocycloalkyl, heterocyclyl-oxy, piperidinylamino, N-methyl-piperidinyl-4-carbonyl, piperazinyl-$C_{1-6}$ alkyl, pyrrolylcarbonylamino, N-methyl-piperidinylcarbonylamino or heterocyclyl-$C_{1-6}$ alkoxy.

17. The compound of claim 16, wherein one or both of $R_3$ and $R_4$ are independently a heterocyclyl-oxy group selected from pyrrolyloxy, piperidinyloxy, furanyloxy and azetidinyloxy.

18. The compound of claim 16, wherein one or both of $R_3$ and $R_4$ are independently an optionally substituted aryl group selected from phenyl and naphthyl.

19. The compound of claim 16, wherein one or both of $R_3$ and $R_4$ are independently an optionally substituted hereroaryl group selected from furyl, pyridinyl, pyridazinyl, pyrimidinyl, pyrazinyl, thienyl, isoxazolyl, oxazolyl, oxadiazolyl, imidazolyl, pyrrolyl, pyrazolyl, triazolyl, tetrazolyl, thiazolyl, isothiazolyl, 1,2,3-thiadiazolyl, benzimidazolyl, indolyl, indazolyl, benzoisothiazolyl, benzoxazolyl, benzoisoxazolyl, quniolinyl and isoquinolinyl.

20. The compound of claim 19, wherein the hereroaryl is pyridinyl, oxazolyl, or triazolyl.

21. The compound of claim 16, wherein one or both of $R_3$ and $R_4$ are independently an optionally substituted heterocyclyl group selected from piperidinyl, piperazinyl, homopiperazinyl, azepinyl, azetidinyl, pyrrolidinyl, pyrazolidinyl, imidazolidinyl, imidazolinyl, oxazolidinyl, isoxazolidinyl, morpholinyl, thiazolidinyl, isothiazolidinyl, quinuclidinyl, thiadiazolidinyl, benzothiazolidinyl, benzopyrrolidinyl, dihydrofuranyl, tetrahydrofuranyl, dihydropyranyl, tetrahydropyranyl, thiomorpholinyl, 1-oxo-thiomorpholinyl, 1,1-dioxothiomorpholinyl, dihydroquinolinyl, dihydroisoquinolinyl, tetrahydroquinolinyl and tetrahydroisoquinolinyl.

22. The compound of claim 21, wherein the optionally substituted heterocyclyl is N($R_7$)piperazinyl, N($R_7$)piperidin-4-yl, pyrrolidinyl, 2-oxopyrrolidinyl, morpholinyl, 2-methylmorpholinyl, 2,6-dimethylmorpholinyl, 2-oxomorpholinyl, 3-(dimethylamino)pyrrolidinyl, 2-oxo-5-methyloxazolidin-3-yl, 3,3-difluoroazetidinyl, fluoropiperidinyl, hydroxylpiperidinyl, or 1,1,-dioxothiomorpholinyl, and $R_7$ is hydrogen, $C_{1-3}$ alkyl, $C_{1-3}$ haloalkyl, $C_{3-6}$ cycloalkyl, $C_{1-5}$ acyl, or $C_{3-6}$ cycloalkylacyl.

23. The compound according to claim 18, wherein B is hydrogen, $C_{1-3}$ alkyl, $C_{1-3}$ haloalkyl, halo, hydroxyl, aryl, amino, $C_{1-3}$ alkylamino, $C_{3-5}$ cycloalkylamino, di-($C_{1-3}$ alkyl)amino, cyano, or $C_{3-5}$ cycloalkyl.

24. The compound of claim 23, wherein B is hydrogen, halo, hydroxyl, $C_{1-3}$ alkyl, $C_{1-3}$ haloalkyl, or di-($C_{1-3}$ alkyl) amino.

25. The compound of claim 16, wherein $R_3$ and $R_4$ are independently halo, cyano or $C_{1-3}$ haloalkyl.

26. The compound according to claim 1, wherein $R_3$ and $R_4$ together form a 3 to 8-membered ring with the atoms in the aromatic ring to which they are attached.

27. The compound according to claim 1, having following structures:

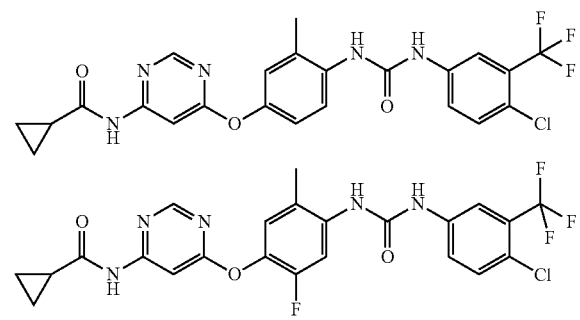

-continued

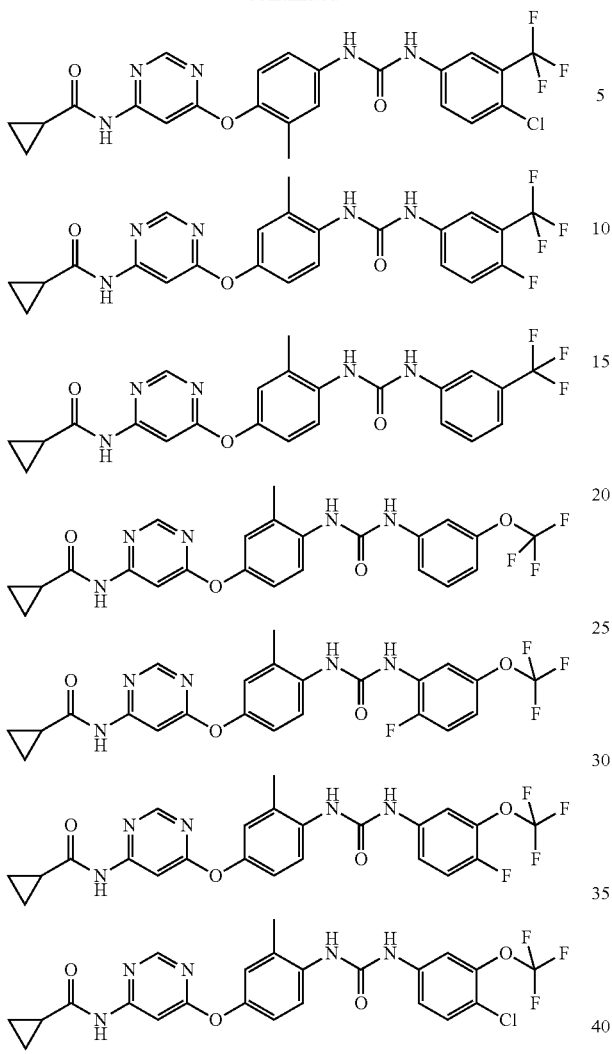

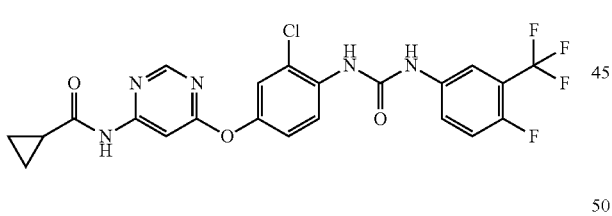

or pharmaceutically acceptable salts thereof.

28. A process of preparing a compound of Formula (I) according to claim 1:

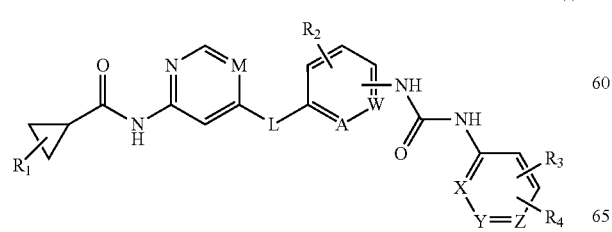
(I)

comprising reacting of compound (II):

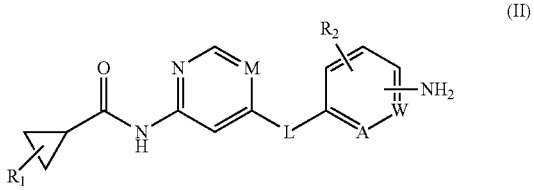
(II)

with compound (III):

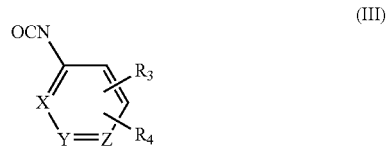
(III)

Wherein M, L, A, W, X, Y, Z and $R_1$ to $R_4$ are as defined in claim 1.

29. A process of preparing a compound of Formula (I) according to claim 1:

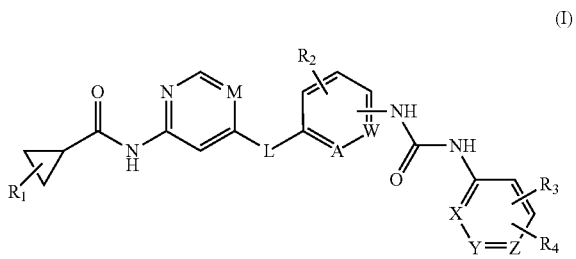
(I)

comprising reacting of compound (II):

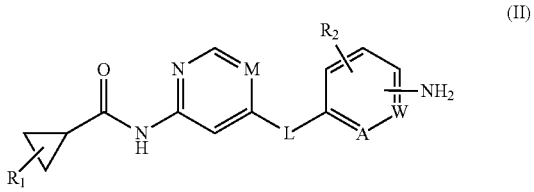
(II)

with compound (IV):

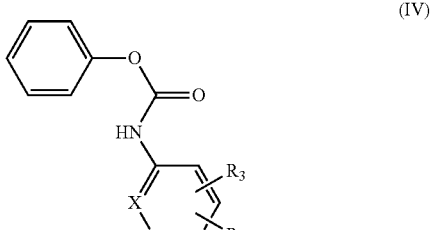
(IV)

Wherein M, L, A, W, X, Y, Z and $R_1$ to $R_4$ are as defined in claim 1.

30. A process of preparing a compound of Formula (I) according to claim 1:

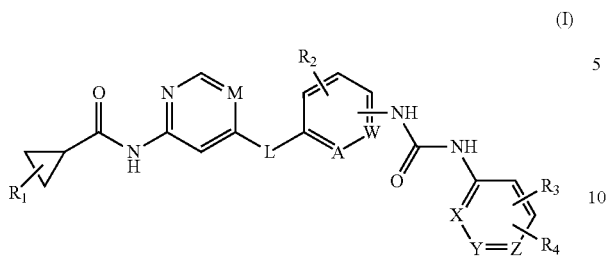
(I)

comprising reacting of compound (V):

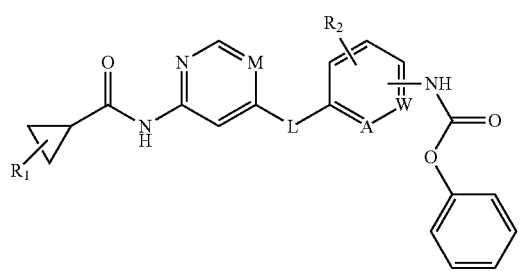
(V)

with compound (VI):

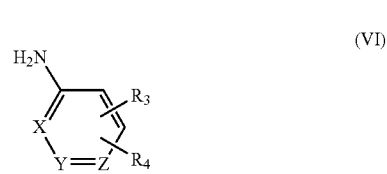
(VI)

Wherein M, L, A, W, X, Y, Z and $R_1$ to $R_4$ are as defined in claim 1.

31. A pharmaceutical composition comprising a compound according claim 1, together with a pharmaceutically acceptable carrier or excipient.

32. A method of treating cancer comprising administering to a mammal in need of such treatment a therapeutically effective amount of a compound according to claim 1, wherein the cancer is breast cancer, colon cancer, lung or prostate cancer.

* * * * *